(12) United States Patent
Bower et al.

(10) Patent No.: US 11,401,522 B2
(45) Date of Patent: Aug. 2, 2022

(54) FUNGAL GENOME MODIFICATION SYSTEMS AND METHODS OF USE

(71) Applicant: Danisco US Inc., Palo Alto, CA (US)

(72) Inventors: Benjamin S. Bower, Palo Alto, CA (US); Jimmy Chan, Palo Alto, CA (US); Jing Ge, Palo Alto, CA (US); Xiaogang Gu, Palo Alto, CA (US); Susan Mampusti Madrid, Palo Alto, CA (US); Danfeng Song, Palo Alto, CA (US); Mingmin Song, Palo Alto, CA (US); Michael Ward, Palo Alto, CA (US); Steven Sungin Kim, Palo Alto, CA (US)

(73) Assignee: DANISCO US INC, Palo Alto, CA (US)

( * ) Notice: Subject to any disclaimer, the term of this patent is extended or adjusted under 35 U.S.C. 154(b) by 642 days.

(21) Appl. No.: 15/536,933

(22) PCT Filed: Dec. 16, 2015

(86) PCT No.: PCT/US2015/066192
§ 371 (c)(1),
(2) Date: Jun. 16, 2017

(87) PCT Pub. No.: WO2016/100568
PCT Pub. Date: Jun. 23, 2016

(65) Prior Publication Data
US 2019/0093114 A1    Mar. 28, 2019

(30) Foreign Application Priority Data

Dec. 16, 2014  (CN) .................. PCT/CN2014/093914
Dec. 16, 2014  (CN) .................. PCT/CN2014/093916
Dec. 16, 2014  (CN) .................. PCT/CN2014/093918

(51) Int. Cl.
*C12N 15/80*  (2006.01)
*C12N 9/22*   (2006.01)
*C12N 15/11*  (2006.01)

(52) U.S. Cl.
CPC .............. *C12N 15/80* (2013.01); *C12N 9/22* (2013.01); *C12N 15/11* (2013.01); *C12N 2310/20* (2017.05)

(58) Field of Classification Search
CPC .................................. C12N 9/22; C12N 15/80
See application file for complete search history.

(56) References Cited

U.S. PATENT DOCUMENTS 8,697,359 B1    4/2014  Zhang et al.
2014/0179006 A1*  6/2014  Zhang .................... C12N 15/63
                                                435/462
2016/0354487 A1* 12/2016  Zhang ................... A61K 38/465
2017/0088845 A1*  3/2017  Ryan ...................... C12N 15/81
2017/0226533 A1*  8/2017  Frisch ................... C12N 15/905

FOREIGN PATENT DOCUMENTS

WO    2013141680 A1    9/2013
WO    2014065596 A1    5/2014
WO    2015054507 A1    4/2015

OTHER PUBLICATIONS

Arazoe et al., FEMS Microbiol. Lett., 352, 2, 221-229 (Year: 2014).*
Di Carlo et al., Nuc. Acids. Res., 41, 7, 4336-4343 (Year: 2013).*
Strathern et al. Genetics (Year: 1995).*
Yang et al., PLoS Genet., 4, 11, e1000264 (Year: 2008).*
Krappmann et al., FUngal Biol. Rev., 21, 25-29 (Year: 2007).*
Kim et. al. Genome Res. Highly efficient RNA-guided genome editing in human cells via delivery of purified Cas9 ribonucleoproteins. 2014 24: 1012-1019 (Year: 2014).*
Accession CL531790. 2010 trib005xe10.g3 T. reesei HindIII BAC library Trichoderma reesei genomic clone trib005xe10 3',genomic survey sequence (Year: 2010).*
Li et al. Achieving efficient protein expression in Trichoderma reesei by using strong constitutive promoters. Microbial Cell Factories 2012, 11:84 (Year: 2012).*
Liang Liu et al., CRISPR-Cas system: a powerful tool for genome editing, Plant Molecular Biology, 2014, pp. 209-218, vol. 85.
Chandler Julie M et al, "Protein profiling of the dimorphic, pathogenic fungus, Penicillium marneffei", Proteome Science, Biomed Central, London, GB,No. 1, Jun. 4, 2008 (Jun. 4, 2008), p. 17.
Giedrius Gasiunas et al., Cas9-crRNA ribonucleoprotein complex mediates specific DNA cleavage for adaptive immunity in bacteria, Proc. Nal. Acad. Sci. USA, 2012, E2579-86, vol. 109.
Martin Jinek et al., A Programmable Dual-RNA-Guided DNA Endonuclease in Adaptive Bacterial Immunity, Science, Aug. 17, 2012, pp. 816-821, vol. 337.
Le Cong et al., Multiplex Genome Engineering Using CRISPR/Cas Systems, Science, Feb. 15, 2013, pp. 819-823, vol. 339.
Prashant Mali et al, RNA Guided Human Genome Engineering via Cas9, Science, Feb. 15, 2013, pp. 823-826, vol. 339.
Fuller Kevin K et al, "Development of the CRISPR/Cas9 System for Targeted Gene Disruption in Aspergillus fumigatus.", Eukaryotic Cell Nov. 2015,vol. 14, No. 11, Nov. 2015 (Nov. 2015), p. 1073-1080.
Rui Liu, Ling Chen, Yanping Jiang, Zhihua Zhou, Gen Zou, "Efficient genome editing in filamentous fungus Trichoderma reesei using the CRISPR/Cas9 system", Cell Discovery,vol. 1, May 12, 2015 (May 12, 2015), p. 1-11.

(Continued)

*Primary Examiner* — Nancy J Leith
*Assistant Examiner* — Tiffany Nicole Grooms

(57) ABSTRACT

Compositions and methods are provided for genome modification at a target site in the genome of a fungal cell. The methods and compositions are drawn to a guide polynucleotide/Cas endonuclease system for promoting modification of the DNA sequence at a target site in a fungal host cell genome.

9 Claims, 12 Drawing Sheets

Specification includes a Sequence Listing.

(56) References Cited

OTHER PUBLICATIONS

Christina S. Nødvig et al, "A CRISPR-Cas9 System for Genetic Engineering of Filamentous Fungi", PLOS ONE, vol. 10, No. 7, Jul. 15, 2015 (Jul. 15, 2015), p. e0133085.
P. Mali et al, "RNA-Guided Human Genome Engineering via Cas9", Science, vol. 339, No. 6121, Jan. 3, 2013 (Jan. 3, 2013), p. 823-826.
Takayuki Arazoe et al, "Tailor-made CRISPR/Cas system for highly efficient targeted gene replacement in the rice blast fungus", Biotechnology and Bioengineering, vol. 112, No. 12, Dec. 14, 2015 (Dec. 14, 2015), p. 2543-2549.
Chi Zhang et al, "Highly efficient CRISPR mutagenesis by microhomology-mediated end joining in Aspergillus fumigatus", Fungal Genetics And Biology,vol. 86, Dec. 14, 2015 (Dec. 14, 2015), p. 47-57.
De Boer P et al, "Highly efficient gene targeting in Penicillium chrysogenum using the bi-partite approach in DELTAlig4 or DELTAku70 mutants", Oct. 1, 2010 (Oct. 1, 2010), vol. 47, No. 10, p. 839-846.
Takayuki Arazoe et al, "Site-specific DNA double-strand break generated by I-SceI endonuclease enhances ectopic homologous recombination in Pyricularia oryzae", FEMS Microbiology Letters,vol. 352, No. 2, Feb. 26, 2014 (Feb. 26, 2014), p. 221-229.
J. E. Dicarlo et al, "Genome engineering in *Saccharomyces cerevisiae* using CRISPR-Cas systems", Nucleic Acids Research,vol. 41, No. 7, Mar. 4, 2013 (Mar. 4, 2013), p. 4336-4343.
Yoshizui Ishino et al., Nucleotide Sequence of the iap Gene, Responsible for Alkaline Phosphatase Isozyme Conversion in *Escherichia coli*, and Identification of the Gene Product, Journal of Bacteriology, Dec. 1987, pp. 5429-5433.
Atsuo Nakata et al., Unusual Nucleotide Arrangement with Repeated Sequences in the *Escherichia coli* K-12 Chromosome, Journal of Bacteriology, Jun. 1989, pp. 3553-3556, vol. 171, No. 6.
Peter M. A. Groenen et al., Nature of DNA polymorphis in the direct repeat cluster of *Mycobacterium* tuberculosis; application for strain differentiation by a novel typing method, Molecular Microbiology, 1993, pp. 1057-1065, vol. 10, No. 5.
Nancy Hoe et al., Rapid Molecular Genetic Subtyping of Serotype M1 Group A *Streptococcus* Strains, Emerging Infectious Diseases, Mar.-Apr. 1999, pp. 254-263, vol. 5, No. 2.
Bernd Masepohl et al., Long tandemly repeated repetitive (LTRR) sequences in the filamentous cyanobacterium *Anabaena* sp. PCC7120, Biochimica et Biophysica Acta, 1996, pp. 26-30.

F. J. M. Mojica et al., Long stretches of short tandem repeats are present in the largest replicons of the Archaea Haloferax mediterranei and Haloferax volcanii and could be involved in replicon partitioning, Molecular Microbiology, 1995, pp. 85-93, vol. 17, No. 1.
Norah Rudin et al., Genetic and Physical Analysis of Double-Strand Break Repair and Recombination in *Saccharomyces cerevisiae*, Genetics, Jul. 1989, pp. 519-534, vol. 122.
Fatima Smih et al., Double-strand breaks at the target locus stimulate gene targeting in embryonic stem cells, Nucleic Acids Research, 1995, pp. 5012-5019, vol. 23, No. 24.
Patrick D. Hsu et al., Development and Applications of CRISPR-Cas9 for Genome Engineering, Cell, Jun. 5, 2014, pp. 1262-1278, vol. 157.
Basak Anindita et al, "A pseudouridine residue in the spliceosome core is part of the filamentous growth program in yeast.", Cell Reports Aug. 21, 2014,vol. 8, No. 4, Aug. 21, 2014 (Aug. 21, 2014), p. 966-973.
Jean-Yves Bleuyard et al., Recent advances in understanding of the DNA double-strand break repair machinery of plants, DNA Repair, 2006, pp. 1-12, vol. 5.
Ralph Siebert et al., Efficient Repair of Genomic Double-Strand Breaks by Homologous Recombination between Directly Repeated Sequences in the Plant Genome, The Plant Cell, May 2002, pp. 1121-1131, vol. 14.
Michael Pacher et al., Two Unlinked Double-Strand Breaks Can Induce Reciprocal Exchanges in Plant Genomes via Homologous Recombination and Nonhomologous End Joining, Genetics, 2007, pp. 21-29, vol. 175.
Dewei Jiang et al, "Molecular tools for functional genomics in filamentous fungi: Recent advances and new strategies", Biotechnology Advances.,vol. 31, No. 8, Dec. 1, 2013 (Dec. 1, 2013), p. 1562-1574.
Prashant Mali et al, "Cas9 as a versatile tool for engineering biology", Nature Method, Oct. 1, 2013 (Oct. 1, 2013), vol. 10, No. 10, p. 957-963.
Marck, Christian et al., The RNA polymerase III-dependent family of genes in hemiascomycetes; comparative RNomics, decoding strategies transcription and evolutionary implications, Nucleic Acids Research, 2006, pp. 1816-1835, vol. 34, No. 6.
International Search Report—PCT/US2015/066192—dated May 2, 2016.

\* cited by examiner

T. reesei U6 gene SEQ ID NO:22

AAAAAACACTAGTAAGTACTACTTATGTATTATTAACTACTTAGCTAACTTCTGCAGTACTACCT
AAGAGGCTAGGGGTAGTTTTATAGCAGACTTATAGCTATTATTTTATTTAGTAAAGTGCTTTTAAA
GTAAGGTCTTTTTATAGCACTTTTTATTTATTTATTATATATATTATATATAATAATTTTAAGCCTGGAATA
GTAAAGAGGCTTATATATAATTATATAGTAATAAAAAGCTTAGCAGCTGTAATATAATTCCTAAAGAA
ACAGCATGAAATGGTATTATGTAAGAGCTATAGTCTAAAGGCACTCTGCTGGATAAAAATAGTGG

"TATA" Box
CTATAAGTCTGCTGCAAAACTACCCCCCAACCTCGTAGG TATATAA GTACTGTTTGATGGTAGTCTA

Intron →

A-Box                        B-Box
Trans. Start
→
TC G CCTTCGGGCATT TGGTCAATTTA TAACGATACAG GTTCGTTTC GGCTTTTCCTCGGAACCC

CCAGAGGTCATCAGTTCGAATCGCTAACAG GTCAACAGAGAAGATTAGCATGGCCCCTGCACT

Terminator
AAGGATGACACGCTCACTCAAAGAGAAGCTAAACA TTTTTTTCTCTT CCAAGTCGTGATGGTTA TCTTTTTGCTTAGAGAATCTATTCTTGTGGACGATTAGTAGTATTGGTAAATCCCTGCTGCACATTGCGGC
GGATGGTCTCAACGGCATAATACCCCATTCGTGATGCAGCGGTGATCTTCAATATGTAGTGTAATACG
TTGCATACACCACCAGTTCGGTGCCCTCCTGTAGTACAGTACGTAGTTCGACTCCTCCGGCAGG
TGGAAACGATTCCCTAGTGGGCAGGTATTTGGCGGGGTCAAGAA

Deletion of 611 nucleotides in pyr4 gene

```
                                                                    Section 12
         (628) 628       640       650       660       670       684
    9-96 (345) CCGCTGACGGCTTACCTGTTCAAGCTCATGGACCTCAAGGCGTCCAACCTGTGCCTG
 pyr4 Tr (628) CCGCTGACGGCTTACCTGTTCAAGCTCATGGACCTCAAGGCGTCCAACCTGTGCCTG
                                                                    Section 13
         (685) 685  690       700       710       720       730  741
    9-96 (402) AGCGCCGACGTGCCGACGGCGCGCGAGCTGCTGTACCTGGCCGACAAGATTGGCCCG
 pyr4 Tr (685) AGCGCCGACGTGCCGACAGCGCGCGAGCTGCTGTACCTGGCCGACAAGATTGGCCCG
                                                                    Section 14
         (742) 742    750       760       770       780       798
    9-96 (459) TCGATTGTCGTGCTCAAGACGCACTACG---(---)-----------------------
 pyr4 Tr (742) TCGATTGTCGTGCTCAAGACGCACTACGACATGGTCTCGGGCTGGGACTTCCACCCG
                                                                    Section 15
         (799) 799       810       820       830       840       855
    9-96 (487) ---------------------------------------------------------
 pyr4 Tr (799) GAGACGGGCACGGGAGCCCAGCTGGCGTCGCTGGCGCGCAAGCACGGCTTCCTCATC
                                                                    Section 16
         (856) 856       870       880       890       900       912
    9-96 (487) ---------------------------------------------------------
 pyr4 Tr (856) TTCGAGGACCGCAAGTTTGGCGACATTGGCCACACCGTCGAGCTGCAGTACACGGGC
        (1084) 1084 1090      1100      1110      1120      1130  1140
    9-96 (487) ---------------------------------------------------------
 pyr4 Tr (1084) GACGCCGACTCCAGGGACGCCGAGCCCGCCGGCGCCGTCAACGGCATGGGCTCCATT
                                                                    Section 21
        (1141) 1141      1150      1160      1170      1180      1197
    9-96 (487) ---------------------------------------------------------
 pyr4 Tr (1141) GGCGTCCTGGACAAGCCCATCTACTCGAACCGGTCCGGCGACGGCCGCAAGGGCAGC
                                                                    Section 22
        (1198) 1198      1210      1220      1230      1240      1254
    9-96 (487) ---------------------------------------------------------
 pyr4 Tr (1198) ATCGTCTCCATCACCACCGTCACCCAGCAGTACGAGTCCGTCTCCTCGCCCCGGTTA
                                                                    Section 23
        (1255) 1255 1260      1270      1280      1290      1300  1311
    9-96 (487) ---------------------------------------------------------
 pyr4 Tr (1255) ACAAAGGCCATCGCCGAGGGCGACGAGTCGCTCTTCCCGGGCATCGAGGAGGCGCCG
                                                                    Section 24
        (1312) 1312      1320      1330      1340      1350      1368
    9-96 (487) ---------------------------------------------------------
 pyr4 Tr (1312) CTGAGCCGCGGCCTCCTGATCCTCGCCCCAAATGTCCAGCCAGGGCAACTTCATGAAC
        (1369) 1369      1380      1390      1400      1410      1425
    9-96 (487) -----------CAGGCCTGCGTCGAGGCCGCCCGGGAGCACAAGGACTTTGTCATG
 pyr4 Tr (1369) AAGGAGTACACGCAGGCCTGCGTCGAGGCCGCCCGGGAGCACAAGGACTTTGTCATG
```

P37 (2.4) #10MH94 1 bp insertion

```
Query 521 CTGGCCGACAAGATTGGCCCGTCGATTGTCGTGCTCAAGACGCACTACG-ACATGGTCTC 579
          |||||||||||||||||||||||||||||||||||||||||||||||||  |||||||||
Sbjct 523 CTGGCCGACAAGATTGGCCCGTCGATTGTCGTGCTCAAGACGCACTACGGACATGGTCTC 464
```

1 bp Insertion

```
              700       710       720       730       740       750       760       770
     pyr4 Tr  GACAGCGCGCGAGCTGCTGTACCTGGCCCTGGCCCGACAAGATTGGCCCCGTCGATTGTCGTGCTCAAGACGCCACTACG
P37 #13 4.2 rc GACAGCGCGCGAGCTGCTGTACCTGGCCCTGGCCCGACAAGATTGGCCCCGTCGATTGTCGTGCTCAAGACGCCACTACG
P37 #14.1 #12 rc GACAGCGCGCGAGCTGCTGTACCTGGCCCTGGCCCGACAAGATTGGCCCCGTCGATTGTCGTGCTCAAGACGCCACTACG
  consensus   GACAGCGCGCGAGCTGCTGTACCTGGCCCTGGCCCGACAAGATTGGCCCCGTCGATTGTCGTGCTCAAGACGCCACTACG 780       790       800
     pyr4 Tr  ACATGGTCTCGGGCTGGGACTTCCACCCGG
P37 #13 4.2 rc GCATGGTCTCGGGCTGGGACTTCCACCCGG
P37 #14.1 #12 rc TACATGGTCTCGGGCTGGGACTTCCACCCGG
  consensus    ACATGGTCTCGGGCTGGGACTTCCACCCGG
```

1 bp deletion

```
              700       710       720       730       740       750       760       770
     pyr4 Tr  GACAGCGCGCGAGCTGCTGTACCTGGCCCTGGCCCGACAAGATTGGCCCCGTCGATTGTCGTGCTCAAGACGCCACTACG
P37 #15 4.4 rc GACAGCGCGCGAGCTGCTGTACCTGGCCCTGGCCCGACAAGATTGGCCCCGTCGATTGTCGTGCTCAAGACGCCACTACG
  consensus   GACAGCGCGCGAGCTGCTGTACCTGGCCCTGGCCCGACAAGATTGGCCCCGTCGATTGTCGTGCTCAAGACGCCACTACG 780       790       800
     pyr4 Tr  ACATGGTCTCGGGCTGGGACTTCCACCCGG
P37 #15 4.4 rc CATGGTCTCGGGCTGGGACTTCCACCCGG
  consensus    CATGGTCTCGGGCTGGGACTTCCACCCGG
```

988 bp DELETION

```
              700       710       720       730       740       750       760       770
     pyr4 Tr  GACAGCGCGCGAGCTGCTGTACCTGGCCCTGGCCCGACAAGATTGGCCCCGTCGATTGTCGTGCTCAAGACGCCACTACG
P37 #14 4.3   GACAGCGCGCGAGCTGCTGTACCTGGCCCTGGCCCGACAAGATTGGCCCCGTCGATTGTCGTGCTCAAGACGCCAAGAAG
  consensus   GACAGCGCGCGAGCTGCTGTACCTGGCCCTGGCCCGACAAGATTGGCCCCGTCGATTGTCGTGCTCAAGACGCCA A G 780       790       800    812
     pyr4 Tr  ACATGGTCTCGGGCTGGGACTTCCACCCGGAGACGGGCACGGG
P37 #14 4.3   G---GGAAAAGGAGGAGGACAAAC-GGAGCTGAGAAAG---
  consensus    G   GG  GGGA    C A C  GGAG  G G A G
```

FUNGAL GENOME MODIFICATION SYSTEMS AND METHODS OF USE

CROSS-REFERENCE TO RELATED APPLICATIONS

The present application claims priority to PCT Patent Appln. Ser. Nos. PCT/CN2014/093918, PCT/CN2014/093916, and PCT/CN2014/093914, all filed Dec. 16, 2014, which are hereby incorporated by reference in their entireties.

SEQUENCE LISTING

The sequence listing submitted via EFS, in compliance with 37 C.F.R. § 1.52(e), is incorporated herein by reference. The sequence listing text file submitted via EFS contains the file "40532-WO-PCT-6_2015-868_Final_ST25.txt" created on Dec. 13, 2015, which is 154,047 bites in size

BACKGROUND

Bacteria and archaea have evolved adaptive immune defenses termed clustered regularly interspaced short palindromic repeats (CRISPR)/CRISPR-associated (Cas) systems that can introduce double strand beaks in DNA in a sequence-specific manner. Cas systems perform their functions through the activity of a ribonucleoprotein complex that includes short RNA sequences (tracrRNA and crRNA) and an RNA dependent endonuclease (Cas endonuclease) that targets a specific DNA sequence (through homology to a portion of the crRNA, called the variable targeting domain) and generates double strand breaks in the target. CRISPR loci were first recognized in *E. coli* (Ishino et al. (1987) J. Bacterial. 169:5429-5433; Nakata et al. (1989) J. Bacterial. 171:3553-3556), with similar interspersed short sequence repeats being subsequently identified in a number of bacterial species, including but not limited to *Haloferax mediterranei, Streptococcus pyogenes, Anabaena,* and *Mycobacterium tuberculosis* (Groenen et al. (1993) Mol. Microbiol. 10:1057-1065; Hoe et al. (1999) Emerg. Infect. Dis. 5:254-263; Masepohl et al. (1996) Biochim. Biophys. Acta 1307:26-30; Mojica et al. (1995) Mol. Microbiol. 17:85-93).

It is well known that inducing cleavage at a specific target site in genomic DNA can be used to introduce modifications at or near that site. For example, homologous recombination for gene targeting has been shown to be enhanced when the targeted DNA site contains a double-strand break (see, e.g., Rudin et al., Genetics 122:519-534; Smih et al., Nucl. Acids Res. 23:5012-5019). Given the site-specific nature of Cas systems, genome modification/engineering technologies based on these systems have been described, including in mammalian cells (see, e.g., Hsu et al.; Cell vol. 157, p 1262-1278, 5 Jun. 2014 entitled "Development and Applications of CRISPR-Cas9 for Genome Engineering"). The power of the Cas-based genome engineering comes from the ability to target virtually any specific location within a complex genome by designing a recombinant crRNA (or equivalently functional polynucleotide) in which the DNA-targeting region (variable targeting domain) of the crRNA is homologous to the desired target site in the genome and combining it with a Cas endonuclease (through any convenient means) into a functional complex in a host cell.

Although Cas-based genome engineering technologies have been applied to a number of different host cell types, the efficient use of such systems in fungal cells has proven to be difficult. Thus, there still remains a need for developing efficient and effective Cas-based genome engineering methods and compositions for modifying/altering a genomic target site in a fungal cell.

BRIEF SUMMARY

Compositions and methods are provided that relate to employing a guide RNA/Cas endonuclease system for modifying the DNA sequence at a target site in the genome of a fungal cell, e.g., a filamentous fungal cell.

Aspects of the present disclosure are drawn to methods for modifying the DNA sequence at a target site in the genome of a fungal cell. In some embodiments, the method includes: a) introducing into a population of fungal cells a Cas endonuclease and a guide RNA, wherein the Cas endonuclease and guide RNA are capable of forming a complex that enables the Cas endonuclease to introduce a double-strand break at a target site in the genome of the fungal cells; and b) identifying at least one fungal cell from the population that has a modification of the DNA sequence at the target site, where the Cas endonuclease, the guide RNA, or both are introduced transiently into the population of fungal cells.

In one aspect, the present disclosure are drawn to a method for modifying the DNA sequence at a target site in the genome of a fungal cell, the method including: a) introducing into a fungal cell a Cas endonuclease and a guide RNA, wherein the Cas endonuclease and guide RNA are capable of forming a complex that enables the Cas endonuclease to introduce a double-strand break at a target site in the genome of the fungal cell; and b) identifying if a modification of the DNA sequence at the target site has occurred in the fungal cell, where the Cas endonuclease, the guide RNA, or both are introduced transiently into the fungal cell.

In another aspect, the present disclosure is drawn to methods for modifying the DNA sequence at a target site in the genome of a fungal cell. In some embodiments, the method includes: a) introducing into a population of fungal cells a Cas endonuclease and a guide RNA, wherein the Cas endonuclease and guide RNA are capable of forming a complex that enables the Cas endonuclease to introduce a double-strand break at a target site in the genome of the fungal cells; and b) identifying at least one fungal cell from the population that has a modification of the DNA sequence at the target site, where both the Cas endonuclease and the guide RNA are introduced non-transiently into the population of fungal cells.

In yet another aspect, the present disclosure are drawn to a method for modifying the DNA sequence at a target site in the genome of a fungal cell, the method including: a) introducing into a fungal cell a Cas endonuclease and a guide RNA, wherein the Cas endonuclease and guide RNA are capable of forming a complex that enables the Cas endonuclease to introduce a double-strand break at a target site in the genome of the fungal cell; and b) identifying if a modification of the DNA sequence at the target site has occurred in the fungal cell, where both the Cas endonuclease and the guide RNA are introduced non-transiently into the fungal cell.

In certain embodiments of the methods described herein, the modification of the DNA sequence at said target site is selected from the group consisting of a deletion of one or more nucleotides, an insertion of one or more nucleotides, a substitution of one or more nucleotides, and any combination thereof.

In certain embodiments, the identifying step comprises culturing the population of fungal cells or the fungal cell from step (a) under conditions to select for or screen for the modification of the DNA sequence at the target site. In certain embodiments, the identifying step comprises culturing the population of fungal cells or the fungal cell from step (a) under conditions to screen for unstable transformants Several different types of CRISPR-Cas systems have been described and can be classified as Type I, Type II, and Type III CRISPR-Cas systems (see, e.g., the description in Liu and Fan, CRISPR-Cas system: a powerful tool for genome editing. Plant Mol Biol (2014) 85:209-218). In certain embodiments, the Cas endonuclease or variant thereof is a Cas9 endonuclease of the Type II CRISPR-Cas system. The Cas9 endonuclease may be any convenient Cas9 endonuclease, including but not limited to Cas9 endonucleases, and functional fragments thereof, from the following bacterial species: *Streptococcus* sp. (e.g., *S. pyogenes, S. mutans*, and *S. thermophilus*), *Campylobacter* sp. (e.g., *C. jejuni*), *Neisseria* sp. (e.g., *N. meningitides*), *Francisella* sp. (e.g., *F. novicida*), and *Pasteurella* sp. (e.g., *P. multocida*). Numerous other species of Cas9 can be used. For example, functional Cas9 endonucleases or variants thereof containing an amino acid sequence that has at least 70% identity to any one of SEQ ID NOs:1 to 7 may be employed, e.g., at least 80% identity, at least 90% identity, at least 95% identity, at least 96% identity, at least 97% identity, at least 98% identity, at least 99% identity, and including up to 100% identity to any one of SEQ ID NOs:1 to 7. In other embodiments, the Cas endonuclease or variant thereof is a Cpf1 endonuclease of the Type II CRISPR-Cas system. Cpf1 mediates robust DNA interference with features distinct from Cas9. Cpf1 lacks tracrRNA and utilizes a T-rich protospacer-adjacent motif. It cleaves DNA via a staggered DNA double-stranded break. See, e.g., Zetsche et al., Cell (2015) 163:759-771.

Introducing the Cas endonuclease or the guide RNA into the population of fungal cells can be achieved using any convenient method, including: transfection, transduction, transformation, electroporation, particle bombardment (biolistic particle delivery), and cell fusion techniques.

In certain embodiments, introducing the Cas endonuclease and/or the guide RNA into the fungal cells includes introducing one or more DNA constructs comprising expression cassettes for the Cas endonuclease, the guide RNA, or both into the fungal cells. The one or more DNA constructs, once in the fungal cells, express the Cas endonuclease and/or the guide RNA. In certain embodiments, the DNA construct is a linear DNA construct. In certain embodiments, the DNA construct is a circular DNA construct. In certain embodiments, the DNA construct is a recombinant DNA construct.

In certain embodiments, the introducing step includes directly introducing a Cas endonuclease polypeptide, a guide RNA, or both into the fungal cells. Any combination of direct introduction and using DNA constructs can be employed (e.g., introducing a DNA construct with an expression cassette for a Cas endonuclease into the fungal cell and directly introducing a guide RNA into the cell, either simultaneously or sequentially as desired).

In certain embodiments of the methods described herein, the Cas expression cassette in the DNA construct includes a Cas endonuclease encoding gene that is optimized for expression in the fungal cell. For example, a Cas endonuclease encoding gene that is optimized for expression in filamentous fungal cells includes a sequence that has at least 70% sequence identity to SEQ ID NO:8 (encoding Cas9 from *S. pyogenes*; SEQ ID NO:1), e.g., at least 80% identity, at least 90% identity, at least 95% identity, at least 96% identity, at least 97% identity, at least 98% identity, at least 99% identity, and including up to 100% identity to SEQ ID NO:8.

In some instances, the Cas endonuclease is operably linked to one or more nuclear targeting signal (also referred to as a nuclear localization signal/sequence; NLS). SEQ ID NO:9 and SEQ ID NO:10 provide an example of a filamentous fungal cell optimized Cas9 gene with NLS sequences at the N- and C-termini and the encoded amino acid sequence, respectively. Many different NLSs are known in eukaryotes. They include monopartite, bipartite and tripartite types. Any convenient NLS can be used, the monopartite type being somewhat more convenient with examples including the SV40 NLS, a NLS derived from the *T. reesei* blr2 (blue light regulator 2) gene, or a combination of both. In some embodiments, the DNA construct is a recombinant one and comprises a promoter operably linked to a filamentous fungal cell optimized polynucleotide sequence encoding a Cas9 endonuclease or variant thereof.

In certain embodiments of the methods described herein, a DNA construct or an expression cassette comprising a guide RNA-encoding sequence and capable of expressing the guide RNA, is introduced into the population of fungal cells or the fungal cell. In some embodiments, the DNA construct or the expression cassette comprises a RNA polymerase III dependent promoter functional in a Euascomycete or Pezizomycete, wherein the promoter is operably linked to the guide RNA-encoding sequence. In some embodiments, the promoter is derived from a *Trichoderma* U6 snRNA gene. In certain embodiments, the promoter comprises a nucleotide sequence with at least 60%, 65%, 70%, 75%, 80%, 85%, 90%, 95%, 96%, 97%, 98%, or 99% identity to SEQ ID NO: 11 or 12. In specific embodiments, the promoter comprises the sequence of SEQ ID NO: 11 or 12. In some embodiments, the DNA construct or the expression cassette for the guide RNA comprises a guide RNA-encoding DNA with an intron sequence from a *Trichoderma* U6 snRNA gene. In some embodiments, the intron sequence derived from *Trichoderma* U6 snRNA gene comprises a nucleotide sequence with at least 60%, 65%, 70%, 75%, 80%, 85%, 90%, 95%, 96%, 97%, 98%, or 99% identity to SEQ ID NO: 90. In specific embodiments, the intron sequence derived from *Trichoderma* U6 snRNA gene comprises the sequence of SEQ ID NO: 90.

In certain embodiments, the modification of the DNA sequence at the target site in the genome of the fungal cells or the fungal cell is caused by non-homologous end joining (NHEJ), either without the presence of a donor DNA or in the presence of a donor DNA that is also introduced into the fungal cells or the fungal cell. In certain other embodiments, the modification of the DNA sequence at the target site is caused by homologous recombination, optionally through the presence of a donor DNA that is also introduced into the fungal cell(s). In some embodiments, the modification (e.g., a deletion of one or more nucleotides, an insertion of one or more nucleotides, insertion of an expression cassette encoding a protein of interest, or a substitution of one or more nucleotides) is originally present in the donor DNA. In some embodiments, the donor DNA has a sequence homologous to a region of the chromosomal DNA on each side of, or at or near, the target site of the Cas/guide RNA complex over at least. In some other embodiments, the donor DNA does not have a sequence homologous to a region of the chromosomal DNA on each side of, or at or near, the target site of the Cas/guide RNA complex. In certain embodiments, the donor DNA comprises an expression cassette encoding a protein of interest. In certain embodiments, the protein of interest encoded by the expression cassette is an enzyme. In particular embodiments, the protein of interest is a hemicellulase, a peroxidase, a protease, a cellulase, a xylanase, a lipase, a phospholipase, an esterase, a cutinase, a pectinase, a keratinase, a reductase, an oxidase, a phenol oxidase, a lipoxygenase, a ligninase, a pullulanase, a tannase, a pentosanase, a mannanase, a beta-glucanase, an arabinosidase, a hyaluronidase, a chondroitinase, a laccase, an amylase, a glucoamylase, a variant thereof, a functional fragment thereof, or a hybrid or mixture of two or more thereof. In yet other particular embodiments, the protein of interest is a peptide hormone, a growth factor, a clotting factor, a chemokine, a cytokine, a lymphokine, an antibody, a receptor, an adhesion molecule, a microbial antigen, a variant thereof, a functional fragment thereof, or a hybrid or mixture of two or more thereof.

In certain embodiments where homologous recombination between the donor DNA and the genome of the fungal cell(s) is desired, the NHEJ pathway in the fungal cell(s) is non-functional (inactivated) or reduced, e.g., where one or more components of the NHEJ pathway are inactivated, nonfunctional, or have reduced activity (e.g., ku80, ku70, rad50, mre11, xrs2, lig4, xrs, or combinations thereof). For example, the fungal cell can have an inactivated/reduced activity form of ku80. In certain other embodiments, the NHEJ pathway in the fungal cell(s) is functional.

Fungal cells that find use in the subject methods can be filamentous fungal cell species. In certain embodiments, the fungal cell is a Eumycotina or Pezizomycotina fungal cell. In some embodiments, the fungal cell is selected from *Trichoderma, Penicillium, Aspergillus, Humicola, Chrysosporium, Fusarium, Neurospora, Myceliophthora, Thermomyces, Hypocrea,* and *Emericella*. The filamentous fungi *Trichoderma reesei, P. chrysogenum, M. thermophila, Thermomyces lanuginosus, A. oryzae* and *A. niger* are of particular interest. Other fungal cells, including species of yeast, can also be employed.

The target site selected by a user of the disclosed methods can be located within a region of a gene of interest selected from the group consisting of: an open reading frame, a promoter, a regulatory sequence, a terminator sequence, a regulatory element sequence, a splice site, a coding sequence, a polyubiquitination site, an intron site, and an intron enhancing motif. Examples of genes of interest include genes encoding acetyl esterases, aminopeptidases, amylases, arabinases, arabinofuranosidases, carboxypeptidases, catalases, cellulases, chitinases, cutinase, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, peroxidases, phenoloxidases, phytases, polygalacturonases, proteases, rhamno-galacturonases, ribonucleases, transferases, transport proteins, transglutaminases, xylanases, hexose oxidases, and combinations thereof. Target genes encoding regulatory proteins such as transcription factors, repressors, proteins that modify other proteins such as kinases, proteins involved in post-translational modification (e.g., glycosylation) can be subjected to Cas mediated editing as well as genes involved in cell signaling, morphology, growth rate, and protein secretion. No limitation in this regard is intended.

In some embodiments of the methods, the step of identifying a fungal cell having a genomic modification at the target site of interest includes culturing the population of cells from step (a) under conditions to select for or screen for the modification at the target site. Such conditions include antibiotic selection conditions, conditions that select for or screen for auxotrophic cells, and the like.

In certain embodiments, the introducing step includes: (i) obtaining a parental fungal cell population that stably expresses the Cas endonuclease, and (ii) transiently introducing the guide RNA into the parental fungal cell population. Conversely, the introducing step can include: (i) obtaining a parental fungal cell population that stably expresses the guide RNA, and (ii) transiently introducing the Cas endonuclease into the parental fungal cell population.

Aspects of the present disclosure are drawn to recombinant fungal cells produced by the methods described above as well as those for use as parental host cells in performing the methods.

Aspects of the present disclosure further include an engineered nucleic acid, e.g., a recombinant DNA construct that can be used in the methods described above or disclosed herein. In one aspect, the engineered nucleic acid encodes a Cas endonuclease or variant thereof. In some embodiments, the Cas endonuclease or variant thereof encoded by the engineered nucleic acid comprises an amino acid sequence that has at least 70%, 75%, 80%, 85%, 90%, or 95% identity to any one of SEQ ID NOs:1 to 7. In some embodiments, the engineered nucleic acid comprises a polynucleotide sequence that is codon-optimized for expression in filamentous fungi. In some embodiments, the engineered nucleic acid comprises a polynucleotide sequence that is at least 70% 75%, 80%, 85%, 90%, 95%, 96%, 97%, 98%, or 99% identical to SEQ ID NO:8. In a particular embodiment, the nucleic acid comprises the sequence of SEQ ID NO:8. In some embodiments, the engineered nucleic acid comprises a promoter for expression of the Cas endonuclease or variant thereof.

In another aspect, the engineered nucleic acid encodes a guide RNA. In some embodiments, the nucleic acid encoding the guide RNA comprises a RNA polymerase III dependent promoter functional in a filamentous fungal cell, a Euascomycete or a Pezizomycete. In some embodiments, the promoter is derived from a *Trichoderma* U6 snRNA gene. In particular embodiments, the promoter comprises a nucleotide sequence with at least 60%, 65%, 70%, 75%, 80%, 85%, 90%, 95%, 96%, 97%, 98%, or 99% identity to SEQ ID NO: 11 or 12 or a functional fragment thereof. In particular embodiments, the nucleic acid comprises the sequence of SEQ ID NO: 11 or 12. In some embodiments, the guide RNA-encoding nucleic acid has a promoter operably linked to at least one heterologous sequence or guide RNA-encoding sequence, where the promoter functions in a filamentous fungal cell as an RNA polymerase III (pol III) dependent promoter to express the heterologous sequence and includes a polynucleotide sequence that has at least 80% sequence identity to SEQ ID NO:11 or 12 (e.g., 80%, 85%, 90%, 95%, 98%, 99%, 100%, or any value there between) or a functional fragment thereof. In certain embodiments, the heterologous sequence or guide RNA-encoding sequence comprises an intron sequence derived from a *Trichoderma* U6 snRNA gene. In particular embodiments, the heterologous sequence or guide RNA-encoding sequence includes an intron that contains a U6 B-Box sequence, e.g., a B-Box sequence having the polynucleotide sequence of GTTCGTTTC. The intron can have a polynucleotide sequence with at least 60%, 65%, 70%, 75%, 80%, 85%, 90%, 95%, 96%, 97%, 98%, or 99% identity to SEQ ID NO: 90. In particular embodiments, the intron comprises a polynucleotide sequence with at least 80% sequence identity to SEQ ID NO:90. In particular embodiments, the nucleic acid comprises the sequence of SEQ ID NO:90. In some embodiments, the guide RNA-encoding nucleic acid comprises both the RNA polymerase III dependent promoter and the intron sequence derived from *Trichoderma* U6 snRNA gene as described herein. In some embodiments, the engineered nucleic acid or the recombinant DNA construct further includes a transcriptional terminator sequence downstream of the heterologous sequence, e.g., the sequence set forth in SEQ ID NO:91 or its derivative.

In certain embodiments, the promoter comprised in the Cas endonuclease-encoding engineered nucleic acid and/or the guide RNA-encoding engineered nucleic acid is derived from a filamentous fungal cell. The filamentous fungal cell can be selected from any of a wide variety of filamentous fungal cells, with specific examples including *T. reesei* and *A. niger*. In some cases, the promoter is derived from a ribosomal RNA (rRNA) promoter.

The recombinant DNA construct operably linked to promoter may encode a functional RNA. In certain aspects, for example, the heterologous sequence encodes a guide RNA polynucleotide, e.g., a guide RNA that includes (i) a first nucleotide sequence domain that is complementary to a polynucleotide sequence in a target DNA (variable targeting domain); and (ii) a second nucleotide sequence domain that interacts with a Cas endonuclease (CER domain).

Aspects of the present disclosure include a vector having the recombinant DNA construct having a promoter operably linked to at least one heterologous sequence as described herein. The vector can further include an expression cassette for a Cas endonuclease.

The present disclosure further provides a filamentous fungal cell containing a recombinant DNA constructs having a promoter operably linked to at least one heterologous sequence as described herein. Methods of expressing a heterologous sequence in a filamentous fungal cell by a) introducing the recombinant DNA construct having a promoter operably linked to at least one heterologous sequence (e.g., as an vector) into a filamentous fungal cell, and b) culturing the filamentous fungal cell of step a) under conditions to allow expression of the heterologous sequence in the recombinant DNA construct (or vector).

Additional embodiments of the methods and compositions of the present disclosure are shown herein.

BRIEF DESCRIPTION OF THE DRAWINGS

The disclosure can be more fully understood from the following detailed description and the accompanying drawings, which form a part of this application.

FIG. 1 depicts the nucleotide sequence of a putative *T. reesei* U6 gene (SEQ ID NO:22). Elements of interest are indicated, including the TATA box (underlined), the transcriptional start site (downward arrow), the A-box (underlined), the Intron (forward arrow), the B-box (underlined; within the Intron of the gene), the sequences that are identical to the human U6 gene (in bold italics), and the terminator (underlined).

FIG. 10. Sequence analysis of the of the pyr4 gene from strains that are resistant to FOA and requires uridine for growth. Alignment with the wild type sequence (K21 control T4; SEQ ID NO:68) revealed the presence of sequence modifications at the target site in the pyr4 gene (insertions of a few (1-2 bps) or many (68 bp) nucleotides). SEQ ID NOs: 69 to 77 are the sequences for strains T4 4-3, T4 4-13, T4 4-11, T4 4-12, T4 4-18, T4 4-20, T4 4-19, T4 4-4, and T4 4-7, respectively. Strains T4 4-13 (SEQ ID NO: 70) and T4 4-12 (SEQ ID NO: 72) have no changes from the wild type sequence at the target site.

FIG. 11A shows agarose gel analysis of pyr4 specific PCR products (encompassing the target site) of two strains (T4 2.2. and T4 4.1) resistant to FOA and that require uridine for growth isolated after direct introduction of in vitro formed Cas9/guide RNA complex followed by growth on Vogel's Uridine/FOA plates. Strain T4 2.2 (Lane 2) showed a PCR product that is of lower molecular weight than the T4 4.1 clone (Lane 3; which is equivalent to the control, shown in Panel B, Lane 2), indicating a large deletion in the pyr4 gene. FIG. 11B shows a similar PCR/agarose gel analysis as in FIG. 11A, but showing T4 strains 4.1, 4.2, 4.3, and 4.4, all of which are resistant to FOA and that require uridine for growth. Strain 4.3 (Lane 5) showed PCR product of the pyr4 gene that is of lower molecular weight than the control (C+; Lane 2).

FIG. 12. Sequence analysis of the pyr4 genes derived from clones T4 2.2 (shown in FIG. 11A) and T4 2.4. Sequence analysis shows that the T4 2.2 clone (top alignment) has a deletion of 611 base pairs at the target site of the introduced Cas9/guide RNA complex. The sequence corresponding to the VT domain sequence of the guide RNA is boxed and the PAM site is circled. The bottom alignment shows a 1 base pair insertion in the pyr4 gene at the target site of the isolated T4 2.4 strain (a "G" residue). The sequence corresponding to the VT domain sequence of the guide RNA is indicated with a line over the alignment and the PAM site is circled. SEQ ID NOs:78 to 81 are the sequences for 9-96 (T4 2.2 strain), Pyr Tr (wild type sequence), Query (wild type sequence), and Sbjct (T4 2.4 strain), respectively.

FIG. 13. Sequence analysis of the pyr4 genes derived from clones T4 4.1 and 4.2 (top alignment), 4.3 (bottom alignment) and 4.4 (middle alignment) (which are shown in FIG. 11B). The wild type pyr4 sequence is the first sequence (top) in all alignments and a consensus is shown on the bottom of all alignments (SEQ ID NO:82). The top alignment shows that the T4 4.1 clone (third sequence in the alignment; SEQ ID NO:84) has an insertion of a T nucleotide while the T4 4.2 clone (second sequence in the alignment; SEQ ID NO:83) has an insertion of a G nucleotide at the target site in the pyr4 gene. (The consensus sequence in this alignment is the same as SEQ ID NO:82.) The middle alignment shows that the T4 4.4 clone (second sequence in the alignment; SEQ ID NO:85) has a deletion of an A nucleotide at the target site in the pyr4 gene. (The consensus sequence in this alignment is the same as SEQ ID NO:85.) The bottom alignment shows that the pyr4 gene sequence in the T4 4.3 clone (second sequence in the alignment; SEQ ID NO: 86) diverges abruptly at the target site. (The consensus sequence in this alignment is SEQ ID NO:87; spaces in the consensus sequence in FIG. 13 are represented by "N" in SEQ ID NO:87.) Further alignment analysis (not shown) confirmed that the T4 4.3 clone has a deletion of 988 base pairs at the target site for the introduced Cas9/guide RNA complex.

DETAILED DESCRIPTION

Figure 2:
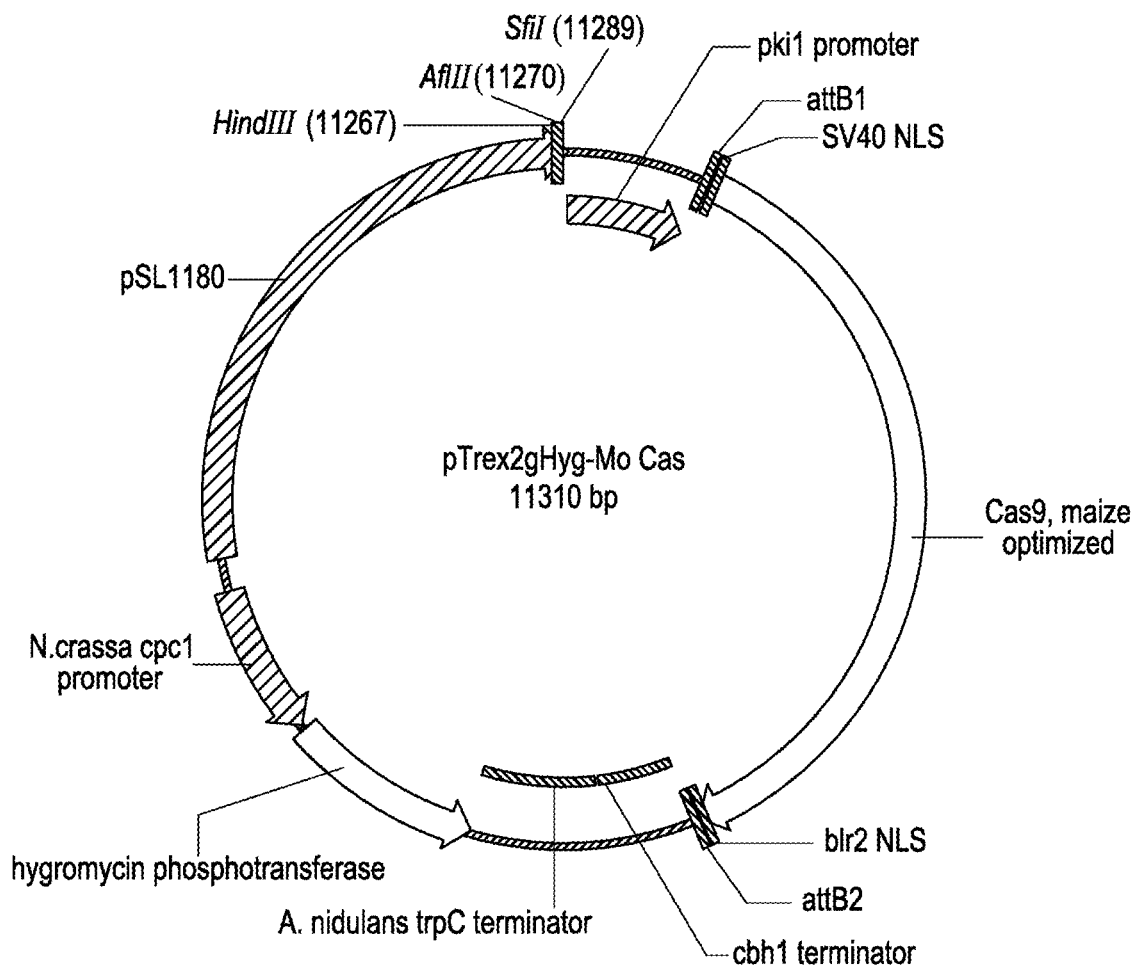
FIG. 2 shows a schematic of the pTrex2gHyg-Mo Cas plasmid.

The present disclosure includes compositions and methods that find use in modifying the DNA sequence at a target site in the genome of a fungal cell. The methods employ a functional guide RNA/Cas endonuclease complex which recognizes a desired target site and introduces a double strand break at the site. Repair of this double-strand break can introduce modifications to the DNA sequence at the target site.

Before the present compositions and methods are described in greater detail, it is to be understood that the present compositions and methods are not limited to particular embodiments described, and as such may, of course, vary. It is also to be understood that the terminology used herein is for the purpose of describing particular embodiments only, and is not intended to be limiting, since the scope of the present compositions and methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the present compositions and methods. The upper and lower limits of these smaller ranges may independently be included in the smaller ranges and are also encompassed within the present compositions and methods, subject to any specifically excluded limit in the stated range. Where the stated range includes one or both of the limits, ranges excluding either or both of those included limits are also included in the present compositions and methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrequited number may be a number which, in the context in which it is presented, provides the substantial equivalent of the specifically recited number. For example, in connection with a numerical value, the term "about" refers to a range of −10% to +10% of the numerical value, unless the term is otherwise specifically defined in context. In another example, the phrase a "pH value of about 6" refers to pH values of from 5.4 to 6.6, unless the pH value is specifically defined otherwise.

The headings provided herein are not limitations of the various aspects or embodiments of the present compositions and methods which can be had by reference to the specification as a whole. Accordingly, the terms defined immediately below are more fully defined by reference to the specification as a whole.

The present document is organized into a number of sections for ease of reading; however, the reader will appreciate that statements made in one section may apply to other sections. In this manner, the headings used for different sections of the disclosure should not be construed as limiting.

Unless defined otherwise, all technical and scientific terms used herein have the same meaning as commonly understood by one of ordinary skill in the art to which the present compositions and methods belongs. Although any methods and materials similar or equivalent to those described herein can also be used in the practice or testing of the present compositions and methods, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present compositions and methods are not entitled to antedate such publication by virtue of prior invention. Further, the dates of publication provided may be different from the actual publication dates which may need to be independently confirmed.

In accordance with this detailed description, the following abbreviations and definitions apply. Note that the singular forms "a," "an," and "the" include plural referents unless the context clearly dictates otherwise. Thus, for example, reference to "an enzyme" includes a plurality of such enzymes, and reference to "the dosage" includes reference to one or more dosages and equivalents thereof known to those skilled in the art, and so forth.

It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present compositions and methods described herein. Any recited method can be carried out in the order of events recited or in any other order which is logically possible.

Definitions

As used herein, a polypeptide referred to as a "Cas endonuclease" or having "Cas endonuclease activity" relates to a CRISPR associated (Cas) polypeptide encoded by a Cas gene where the Cas protein is capable of cutting a target DNA sequence when functionally coupled with one or more guide polynucleotides (see, e.g., U.S. Pat. No. 8,697,359 entitled "CRISPR-Cas systems and methods for altering expression of gene products"). Variants of Cas endonucleases that retain guide polynucleotide directed endonuclease activity are also included in this definition. The Cas endonucleases employed in the donor DNA insertion methods detailed herein are endonucleases that introduce double-strand breaks into the DNA at the target site. A Cas endonuclease is guided by the guide polynucleotide to recognize and cleave a specific target site in double stranded DNA, e.g., at a target site in the genome of a cell.

As used herein, the term "guide polynucleotide" relates to a polynucleotide sequence that can form a complex with a Cas endonuclease and enables the Cas endonuclease to recognize and cleave a DNA target site. The guide polynucleotide can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA".

The guide polynucleotide can be a double molecule (also referred to as duplex guide polynucleotide) comprising a first nucleotide sequence domain (referred to as Variable Targeting domain or VT domain) that is complementary to a nucleotide sequence in a target DNA and a second nucleotide sequence domain (referred to as Cas endonuclease recognition domain or CER domain) that interacts with a Cas endonuclease polypeptide. The CER domain of the double molecule guide polynucleotide comprises two separate molecules that are hybridized along a region of complementarity. The two separate molecules can be RNA, DNA, and/or RNA-DNA-combination sequences. In some embodiments, the first molecule of the duplex guide polynucleotide comprising a VT domain linked to a CER domain is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the crRNA naturally occurring in Bacteria and Archaea. In one embodiment, the size of the fragment of the crRNA naturally occurring in Bacteria and Archaea that is present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides. In some embodiments the second molecule of the duplex guide polynucleotide comprising a CER domain is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides). In certain embodiments, the RNA that guides the RNA/Cas9 endonuclease complex is a duplexed RNA comprising a duplex crRNA-tracrRNA.

The guide polynucleotide can also be a single molecule comprising a first nucleotide sequence domain (referred to as Variable Targeting domain or VT domain) that is complementary to a nucleotide sequence in a target DNA and a second nucleotide domain (referred to as Cas endonuclease recognition domain or CER domain) that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. In some embodiments the single guide polynucleotide comprises a crNucleotide (comprising a VT domain linked to a CER domain) linked to a tracrNucleotide (comprising a CER domain), wherein the linkage is a nucleotide sequence comprising a RNA sequence, a DNA sequence, or a RNA-DNA combination sequence. The single guide polynucleotide being comprised of sequences from the crNucleotide and tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). In one embodiment of the disclosure, the single guide RNA comprises a crRNA or crRNA fragment and a tracrRNA or tracrRNA fragment of the type II CRISPR/Cas system that can form a complex with a type II Cas endonuclease, wherein the guide RNA/Cas endonuclease complex can direct the Cas endonuclease to a fungal cell genomic target site, enabling the Cas endonuclease to introduce a double strand break into the genomic target site.

One aspect of using a single guide polynucleotide versus a duplex guide polynucleotide is that only one expression cassette needs to be made to express the single guide polynucleotide in a target cell.

The term "variable targeting domain" or "VT domain" is used interchangeably herein and includes a nucleotide sequence that is complementary to one strand (nucleotide sequence) of a double strand DNA target site. The % complementation between the first nucleotide sequence domain (VT domain) and the target sequence is at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 7%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or is 100% complementary. The VT domain can be at least 12, 13, 14, 15, 16, 17, 18, 19, 20, 21, 22, 23, 24, 25, 26, 27, 28, 29 or 30 nucleotides in length. In some embodiments, the VT domain comprises a contiguous stretch of 12 to 30 nucleotides. The VT domain can be composed of a DNA sequence, a RNA sequence, a modified DNA sequence, a modified RNA sequence, or any combination thereof.

The term "Cas endonuclease recognition domain" or "CER domain" of a guide polynucleotide is used interchangeably herein and includes a nucleotide sequence (such as a second nucleotide sequence domain of a guide polynucleotide), that interacts with a Cas endonuclease polypeptide. The CER domain can be composed of a DNA sequence, a RNA sequence, a modified DNA sequence, a modified RNA sequence (see for example modifications described herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence, such as, but not limiting to a GAAA tetraloop sequence.

Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide polynucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

As used herein, the term "guide polynucleotide/Cas endonuclease system" (and equivalents) includes a complex of a Cas endonuclease and a guide polynucleotide (single or double) that is capable of introducing a double strand break into a DNA target sequence. The Cas endonuclease unwinds the DNA duplex in close proximity of the genomic target site and cleaves both DNA strands upon recognition of a target sequence by a guide RNA, but only if the correct protospacer-adjacent motif (PAM) is appropriately oriented at the 3' end of the target sequence.

The terms "functional fragment", "fragment that is functionally equivalent", "functionally equivalent fragment", and the like, are used interchangeably and refer to a portion or subsequence of a parent biological sequence, e.g., a polypeptide that retains the qualitative enzymatic activity of the parent polypeptide, or a polynucleotide that retains the main function of the parent polynucleotide. For example, a functional fragment of a Cas endonuclease retains the ability to create a double-strand break with a guide polynucleotide. It is noted here that a functional fragment may have altered quantitative enzymatic activity as compared to the parent polypeptide. Other examples include a functional fragment of a gene promoter which retains the ability to promote transcription, a functional fragment of an intron which retains the ability to facilitate transcription, and a functional fragment of an enzyme-encoding gene sequence which encodes a functional fragment of an enzyme.

The terms "functional variant", "variant that is functionally equivalent", "functionally equivalent variant", and the like are used interchangeably and refer to a variant of a parent polypeptide that retains the qualitative enzymatic activity of the parent polypeptide. For example, a functional variant of a Cas endonuclease retains the ability to create a double-strand break with a guide polynucleotide. It is noted here that a functional variant may have altered quantitative enzymatic activity as compared to the parent polypeptide.

Fragments and variants can be obtained via any convenient method, including site-directed mutagenesis and synthetic construction.

The term "genome" as it applies to fungal cells encompasses not only chromosomal DNA found within the nucleus, but organelle DNA found within subcellular components (e.g., mitochondria) of the cell.

A "codon-modified gene" or "codon-preferred gene" or "codon-optimized gene" is a gene having its frequency of codon usage designed to mimic the frequency of preferred codon usage of the host cell. The nucleic acid changes made to codon-optimize a gene are "synonymous", meaning that they do not alter the amino acid sequence of the encoded polypeptide of the parent gene. However, both native and variant genes can be codon-optimized for a particular host cell, and as such no limitation in this regard is intended.

"Coding sequence" refers to a polynucleotide sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, 5' untranslated sequences, 3' untranslated sequences, introns, polyadenylation target sequences, RNA processing sites, effector binding sites, and stem-loop structures.

"Promoter" refers to a DNA sequence capable of controlling the expression of a coding sequence or functional RNA. The promoter sequence consists of proximal and more distal upstream elements, the latter elements often referred to as enhancers. An "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, and/or comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. As is well-known in the art, promoters can be categorized according to their strength and/or the conditions under which they are active, e.g., constitutive promoters, strong promoters, weak promoters, inducible/repressible promoters, tissue-specific/developmentally regulated promoters, cell-cycle dependent promoters, etc.

"RNA transcript" refers to the product resulting from RNA polymerase-catalyzed transcription of a DNA sequence. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. "Sense" RNA refers to RNA transcript that includes the mRNA and can be translated into protein within a cell or in vitro. "Antisense RNA" refers to an RNA transcript that is complementary to all or part of a target primary transcript or mRNA, and that, under certain conditions, blocks the expression of a target gene (see, e.g., U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated into a polypeptide but yet has an effect on cellular processes. The terms "complement" and "reverse complement" are used interchangeably herein with respect to mRNA transcripts, and are meant to define the antisense RNA of the message.

As used herein, "functionally attached" or "operably linked" means that a regulatory region or functional domain of a polypeptide or polynucleotide sequence having a known or desired activity, such as a promoter, enhancer region, terminator, signal sequence, epitope tag, etc., is attached to or linked to a target (e.g., a gene or polypeptide) in such a manner as to allow the regulatory region or functional domain to control the expression, secretion or function of that target according to its known or desired activity. For example, a promoter is operably linked with a coding sequence when it is capable of regulating the expression of that coding sequence (i.e., the coding sequence is under the transcriptional control of the promoter).

Standard recombinant DNA and molecular cloning techniques used herein are well known in the art.

"PCR" or "polymerase chain reaction" is a technique for the synthesis of specific DNA segments and consists of a series of repetitive denaturation, annealing, and extension cycles and is well known in the art.

The term "recombinant," when used in reference to a biological component or composition (e.g., a cell, nucleic acid, polypeptide/enzyme, vector, etc.) indicates that the biological component or composition is in a state that is not found in nature. In other words, the biological component or composition has been modified by human intervention from its natural state. For example, a recombinant cell encompass a cell that expresses one or more genes that are not found in its native parent (i.e., non-recombinant) cell, a cell that expresses one or more native genes in an amount that is different than its native parent cell, and/or a cell that expresses one or more native genes under different conditions than its native parent cell. Recombinant nucleic acids may differ from a native sequence by one or more nucleotides, be operably linked to heterologous sequences (e.g., a heterologous promoter, a sequence encoding a non-native or variant signal sequence, etc.), be devoid of intronic sequences, and/or be in an isolated form. Recombinant polypeptides/enzymes may differ from a native sequence by one or more amino acids, may be fused with heterologous sequences, may be truncated or have internal deletions of amino acids, may be expressed in a manner not found in a native cell (e.g., from a recombinant cell that over-expresses the polypeptide due to the presence in the cell of an expression vector encoding the polypeptide), and/or be in an isolated form. It is emphasized that in some embodiments, a recombinant polynucleotide or polypeptide/enzyme has a sequence that is identical to its wild-type counterpart but is in a non-native form (e.g., in an isolated or enriched form).

The term "engineered", when used in reference to a biological component or composition (e.g., a cell, nucleic acid, polypeptide/enzyme, vector, etc.) indicates that the biological component or composition is designed by human and is at least not completely derived from or completely identical to biological component or composition in nature, as far as the person who designs the "engineered" biological component or composition is aware at the time of designing. An engineered biological component or composition, e.g., an engineered nucleic acid, may be derived from various parts of different naturally existing biological components or compositions. An engineered biological component or composition may be a recombinant biological component or composition.

The terms "plasmid", "vector" and "cassette" refer to an extra chromosomal element that carries a polynucleotide sequence of interest, e.g., a gene of interest to be expressed in a cell (an "expression vector" or "expression cassette"). Such elements are generally in the form of double-stranded DNA and may be autonomously replicating sequences, genome integrating sequences, phage, or nucleotide sequences, in linear or circular form, of a single- or double-stranded DNA or RNA, derived from any source, in which a number of nucleotide sequences have been joined or recombined into a unique construction which is capable of introducing a polynucleotide of interest into a cell. The polynucleotide sequence of interest may be a gene encoding a polypeptide or functional RNA that is to be expressed in the target cell. Expression cassettes/vectors generally contain a gene with operably linked elements that allow for expression of that gene in a host cell.

The term "expression", as used herein, refers to the production of a functional end-product (e.g., an mRNA, guide RNA, or a protein) in either precursor or mature form.

"Introduced" in the context of inserting a polynucleotide or polypeptide into a cell (e.g., a recombinant DNA construct/expression construct) refers to any method for performing such a task, and includes any means of "transfection", "transformation", "transduction", physical means, or the like, to achieve introduction of the desired biomolecule.

By "introduced transiently", "transiently introduced", "transient introduction", "transiently express" and the like is meant that a biomolecule is introduced into a host cell (or a population of host cells) in a non-permanent manner. With respect to double stranded DNA, transient introduction includes situations in which the introduced DNA does not integrate into the chromosome of the host cell and thus is not transmitted to all daughter cells during growth as well as situations in which an introduced DNA molecule that may have integrated into the chromosome is removed at a desired time using any convenient method (e.g., employing a cre-lox system, by removing positive selective pressure for an episomal DNA construct, by promoting looping out of all or part of the integrated polynucleotide from the chromosome using a selection media, etc.). No limitation in this regard is intended. In general, introduction of RNA (e.g., a guide RNA, a messenger RNA, ribozyme, etc.) or a polypeptide (e.g., a Cas polypeptide) into host cells is considered transient in that these biomolecules are not replicated and indefinitely passed down to daughter cells during cell growth. With respect to the Cas/guide RNA complex, transient introduction covers situations when either of the components is introduced transiently, as both biomolecules are needed to exert targeted Cas endonuclease activity. Thus, transient introduction of a Cas/guide RNA complex includes embodiments where either one or both of the Cas endonuclease and the guide RNA are introduced transiently. For example, a host cell having a genome-integrated expression cassette for the Cas endonuclease (and thus not transiently introduced) into which a guide RNA is transiently introduced can be said to have a transiently introduced Cas/guide RNA complex (or system) because the functional complex is present in the host cell in a transient manner. In certain embodiments, the introducing step includes: (i) obtaining a parental fungal cell population that stably expresses the Cas endonuclease, and (ii) transiently introducing the guide RNA into the parental fungal cell population. Conversely, the introducing step can include: (i) obtaining a parental fungal cell population that stably expresses the guide RNA, and (ii) transiently introducing the Cas endonuclease into the parental fungal cell population.

"Mature" protein refers to a post-translationally processed polypeptide (i.e., one from which any pre- or propeptides. present in the primary translation product have been removed). "Precursor" protein refers to the primary product of translation of mRNA (i.e., with pre- and propeptides still present). Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance (the resulting host cell is sometimes referred to herein as a "stable transformant"). In contrast, "transient transformation" refers to the transfer of a nucleic acid fragment into the nucleus, or other DNA-containing organelle, of a host organism resulting in gene expression without integration or stable inheritance (sometimes referred to herein as "unstable transformation", and the resulting host cell sometimes referred to herein as an "unstable transformant"). Host organisms containing the transformed nucleic acid fragments are referred to as "transgenic" organisms.

"Fungal cell", "fungi", "fungal host cell", and the like, as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., supra) and all mitosporic fungi (Hawksworth et al., supra). In certain embodiments, the fungal host cell is a yeast cell, where by "yeast" is meant ascosporogenous yeast (Endomycetales), basidiosporogenous yeast, and yeast belonging to the Fungi Imperfecti (Blastomycetes). As such, a yeast host cell includes a *Candida, Hansenula, Kluyveromyces, Pichia, Saccharomyces, Schizosaccharomyces*, or *Yarrowia* cell. Species of yeast include, but are not limited to, the following: *Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, Kluyveromyces lactis*, and *Yarrowia lipolytica* cell.

The term "filamentous fungal cell" includes all filamentous forms of the subdivision Eumycotina or Pezizomycotina. Suitable cells of filamentous fungal genera include, but are not limited to, cells of *Acremonium, Aspergillus, Chrysosporium, Corynascus, Chaetomium, Fusarium, Gibberella, Humicola, Magnaporthe, Myceliophthora, Neurospora, Paecilomyces, Penicillium, Scytaldium, Talaromyces, Thermoascus, Thielavia, Tolypocladium, Hypocrea*, and *Trichoderma*.

Suitable cells of filamentous fungal species include, but are not limited to, cells of *Aspergillus awamori, Aspergillus fumigatus, Aspergillus foetidus, Aspergillus japonicus, Aspergillus nidulans, Aspergillus niger, Aspergillus oryzae, Chrysosporium lucknowense, Hypocrea jecorina, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Myceliophthora thermophila, Neurospora crassa, Neurospora intermedia, Penicillium purpurogenum, Penicillium canescens, Penicillium solitum, Penicillium funiculosum, Phanerochaete chrysosporium, Talaromyces flavus, Thielavia terrestris, Trichoderma harzianum, Trichoderma koningii, Trichoderma longibrachiatum, Trichoderma reesei,* and *Trichoderma viride*.

The terms "target site", "target sequence", "genomic target site", "genomic target sequence" (and equivalents) are used interchangeably herein and refer to a polynucleotide sequence in the genome of a fungal cell at which a Cas endonuclease cleavage is desired to promote a genome modification, e.g., modification of the DNA sequence at the target site. The context in which this term is used, however, can slightly alter its meaning. For example, the target site for a Cas endonuclease is generally very specific and can often be defined to the exact nucleotide position, whereas in some cases the target site for a desired genome modification can be defined more broadly than merely the site at which DNA cleavage occurs. The target site can be an endogenous site in the fungal cell genome, or alternatively, the target site can be heterologous to the fungal cell and thereby not be naturally occurring in the genome, or the target site can be found in a heterologous genomic location compared to where it occurs in nature.

As used herein, "nucleic acid" means a polynucleotide and includes a single or a double-stranded polymer of deoxyribonucleotide or ribonucleotide bases. Nucleic acids may also include fragments and modified nucleotides. Thus, the terms "polynucleotide", "nucleic acid sequence", "nucleotide sequence" and "nucleic acid fragment" are used interchangeably to denote a polymer of RNA and/or DNA that is single- or double-stranded, optionally containing synthetic, non-natural, or altered nucleotide bases. Nucleotides (usually found in their 5'-monophosphate form) are referred to by their single letter designation as follows: "A" for adenosine or deoxyadenosine (for RNA or DNA, respectively), "C" for cytosine or deoxycytosine, "G" for guanosine or deoxyguanosine, "U" for uridine, "T" for deoxythymidine, "R" for purines (A or G), "Y" for pyrimidines (C or T), "K" for G or T, "H" for A or C or T, "I" for inosine, and "N" for any nucleotide.

The term "derived from" encompasses the terms "originated from," "obtained from," "obtainable from," "isolated from," and "created from," and generally indicates that one specified material find its origin in another specified material or has features that can be described with reference to the another specified material.

As used herein, the term "hybridization conditions" refers to the conditions under which hybridization reactions are conducted. These conditions are typically classified by degree of "stringency" of the conditions under which hybridization is measured. The degree of stringency can be based, for example, on the melting temperature (Tm) of the nucleic acid binding complex or probe. For example, "maximum stringency" typically occurs at about Tm −5° C. (5° C. below the Tm of the probe); "high stringency" at about 5-10° C. below the Tm; "intermediate stringency" at about 10-20° C. below the Tm of the probe; and "low stringency" at about 20-25° C. below the Tm. Alternatively, or in addition, hybridization conditions can be based upon the salt or ionic strength conditions of hybridization, and/or upon one or more stringency washes, e.g.: 6×SSC=very low stringency; 3×SSC=low to medium stringency; 1×SSC=medium stringency; and 0.5×SSC=high stringency. Functionally, maximum stringency conditions may be used to identify nucleic acid sequences having strict identity or near-strict identity with the hybridization probe; while high stringency conditions are used to identify nucleic acid sequences having about 80% or more sequence identity with the probe. For applications requiring high selectivity, it is typically desirable to use relatively stringent conditions to form the hybrids (e.g., relatively low salt and/or high temperature conditions are used).

As used herein, the term "hybridization" refers to the process by which a strand of nucleic acid joins with a complementary strand through base pairing, as known in the art. More specifically, "hybridization" refers to the process by which one strand of nucleic acid forms a duplex with, i.e., base pairs with, a complementary strand, as occurs during blot hybridization techniques and PCR techniques. A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm −5° C. (5° below the Tm of the probe); "high stringency" at about 5-10° C. below the Tm; "intermediate stringency" at about 10-20° C. below the Tm of the probe; and "low stringency" at about 20-25° C. below the Tm. Functionally, maximum stringency conditions may be used to identify sequences having strict identity or near-strict identity with the hybridization probe; while intermediate or low stringency hybridization can be used to identify or detect polynucleotide sequence homologs.

Intermediate and high stringency hybridization conditions are well known in the art. For example, intermediate stringency hybridizations may be carried out with an overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/mL denatured sheared salmon sperm DNA, followed by washing the filters in 1×SSC at about 37-50° C. High stringency hybridization conditions may be hybridization at 65° C. and 0.1×SSC (where 1×SSC=0.15 M NaCl, 0.015 M Na citrate, pH 7.0). Alternatively, high stringency hybridization conditions can be carried out at about 42° C. in 50% formamide, 5×SSC, 5×Denhardt's solution, 0.5% SDS and 100 µg/mL denatured carrier DNA followed by washing two times in 2×SSC and 0.5% SDS at room temperature and two additional times in 0.1×SSC and 0.5% SDS at 42° C. And very high stringent hybridization conditions may be hybridization at 68° C. and 0.1×SSC. Those of skill in the art know how to adjust the temperature, ionic strength, etc. as necessary to accommodate factors such as probe length and the like.

The phrase "substantially similar" or "substantially identical," in the context of at least two nucleic acids or polypeptides, means that a polynucleotide or polypeptide comprises a sequence that has at least 90%, at least 91%, at least 92%, at least 93%, at least 94%, at least 95%, at least 96%, at least 97%, at least 98%, or even at least 99% identical to a parent or reference sequence, or does not include amino acid substitutions, insertions, deletions, or modifications made only to circumvent the present description without adding functionality.

"Sequence identity" or "identity" in the context of nucleic acid or polypeptide sequences refers to the nucleic acid bases or amino acid residues in two sequences that are the same when aligned for maximum correspondence over a specified comparison window.

The term "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90% or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, (1989) CABIOS 5:151-153; Higgins et al., (1992) Comput Appl Biosci 8:189-191) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

The "Clustal W method of alignment" corresponds to the alignment method labeled Clustal W (described by Higgins and Sharp, (1989) CABIOS 5:151-153; Higgins et al., (1992) Comput Appl Biosci 8:189-191) and found in the MegAlign™ v6.1 program of the LASERGENE bioinformatics computing suite (DNASTAR Inc., Madison, Wis.). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

Unless otherwise stated, sequence identity/similarity values provided herein refer to the value obtained using GAP Version 10 (GCG, Accelrys, San Diego, Calif.) using the following parameters: % identity and % similarity for a nucleotide sequence using a gap creation penalty weight of 50 and a gap length extension penalty weight of 3, and the nwsgapdna.cmp scoring matrix; % identity and % similarity for an amino acid sequence using a GAP creation penalty weight of 8 and a gap length extension penalty of 2, and the BLOSUM62 scoring matrix (Henikoff and Henikoff, (1989) Proc. Natl. Acad. Sci. USA 89:10915). GAP uses the algorithm of Needleman and Wunsch, (1970) J Mol Biol 48:443-53, to find an alignment of two complete sequences that maximizes the number of matches and minimizes the number of gaps. GAP considers all possible alignments and gap positions and creates the alignment with the largest number of matched bases and the fewest gaps, using a gap creation penalty and a gap extension penalty in units of matched bases.

It is well understood by one skilled in the art that many levels of sequence identity are useful in identifying polypeptides from other species or modified naturally or synthetically wherein such polypeptides have the same or similar function or activity. Useful examples of percent identities include, but are not limited to, 50%, 55%, 60%, 65%, 70%, 75%, 80%, 85%, 90% or 95%, or any integer percentage from 50% to 100%. Indeed, any integer amino acid identity from 50% to 100% may be useful in describing the present disclosure, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

"Gene" includes a nucleic acid fragment that encodes and is capable to express a functional molecule such as, but not limited to, a specific polypeptide (e.g., an enzyme) or a functional RNA molecule (e.g., a guide RNA, an anti-sense RNA, ribozyme, etc.), and includes regulatory sequences preceding (5' non-coding sequences) and/or following (3' non-coding sequences) the coding sequence. "Native gene" refers to a gene as found in nature with its own regulatory sequences. A recombinant gene refers to a gene that is regulated by a different gene's regulatory sequences which could be from a different organism or the same organism.

A "mutated gene" is a gene that has been altered through human intervention. Such a "mutated gene" has a sequence that differs from the sequence of the corresponding non-mutated gene by at least one nucleotide addition, deletion, or substitution. In certain embodiments of the disclosure, the mutated gene comprises an alteration that results from a guide polynucleotide/Cas endonuclease system as disclosed herein. A mutated fungal cell is a fungal cell comprising a mutated gene.

As used herein, a "targeted mutation" is a mutation in a native gene that was made by altering a target sequence within the native gene using a method involving a double-strand-break-inducing agent that is capable of inducing a double-strand break in the DNA of the target sequence as disclosed herein or known in the art.

The term "donor DNA" or "donor nucleic acid sequence" or "donor polynucleotide" refers to a polynucleotide that contains a polynucleotide sequence of interest that is to be inserted at or near a target site or to replace a region at or near a target site, generally in conjunction with the activity of a Cas/guide polynucleotide complex (where the guide polynucleotide defines the target site, as detailed above). As such, the polynucleotide sequence of interest in the donor DNA may include a novel region to be inserted at or near the target site and/or a modified polynucleotide sequence when compared to the nucleotide sequence to be replaced/edited at or near the target site. In certain embodiments, the donor DNA construct further comprises a first and a second region of homology that flank the polynucleotide sequence of interest. The first and second regions of homology of the donor DNA share homology to a first and a second genomic region, respectively, present in or flanking the target site of the fungal cell genome. By "homology" is meant DNA sequences that are similar. For example, a "region of homology to a genomic region" that is found on the donor DNA is a region of DNA that has a similar sequence to a given "genomic region" in the fungal cell genome. A region of homology can be of any length that is sufficient to promote homologous recombination at the cleaved target site. For example, the region of homology can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800, 5-2900, 5-3000, 5-3100 or more bases in length such that the region of homology has sufficient homology to undergo homologous recombination with the corresponding genomic region. "Sufficient homology" indicates that two polynucleotide sequences have sufficient structural similarity to act as substrates for a homologous recombination reaction. The structural similarity includes overall length of each polynucleotide fragment, as well as the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

The amount of homology or sequence identity shared by a target and a donor polynucleotide can vary and includes total lengths and/or regions having unit integral values in the ranges of about 1-20 bp, 20-50 bp, 50-100 bp, 75-150 bp, 100-250 bp, 150-300 bp, 200-400 bp, 250-500 bp, 300-600 bp, 350-750 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, 5-10 kb, or up to and including the total length of the target site. These ranges include every integer within the range, for example, the range of 1-20 bp includes 1, 2, 3, 4, 5, 6, 7, 8, 9, 10, 11, 12, 13, 14, 15, 16, 17, 18, 19 and 20 bp. The amount of homology can also described by percent sequence identity over the full aligned length of the two polynucleotides which includes percent sequence identity of about at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%.

Sufficient homology includes any combination of polynucleotide length, global percent sequence identity, and optionally conserved regions of contiguous nucleotides or local percent sequence identity, for example sufficient homology can be described as a region of 75-150 bp having at least 80% sequence identity to a region of the target locus. Sufficient homology can also be described by the predicted ability of two polynucleotides to specifically hybridize under high stringency conditions, see, for example, Sambrook et al., (1989) Molecular Cloning: A Laboratory Manual, (Cold Spring Harbor Laboratory Press, NY); Current Protocols in Molecular Biology, Ausubel et al., Eds (1994) Current Protocols, (Greene Publishing Associates, Inc. and John Wiley & Sons, Inc); and, Tijssen (1993) Laboratory Techniques in Biochemistry and Molecular Biology—Hybridization with Nucleic Acid Probes, (Elsevier, New York).

A "phenotypic marker" is a screenable or selectable marker that includes visual markers and selectable markers whether it is a positive or negative selectable marker. Any phenotypic marker can be used. Specifically, a selectable or screenable marker comprises a DNA segment that allows one to identify, select for, or screen for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products which provide resistance against otherwise toxic compounds and antibiotics, such as, chlorimuron ethyl, benomyl, Basta, and hygromycin phosphotransferase (HPT); DNA segments that encode products which are otherwise lacking in the recipient cell (e.g., tRNA genes, auxotrophic markers, dominant heterologous marker-amdS); DNA segments that encode products which can be readily identified (e.g., phenotypic markers such as β-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Methods and Compositions for Modifying a Fungal Cell Genome

Methods are provided employing a guide RNA/Cas endonuclease system for modifying the DNA sequence at a target site in the genome of a fungal cell, e.g., a filamentous fungal cell.

Aspects of the present disclosure include methods for modifying the DNA sequence at a target site in the genome of a fungal cell by transiently introducing a Cas endonuclease/guide polynucleotide complex into the cell. The Cas endonuclease/guide polynucleotide complex is capable of introducing a double-strand break at the target site in the genome of the fungal cell, and repair of this break can result in sequence modification (e.g., insertions or deletions).

Introduction of the Cas endonuclease or guide polynucleotide (or other biomolecule) can be done in any convenient manner, including transfection, transduction, transformation, electroporation, particle bombardment (biolistic particle delivery), cell fusion techniques, etc. Each of these components can be introduced simultaneously or sequentially as desired by the user. For example, a fungal cell can first be stably transfected with a Cas expression DNA construct followed by introduction of a guide polynucleotide into the stable transfectant (either directly or using a guide polynucleotide expressing DNA construct). This set up may even be advantageous as the user can generate a population of stable Cas transfectant fungal cells into which different guide polynucleotides can be introduced independently (in some cases, more than one guide polynucleotide can be introduced into the same cells should this be desired). In some embodiments, a Cas expressing fungal cell is obtained by the user, and thus the user does not need to introduce a recombinant DNA construct capable of expressing a Cas endonuclease into the cell, but rather only need introduce a guide polynucleotide into the Cas expressing cell.

In certain embodiments, a guide polynucleotide is introduced into the fungal cell by introducing a recombinant DNA construct that includes an expression cassette (or gene) encoding the guide polynucleotide. In some embodiments, the expression cassette is operably linked to a eukaryotic RNA pol III promoter. These promoters are of particular interest as transcription by RNA pol III does not lead to the addition of a 5' cap structure or polyadenylation that occurs upon transcription by RNA polymerase II from an RNA pol II dependent promoter. In certain embodiments, the RNA pol III promoter is a filamentous fungal cell U6 polymerase III promoter (e.g., SEQ ID NO:11 and functional variants thereof, e.g., SEQ ID NO:12).

When a double-strand break is induced in the genomic DNA of a host cell (e.g., by the activity of a Cas endonuclease/guide RNA complex at a target site, the complex having double-strand endonuclease activity), the cell's DNA repair mechanism is activated to repair the break which, due to its error-prone nature, can produce mutations at double-strand break sites. The most common repair mechanism to bring the broken ends together is the nonhomologous end-joining (NHEJ) pathway (Bleuyard et al., (2006) DNA Repair 5:1-12). The structural integrity of chromosomes is typically preserved by the repair, but deletions, insertions, or other rearrangements are possible (Siebert and Puchta, (2002) Plant Cell 14:1121-31; Pacher et al., (2007) Genetics 175:21-9).

Surprisingly, we have found in filamentous fungi that non-homologous insertion of transformed DNA at the double-strand break is highly favored over simple end-joining between the two ends of the chromosomal DNA at a double-strand break. Therefore, in cases where the Cas endonuclease or guide RNA is provided by transformation with an expression cassette containing DNA construct or constructs, those DNA constructs, or fragments thereof, are inserted at the double-strand break at high frequency. This insertion occurs in the absence of homology between DNA sequences on the Cas endonuclease or guide RNA expression constructs and the sequences around the double-strand break.

DNA taken up by transformation may integrate in a stable fashion in the genome or it may be transiently maintained. Transient maintenance can be recognized by an unstable phenotype. For example, DNA uptake can be recognized by selection for a marker gene present on the transforming DNA. After transformation and selection, the transformants may be grown under non-selective conditions for several generations before transfer back to selective conditions. A stable transformant will be able to grow after transfer back to selective conditions whereas an unstable transformant will be unable to grow after transfer back to selective conditions due to loss of the transforming DNA. We have demonstrated that it is possible to transiently express Cas endonuclease and/or guide RNA in fungal cells.

In embodiments where unstable transformants are desired, a plasmid with telomere sequences to encourage autonomous replication can be used. Other types of plasmids that are designed for autonomous replication, such as those with autonomous replication sequences, centromere sequences or other sequences, can also be employed. Surprisingly, in *Trichoderma reesei* we have found that one can use plasmids with no known origin of replication, autonomous replication sequence, centromere or telomere sequences. By screening those transformants that show an unstable phenotype with respect to the selectable marker, efficient target site gene modification without vector DNA insertion is obtained.

Certain embodiments of the present disclosure include integrating a Cas endonuclease expression cassette and first selectable marker in the genome of a fungus, optionally flanked by repeats to allow subsequent removal (loop-out) of the expression cassette and first selectable marker, to produce a Cas endonuclease expressing host cell. These cells can be employed in numerous ways to obtain a genetic modification of interest, including modification of the DNA sequence at a desired target site.

For example, a Cas endonuclease expressing host cell can be transformed with a DNA construct including a guide RNA expression cassette containing a second selectable marker. Host cells that are selected for using the second selectable marker will express the guide RNA from this DNA construct, which enables Cas endonuclease activity and targeting to a defined target site of interest in the genome. Screening these host cells for transformants that show an unstable phenotype with respect to the second selectable marker will enable obtaining host cells with a modified site of interest without DNA construct insertion.

As another example, a Cas endonuclease expressing host cell can be induced to uptake an in vitro synthesized guide RNA to enable Cas endonuclease activity and targeting to a defined site in the genome. In some cases, it will be desirable to induce uptake of both guide RNA and a separate DNA construct bearing a selectable marker gene to allow for selection of those cells that have taken up DNA and, at high frequency, are expected to have simultaneously taken up guide RNA. As above, screening those transformants that show an unstable phenotype with respect to the selectable marker for the genetic modification of interest without vector DNA insertion is obtained.

As yet another example, a Cas endonuclease expressing host cell can be used to create a "helper strain" that can provide, in trans, the Cas endonuclease to a "target strain". In brief, a heterokaryon can be created between the helper strain and the target strain, e.g., by fusion of protoplasts from each strain or by anastomosis of hyphae depending on the species of filamentous fungus. Maintenance of the heterokaryon will depend on appropriate nutritional or other marker genes or mutations in each parental strain and growth on suitable selective medium such that the parental strains are unable to grow whereas the heterokaryon, due to complementation, is able to grow. Either at the time of heterokaryon formation or subsequently, a guide RNA is introduced by transfection. The guide RNA may be directly introduced or introduced via a DNA construct having a Cas endonuclease expression cassette and a selectable marker gene. Cas endonuclease is expressed from the gene in the helper strain nucleus and is present in the cytoplasm of the heterokaryon. The Cas endonuclease associates with the guide RNA to create an active complex that is targeted to the desired target site(s) in the genome to induce modification of the DNA sequence. Subsequently, spores are recovered from the heterokaryon and subjected to selection or screening to recover the target strain with modification of the DNA sequence at the target site. In cases in which an expression cassette is used to introduce the guide RNA, heterokaryons are chosen in which the guide RNA expression construct is not stably maintained.

In certain embodiments, the Cas endonuclease is a Cas9 endonuclease (see, e.g., WO 2013141680 entitled "RNA-directed DNA Cleavage by the Cas9-crRNA Complex"). Examples of Cas9 endonucleases include those from *Streptococcus* sp. (e.g., *S. pyogenes, S. mutans*, and *S. thermophilus*), *Campylobacter* sp. (e.g., *C. jejuni*), *Neisseria* sp. (e.g., *N. meningitides*), *Francisella* sp. (e.g., *F. novicida*), and *Pasteurella* sp. (e.g., *P. multocida*) (see, e.g., Cas9 endonucleases described in Fonfara et al., Nucleic Acids Res., 2013, pages 1-14: incorporated herein by reference). In some embodiments, the Cas endonuclease is encoded by an optimized Cas9 endonuclease gene, e.g., optimized for expression in a fungal cell (e.g., Cas9 encoding genes containing SEQ ID NO:8, e.g., SEQ ID NO:9, as described below).

In certain instances, the Cas endonuclease gene is operably linked to one or more polynucleotides encoding nuclear localization signals such that the Cas endonuclease/guide polynucleotide complex that is expressed in the cell is efficiently transported to the nucleus. Any convenient nuclear localization signal may be used, e.g., a polynucleotide encoding an SV40 nuclear localization signal present upstream of and in-frame with the Cas codon region and a polynucleotide encoding a nuclear localization signal derived from the *T. reesei* blr2 (blue light regulator 2) gene present downstream and in frame with the Cas codon region. Other nuclear localization signals can be employed.

In certain embodiments of the disclosure, the guide polynucleotide is a guide RNA that includes a crRNA region (or crRNA fragment) and a tracrRNA region (or tracrRNA fragment) of the type II CRISPR/Cas system that can form a complex with a type II Cas endonuclease. As indicated above, the guide RNA/Cas endonuclease complex can direct the Cas endonuclease to a fungal cell genomic target site, enabling the Cas endonuclease to introduce a double strand break into the genomic target site. In some cases, the RNA that guides the RNA/Cas9 endonuclease complex is a duplex that includes a crRNA and a separate tracrRNA. In other instances, the guide RNA is a single RNA molecule that includes both a crRNA region and a tracrRNA region (sometimes referred to herein as a fused guide RNA). One advantage of using a fused guide RNA versus a duplexed crRNA-tracrRNA is that only one expression cassette needs to be made to express the fused guide RNA.

Host cells employed in the methods disclosed herein may be any fungal host cells are from the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., supra) and all mitosporic fungi (Hawksworth et al., supra). In certain embodiments, the fungal host cells are yeast cells, e.g., *Candida, Hansenula, Kluyveromyces, Pichia, Saccharomyces, Schizosaccharomyces*, or *Yarrowia* cell. Species of yeast include, but are not limited to, the following: *Saccharomyces* carlsbergensis, Saccharomyces cerevisiae, Saccharomyces diastaticus, Saccharomyces douglasii, Saccharomyces kluyveri, Saccharomyces norbensis, Saccharomyces oviformis, Kluyveromyces lactis, and Yarrowia lipolytica cell. In additional embodiments, the fungal cells are filamentous fungal cells including but not limited to species of Trichoderma, Penicillium, Aspergillus, Humicola, Chrysosporium, Fusarium, Neurospora, Myceliophthora, Hypocrea, and Emericella. For example, the filamentous fungi T. reesei and A. niger find use in aspects of the disclosed methods.

Virtually any site in a fungal cell genome may be targeted using the disclosed methods, so long as the target site includes the required protospacer adjacent motif, or PAM. In the case of the S. pyogenes Cas9, the PAM has the sequence NGG (5' to 3'; where N is A, G, C or T), and thus does not impose significant restrictions on the selection of a target site in the genome. Other known Cas9 endonucleases have different PAM sites (see, e.g., Cas9 endonuclease PAM sites described in Fonfara et al., Nucleic Acids Res., 2013, pages 1-14: incorporated herein by reference).

The length of the target site can vary, and includes, for example, target sites that are at least 12, 13, 14, 15, 16, 17, 18, 19, 20, 21, 22, 23, 24, 25, 26, 27, 28, 29, 30 or more nucleotides in length. It is further possible that the target site can be palindromic, that is, the sequence on one strand reads the same in the opposite direction on the complementary strand. The cleavage site can be within the target sequence or the cleavage site could be outside of the target sequence. In another variation, the cleavage could occur at nucleotide positions immediately opposite each other to produce a blunt end cut or, in other cases, the incisions could be staggered to produce single-stranded overhangs, also called "sticky ends", which can be either 5' overhangs, or 3' overhangs.

In some cases, active variant target sequences in the genome of the fungal cell can also be used, meaning that the target site is not 100% identical to the relevant sequence in the guide polynucleotide (within the crRNA sequence of the guide polynucleotide). Such active variants can comprise at least 65%, 70%, 75%, 80%, 85%, 90%, 91%, 92%, 93%, 94%, 95%, 96%, 97%, 98%, 99% or more sequence identity to the given target site, wherein the active variant target sequences retain biological activity and hence are capable of being recognized and cleaved by a Cas endonuclease. Assays to measure the double-strand break of a target site by an endonuclease are known in the art and generally measure the overall activity and specificity of the agent on DNA substrates containing recognition sites.

Target sites of interest include those located within a region of a gene of interest. Non-limiting examples of regions within a gene of interest include an open reading frame, a promoter, a transcriptional regulatory element, a translational regulatory element, a transcriptional terminator sequence, an mRNA splice site, a protein coding sequence, an intron site, and an intron enhancing motif.

In certain embodiments, modification of the genome of the fungal cell results in a phenotypic effect that can be detected and, in many instances, is a desired outcome of the user. Non-limiting examples include acquisition of a selectable cell growth phenotype (e.g., resistance to or sensitivity to an antibiotic, gain or loss of an auxotrophic characteristic, increased or decreased rate of growth, etc.), expression of a detectable marker (e.g., fluorescent marker, cell-surface molecule, chromogenic enzyme, etc.), and the secretion of an enzyme whose activity can be detected in culture supernatant.

In some instances, the genomic modification in the fungal cells is detected directly using any convenient method, including sequencing, PCR, Southern blot, restriction enzyme analysis, and the like, including combinations of such methods.

In some embodiments, specific genes are targeted for modification using the disclosed methods, including genes encoding enzymes, e.g., acetyl esterases, aminopeptidases, amylases, arabinases, arabinofuranosidases, carboxypeptidases, catalases, cellulases, chitinases, cutinase, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, peroxidases, phenoloxidases, phytases, polygalacturonases, proteases, rhamno-galacturonases, ribonucleases, transferases, transport proteins, transglutaminases, xylanases, hexose oxidases, and combinations thereof.

There are numerous variations for implementing the methods described herein. For example, instead of having the Cas expression cassette present as an exogenous sequence in the fungal host cell, this cassette can be integrated into the genome of the fungal host cell. Generating this parental cell line would allow a user to simply introduce a desired guide RNA (e.g., as a guide RNA expression vector) which would then target the genomic site of interest as detailed elsewhere herein. In some of these embodiments, the integrated Cas gene can be designed to include polynucleotide repeats flanking it for subsequent loop-out/removal from the genome if needed.

Non-limiting examples or embodiments of compositions and methods disclosed herein are as follows:

1. A method for modifying the DNA sequence at a target site in the genome of a filamentous fungal cell, the method comprising:
   a) introducing into a population of filamentous fungal cells a Cas endonuclease and a guide RNA, wherein the Cas endonuclease and guide RNA are capable of forming a complex that enables the Cas endonuclease to introduce a double-strand break at a target site in the genome of the fungal cells; and
   b) identifying at least one fungal cell from the population that has a modification of the DNA sequence at the target site,
   wherein the Cas endonuclease, the guide RNA, or both are introduced transiently into the population of fungal cells.
2. The method of embodiment 1, wherein the modification of the DNA sequence at said target site is selected from the group consisting of a deletion of one or more nucleotides, an insertion of one or more nucleotides, a substitution of one or more nucleotides, and any combination thereof.
3. The method of embodiment 1 or 2, wherein introducing the Cas endonuclease into the population of fungal cells is achieved using a method selected from the group consisting of transfection, transduction, transformation, electroporation, particle bombardment (biolistic particle delivery), and cell fusion techniques.
4. The method of any preceding embodiment, wherein introducing the guide RNA into the population of fungal cells is achieved using a method selected from the group consisting of transfection, transduction, transformation, electroporation, particle bombardment (biolistic particle delivery), and cell fusion techniques.

5. The method of any preceding embodiment, wherein the identifying step comprises culturing the population of fungal cells from step (a) under conditions to select for or screen for the modification of the DNA sequence at the target site.
6. The method of any preceding embodiment, wherein the identifying step comprises culturing the population of cells from step (a) under conditions to screen for unstable transformants.
7. The method of any preceding embodiment, wherein the Cas endonuclease is a Cas9 endonuclease or variant thereof.
8. The method of embodiment 7, wherein the Cas9 endonuclease or variant thereof comprises a full length Cas9 or a functional fragment thereof from a species selected from the group consisting of: *Streptococcus* sp., *S. pyogenes*, *S. mutans*, *S. thermophilus*, *Campylobacter* sp., *C. jejuni*, *Neisseria* sp., *N. meningitides*, *Francisella* sp., *F. novicida*, and *Pasteurella* sp., *P. multocida*.
9. The method of embodiment 8, wherein the Cas9 endonuclease or variant thereof comprises an amino acid sequence that has at least 70% identity to any one of SEQ ID NOs:1 to 7 or a functional fragment thereof.
10. The method of any preceding embodiment, wherein the introducing step comprises introducing a DNA construct comprising an expression cassette for the Cas endonuclease into the fungal cells.
11. The method of any preceding embodiment, wherein the introducing step comprises introducing a DNA construct comprising an expression cassette for the guide RNA into the fungal cells.
12. The method of any one of embodiments 1 to 9 and 11, wherein the introducing step comprises directly introducing the Cas endonuclease into the fungal cells.
13. The method of any one of embodiments 1 to 10 and 12, wherein the introducing step comprises directly introducing the guide RNA into the fungal cells.
14. The method of embodiment 10, wherein the expression cassette for the Cas endonuclease comprises a Cas coding sequence that is optimized for expression in the fungal cell.
15. The method of embodiment 14, wherein the Cas coding sequence is a Cas9 coding sequence comprising a polynucleotide sequence that is at least 70% identical to SEQ ID NO:8 or a functional fragment thereof.
16. The method of any preceding embodiment, wherein the Cas endonuclease is operably linked to a nuclear localization signal.
17. The method of embodiment 11, wherein the expression cassette for the guide RNA comprises a RNA polymerase III dependent promoter functional in a Euascomycete or Pezizomycete, and wherein the promoter is operably linked to the DNA encoding the guide RNA.
18. The method of embodiment 17, wherein the promoter is derived from a *Trichoderma* U6 snRNA gene.
19. The method of embodiment 17 or 18, wherein the promoter comprises a nucleotide sequence with at least 60%, 65%, 70%, 75%, 80%, 85%, 90%, 95%, 96%, 97%, 98%, or 99% identity to SEQ ID NO: 11 or 12 or a functional fragment thereof.
20. The method of embodiment 19, wherein the promoter comprises the sequence of SEQ ID NO: 11 or 12.
21. The method of any one of embodiments 11 and 17-20, wherein the expression cassette for the guide RNA comprises a guide RNA-encoding DNA with an intron sequence from a *Trichoderma* U6 snRNA gene.
22. The method of embodiment 21, wherein the intron sequence derived from *Trichoderma* U6 snRNA gene comprises a nucleotide sequence with at least 60%, 65%, 70%, 75%, 80%, 85%, 90%, 95%, 96%, 97%, 98%, or 99% identity to SEQ ID NO: 90 or a functional fragment thereof.
23. The method of embodiment 22, wherein the intron sequence derived from *Trichoderma* U6 snRNA gene comprises the sequence of SEQ ID NO: 90.
24. The method of any preceding embodiment, wherein the filamentous fungal cell is a Eumycotina or Pezizomycotina fungal cell.
25. The method of any preceding embodiment, wherein filamentous fungal cell is selected from the group consisting of *Trichoderma*, *Penicillium*, *Aspergillus*, *Humicola*, *Chrysosporium*, *Fusarium*, *Myceliophthora*, *Neurospora*, *Hypocrea*, and *Emericella*.
26. The method of any preceding embodiment, wherein the target site is located within a region of a gene of interest selected from the group consisting of: an open reading frame, a promoter, a regulatory sequence, a terminator sequence, a regulatory element sequence, a splice site, a coding sequence, a polyubiquitination site, an intron site, and an intron enhancing motif.
27. The method of any one of embodiments 1, 2, 4-9, 11, 13, and 16-19, wherein the introducing step comprises: (i) obtaining a parental fungal cell population that stably expresses the Cas endonuclease, and (ii) transiently introducing the guide RNA into the parental fungal cell population.
28. The method of any one of embodiments 1-3, 5-10, 12, and 14-19, wherein the introducing step comprises: (i) obtaining a parental fungal cell population that stably expresses the guide RNA, and (ii) transiently introducing the Cas endonuclease into the parental fungal cell population.
29. The method of any preceding embodiment, wherein the modification of the DNA sequence at the target site is not caused by a homologous recombination.
30. The method of any preceding embodiment, wherein the method does not involve introducing a donor DNA into the population of fungal cells.
31. A recombinant fungal cell produced by the method of any preceding embodiment.
32. An engineered nucleic acid encoding a Cas endonuclease or variant thereof, wherein the Cas endonuclease or variant thereof comprises an amino acid sequence that has at least 70%, 75%, 80%, 85%, 90%, or 95% identity to any one of SEQ ID NOs:1 to 7 or a functional fragment thereof, and wherein the nucleic acid comprises a polynucleotide sequence that is at least 70% 75%, 80%, 85%, 90%, 95%, 96%, 97%, 98%, or 99% identical to SEQ ID NO:8 or a functional fragment thereof.
33. The engineered nucleic acid of embodiment 32, wherein the nucleic acid comprises the sequence of SEQ ID NO:8.
34. An engineered nucleic acid encoding a guide RNA which enables a Cas endonuclease to introduce a double-strand break at a target site in the genome of a filamentous fungal cell, wherein the nucleic acid encoding the guide RNA comprises a RNA polymerase III dependent promoter functional in a Euascomycete or Pezizomycete, and the promoter is derived from a *Trichoderma* U6 snRNA gene 35. The engineered nucleic acid of embodiment 34, wherein the promoter comprises a nucleotide sequence with at least 60%, 65%, 70%, 75%, 80%, 85%, 90%, 95%, 96%, 97%, 98%, 99%, or 100% identity to SEQ ID NO: 11 or 12 or a functional fragment thereof.

36. An engineered nucleic acid encoding a guide RNA which enables a Cas endonuclease to introduce a double-strand break at a target site in the genome of a filamentous fungal cell, wherein the nucleic acid encoding the guide RNA comprises a guide RNA-encoding DNA with an intron sequence derived from a *Trichoderma* U6 snRNA gene.

37. The engineered nucleic acid of embodiment 36, wherein the intron sequence derived from *Trichoderma* U6 snRNA gene comprises a nucleotide sequence with at least 60%, 65%, 70%, 75%, 80%, 85%, 90%, 95%, 96%, 97%, 98%, or 100% identity to SEQ ID NO: 90 or a functional fragment thereof.

38. The engineered nucleic acid of embodiment 34 or 36, wherein the nucleic acid encoding the guide RNA comprises both a promoter derived from a *Trichoderma* U6 snRNA gene and an intron sequence derived from a *Trichoderma* U6 snRNA gene, wherein the promoter comprises a nucleotide sequence with at least 60%, 65%, 70%, 75%, 80%, 85%, 90%, 95%, 96%, 97%, 98%, 99%, or 100% identity to SEQ ID NO: 11 or 12 or a functional fragment thereof, and wherein the intron sequence derived from *Trichoderma* U6 snRNA gene comprises a nucleotide sequence with at least 60%, 65%, 70%, 75%, 80%, 85%, 90%, 95%, 96%, 97%, 98%, 99%, or 100% identity to SEQ ID NO: 90 or a functional fragment thereof.

EXAMPLES

In the following Examples, unless otherwise stated, parts and percentages are by weight and degrees are Celsius. It should be understood that these Examples, while indicating embodiments of the disclosure, are given by way of illustration only. From the above discussion and these Examples, one skilled in the art can make various changes and modifications of the disclosure to adapt it to various usages and conditions. Such modifications are also intended to fall within the scope of the appended claims.

Section A: Introduction of Cas/Guide RNA by Expression Vectors

Example 1: Identification of *T. reesei* U6 snRNA Gene

An RNA polymerase III directed promoter is desired for production of guide RNA in *T. reesei* without the addition of a 5' cap structure or polyadenylation that would result from the use of a RNA polymerase II dependent promoter. However, no RNA polymerase III dependent promoter that is functional in *T. reesei* has been described. Known RNA polymerase III dependent promoters from other species were considered to be tested for their ability to function in *T. reesei* including the 5' upstream regions from the *Saccharomyces cerevisiae* snr52 gene, the human U6 snRNA gene, or the corn U6 snRNA gene.

More desirable was to identify a native *T. reesei* sequence that would function as an RNA polymerase III dependent promoter. The DNA sequence encoding the human U6 small nuclear RNA (snRNA; GenBank accession number M14486) was used to search the *T. reesei* v2 genome sequence (www.jgi.doe.gov) using the BLAST algorithm. A short region of *T. reesei* DNA sequence was identified with similarity to the human sequence. Examination of the surrounding DNA sequence and comparison with the U6 genes of yeasts, particularly *Schizosaccharomyces pombe* (Marck et al., 2006, Nucleic Acids Research 34:1816-1835), allowed a number of features of the *T. reesei* U6 gene to be putatively identified (SEQ ID NO:22, shown below). The start of the transcribed sequence and the terminator were identified as were an upstream TATA box. An intron apparently interrupts the transcribed region and possible A-box and B-box promoter elements can be recognized within the transcribed region, the latter within the intron. (see FIG. 1).

(SEQ ID NO: 22)
AAAAAACACTAGTAAGTACTTACTTATGTATTATTAACTACTTTAGCTAA

CTTCTGCAGTACTACCTAAGAGGCTAGGGGTAGTTTTATAGCAGACTTAT

AGCTATTATTTTTATTTAGTAAAGTGCTTTTAAAGTAAGGTCTTTTTTAT

AGCACTTTTTATTTATTATAATATATATTATATAATAATTTTAAGCCTGG

AATAGTAAAGAGGCTTATATAATAATTTATAGTAATAAAAGCTTAGCAGC

TGTAATATAATTCCTAAAGAAACAGCATGAAATGGTATTATGTAAGAGCT

ATAGTCTAAAGGCACTCTGCTGGATAAAAATAGTGGCTATAAGTCTGCTG

CAAAACTACCCCCAACCTCGTAGGTATATAAGTACTGTTTGATGGTAGTC

TATCGCCTTCGGGCATTTGGTCAATTTATAACGATACAGGTTCGTTTCGG

CTTTTCCTCGGAACCCCCAGAGGTCATCAGTTCGAATCGCTAACAGGTCA

ACAGAGAAGATTAGCATGGCCCCTGCACTAAGGATGACACGCTCACTCAA

AGAGAAGCTAAACATTTTTTTCTCTTCCAAGTCGTGATGGTTATCTTTT

TGCTTAGAGAATCTATTCTTGTGGACGATTAGTATTGGTAAATCCCTGCT

GCACATTGCGGCGGATGGTCTCAACGGCATAATACCCCATTCGTGATGCA

GCGGTGATCTTCAATATGTAGTGTAATACGTTGCATACACCACCAGGTTC

GGTGCCTCCTGTATGTACAGTACTGTAGTTCGACTCCTCCGCGCAGGTGG

AAACGATTCCCTAGTGGGCAGGTATTTTGGCGGGGTCAAGAA

Example 2: sgRNA Sequences to Target *T. reesei* Genes

It has been shown that a single guide RNA (sgRNA) molecule can interact with the *Streptococcus pyogenes* Cas9 protein to target this endonuclease in vivo to a specific locus in a eukaryote genome (REFS). The sgRNA is a hybrid molecule designed as a fusion between the tracrRNA and crRNA observed naturally to be components of the *Streptococcus pyogenes* type II CRISPR-Cas system (Gasiunas et al. (2012) Proc. Natl. Acad. Sci. USA 109:E2579-86, Jinek et al. (2012) Science 337:816-21, Mali et al. (2013) Science 339:823-26, and Cong et al. (2013) Science 339:819-23). The first 20 nucleotides of the sgRNA are complementary to the target site in the genome. An additional sequence (PAM, protospacer adjacent motif) is also required to be present at the target site in the genome adjacent to the sgRNA-complementary region. In the case of the *S. pyogenes* Cas9 the PAM has the sequence NGG (where N is A, G, C or T).

The sequence of sgRNA used in these experiments is shown below where the 20 nucleotides designed to be complementary to the target site are shown as N residues (SEQ ID NO:23) (N=A, G, C, or U).

NNNNNNNNNNNNNNNNNNNNGUUUUAGAGCUAGAAAUAGCAAGUUAAAAU

AAGGCUAGUCCGUUAUCAACUUGAAAAAGUGGCACCGAGUCGGUGGUGC sgRNAs were designed to target different loci in the *T. reesei* genome. The sequence of an sgRNA (called gAd3A TS1) to target the *T. reesei* ad3A gene (Phosphoribosylamidoimidazole-succinocarboxamide synthase) at a site designated as target site 1 (TS1) is shown below (SEQ ID NO:24). The 20 nucleotide region that is complementary to the *T. reesei* genome sequence is shown in lower case.

guccucgagcaaaaggugccGUUUUAGAGCUAGAAAUAGCAAGUUAAAAU

AAGGCUAGUCCGUUAUCAACUUGAAAAAGUGGCACCGAGUCGGUGGUGC

The sequence of an sgRNA (called gTrGA TS2) to target the *T. reesei* gla1 (glucoamylase) gene at a site designated as target site 2 (TS2) is shown below (SEQ ID NO:25). The 20 nucleotide region that is complementary to the *T. reesei* genome sequence is shown in lower case.

guucagugcaauaggcgucuGUUUUAGAGCUAGAAAUAGCAAGUUAAAAU

AAGGCUAGUCCGUUAUCAACUUGAAAAAGUGGCACCGAGUCGGUGGUGC

The sequence of an sgRNA (called gTrGA TS11) to target the *T. reesei* gla1 (glucoamylase) gene at a site designated as target site 11 (TS11) is shown below (SEQ ID NO:26). The 20 nucleotide region that is complementary to the *T. reesei* genome sequence is shown in lower case.

gccaauggcgacggcagcacGUUUUAGAGCUAGAAAUAGCAAGUUAAAAU

AAGGCUAGUCCGUUAUCAACUUGAAAAAGUGGCACCGAGUCGGUGGUGC

The sequence of an sgRNA (called gPyr2 TS6) to target the *T. reesei* pyr2 (orotate phosphoribosyltransferase) gene at a site designated as target site 6 (TS6) is shown below (SEQ ID NO:27). The 20 nucleotide region that is complementary to the *T. reesei* genome sequence is shown in lower case.

gcacagcgggaugcccuuguGUUUUAGAGCUAGAAAUAGCAAGUUAAAAU

AAGGCUAGUCCGUUAUCAACUUGAAAAAGUGGCACCGAGUCGGUGGUGC

Example 3: Cas9 DNA and Protein Sequences for Expression in *T. reesei*

A codon optimized *Streptococcus pyogenes* Cas9-encoding gene, including NLS sequences, was designed, synthesized and tested for expression in *T. reesei* (SEQ ID NO:9). The encoded protein (SEQ ID NO:10) has an N-terminal SV40 nuclear localization signal (NLS; SEQ ID NO:19) and a C-terminal NLS derived from the *T. reesei* blr2 (blue light regulator 2) gene (SEQ ID NO:20; both are underlined in SEQ ID NO:10 below).

```
                                       SEQ ID NO: 9
atggcaccgaagaagaagcgcaaggtgatggacaagaagtacagcatcgg cctcgacatcggcaccaactcggtgggctggccgtcatcacggacgaat ataaggtcccgtcgaagaagttcaaggtcctcggcaatacagaccgccac agcatcaagaaaaacttgatcggcgccctcctgttcgatagcggcgagac cgcggaggcgaccaggctcaagaggaccgccaggagacggtacactaggc gcaagaacaggatctgctacctgcaggagatcttcagcaacgagatggcg aaggtggacgactccttcttccaccgcctggaggaatcattcctggtgga ggaggacaagaagcatgagcggcacccaatcttcggcaacatcgtcgacg aggtggcctaccacgagaagtacccgacaatctaccacctccggaagaaa ctggtggacagcacagacaaggcggacctccggctcatctaccttgccct cgcgcatatgatcaagttccgcggccacttcctcatcgagggcgacctga acccggacaactccgacgtggacaagctgttcatccagctcgtgcagacg tacaatcaactgttcgaggagaacccatcaaacgctagcggcgtggacgc caaggccatcctctcggccaggctctcgaaatcaagaaggctggagaacc ttatcgcgcagttgccaggcgaaaagaagaacggcctcttcggcaaccttt attgcgctcagcctcggcctgacgccgaacttcaaatcaaacttcgacct cgcggaggacgccaagctccagctctcaaaggacacctacgacgacgacc tcgacaacctcctggcccagataggagaccagtacgcggaccctcttcctc gccgccaagaacctctccgacgctatcctgctcagcgacatccttcgggt caacaccgaaattaccaaggcaccgctgtccgccagcatgattaaacgct acgacgagcaccatcaggacctcacgctgctcaaggcactcgtccgccag cagctccccgagaagtacaaggagatcttcttcgaccaatcaaaaaacgg ctacgcgggatatatcgacggcggtgccagccaggaagagttctacaagt tcatcaaaccaatcctggagaagatggacggcaccgaggagttgctggtc aagctcaacagggaggacctcctcaggaagcagaggaccttcgacaacgg ctccatcccgcatcagatccacctgggcgaactgcatgccatcctgcggc gccaggaggacttctacccgttcctgaaggataaccgggagaagatcgag aagatcttgacgttccgcatcccatactacgtgggccgctggctcgcgg caactcccggttcgcctggatgacccggaagtcggaggagaccatcacac cctggaactttgaggaggtggtcgataagggcgctagcgctcagagcttc atcgagcgcatgaccaacttcgataaaaacctgcccaatgaaaaagtcct ccccaagcactcgctgctctacgagtacttcaccgtgtacaacgagctca ccaaggtcaaatacgtcaccgagggcatgcggaagccggcgttcctgagc ggcgagcagaagaaggcgatagtggacctcctcttcaagaccaacaggaa ggtgaccgtgaagcaattaaaagaggactacttcaagaaaatagagtgct tcgactccgtggagatctcgggcgtggaggatcggttcaacgcctcactc ggcacgtatcacgacctcctcaagatcattaaagacaaggacttcctcga caacgaggagaacgaggacatcctcgaggacatcgtcctcaccctgaccc tgttcgaggaccgcgaaatgatcgaggagaggctgaagacctacgcgcac ctgttcgacgacaaggtcatgaaacagctcaagaggcgccgctacactgg ttggggaaggctgtcccgcaagctcattaatggcatcagggacaagaga gcggcaagaccatcctggacttcctcaagtccgacgggttcgccaaccgc aacttcatgcagctcattcacgacgactcgctcacgttcaaggaagacat
```

-continued
```
ccagaaggcacaggtgagcgggcagggtgactccctccacgaacacatcg
ccaacctggccggctcgccggccattaaaaagggcatcctgcagacggtc
aaggtcgtcgacgagctcgtgaaggtgatgggccggcacaagcccgaaaa
tatcgtcatagagatggccagggagaaccagaccacccaaaaagggcaga
agaactcgcgcgagcggatgaaacggatcgaggagggcattaagagctc
gggtcccagatcctgaaggagcacccgtggaaaatacccagctccagaa
tgaaaagctctacctctactacctgcagaacggccgcgacatgtacgtgg
accaggagctggacattaatcggctatcggactacgacgtcgaccacatc
gtgccgcagtcgttcctcaaggacgatagcatcgacaacaaggtgctcac
ccggtcggataaaaatcggggcaagagcgacaacgtgcccagcgaggagg
tcgtgaagaagatgaaaaactactggcgccagctcctcaacgcgaaactg
atcacccagcgcaagttcgacaacctgacgaaggcggaacgcggtggctt
gagcgaactcgataaggcgggcttcataaaaaggcagctggtcgagacgc
gccagatcacgaagcatgtcgcccagatcctggacagccgcatgaatact
aagtacgatgaaaacgacaagctgatccgggaggtgaaggtgatcacgct
gaagtccaagctcgtgtcggacttccgcaaggacttccagttctacaagg
tccgcgagatcaacaactaccaccacgcccacgacgcctacctgaatgcg
gtggtcgggaccgccctgatcaagaagtacccgaagctggagtcggagtt
cgtgtacggcgactacaaggtctacgacgtgcgcaaaatgatcgccaagt
ccgagcaggagatcggcaaggccacggcaaaatacttcttctactcgaac
atcatgaacttcttcaagaccgagatcaccctcgcgaacggcgagatccg
caagcgcccgctcatcgaaaccaacggcgagacgggcgagatcgtctggg
ataagggccgggatttcgcgacggtccgcaaggtgctctccatgccgcaa
gtcaatatcgtgaaaaagacggaggtccagacgggcgggttcagcaagga
gtccatcctcccgaagcgcaactccgacaagctcatcgcgaggaagaagg
attgggacccgaaaaaatatggcggcttcgacagcccgaccgtcgcatac
agcgtcctcgtcgtggcgaaggtggagaagggcaagtcaaagaagctcaa
gtccgtgaaggagctgctcgggatcacgattatggagcggtcctccttcg
agaagaacccgatcgacttcctagaggccaagggatataaggaggtcaag
aaggacctgattattaaactgccgaagtactcgctcttcgagctggaaaa
cggccgcaagaggatgctcgcctccgcaggcgagttgcagaagggcaacg
agctcgccctcccgagcaaatacgtcaatttcctgtacctcgctagccac
tatgaaaagctcaagggcagcccggaggacaacgagcagaagcagctctt
cgtggagcagcacaagcattaccTggacgagatcatcgagcagatcagcg
agttctcgaagcgggtgatcctcgccgacgcgaacctggacaaggtgctg
tcggcatataacaagcaccgcgacaaaccaatacgcgagcaggccgaaa
tatcatccacctcttcaccctcaccaacctcggcgctccggcagccttca
agtacttcgacaccacgattgaccggaagcggtacacgagcacgaaggag
gtgctcgatgcgacgctgatccaccagagcatcacagggctctatgaaac
acgcatcgacctgagccagctgggcggagacaagaagaagaagctcaagc
tctag
```

SEQ ID NO: 10

MAPKKKRKVMDKKYSIGLDIGTNSVGWAVITDEYKVPSKKFKVLGNTDRH

SIKKNLIGALLFDSGETAEATRLKRTARRRYTRRKNRICYLQEIFSNEMA

KVDDSFFHRLEESFLVEEDKKHERHPIFGNIVDEVAYHEKYPTIYHLRKK

LVDSTDKADLRLIYLALAHMIKFRGHFLIEGDLNPDNSDVDKLFIQLVQT

YNQLFEENPINASGVDAKAILSARLSKSRRLENLIAQLPGEKKNGLFGNL

IALSLGLTPNFKSNFDLAEDAKLQLSKDTYDDDLDNLLAQIGDQYADLFL

AAKNLSDAILLSDILRVNTEITKAPLSASMIKRYDEHHQDLTLLKALVRQ

QLPEKYKEIFFDQSKNGYAGYIDGGASQEEFYKFIKPILEKMDGTEELLV

KLNREDLLRKQRTFDNGSIPHQIHLGELHAILRRQEDFYPFLKDNREKIE

KILTFRIPYYVGPLARGNSRFAWMTRKSEETITPWNFEEVVDKGASAQSF

IERMTNFDKNLPNEKVLPKHSLLYEYFTVYNELTKVKYVTEGMRKPAFLS

GEQKKAIVDLLFKTNRKVIVKQLKEDYFKKIECFDSVEISGVEDRFNASL

GTYHDLLKIIKDKDFLDNEENEDILEDIVLTLTLFEDREMIEERLKTYAH

LFDDKVMKQLKRRRYTGWGRLSRKLINGIRDKQSGKTILDFLKSDGFANR

NFMQLIHDDSLTFKEDIQKAQVSGQGDSLHEHIANLAGSPAIKKGILQTV

KVVDELVKVMGRHKPENIVIEMARENQTTQKGQKNSRERMKRIEEGIKEL

GSQILKEHPVENTQLQNEKLYLYYLQNGRDMYVDQELDINRLSDYDVDHI

VPQSFLKDDSIDNKVLTRSDKNRGKSDNVPSEEVVKKMKNYWRQLLNAKL

ITQRKFDNLTKAERGGLSELDKAGFIKRQLVETRQITKHVAQILDSRMNT

KYDENDKLIREVKVITLKSKLVSDFRKDFQFYKVREINNYHHAHDAYLNA

VVGTALIKKYPKLESEFVYGDYKVYDVRKMIAKSEQEIGKATAKYFFYSN

IMNFFKTEITLANGEIRKRPLIETNGETGEIVWDKGRDFATVRKVLSMPQ

VNIVKKTEVQTGGFSKESILPKRNSDKLIARKKDWDPKKYGGFDSPTVAY

SVLVVAKVEKGKSKKLKSVKELLGITIMERSSFEKNPIDFLEAKGYKEVK

KDLIIKLPKYSLFELENGRKRMLASAGELQKGNELALPSKYVNFLYLASH

YEKLKGSPEDNEQKQLFVEQHKHYLDEIIEQISEFSKRVILADANLDKVL

SAYNKHRDKPIREQAENIIHLFTLTNLGAPAAFKYFDTTIDRKRYTSTKE

VLDATLIHQSITGLYETRIDLSQLGGDKKKKLKL

Example 4: Construction of Cas9 Expression Vectors

The synthetic DNA sequence encoding Cas9 shown above was inserted into pENTR/D-TOPO so that it would be between flanking attL1 and attL2 sites to enable transfer by Gateway cloning (InVitrogen) into suitable expression vectors. A Gateway compatible expression vector, pTrex2gHyg, was available that comprises the following features; the promoter region from the *T. reesei* pki1 (pyruvate kinase) gene and terminator region from the *T. reesei* cbh1 (cellobiohydrolase I) gene separated by Gateway cloning sites, a bacterial hygromycin phosphotransferase gene functionally linked to the *Neurospora crassa* cpc1 (cross pathway control 1) promoter region and the *Aspergillus nidulans* trpC (trifunctional protein with glutamine amido transferase, indoleglycerolphosphate synthase and phosphoribosylanthranilate isomerase activity) terminator region, and bacterial vector sequences for selection and maintenance in *E. coli*. The cas9 gene was cloned into pTrex2gHyg using the Gateway cloning procedure (InVitrogen) to give pTrex2gHyg MoCas (see FIG. 2).

Example 5: Construction of sgRNA Expression Vectors

Synthetic DNA sequences were obtained that encode the gAd3A TS1 sgRNA flanked by different putative RNA polymerase III dependent promoters and terminators. Each of these synthetic DNA sequences also had restriction enzyme recognition sites (EcoRI and BamHI) at either end.

The following sequence encodes the gAd3ATS1 sgRNA (underlined) with the *Saccharomyces cerevisiae* snr52 promoter and *S. cerevisiae* sup4 terminator (denoted gAd3ATS1-1; SEQ ID NO:28):

gaattcggatccTCTTTGAAAAGATAATGTATGATTATGCTTTCACTCAT

ATTTATACAGAAACTTGATGTTTTCTTTCGAGTATATACAAGGTGATTAC

ATGTACGTTTGAAGTACAACTCTAGATTTTGTAGTGCCCTCTTGGGCTAG

CGGTAAAGGTGCGCATTTTTTCACACCCTACAATGTTCTGTTCAAAAGAT

TTTGGTCAAACGCTGTAGAAGTGAAAGTTGGTGCGCATGTTTCGGCGTTC

GAAACTTCTCCGCAGTGAAAGATAAATGATC<u>gtcctcgagcaaaaggtgc</u>

<u>cGTTTTAGAGCTAGAAATAGCAAGTTAAAATAAGGCTAGTCCGTTATCAA</u>

<u>CTTGAAAAAGTGGCACCGAGTCGGTGGTGCTTTTTTTGTTTTTATGTCT</u> gaattcggatcc

The following sequence encodes the gAd3ATS1 sgRNA (underlined) with the *T. reesei* U6 promoter and terminator (denoted gAd3A TS1-2; SEQ ID NO:29):

gaattcggatccAAAAAACACTAGTAAGTACTTACTTATGTATTATTAAC

TACTTTAGCTAACTTCTGCAGTACTACCTAAGAGGCTAGGGGTAGTTTTA

TAGCAGACTTATAGCTATTATTTTTATTTAGTAAAGTGCTTTTAAAGTAA

GGTCTTTTTTATAGCACTTTTTATTTATTATAATATATATTATATAATAA

TTTTAAGCCTGGAATAGTAAAGAGGCTTATATAATAATTTATAGTAATAA

AAGCTTAGCAGCTGTAATATAATTCCTAAAGAAACAGCATGAAATGGTAT

TATGTAAGAGCTATAGTCTAAAGGCACTCTGCTGGATAAAAATAGTGGCT

ATAAGTCTGCTGCAAAACTACCCCCAACCTCGTAGGTATATAAGTACTGT

TTGATGGTAGTCTATC<u>gtcctcgagcaaaaggtgccGTTTTAGAGCTAGA</u>

<u>AATAGCAAGTTAAAATAAGGCTAGTCCGTTATCAACTTGAAAAAGTGGCA</u>

<u>CCGAGTCGGTGGTGCTTTTTTTCTCTT</u>gaattcggatcc

The following sequence encodes the gAd3ATS1 sgRNA (underlined) with the *T. reesei* U6 promoter, terminator and an intron (in italics) (denoted gAd3A TS1-3; SEQ ID NO:30):

gaattcggatccAAAAAACACTAGTAAGTACTTACTTATGTATTATTAAC

TACTTTAGCTAACTTCTGCAGTACTACCTAAGAGGCTAGGGGTAGTTTTA

TAGCAGACTTATAGCTATTATTTTTATTTAGTAAAGTGCTTTTAAAGTAA

-continued

GGTCTTTTTTATAGCACTTTTTATTTATTATAATATATATTATATAATAA

TTTTAAGCCTGGAATAGTAAAGAGGCTTATATAATAATTTATAGTAATAA

AAGCTTAGCAGCTGTAATATAATTCCTAAAGAAACAGCATGAAATGGTAT

TATGTAAGAGCTATAGTCTAAAGGCACTCTGCTGGATAAAAATAGTGGCT

ATAAGTCTGCTGCAAAACTACCCCCAACCTCGTAGGTATATAAGTACTGT

TTGATGGTAGTCTATC*gtcctcgagcaaaaggtgcc*<u>GTTTTAGAGCTAGA</u>

<u>GTTCGTTTCGGCTTTTCCTCGGAACCCCCAGAGGTCATCAGTTCGAATCG</u>

<u>CTAACAG</u>*AATAGCAAGTTAAAATAAGGCTAGTCCGTTATCAACTTGAAAA*

<u>AGTGGCACCGAGTCGGTGGTGCTTTTTTTCTCTT</u>gaattcggatcc

Figure 3:
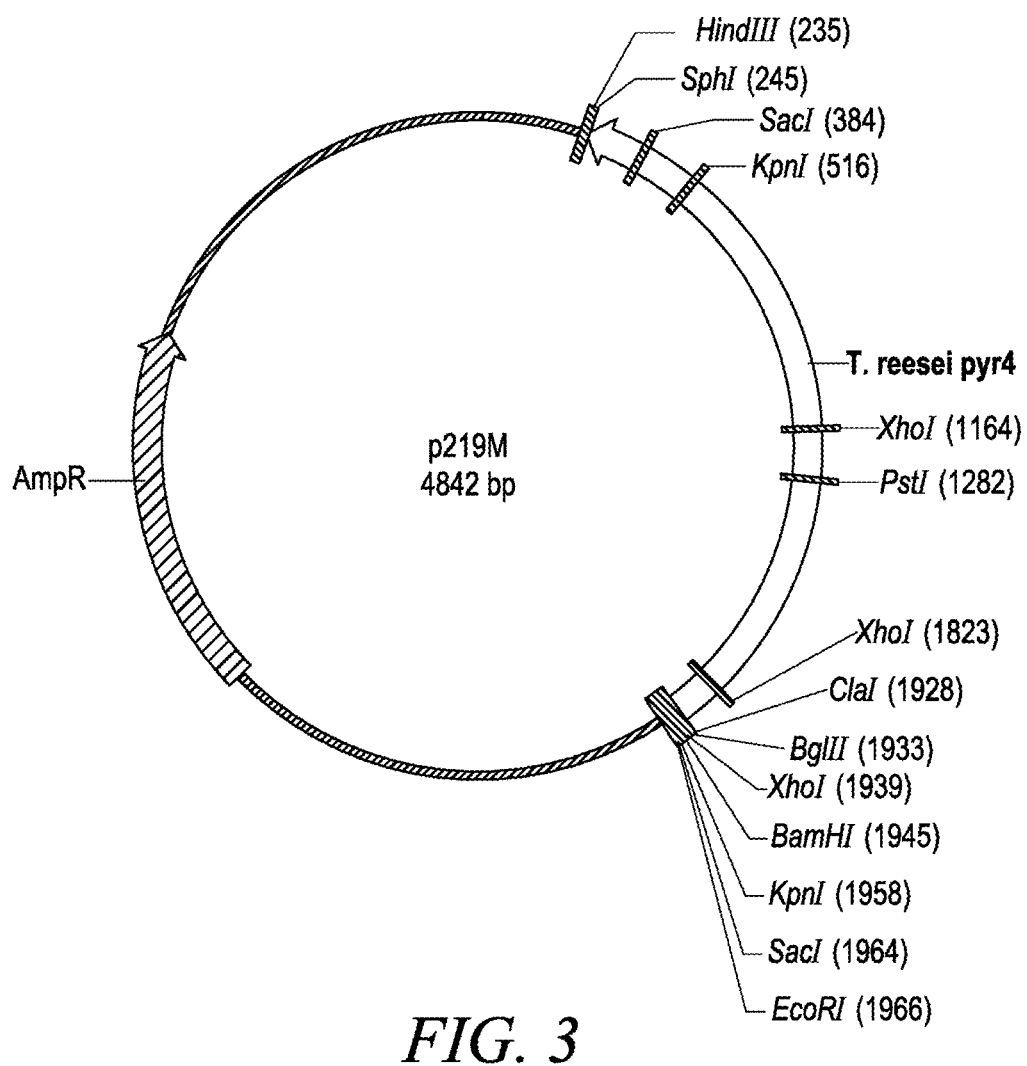
FIG. 3 shows a schematic of the p219M plasmid.
Figure 4:
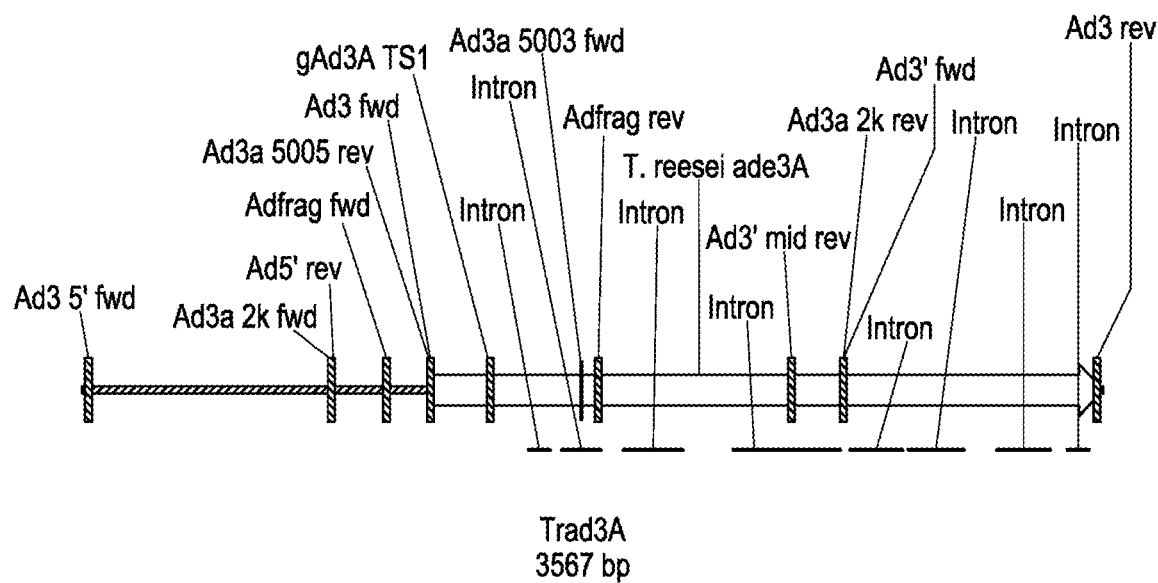
FIG. 4 shows a schematic of the *T. reesei* ad3A gene with PCR primer sites and intronic regions shown.
Figure 5:
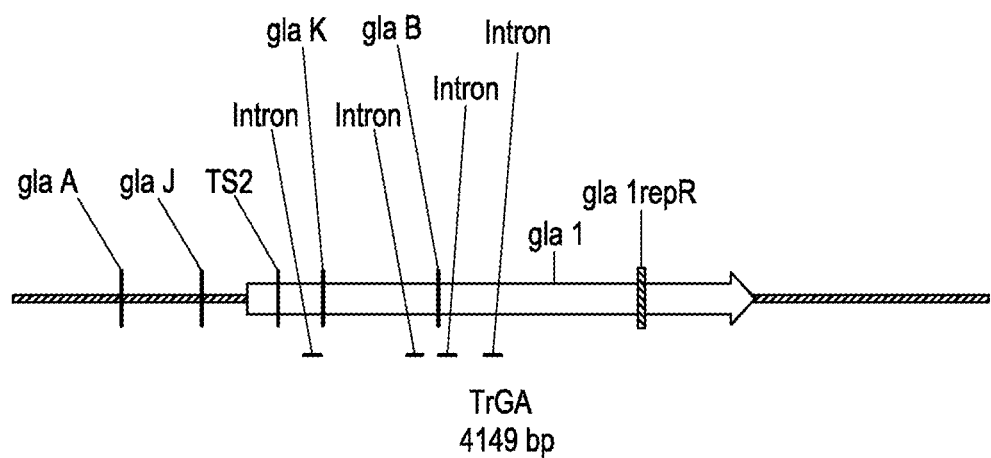
FIG. 5 shows a schematic of the *T. reesei* glucoamylase gene (TrGA) with PCR primer and intronic regions shown.

Plasmid p219M (FIG. 3) is an *E. coli* vector containing the *T. reesei* pyr4 (orotidine monophosphate decarboxylase) gene including its native promoter and terminator. This vector was digested with EcoRI and BamHI and the ends were dephosphorylated. Each of the above synthetic DNA molecules was digested with EcoRI and BamHI and ligated with the cut p219M to create a series of vectors containing an sgRNA expression cassette and the pyr4 gene. Each vector was designated by the name of the sgRNA that it encoded (for example, p219M gAd3A TS1-1 incorporates the gAd3A expression cassette with the *S. cerevisiae* snr52 promoter and sup4 terminator).

Guide RNA expression cassettes with a shorter *T. reesei* U6 promoter region were obtained as synthetic DNA. An example is provided here that includes the sequence for an sgRNA targeting the *T. reesei* gla1 gene at TS11 (SEQ ID NO:31; intron sequence is underlined).

AATTCCTAAAGAAACAGCATGAAATGGTATTATGTAAGAGCTATAGTCTA

AAGGCACTCTGCTGGATAAAAATAGTGGCTATAAGTCTGCTGCAAAACTA

CCCCCAACCTCGTAGGTATATAAGTACTGTTTGATGGTAGTCTATCgcca atggcgacggcagcacGTTTTAGAGCTAGA<u>GTTCGTTTCGGCTTTTCCTC</u>

<u>GGAACCCCCAGAGGTCATCAGTTCGAATCGCTAACAG</u>AATAGCAAGTTAA

AATAAGGCTAGTCCGTTATCAACTTGAAAAAGTGGCACCGAGTCGGTGGT

GCTTTTTTTCTCTT

The above gRNA expression cassette was amplified by PCR using primers gRNA fwd aflII
(5'-cgtcagcttaagaattcctaaagAACAGCATGAAATGG;
SEQ ID NO: 32)
and gRNA rev sfi1
(5'-cgtcagggccacgtgggccAAGAGAAAAAAAGCACCACCGACTC
GG, SEQ ID NO : 33).

These primers add an 011 to the 5' end and an sfiI site to the 3' end of the guide RNA expression cassette. The PCR product was purified using a Qiagen PCR Purification Kit according to the manufacturer's directions. The PCR product was then digested with SfiI and AflIII and cleaned again on a Qiagen PCR Purification Kit. Plasmid pTrex2g/Hyg MoCas was digested with SfiI and AflIII and dephosphorylated using the Roche Rapid alkaline phosphatase kit (Roche Diagnostics Corp., IN). The digested plasmid and PCR product were finally ligated using the Roche Rapid DNA ligase kit to create pTrex2g/Hyg MoCas gTrGA TS11B. Other sgRNA expression cassettes were inserted into pTrex2g/Hyg MoCas in a similar manner.

Example 6: Cas9-Mediated Gene Inactivation in *Trichoderma reesei*

A series of experiments are described below in which a *Trichoderma reesei* strain is either co-transformed with two separate expression vectors, one for production of Cas9 and one for production of gRNA, or is transformed with a single vector for expression of both Cas9 and gRNA. These experiments demonstrate that the 5' upstream region from the *T. reesei* U6 gene promotes gRNA transcription only when the U6 intron is also present within the gRNA transcribed region. The experiments also demonstrate that targeted gene inactivation can occur with high efficiency in *T. reesei* transformants.

Inactivation of the ad3A Gene

A strain of *Trichoderma reesei* derived from the publicly available strain RL-P37 in which the genes (cbh1, cbh2, egl1, and egl2) encoding the four major secreted cellulases were deleted was used. This strain also lacked a functional pyr4 gene. Biolistic transformation (as described in US20060003408A1) was used to co-transform with a mixture of equal amounts of pTrex2gHyg MoCas and either p219M gAd3ATS1-1, p219M gAd3ATS1-2 or p219M gAd3ATS1-3. Transformants were selected on agar plates with Vogel's minimal medium containing 2% glucose, 100 mg/L hygromycin B and 200 mg/L adenine. After selection on the first plates transformant colonies were picked to fresh plates of the same selective medium. During growth on the second plate it was possible to distinguish between stable and unstable hygromycin-resistant transformants. Stable transformants grew more rapidly, the colonies had a smooth outline and the mycelium was more dense. Unstable transformants grew slower, had less dense mycelium and colonies had a ragged irregular outline. After growth on the second plate transformants were transferred to Vogel's medium with glucose, without hygromycin and with 14 mg/L adenine to screen for those which exhibited a red/brown color indicating that they were adenine auxotrophs. Five stable and 23 unstable transformants were obtained with p219M gAd3ATS1-1 and all were adenine prototrophs. Eleven stable and 38 unstable transformants were obtained with p219M gAd3ATS1-2 and all 11 stable and 29 of the unstable transformants were adenine prototrophs. Nineteen stable and 2 unstable transformants were obtained with p219M gAd3ATS1-3 and all were adenine auxotrophs. Clearly, adenine auxotrophs were only obtained with gAd3ATS1-3 that utilizes the *T. reesei* U6 promoter, intron and terminator to control transcription of sgAd3A TS1. Adenine auxotrophy indicates targeted Cas9 cleavage at the native *T. reesei* ad3A locus. It can be concluded that Cas9-mediated gene inactivation is efficient because all transformants with gAd3ATS1-3 that were tested were adenine auxotrophs.

In order to determine the mutations at the ad3A locus in co-transformants with pTrex2gHyg MoCas and p219M gAd3ATS1-3 genomic DNA was extracted from 10 stable adenine auxotrophic transformants. This DNA was used as template for PCR using several different primer pairs designed to generate products that spanned the Cas9 target site or were upstream or downstream of the target site. PfuUltra II Fusion HS DNA polymerase (Agilent Technologies) was used for the PCR according to the manufacturer's directions. In each case, the extension time was that suggested by the manufacturer for the expected size of the PCR product as described below. The sizes of the PCR products were evaluated by agarose gel electrophoresis.

A PCR product of the expected size (872 bp) was obtained in all transformants using Ad3 5' fwd+Ad3 5' rev primers (5'-tgaacacagccaccgacatcagc [SEQ ID NO:34] and 5'-gctggtgagggtttgtgctattg [SEQ ID NO:35] respectively) that amplify a region on the 5' side of the TS1 target site.

A PCR product of the expected size (1214 bp) was obtained in all transformants using Ad3 5' fwd+Ad3a 5005 rev primers (5'-tgaacacagccaccgacatcagc [SEQ ID NO:34] and 5'-gattgcttgggaggaggacat [SEQ ID NO:36] respectively) that amplify a region on the 5' side of the TS1 target site.

A PCR product of the expected size (904 bp) was obtained in all transformants using Ad3 3' fwd+Ad3 3' rev primers (5'-cgaggccactgatgaagttgttc [SEQ ID NO:37] and 5'-cagttttccaaggctgccaacgc [SEQ ID NO:38] respectively) that amplify a region on the 3' side of the TS1 target site.

A PCR product of the expected size (757 bp) was obtained in all transformants using Ad3a 5003 fwd+Ad3mid rev primers (5'-ctgatcttgcaccctggaaatc [SEQ ID NO:39] and 5'-ctctctatcatttgccaccctcc [SEQ ID NO:40] respectively) that amplify a region on the 3' side of the TS1 target site.

The above PCR results demonstrated that the genomic DNA preparations were of a quality sufficient to obtain PCR products from either upstream or downstream of the Cas9 target site.

No PCR product could be obtained for any transformants using Adfrag fwd+Adfrag rev primers (5'-ctccattcaccctcaattctcc [SEQ ID NO:41] and 5'-gttcccttggcggtgcttggatc [SEQ ID NO:42] respectively) spanning the TS1 target site in ad3A. The expected size for this PCR product presuming no large size change caused by Cas9 activity was approximately 764 bp.

No PCR product could be obtained for any transformants using Adfrag fwd+Ad3 3' rev primers (5'-ctccattcaccctcaattctcc [SEQ ID NO:41] and 5'-cagttttccaaggctgccaacgc [SEQ ID NO:38] respectively) spanning the TS1 target site in ad3A. The expected size for this PCR product presuming no large size change caused by Cas9 activity was approximately 2504 bp.

No PCR product could be obtained for any transformants using Ad3a 2k fwd+Ad3a 2k rev primers (5'-caatagcacaaaccctcaccagc [SEQ ID NO:43] and 5'-gaacaactt-catcagtggcctcg [SEQ ID NO:44] respectively) spanning the TS1 target site in ad3A. The expected size for this PCR product presuming no large size change caused by Cas9 activity was approximately 1813 bp.

Five of the transformants also gave no PCR product using Adfrag fwd+Ad3 mid rev primers (5'-ctccattcaccctcaattctcc [SEQ ID NO:41] and 5'-ctctctatcatttgccaccctcc [SEQ ID NO:40] respectively) spanning the TS1 target site. The expected size for this PCR product presuming no large size change caused by Cas9 activity was approximately 1438 bp.

Based on published data, Cas9-mediated inactivation of genes typically involves error-prone repair of a double-strand break in the DNA at the target site. The end result is small deletions or insertions (indels) at the target site. The above results from PCR analysis were surprising in that it was not possible to obtain a PCR product of the expected size that spanned the target site suggesting that inactivation of ad3A was not due to small insertions or deletions (indels) at the target site. Instead, these data are consistent with the possibilities that inactivation of ad3A was caused by a chromosomal rearrangement or large insertion at the target site.

Inactivation of the Glucoamylase (GA) Gene

A strain of *Trichoderma reesei* derived from the publicly available strain RL-P37 in which the genes (cbh1, cbh2, egl1, and egl2) encoding the four major secreted cellulases were deleted was used. This strain also lacked a functional pyr4 gene. This strain was co-transformed using the biolistic method with a mixture of equal amounts of pTrex2gHyg MoCas and p219M gTrGA TS2. Transformants were selected on agar plates with Vogel's minimal medium containing 1% glucose, 100 ug/ml hygromycin B and 2 mg/ml uridine. After selection on the first plates transformant colonies were picked to fresh plates of the same selective medium. During growth on the second plate it was possible to distinguish between stable and unstable hygromycin-resistant transformants. Seventeen stable and 4 unstable transformants were obtained. These transformants were transferred to Vogel's agar plates without glucose and with 1% insoluble starch to screen for presence or absence of secreted glucoamylase. Colonies able to secrete glucoamylase grow well and sporulate. Colonies unable to secrete glucoamylase grow with very sparse mycelium and are clearly distinguishable. Fourteen of the 17 stable transformants were unable to secrete glucoamylase and all 4 of the unstable transformants did not secrete glucoamylase.

In order to determine the mutations at the gla1 (glucoamylase) locus in co-transformants with pTrex2gHyg MoCas and p219M gTrGA TS2 genomic DNA was extracted from 5 stable glucoamylase non-producing transformants. This DNA was used as template for PCR using different primer pairs designed to generate products that spanned the Cas9 target site or were upstream or downstream of the target site. PfuUltra II Fusion HS DNA polymerase (Agilent Technologies) was used for the PCR according to the manufacturer's directions. In each case, the extension time was that suggested by the manufacturer for the expected size of the PCR product as described below. The sizes of the PCR products were evaluated by agarose gel electrophoresis.

No PCR product could be obtained for any transformants using glaA+glaB primers (5'-ccgttagttgaagatccttgccg [SEQ ID NO:45] and 5'-gtcgaggatttgcttcatacctc [SEQ ID NO:46] respectively) spanning the TS2 target site in gla1. The expected size for this PCR product presuming no large size change caused by Cas9 activity was approximately 1371 bp.

A band of the expected size (364 bp) was obtained in all transformants using glaA+glaJ primers (5'-ccgttagttgaagatccttgccg [SEQ ID NO:45] and 5'-tgccgactttgtccagtgattcg [SEQ ID NO:47] respectively) that amplify a region on the 5' side of the TS2 target site.

A band of the expected size (520 bp) was obtained in 4 of the transformants using glaK+glaB primers (5'-ttacatgtggacgcgagatagcg [SEQ ID NO:48] and 5'-gtcgaggatttgcttcatacctc [SEQ ID NO:46] respectively) that amplify a region on the 3' side of the TS2 target site. One of the transformants gave no PCR product with this primer pair.

A separate experiment intended to demonstrate inactivation of the gla1 gene by targeted Cas9 action was performed using a strain of *T. reesei* derived from RL-P37 and having an inactive pyr4 gene. Protoplasts of this strain were transformed with pTrex2gHyg MoCas gTrGA TS11 using a polyethylene glycol-mediated procedure (as described below). Transformants were selected on agar plates of Vogel's minimal medium with 2% glucose, 2 mg/ml uridine, 1.1M sorbitol and 100 ug/ml hygromycin B. After selection on the first plates transformant colonies were picked to fresh plates of the same selective medium without sorbitol. During growth on the second plate it was possible to distinguish between stable and unstable hygromycin-resistant transformants. Transformants were transferred to Vogel's agar plates without glucose and with 1% insoluble starch to screen for presence or absence of secreted glucoamylase. Five stable transformants, designated B#1, B#2, B#4, B#5 and B#6, which did not secrete glucoamylase were selected for further analysis. Genomic DNA was extracted from each of these transformants.

PCR was performed using genomic DNA as template and primers gla1repF and gla1repR (5'-gtgtgtctaatgcctccaccac [SEQ ID NO:49] and 5'-gatcgtgctagcgctgctgttg [SEQ ID NO:50] respectively) that generate a product of 983 bp from the wild-type gla1 locus spanning the TS11 target site. The PCR conditions included gradually reducing the primer annealing temperature with each PCR cycle and a long extension time to determine if there had been a large insertion at the target site. The specific PCR conditions were as follows.

Step 1: 94 C for 1 minute
Step 2: 94 C for 25 seconds
Step 3: 63 C for 30 seconds (temperature reduced by 0.2 C per cycle)
Step 4: 70 C for 8 minutes
Steps 2-4 repeated 24 more times
Step 5: Hold at 4 C A clear PCR product of greater than 12 kb was obtained from two of the transformants (B#1 and B#6) suggesting an increase of greater than 11 kb in the DNA region spanning the target site. The other three transformants gave only non-specific PCR products that appeared as low intensity bands on agarose gel electrophoresis. Sequence analysis of the >12 kb PCR product from B#6 demonstrated that DNA derived from plasmid pTrex2gHyg MoCas gTrGA TS11 was inserted at the TS11 target site.

PCR was performed using genomic DNA samples B#2, B#4, and B#5 and primer pair 1553R and 1555F (5'-CCGTGATGGAGCCCGTCTTCT [SEQ ID NO:51] and 5'-CGCGGTGAGTTCAGGCTTTTC [SEQ ID NO:52] respectively). Primer 1553R binds to the gla1 gene on the 3' side of target site 11. Primer 1555F binds near the start codon of the hygromycin phosphotransferase (hygB) gene on the plasmid pTrex2gHyg MoCas gTrGA TS11. The same PCR conditions were used as above. PCR products of 4.5 kb and 6.5 were obtained for transformants B#4 and B#5 respectively. PCR products should only be obtained if the plasmid with the hygB gene had inserted into the gla1 gene. Presumably, the inserted plasmid DNA in transformants B#4, and B#5 was so large that it was not possible to obtain a PCR product using primers gla1 repF and gla1repR.

Taken together, the PCR data demonstrated that stable hygromycin-resistant transformants with glucoamylase inactivation have arisen through insertion of large segments of the Cas9 and guide RNA expression vector at the target site in the gla1 gene.

Inactivation of the Pyr2 Gene

Transformants of *T. reesei* strains QM6a or RL-P37 were generated by PEG-mediated transformation of protoplasts with derivatives of plasmid pTrex2gHyg MoCas that included guide RNA expression cassettes targeting different positions within the *T. reesei* pyr2 gene. Inactivation of this gene confers uridine auxotrophy and resistance to 5-fluoroorotic acid (FOA). Transformants were initially selected on medium containing hygromycin B. Upon transfer to fresh agar plates containing hygromycin B they were scored as stable or unstable. Transformants were then transferred to agar plates of Vogel's minimal medium with 2 mg/ml uridine and 1.2 mg/ml FOA. The ability to grow in the presence of FOA is indicative of uridine auxotrophy due to Cas9-mediated inactivation of the pyr2 gene.

Genomic DNA was extracted from some of the FOA resistant hygromycin stable and unstable transformants for PCR analysis. The primers used for this analysis were pyr2F (5'-gtataagagcaggaggagggag [SEQ ID NO:53]) and pyr2R (5'-gaacgcctcaatcagtcagtcg [SEQ ID NO:54]) designed to amplify a region of the pyr2 locus spanning the target sites and approximately 0.8 kb in length.

Among the QM6a transformants shown to be FOA resistant 18 stable and 5 unstable hygromycin resistant transformants were tested using the PCR protocol with an extension time sufficient to amplify the region of the pyr2 locus presuming the size to be similar to that in a wild-type strain. None of the stable transformants gave a PCR product with this short extension time whereas 2 of the unstable transformants did give a PCR product. DNA sequence analysis of these two PCR products showed that one had a single nucleotide deletion and the other had a 111 nucleotide deletion at the expected target site.

Among the RL-P37 transformants shown to be FOA resistant 4 stable and 2 unstable hygromycin resistant transformants were tested using the PCR protocol with a short extension time. None of the stable transformants gave a PCR product with this short extension time whereas both of the unstable transformants did give a PCR product. DNA sequence analysis of these two PCR products showed that one had a single nucleotide deletion and the other had an insertion of 134 nucleotides at the expected target site. This insertion consisted of two small fragments of the pTrex2gHyg vector.

A different 6 stable hygromycin resistant RL-P37 transformants were analyzed using the PCR protocol described earlier designed to enable amplification of the region of the pyr2 locus presuming a large DNA fragment was inserted at the target site in the pyr2 locus. All 6 transformants gave a large PCR product (between approximately 5 kb and >12 kb depending on the transformant) with this long extension time protocol. DNA sequence analysis of 5 of these PCR products showed that pTrex2gHyg vector DNA, or fragments thereof, was integrated in all cases.

Taken together, these data show that repair of a double strand break caused by Cas9 predominantly involves integration of large vector fragments in stable transformants. This can be a very efficient method of gene inactivation. This also demonstrates that a DNA fragment or vector bearing a functional gene and having no sequence homology with the target site can integrate in a site-specific manner at the target site following Cas9 cleavage and double strand break formation. In contrast, small deletions or insertions (indels) are associated with inactivation of a gene by Cas9 in unstable transformants. This is the method of choice for gene inactivation if vector integration is undesirable.

Figure 6:
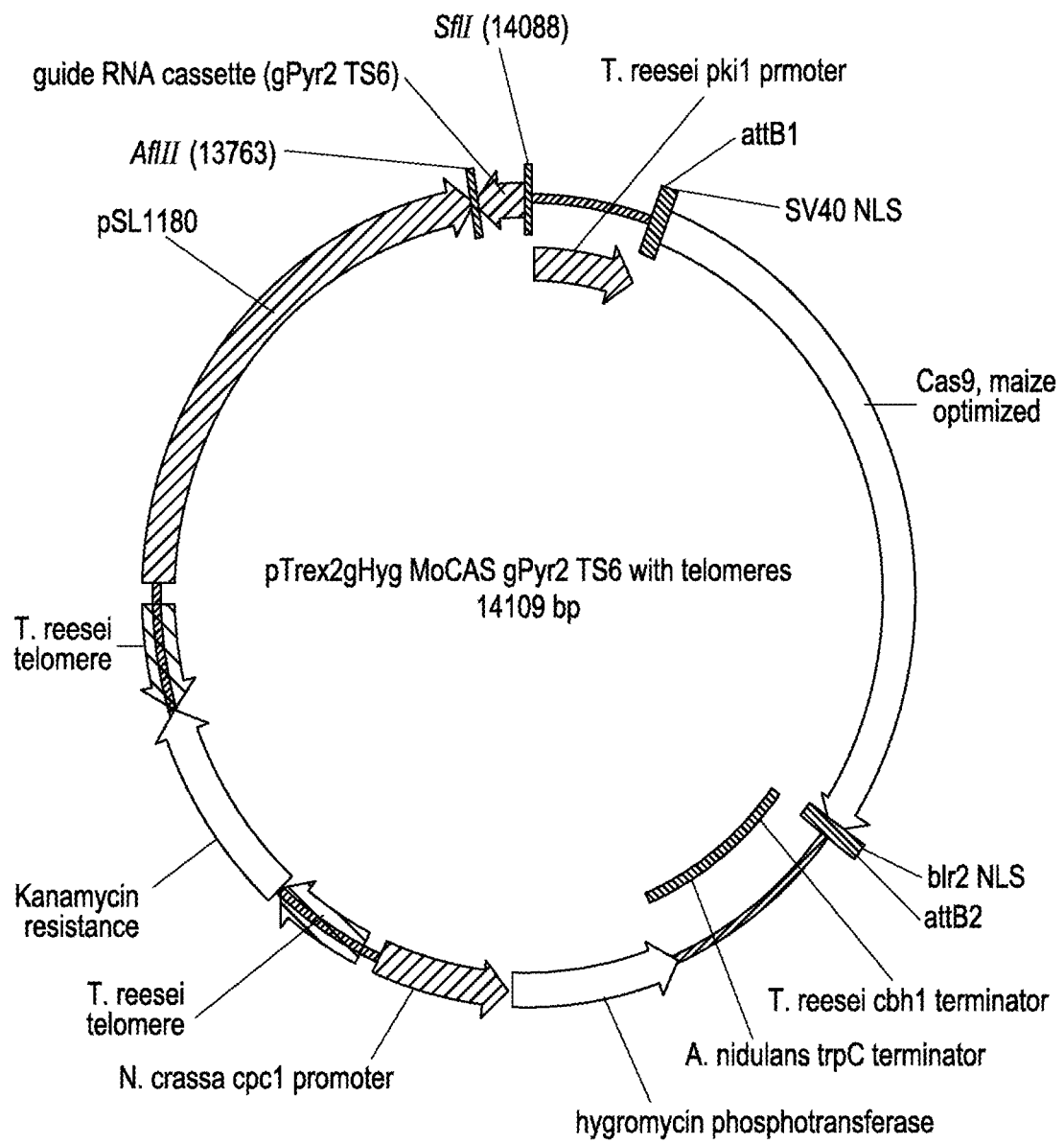
FIG. 6 shows a schematic of the pTrex2gHygMoCasgPyr2TS6 plasmid which includes telomere sequences.

Example 7: Expression of Cas9 and sgRNA Using Expression Vector with Telomeres A version of the Cas9 and guide RNA expression vector pTrex2gHyg MoCAS gPyr2 TS6 was constructed that contained *Trichoderma reesei* telomere sequences (shown in FIG. 6). The DNA sequence shown below (SEQ ID NO:55) was inserted into the vector. The underlined regions contain the repeated telomere sequences, each reading in towards center of this fragment. The central portion is a bacterial kanamycin resistance gene with promoter and terminator that enables selection in *E. coli* to ensure maintenance of the telomere repeats. In *Trichoderma*, a vector with telomeres is expected to linearize with the telomere sequences at each end and should be maintained autonomously at low copy number although occasional integration into the chromosomal DNA can also occur.

(SEQ ID NO: 55)
<u>tcaggaaatagctttaagtagcttattaagtattaaaattatatatt</u>

<u>tttaatataactatatttctttaataaataggtattttaagctttatat</u>

<u>ataaatataataataaaataatatattatatagcttttttattaataaat</u>

<u>aaaatagctaaaaatataaaaaaaatagctttaaaatacttatttttaa</u>

<u>ttagaattttatatattttaatatataagatcttttactttttttataa</u>

<u>gcttcctaccttaaattaaattttttactttttttttactattttactata</u>

<u>tcttaaataaaggctttaaaaatataaaaaaaatcttcttatatattat</u>

<u>aagctataaggattatatatatttttttttaattttttaaagtaagta</u>

<u>ttaaagctagaattaaagtttttaatttttttaaggctttatttaaaaaaa</u>

<u>ggcagtaatagcttataaaagaaatttcttttctttttatactaaaagt</u> acttttttttttaataaggttagggttagggtttactcacaccgaccatc ccaaccacatcttagggttagggttagggttagggttagggttagggtt agggttagggtaagggtttaaacaaagccacgttgtgtctcaaaatctc tgatgttacattgcacaagataaaaatatatcatcatgaacaataaaac tgtctgcttacataaacagtaatacaaggggtgttatgagccatattca acgggaaacgtcttgctcgaggccgcgattaaattccaacatggatgct gatttatatgggtataaatgggctcgcgataatgtcgggcaatcaggtg cgacaatctatcgattgtatgggaagcccgatgcgccagagttgtttct gaaacatggcaaaggtagcgttgccaatgatgttacagatgagatggtc agactaaactggctgacggaatttatgcctcttccgaccatcaagcatt ttatccgtactcctgatgatgcatggttactcaccactgcgatccccgg gaaaacagcattccaggtattagaagaatatcctgattcaggtgaaaat attgttgatgcgctggcagtgttcctgcgccggttgcattcgattcctg tttgtaattgtccttttaacagcgatcgcgtatttcgtctcgctcaggc gcaatcacgaatgaataacggtttggttgatgcgagtgattttgatgac gagcgtaatggctggcctgttgaacaagtctggaaagaaatgcataagc ttttgccattctcaccggattcagtcgtcactcatggtgatttctcact tgataaccttattttttgacgaggggaaattaataggttgtattgatgtt ggacgagtcggaatcgcagaccgataccaggatcttgccatcctatgga actgcctcggtgagttttctccttcattacagaaacggcttttcaaaa atatggtattgataatcctgatatgaataaattgcagtttcatttgatg ctcgatgagttttctaatcagaattggttaattggttgtaacactggc agagcattacgctgacttgacgggacggcggctttgttgaataaatcga acttttgctgagttgaaggatcagatcacgcatcttcccgacaacgcag accgttccgtggcaaagcaaaagttcaaaatcaccaactggtccaccta caacaaagctctcatcaaccgtggctccctcactttctggctggatgat gggggcgattcaggcctggtatgagtcagcaacaccttcttcacgaggca -continued
```
gacctcagcggtttaaacctaaccctaaccctaaccctaaccctaaccc taaccctaaccctaaccctaaccctaaccctaaccctaaccctaaccct aacctaaccctaatggggtcgatctgaaccgaggatgagggttctatag actaatctacaggccgtacatggtgtgattgcagatgcgacgggcaagg tgtacagtgtccagaaggaggagagcggcataggtattgtaatagacca gctttacataataatcgcctgttgctactgactgatgaccttcttccct aaccagtttcctaattaccactgcagtgaggataaccctaactcgctct ggggttattattatactgattagcaggtggcttatatagtgctgaagta ctataagagtttctgcgggaggaggtggaaggactataaactggacaca gttagggatagagtgatgacaagacctgaatgttatcctccggtgtggt atagcgaattggctgaccttgcagatggtaatggtttaggcagggtttt tgcagaggggacgagaacgcgttctgcgatttaacggctgctgccgcc aagctttacggttctctaatgggcggccgc
```

This vector was inserted into *T. reesei* strain RL-P37 by PEG-mediated transformation of protoplasts. Transformants were selected for hygromycin resistance and transferred to fresh agar plates with hygromycin. The majority of transformants showed an unstable hygromycin resistance phenotype. Individual transformed colonies were transferred to minimal medium agar plates containing 2 mg/ml uridine and 1.2 mg/ml 5-fluoroorotic acid to select for those that were able to grow and thus had a Pyr-minus phenotype. Eight out of 142 (6%) of the unstable transformants were Pyr-minus. Analysis by PCR of the pyr2 locus and sequencing of three of these transformants showed that two had small deletions at the target site (1 bp and 27 bp respectively) and one had a 1 bp deletion combined with an insertion of 68 bp derived from the bacterial vector portion of pTrex2gHyg MoCAS gPyr2 TS6. The other 5 transformants did not give a PCR product despite using PCR conditions designed to amplify large DNA fragments [PCR conditions: Step 1: 94° C. for 1 minute; Step 2: 94° C. for 25 seconds; Step 3: 63 C for 30 seconds (temperature reduced by 0.2 C per cycle); Step 4: 70° C. for 8 minutes; Steps 2-4 repeated 24 more times; Step 5: Hold at 4° C. Polymerase: PfuUltra II Fusion HS DNA polymerase (Agilent Technologies)].

These results demonstrate that expression of Cas9 and guide RNA from an autonomously replicating vector enables Cas9 targeting to a specific locus (pyr2 in this case). The resulting gene inactivation can occur without insertion of vector DNA at the target site.

Section B: Direct Introduction of Cas and/or Guide RNA

Example 8: Heterologous Expression of CRISPR SpyCas9 in *E. coli*

Figure 7:
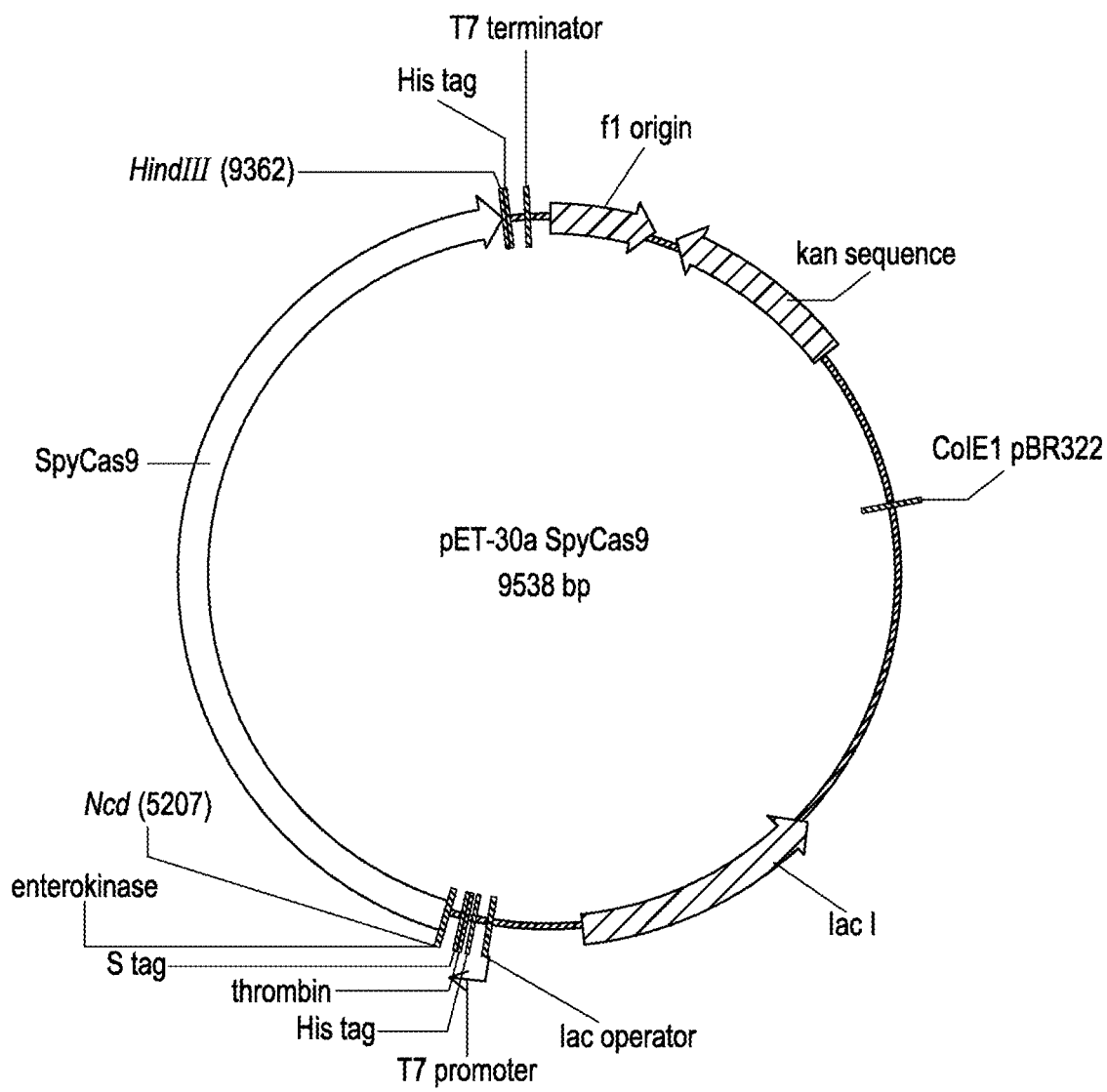
FIG. 7. Plasmid map of pET30a-SpyCas9.
Figure 8A:
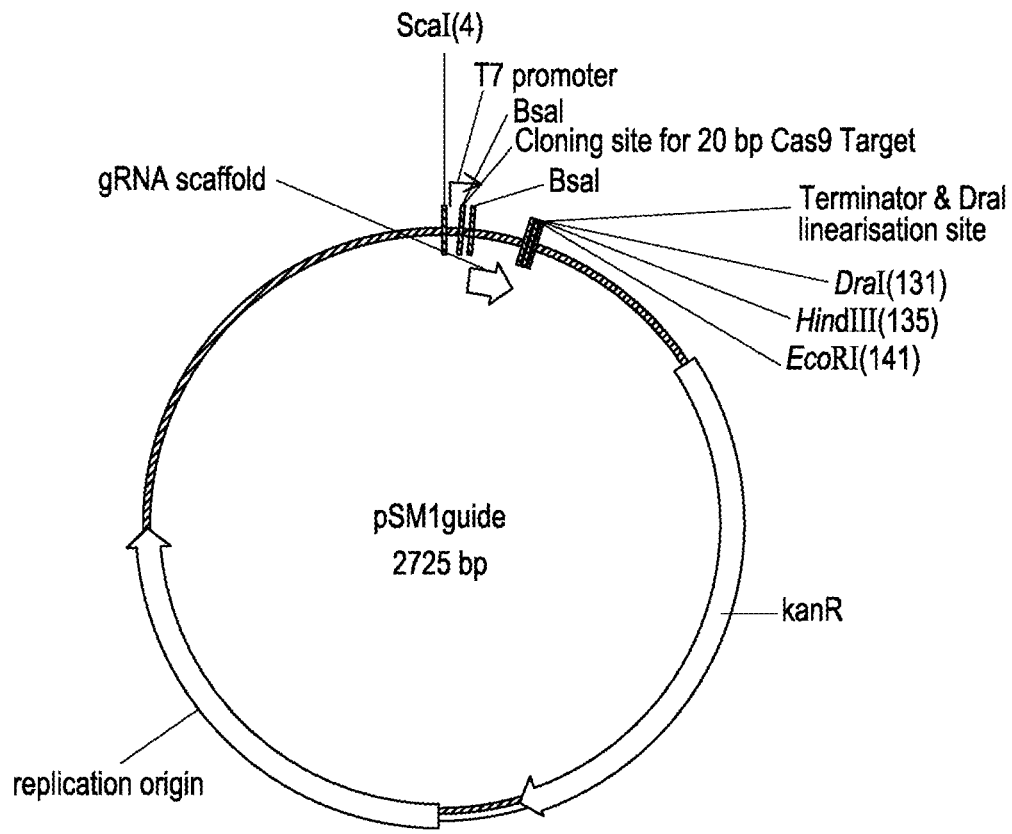
FIG. 8A shows a plasmid map for pSM1guide which is used for flexible cloning of any potential guide RNA variable targeting (VT) domain matching the sequence pattern GGN18NGG or GN19NGG.
Figure 8B:
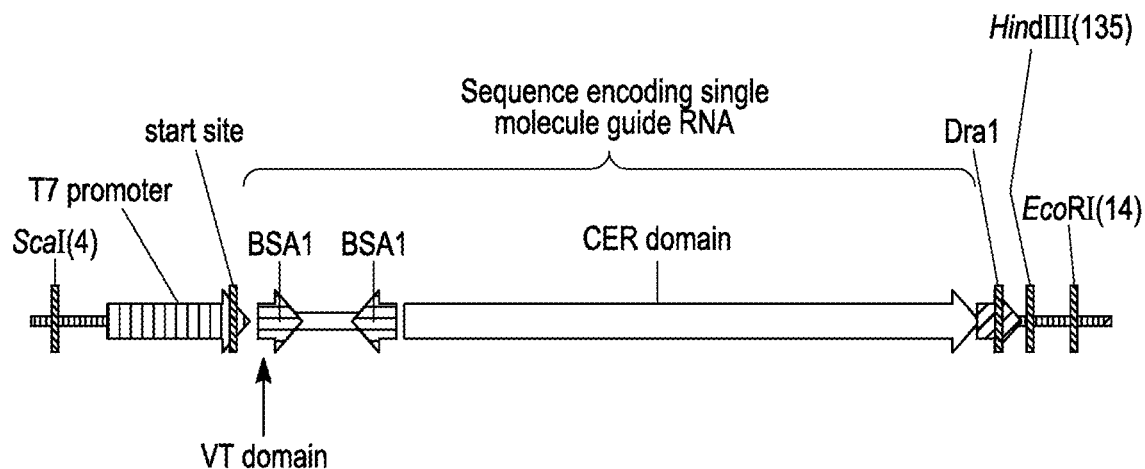
FIG. 8B is a more detailed map of the single molecule guide RNA expression cassette region of the pSM1guide plasmid in panel A and shows the configuration of the T7 promoter, the transcriptional start site, the type II restriction endonuclease sites of Bsa1 (used to insert the desired VT domain, e.g., using annealed oligos), the CER domain (which includes the transcriptional terminator sequence TTTTT; not shown), and the full region encoding the single molecule guide RNA. Restriction enzyme DRA1 is used to linearize this plasmid before in vitro transcription. When transcribed, the CER domain of the guide RNA will form a hairpin structure that is able to bind to a cognate Cas9 polypeptide, thus generating a functional Cas9/guide RNA complex that can induce a double strand break at a DNA target site (one having a sequence complementary to the VT domain and the appropriate PAM site).

*E. coli* codon-optimized *Streptococcus pyogenes* Cas9 (SpyCas9) gene was synthesized and inserted into the expression vector pET30a at NcoI and HindIII sites by Generay (Shanghai, China), resulting in the plasmid pET30a-SpyCas9 (FIG. 7). As indicated in the plasmid map in FIG. 8A, the full coding sequence of the expression cassette contains, in 5' to 3' orientation, a sequence encoding an N-terminal His6 tag/thrombin/S•Tag™ enterokinase region (SEQ ID NO:13; includes a start codon methionine), a sequence encoding an SV40 nuclear localization signal (SEQ ID NO:14), a sequence encoding the SpyCas9 (SEQ ID NO:15), and a sequence encoding the BLR nuclear localization signal (SEQ ID NO:16) all in operable linkage. This entire coding sequence is shown in SEQ ID NO:17. The amino acid sequence of the N-terminal His6 tag/thrombin/S•Tag™ enterokinase region encoded by SEQ ID NO:13 is shown in SEQ ID NO:18 (including the methionine at position 1), the amino acid sequence of the SV40 nuclear localization signal encoded by SEQ ID NO:14 is shown in SEQ ID NO:19, the amino acid sequence of the SpyCas9 encoded by SEQ ID NO:15 is shown in SEQ ID NO:1, and the amino acid sequence of the BLR nuclear localization signal encoded by SEQ ID NO:16 is shown in SEQ ID NO:20. The amino acid sequence encoded by SEQ ID NO:17 is shown in SEQ ID NO:21.

The pET30a-SpyCas9 plasmid was transformed into Rosetta2 (De3)plysS *E. coli* strain (Novagen®, EMD Biosciences, Inc., Merck KGaA, Darmstadt, Germany) and the transformation products were spread on Luria Agar plates supplemented with 34 ppm Chloramphenicol and 50 ppm Kanamycin. Colonies were picked and cultivated for 24 hours in a 250 ml shake flask with 25 ml of the Invitrogen MagicMedia™ *E. coli* Expression Medium (Thermo Fisher Scientific Inc., Grand Island, N.Y.).

Example 9: Purification of SpyCas9

For purification of SpyCas9, a combination of affinity, hydrophobic interaction and size exclusion chromatographic steps were applied. Briefly, SpyCas9 expressing *E. coli* cells (Rosetta2 (De3)plysS, as described above) were cultured in a 250 ml shake flask with 25 ml MagicMedian™ for 24 hours and harvested by centrifugation. Cells (approximately 40 grams) were pelleted and resuspended in 400 ml lysis buffer (20 mM HEPES, pH7.5, 500 mM NaCl, 0.1% Triton X-100, 1 mM DTT and 1 mM TCEP, protease inhibitor cocktail purchased from Roche) and lysed via ultra-sonicator (35% power, 20 min, 2s on/3s off) (SCIENT2-II D, Ningbo Scientz Biotechnology Co., LTD). The lysate was cleared by centrifugation at 20000g for 40 min.

Approximately 400 ml of clarified lysate was incubated with 5 ml Ni-NTA resin (GE Healthcare) overnight at 4° C. with shaking at 30 rpm/min using a Rolling Incubator (Kylin-Bell Lab. Instruments Co., Ltd. Haimen, China). After centrifugation, the resin was transferred to a XK26/20 column (GE Healthcare) and connected to AKTA Explorer system (GE Healthcare). After being washed extensively with equilibration buffer (20 mM HEPES, pH 7.5, 300 mM NaCl, 0.1% Triton X-100) followed by wash buffer (25 mM imidazole in equilibration buffer), the target protein was eluted with 250 mM imidazole in equilibration buffer.

To the active fraction collected from the affinity step, ammonium sulfate was added to a final concentration of 0.8 M and loaded onto a 20 ml phenyl-Sepharose HP column (GE Healthcare). The column was eluted with a gradient of 0.8 M to 0.0 M ammonium sulfate in 50 mM HEPES buffer pH 7.5 and the flow through was collected.

Finally, the protein was further purified by size exclusion chromatography on a Superdex 200 16/60 column (GE Healthcare) in 20 mM HEPES pH7.5, 150 mM KCl and 10% glycerol. The fraction with the highest purity were pooled and concentrated via Amicon 30 KDa membrane filter (Millipore). The final protein sample was stored at −20° C. freezer in the 40% glycerol until use.

Example 10: Guide RNA Design and Expression Vector Cloning

We used the Cas9 Target Finder to identify viable target sites. Target sequences with an appropriate PAM site were identified on the sense or antisense strand of the xyr1 gene of *Trichoderma reesei* (Transcription factor Xylanase regulator 1 involved in Xylan degradation (Protein ID 122208)) as well as the pyr4 gene of *Trichoderma reesei* (orotidine-5'-monophosphate decarboxylase (Protein ID 74020)). Using this program, we identified all 20-nucleotide long target sequences followed by a 3-nucleotide PAM sequence (NGG) that matches the sequence pattern GGN18NGG or GN19NGG. Basic local alignment search tool (BLAST) was performed using the *Trichoderma reesei* genome sequence database (genome4gi-psf.org/Trire2/Trire2.home) to check for uniqueness of the 20-nt sequence and to avoid off target effects. The following sequences were used to generate in vitro guide RNA expression constructs in the pSM1guide plasmid (shown in FIG. 8A) for two xyr1 specific target sites (xyr1 Ta and xyr1 Tc) and for one pyr4 specific target site (pyr4 TS2). The target sequences with the associated PAM sites as well as the oligos used for annealing and cloning into the pSM1guide plasmid at the BSA1 restriction sites are shown:

```
Xyr1 Ta
(1) Target sequence (5'-3', PAM bold underlined):
                                          (SEQ ID NO: 56)
GCAGCACCTCGCACAGCATGCGG (SEQ ID NO: 57)
(2) oligo 1: TAGGCAGCACCTCGCACAGCATG (SEQ ID NO: 58)
(3) oligo 2: AAACCATGCTGTGCGAGGTGCT Xyr1 Tc
(1) Target sequence (5'-3', PAM bold underlined):
                                          (SEQ ID NO: 59)
GCTGCCAGGAAGAATTCAACGGG (SEQ ID NO: 60)
(2) oligo 1: TAGGCTGCCAGGAAGAATTCAAC (SEQ ID NO: 61)
(3) oligo 2: AAACGTTGAATTCTTCCTGGCA Pyr4 TS2
(1) Target sequence (5'-3', PAM bold underlined):
                                          (SEQ ID NO: 62)
GCTCAAGACGCACTACGACATGG (SEQ ID NO: 63)
(2) oligo 1: TAGGCTCAAGACGCACTACGACA (SEQ ID NO: 64)
(3) oligo 2: AAACTGTCGTAGTGCGTCTTGAGC
```

The sequences below show the template sequence derived from the respective pSM1guide plasmid constructs for transcription of each of the three guide RNAs (i.e., for the xyr1 Ta, xyr1 Tc and pyr4 TS2 target sites above). Each sequence below shows the T7 promoter (bold), the VT domain (shown in uppercase), the CER domain (shown in lowercase), and a transcriptional terminator (bold underline).

```
Xyr-1 Ta
                                          (SEQ ID NO: 65)
taatacgactcactataggGCAGCACCTCGCACAGCATGgttttagagct agaaatagcaagttaaaataaggctagtccgttatcaacttgaaaaagtg gcaccgagtcggtgcttttttacg Xyr-1 Tc
                                          (SEQ ID NO: 66)
taatacgactcactataggGCTGCCAGGAAGAATTCAACgttttagagct agaaatagcaagttaaaataaggctagtccgttatcaacttgaaaaagtg gcaccgagtcggtgcttttttacg Pyr4 TS2
                                          (SEQ ID NO: 67)
taatacgactcactataggGCTCAAGACGCACTACGACAgttttagagct agaaatagcaagttaaaataaggctagtccgttatcaacttgaaaaagtg gcaccgagtcggtgcttttttacg
```

Example 11: In Vitro DNA Cleavage Assay

Guide RNAs were produced in vitro from templates for xyr1 Ta and xyr1 Tc using the MEGAshortscript™ T7 transcription kit from Thermo Fisher according to the manufacturer's instructions. In vitro transcription was carried out at 37° C. for at least 5 hours. Transcribed guide RNAs were purified using MEGAclear™ Transcription Clean-Up kit from Thermo Fisher. The RNA concentration was measured with NanoDrop™ (Thermo Fisher). Denaturing urea-PAGE gel (10%) was used to confirm the quality of the guide RNA produced (data not shown).

Figure 9A:
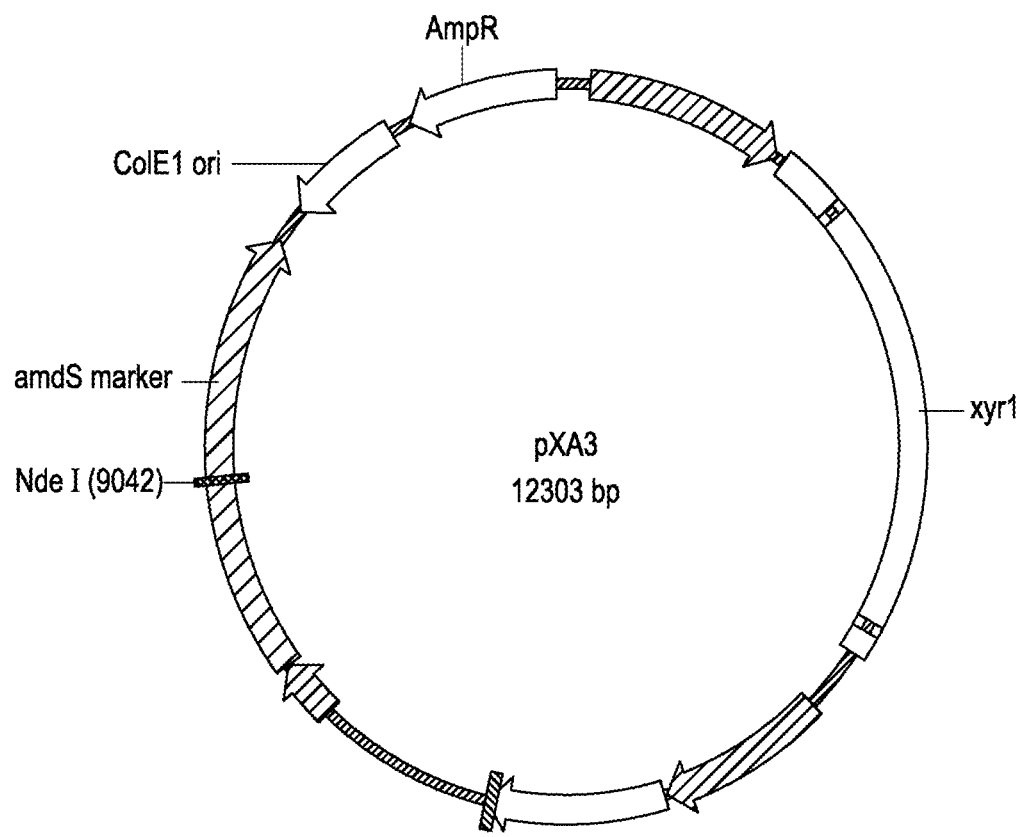
FIG. 9A shows a map of the pXA3 plasmid which was used for creating linearized DNA substrate. This plasmid contains the coding sequence for the xyr1 gene (SEQ ID NO:89) and was linearized by digestion with the restriction enzyme NdeI to produce the DNA substrate.

Purified Cas9 protein (200 ng) was incubated with: (1) 300 ng substrate DNA alone (substrate DNA is plasmid pXA3 [shown in FIG. 9A] linearized with NdeI; pXA3 contains the xyr1 gene [SEQ ID NO:89] that has the 20 bp target sequence and appropriately spaced PAM site for both of the xyr1 guide RNAs)(2) 300 ng substrate DNA in the presence of 100 ng in vitro synthesized xyr1 Ta guide RNA; and (3) 300 ng substrate DNA in the presence of 100 ng in vitro synthesized xyr1 Tc guide RNA. The reactions were carried out in NEB buffer 3 in a reaction volume of 20 ul for 1 h at 37° C. (1×NEB3 Buffer Components consists of 100 mM NaCl, 50 mM Tris-HCl, 10 mM MgCl2 10 mM MgCl2, 1 mM DTT, pH 7.9 at 25° C.)

Figure 9B:
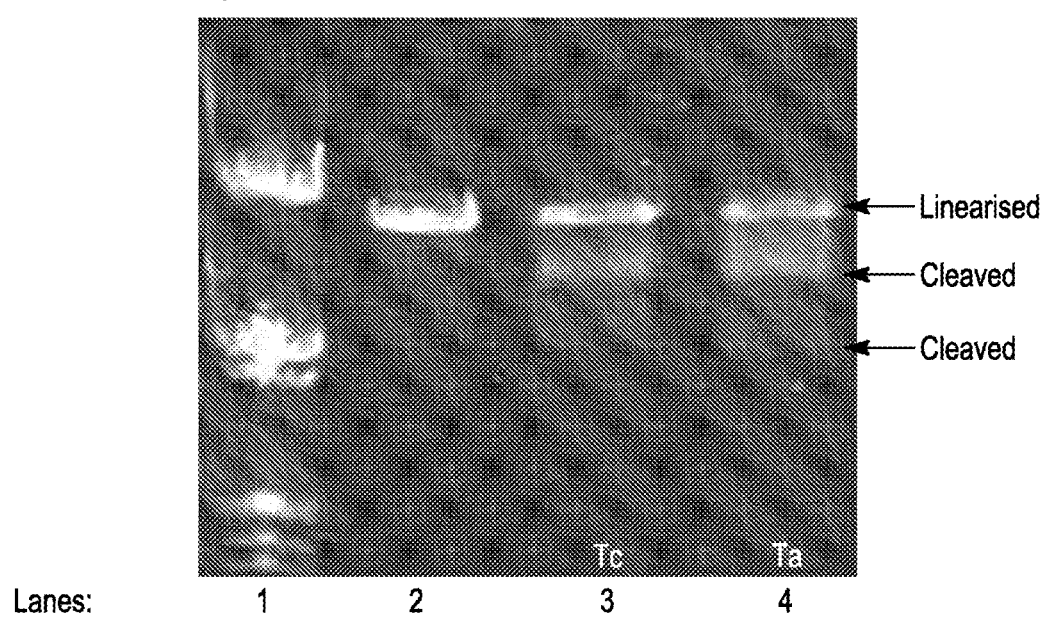
FIG. 9B shows the results of guide RNA/Cas9 cleavage assay (visualized by ethidium bromide staining). Agarose gel analysis of xyr1-specific in vitro cleavage assay is shown in this figure. Lane 1 shows molecular weight markers; Lane 2 shows linearized plasmid substrate (containing the xyr1 gene) in the absence of Cas9 and guide RNA; Lane 3 shows cleavage of the plasmid substrate in the presence of Cas9 and a guide RNA with the xyr1Ta VT domain; Lane 4 shows cleavage of the plasmid substrate in the presence of Cas9 and a guide RNA with the xyr1Tc VT. Positions of the linearized plasmid substrate and the cleaved products are indicated at the right.

As shown in FIG. 9B, each of the xyr1 specific guide RNA with purified SpyCas9 can successfully cut substrate DNA into the expected fragments (Lanes 3 and 4), confirming the function of the synthesized guide RNA/Cas9 complex. Lane 1 shows molecular weight markers; Lane 2 shows NdeI-linearized plasmid pXA3 substrate in the absence of Cas9 and guide RNA; Lane 3 shows cleavage of linearized plasmid pXA3 substrate in the presence of Cas9 and a guide RNA with the xyr1 Ta VT domain; Lane 4 shows cleavage of the linearized plasmid pXA3 substrate in the presence of Cas9 and a guide RNA with the xyr1 Tc VT domain. Positions of the linearized plasmid pXA3 substrate and products are indicated at the right.

Example 12: Guide RNA Introduction into Cas9-Expressing Fungal Cells

Methods
(i) Protoplast Preparation

For protoplast preparation, 5×108 spores of the desired *T. reesei* strain are inoculated into 50 ml germination medium (recipe described in U.S. Pat. No. 8,679,815) in a 250 ml shake flask with 4 baffles and incubated at 27° C. for 17 hours at 170 rpm. The mycelia are recovered by transferring the liquid volume into 50 ml conical tubes and spinning at 3000 rpm for 10 minutes. The supernatant is decanted and the mycelial pellets are washed twice using 1.2 M MgSO4—

10 mM Na-phosphate buffer and resuspended in 15 ml lysing enzyme buffer (lysing Enzyme from *Trichoderma harzianum* (Sigma catalog #L1412)) dissolved in 1.2 M MgSO4—10 mM Na-phosphate buffer (pH 5.8), 50 mg/ml). The cell suspension is transferred into a 250 ml shake flask with 4 baffles and shaken at room temperature for at least 2 hours at 200 rpm. The protoplasts are harvested by filtration through Miracloth (Calbiochem Art. No. 475855) folded in a glass funnel into a Greiner tube. 0.6 M Sorbitol—0.1 M Tris-HCl buffer is added carefully on top of the filtered protoplasts. The protoplasts are collected by centrifugation for 15 minutes at 4000 rpm. The middle phase containing the protoplasts is transferred into a new tube and added at least an equal volume of 1.2 M Sorbitol—10 mM Tris-HCl buffer. The protoplasts are collected by centrifugation for 5 minutes at 4000 rpm, and washed two times with 1.2M sorbitol-10 mM Tris-HCl buffer. The pellet is resuspended into at least 1 ml 1.2 M Sorbitol—10 mM Tris-HCl pH 7.5-10 mM CaCl2) buffer and the number of protoplasts counted under a microscope. The protoplast suspension is diluted using 4 parts of 1.2 M Sorbitol—10 mM Tris-HCl—10 mM CaCl2) and 1 part of 25% PEG6000—50 mM CaCl2—10 mM Tris-HCl until 5×108 per ml for use in subsequent transformation.

(ii) Transformation

The desired cargo (e.g., a DNA construct, guide RNA, Cas9/guide RNA complex, etc.) is added to 200 μL protoplast (~1×108) and kept on ice for 30 min. After incubation, protoplasts are added to cooled molten sorbitol/Vogel agar (1.1 M sorbitol of minimal Vogel agar) to be as the top layer of the minimal Vogel plate (Davis et al., (1970) Methods in Enzymology 17A, pp. 79-143 and Davis, Rowland, NEUROSPORA, CONTRIBUTIONS OF A MODEL ORGANISM, Oxford University Press, (2000)). The plates are incubated at 30° C. for a week. The detailed steps are described in U.S. Pat. No. 8,679,815 (incorporated herein by reference).

Experimental

Protoplasts of a *Trichoderma reesei* strain having an inactivated pyr2 gene (encoding orotate phosphoribosyl transferase, Protein ID 21435) (strain T4 mpg1 Δpyr2) was transformed as described above with a DNA construct containing an expression cassette for Cas9 under the control of the pyruvate kinase (pki) promoter and an expression cassette for the pyr2 gene from *T. reesei* under the control of the its native promoter. A transformant with the Cas9-pyr2 cassette integrated into the genome and constitutively expressing the Cas9 gene was identified by selecting for cells having a functional pyr2 gene (growth without uridine supplementation on Vogels media).

Figure 10:
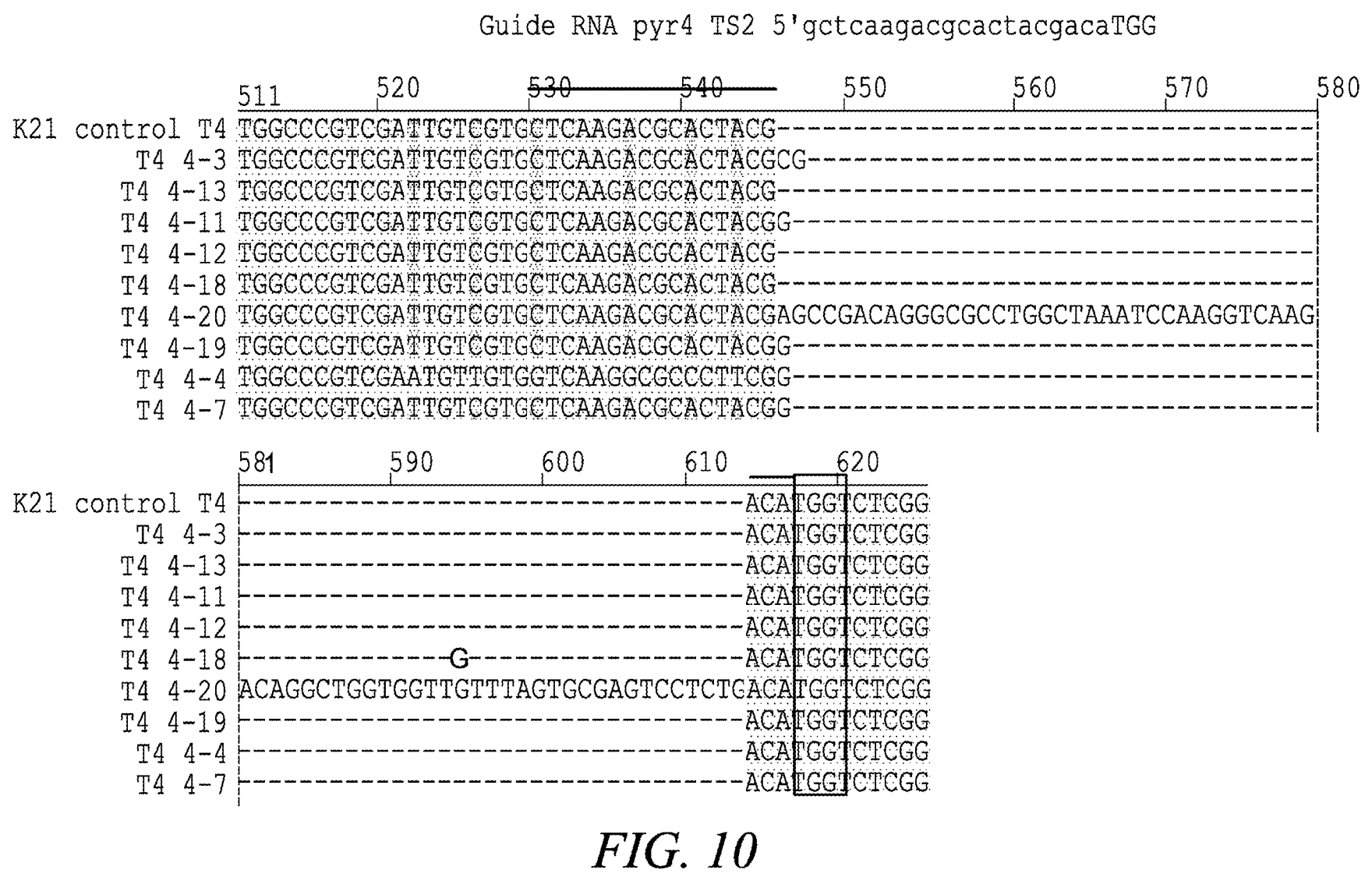

Twenty (20) ug of in vitro synthesized Pyr4 TS2 guide RNA as described above (with target site 5'GCTCAAGACGCACTACGACA3', SEQ ID NO:92) was introduced into the Cas9 expressing *T. reesei* cells by the protoplast transformation method described above. Analysis of the pyr4 gene from isolated strains that are resistant to FOA and require uridine for growth by sequencing and alignment showed the presence of changes to the DNA sequence at the pyr4 gene target site. Sequence changes included insertions of a few nucleotides (1-2 nucleotides; clones T4 4-3, T4 4-11, T4 4-18, T4 4-19, T4 4-4, and T4 4-7) as well as larger insertions (68 nucleotides, clone T4 4-20) (FIG. 10). This demonstrates that direct, transient introduction of guide RNA into a Cas-expressing fungal host cell can be used to modify the DNA sequence at a desired target site in the genome of the cell.

Example 13: In Vivo SpyCas9/Guide RNA Uptake Experiment

To form the Cas9/guide RNA complex in vitro, purified Cas9 protein 20 μg was mixed with Pyr4 TS2 guide RNA 20 μg in 20 mM Hepes, 100 mM NaCl, 5 mM MgCl2, 0.1 mM EDTA pH6.5 (final volume is 40 pt), and incubated at room temperature from 1 5-30 minutes to allow for complex formation. The Cas9/guide RNA complex was transformed into *T. reesei* protoplasts as described above and grown on Vogel's Uridine FOA plates.

Figure 11A:
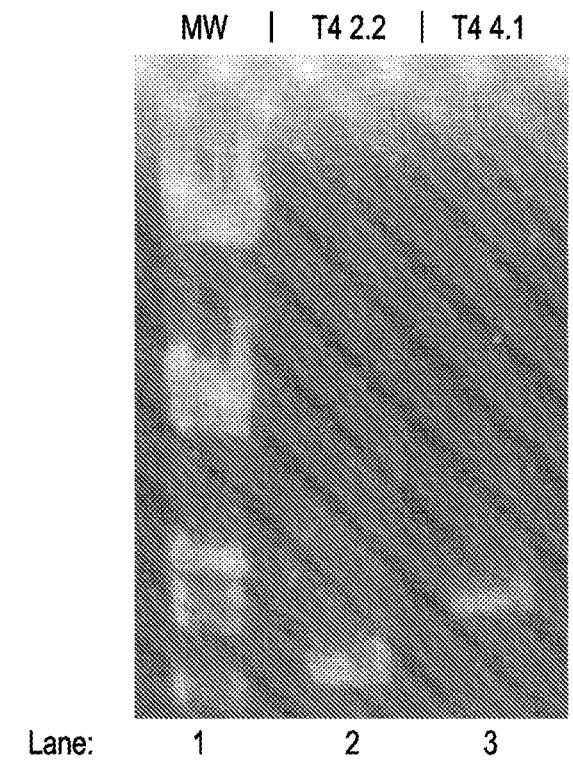
FIGS. 11A and 11B. DNA sequence modification at a target site by uptake of in vitro formed Cas9/guide RNA complex.
Figure 11B:
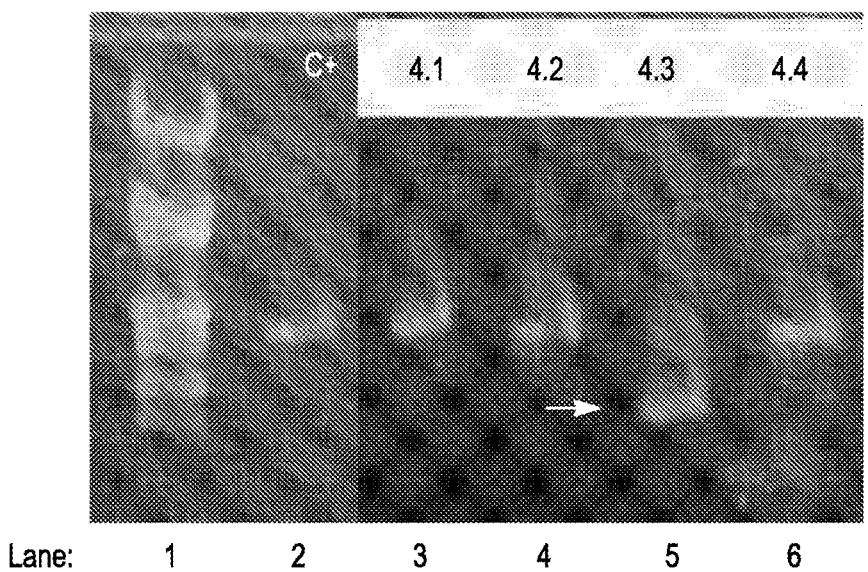

PCR analysis of the isolated strains from this transformation is shown in FIGS. 11A and B. FIG. 11A shows agarose gel analysis of pyr4 specific PCR products (encompassing the target site) of two isolated strains (P37 2.2. and P37 4.1; both resistant to FOA and that require uridine for growth). Strain P37 2.2 (Lane 2) showed a PCR product that is of lower molecular weight than the T4 4.1 clone (Lane 3; which is equivalent to the control, shown in FIG. 11B, Lane 2), indicating a large deletion in the pyr4 gene. FIG. 11B shows similar PCR/agarose gel analysis as in FIG. 11A, and includes analysis of P37 strains 4.1, 4.2, 4.3, and 4.4 (all of which are resistant to FOA and require uridine for growth). Strain 4.3 (Lane 5) showed PCR product of the pyr4 gene that is of lower molecular weight than the control (C+; Lane 2), indicating a large deletion in the pyr4 gene.

Sequence analysis of the pyr4 genes derived from clones T4 2.2 (shown in FIG. 11A) and T4 2.4 (not shown in FIG. 11A or 11B) is shown in FIG. 12. Note that the wild type pyr4 sequence is the first sequence (top) in the alignments. This analysis shows that the T4 2.2 clone (top alignment) has a deletion of 611 base pairs at the target site of the introduced Cas9/guide RNA complex. The sequence corresponding to the VT domain sequence of the guide RNA is boxed and the PAM site is circled. The bottom alignment shows a 1 base pair insertion in the pyr4 gene at the target site of the isolated T4 2.4 strain (a "G" residue). The sequence corresponding to the VT domain sequence of the guide RNA is indicated with a line over the alignment and the PAM site is circled.

FIG. 13 shows sequence analysis of the pyr4 genes derived from clones P37 4.1 and 4.2 (top alignment), 4.3 (bottom alignment) and 4.4 (middle alignment) (which were shown in FIG. 11B). The wild type pyr4 sequence is the first sequence (top) in all alignments and a consensus is shown on the bottom of all alignments. The top alignment shows that the P37 4.1 clone (third sequence in the alignment) has an insertion of a T nucleotide while the P37 4.2 clone (second sequence in the alignment) has an insertion of a G nucleotide at the target site in the pyr4 gene. The middle alignment shows that the P37 4.4 clone (second sequence in the alignment) has a deletion of an A nucleotide at the target site in the pyr4 gene. The bottom alignment shows that the pyr4 gene sequence in the P37 4.3 clone (second sequence in the alignment) diverges abruptly at the target site. Further alignment analysis (not shown) confirmed that the P37 4.3 clone has a deletion of 988 base pairs at the target site of the introduced Cas9/guide RNA complex.

This demonstrates that direct, transient introduction of a Cas9/guide RNA complex into a fungal host cell can be used to modify the DNA sequence at a desired target site in the genome of the cell.

Although the foregoing compositions and methods have been described in some detail by way of illustration and example for purposes of clarity of understanding, it is readily apparent to those of ordinary skill in the art in light of the teachings herein that certain changes and modifications may be made thereto without departing from the spirit or scope of the appended claims.

Accordingly, the preceding merely illustrates the principles of the present compositions and methods. It will be appreciated that those skilled in the art will be able to devise various arrangements which, although not explicitly described or shown herein, embody the principles of the present compositions and methods and are included within its spirit and scope. Furthermore, all examples and conditional language recited herein are principally intended to aid the reader in understanding the principles of the present compositions and methods and the concepts contributed by the inventors to furthering the art, and are to be construed as being without limitation to such specifically recited examples and conditions. Moreover, all statements herein reciting principles, aspects, and embodiments of the present compositions and methods as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present compositions and methods, therefore, is not intended to be limited to the exemplary embodiments shown and described herein.

```
Sequences:

SEQ ID NO: 1
Streptococcus pyogenes Cas9, no NLS (encoded by SEQ ID NO: 8 and SEQ ID NO: 15)
MDKKYSIGLDIGTNSVGWAVITDEYKVPSKKFKVLGNTDRHSIKKNLIGALLFDSGETAEATRLKRTARRRYTRRKNRICY
LQEIFSNEMAKVDDSFFHRLEESFLVEEDKKHERHPIFGNIVDEVAYHEKYPTIYHLRKKLVDSTDKADLRLIYLALAHMI
KFRGHFLIEGDLNPDNSDVDKLFIQLVQTYNQLFEENPINASGVDAKAILSARLSKSRRLENLIAQLPGEKKNGLFGNLIA
LSLGLTPNFKSNFDLAEDAKLQLSKDTYDDDLDNLLAQIGDQYADLFLAAKNLSDAILLSDILRVNTEITKAPLSASMIKR
YDEHHQDLTLLKALVRQQLPEKYKEIFFDQSKNGYAGYIDGGASQEEFYKFIKPILEKMDGTEELLVKLNREDLLRKQRTF
DNGSIPHQIHLGELHAILRRQEDFYPFLKDNREKIEKILTFRIPYYVGPLARGNSRFAWMTRKSEETITPWNFEEVVDKGA
SAQSFIERMTNFDKNLPNEKVLPKHSLLYEYFTVYNELTKVKYVTEGMRKPAFLSGEQKKAIVDLLFKTNRKVTVKQLKED
YFKKIECFDSVEISGVEDRFNASLGTYHDLLKIIKDKDFLDNEENEDILEDIVLTLTLFEDREMIEERLKTYAHLEDDKVM
KQLKRRRYTGWGRLSRKLINGIRDKQSGKTILDFLKSDGFANRNFMQLIHDDSLTFKEDIQKAQVSGQGDSLHEHIANLAG
SPAIKKGILQTVKVVDELVKVMGRHKPENIVIEMARENQTTQKGQKNSRERMKRIEEGIKELGSQILKEHPVENTQLQNEK
LYLYYLQNGRDMYVDQELDINRLSDYDVDHIVPQSFLKDDSIDNKVLTRSDKNRGKSDNVPSEEVVKKMKNYWRQLLNAKL
ITQRKFDNLTKAERGGLSELDKAGFIKRQLVETRQITKHVAQILDSRMNTKYDENDKLIREVKVITLKSKLVSDFRKDFQF
YKVREINNYHHAHDAYLNAVVGTALIKKYPKLESEFVYGDYKVYDVRKMIAKSEQEIGKATAKYFFYSNIMNFFKTEITLA
NGEIRKRPLIETNGETGEIVWDKGRDFATVRKVLSMPQVNIVKKTEVQTGGFSKESILPKRNSDKLIARKKDWDPKKYGGF
DSPTVAYSVLVVAKVEKGKSKKLKSVKELLGITIMERSSFEKNPIDFLEAKGYKEVKKDLIIKLPKYSLFELENGRKRMLA
SAGELQKGNELALPSKYVNFLYLASHYEKLKGSPEDNEQKQLFVEQHKHYLDEIIEQISEFSKRVILADANLDKVLSAYNK
HRDKPIREQAENIIHLFTLTNLGAPAAFKYFDTTIDRKRYTSTKEVLDATLIHQSITGLYETRIDLSQLGGD SEQ ID NO: 2
Streptococcus thermophilus LMD-9 Cas9
MTKPYSIGLDIGTNSVGWAVTIDNYKVPSKKMKVLGNTSKKYIKKNLLGVLLFDSGITAEGRRLKRTARRRYTRRRNRILY
LQEIFSTEMATLDDAFFQRLDDSFLVPDDKRDSKYPIFGNLVEEKAYHDEFPTIYHLRKYLADSTKKADLRLVYLALAHMI
KYRGHFLIEGEFNSKNNDIQKNFQDFLDTYNAIFESDLSLENSKQLEEIVKDKISKLEKKDRILKLFPGEKNSGIFSEFLK
LIVGNQADFRKCFNLDEKASLHFSKESYDEDLETLLGYIGDDYSDVFLKAKKLYDAILLSGFLTVTDNETEAPLSSAMIKR
YNEHKEDLALLKEYIRNISLKTYNEVFKDDTKNGYAGYIDGKTNQEDFYVYLKKLLAEFEGADYFLEKIDREDFLRKQRTF
DNGSIPYQIHLQEMRAILDKQAKFYPFLAKNKERIEKILTFRIPYYVGPLARGNSDFAWSIRKRNEKITPWNFEDVIDKES
SAEAFINRMTSFDLYLPEEKVLPKHSLLYETFNVYNELTKVRFIAESMRDYQFLDSKQKKDIVRLYFKDKRKVTDKDIIEY
LHAIYGYDGIELKGIEKQFNSSLSTYHDLLNIINDKEFLDDSSNEAIIEEIIHTLTIFEDREMIKQRLSKFENIFDKSVLK
KLSRRHYTGWGKLSAKLINGIRDEKSGNTILDYLIDDGISNRNFMQLIHDDALSFKKKIQKAQIIGDEDKGNIKEVVKSLP
GSPAIKKGILQSIKIVDELVKVMGGRKPESIVVEMARENQYTNQGKSNSQQRLKRLEKSLKELGSKILKENIPAKLSKIDN
NALQNDRLYLYYLQNGKDMYTGDDLDIDRLSNYDIDHIIPQAFLKDNSIDNKVLVSSASNRGKSDDVPSLEVVKKRKTFWY
QLLKSKLISQRKFDNLTKAERGGLSPEDKAGFIQRQLVETRQITKHVARLLDEKFNNKKDENNRAVRTVKIITLKSTLVSQ
FRKDFELYKVREINDFHHAHDAYLNAVVASALLKKYPKLEPEFVYGDYPKYNSFRERKSATEKVYFYSNIMNIFKKSISLA
DGRVIERPLIEVNEETGESVWNKESDLATVRRVLSYPQVNVVKKVEEQNHGLDRGKPKGLFNANLSSKPKPNSNENLVGAK
EYLDPKKYGGYAGISNSFTVLVKGTIEKGAKKKITNVLEFQGISILDRINYRKDKLNFLLEKGYKDIELIIELPKYSLFEL
SDGSRRMLASILSTNNKRGEIHKGNQIFLSQKFVKLLYHAKRISNTINENHRKYVENHKKEFEELFYYILEFNENYVGAKK
NGKLLNSAFQSWQNHSIDELCSSFIGPTGSERKGLFELTSRGSAADFEFLGVKIPRYRDYTPSSLLKDATLIHQSVTGLYE
TRIDLAKLGEG SEQ ID NO: 3
Streptococcus mutans UA159 Cas9
MKKPYSIGLDIGTNSVGWAVVTDDYKVPAKKMKVLGNTDKSHIEKNLLGALLFDSGNTAEDRRLKRTARRRYTRRRNRILY
LQEIFSEEMGKVDDSFFHRLEDSFLVTEDKRGERHPIFGNLEEEVKYHENFPTIYHLRQYLADNPEKVDLRLVYLALAHII
KFRGHFLIEGKFDTRNNDVQRLFQEFLAVYDNTFENSSLQEQNVQVEEILTDKISKSAKKDRVLKLFPNEKSNGRFAEFLK
LIVGNQADFKKHFELEEKAPLQFSKDTYEEELEVLLAQIGDNYAELFLSAKKLYDSILLSGILTVTDVGTKAPLSASMIQR
YNEHQMDLAQLKQFIRQKLSDKYNEVFSDVSKDGYAGYIDGKTNQEAFYKYLKGLLNKIEGSGYFLDKIEREDFLRKQRTF
DNGSIPHQIHLQEMRAIIRRQAEFYPFLADNQDRIEKLLTFRIPYYVGPLARGKSDFAWLSRKSADKITPWNFDEIVDKES
SAEAFINRMTNYDLYLPNQKVLPKHSLLYEKFTVYNELTKVKYKTEQGKTAFFDANMKQEIPDGVFKVYRKVTKDKLMDFL
EKEFDEFRIVDLTGLDKENKVFNASYGTYHDLCKILDKDFLDNSKNEKILEDIVLTLTLFEDREMIRKRLENYSDLLTKEQ
VKKLERRHYTGWGRLSAELIHGIRNKESRKTILDYLIDDGNSNRNFMQLINDDALSFKEEIAKAQVIGETDNLNQVVSDIA
GSPAIKKGILQSLKIVDELVKIMGHQPENIVVEMARENQFTNQGRRNSQQRLKGLTDSIKEFGSQILKEHPVENSQLQNDR
LFLYYLQNGRDMYTGEELDIDYLSQYDIDHIIPQAFIKDNSIDNRVLTSSKENRGKSDDVPSKDVVRKMKSYWSKLLSAKL
ITQRKFDNLTKAERGGLTDDDKAGFIKRQLVETRUTKHVARILDERFNTETDENNKKIRQVKIVTLKSNLVSNFRKEFELY
KVREINDYHHAHDAYLNAVIGKALLGVYPQLEPEFVYGDYPHFHGHKENKATAKKFFYSNIMNFFKKDDVRTDKNGEIIWK
KDEHISNIKKVLSYPQVNIVKKVEEQTGGFSKESILPKGNSDKLIPRKTKKFYWDTKKYGGFDSPIVAYSILVIADIEKGK
SKKLKTVKALVGVTIMEKMTFERDPVAFLERKGYRNVQEENIIKLPKYSLFKLENGRKRLLASARELQKGNEIVLPNHLGT
LLYHAKNIHKVDEPKHLDYVDKHKDEFKELLDVVSNFSKKYTLAEGNLEKIKELYAMINGEDLKELASSFINLLTFTAIGA
PATFKFFDKNIDRKRYTSTTEILNATLIHQSITGLYETRIDLNKLGGD
```

-continued

Sequences:

SEQ ID NO: 4
*Campylobacter jejuni* Cas9
MARILAFDIGISSIGWAFSENDELKDCGVRIFTKVENPKTGESLALPRRLARSARKRLARRKARLNHLKHLIANEFKLNYE
DYQSFDESLAKAYKGSLISPYELRFRALNELLSKQDFARVILHIAKRRGYDDIKNSDDKEKGAILKAIKQNEEKLANYQSV
GEYLYKEYFQKFKENSKEFTNVRNKKESYERCIAQSFLKDELKLIFKKQREFGFSFSKKFEEEVLSVAFYKRALKDFSHLV
GNCSFFTDEKRAPKNSPLAFMFVALTRIINLLNNLKNTEGILYTKDDLNALLNEVLKNGTLTYKQTKKLLGLSDDYEFKGE
KGTYFIEFKKYKEFIKALGEHNLSQDDLNEIAKDITLIKDEIKLKKALAKYDLNQNQIDSLSKLEFKDHLNISFKALKLVT
PLMLEGKKYDEACNELNLKVAINEDKKDFLPAFNETYYKDEVTNPVVLRAIKEYRKVLNALLKKYGKVHKINIELAREVGK
NHSQRAKIEKEQNENYKAKKDAELECEKLGLKINSKNILKLRLFKEQKEFCAYSGEKIKISDLQDEKMLEIDHIYPYSRSF
DDSYMNKVLVFTKQNQEKLNQTPFEAFGNDSAKWQKIEVLAKNLPTKKQKRILDKNYKDKEQKNFKDRNLNDTRYIARLVL
NYTKDYLDFLPLSDDENTKLNDTQKGSKVHVEAKSGMLTSALRHTWGFSAKDRNNHLHHAIDAVIIAYANNSIVKAFSDFK
KEQESNSAELYAKKISELDYKNKRKFFEPFSGFRQKVLDKIDEIFVSKPERKKPSGALHEETFRKEEEFYQSYGGKEGVLK
ALELGKIRKVNGKIVKNGDMFRVDIFKHKKTNKFYAVPIYTMDFALKVLPNKAVARSKKGEIKDWILMDENYEFCFSLYKD
SLILIQTKDMQEPEFVYYNAFTSSTVSLIVSKHDNKFETLSKNQKILFKNANEKEVIAKSIGIQNLKVFEKYIVSALGEVT
KAEFRQREDFKK SEQ ID NO: 5
*Neisseria meningitides* Cas9
MAAFKPNSINYILGLDIGIASVGWAMVEIDEEENPIRLIDLGVRVFERAEVPKTGDSLAMARRLARSVRRLTRRRAHRLLR
TRRLLKREGVLQAANFDENGLIKSLPNTPWQLRAAALDRKLTPLEWSAVLLHLIKHRGYLSQRKNEGETADKELGALLKGV
AGNAHALQTGDFRTPAELALNKFEKESGHIRNQRSDYSHTFSRKDLQAELILLLFEKQKEFGNPHVSGGLKEGIETLLMTQR
PALSGDAVQKMLGHCTFEPAEPKAAKNTYTAERFIWLTKLNNLRILEQGSERPLTDTERATLMDEPYRKSKLTYAQARKLL
GLEDTAFFKGLRYGKDNAEASTLMEMKAYHAISRALEKEGLKDKKSPLNLSPELQDEIGTAFSLFKTDEDITGRLKDRIQP
EILEALLKHISFDKFVQISLKALRRIVPLMEQGKRYDEACAEIYGDHYGKKNTEEKIYLPPIPADEIRNPVVLRALSQARK
VINGVVRRYGSPARIHIETAREVGKSFKDRKEIEKRQEENRKDREKAAAKFREYFPNFVGEPKSKDILKLRLYEQQHGKCL
YSGKEINLGRLNEKGYVEIDHALPFSRTWDDSFNNKVLVLGSENQNKGNQTPYEYFNGKDNSREWQEFKARVETSRFPRSK
KQRILLQKFDEDGFKERNLNDTRYVNRFLCQFVADRMRLTGKGKKRVFASNGQITNLLRGFWGLRKVRAENDRHHALDAVV
VACSTVAMQQKITRFVRYKEMNAFDGKTIDKETGEVLHQKTHFPQPWEFFAQEVMIRVFGKPDGKPEFEEADTLEKLRTLL
AEKLSSRPEAVHEYVTPLFVSRAPNRKMSGQGHMETVKSAKRLDEGVSVLRVPLTQLKLKDLEKMVNREREPKLYEALKAR
LEAHKDDPAKAFAEPFYKYDKAGNRTQQVKAVRVEQVQKTGVWVRNHNGIADNATMVRVDVFEKGDKYYLVPIYSWQVAKG
ILPDRAVVQGKDEEDWQLIDDSFNFKFSLHPNDLVEVITKKARMFGYFASCHRGTGNINIRIHDLDHKIGKNGILEGIGVK
TALSFQKYQIDELGKEIRPCRLKKRPPVR SEQ ID NO: 6
*Francisella tularensis* subsp. *novicida* Cas9
MNFKILPIAIDLGVKNTGVFSAFYQKGTSLERLDNKNGKVYELSKDSYTLLMNNRTARRHQRRGIDRKQLVKRLFKLIWTE
QLNLEWDKDTQQAISFLFNRRGFSFITDGYSPEYLNIVPEQVKAILMDIFDDYNGEDDLDSYLKLATEQESKISEIYNKLM
QKILEFKLMKLCTDIKDDKVSTKTLKEITSYEFELLADYLANYSESLKTQKFSYTDKQGNLKELSYYHHDKYNIQEFLKRH
ATINDRILDTLLTDDLDIWNFNFEKFDFDKNEEKLQNQEDKDHIQAHLHHFVFAVNKIKSEMASGGRHRSQYFQEITNVLD
ENNHQEGYLKNFCENLHNKKYSNLSVKNLVNLIGNLSNLELKPLRKYFNDKIHAKADHWDEQKFTETYCHWILGEWRVGVK
DQDKKDGAKYSYKDLCNELKQKVTKAGLVDFLLELDPCRTIPPYLDNNNRKPPKCQSLILNPKFLDNQYPNWQQYWELKKL
QSIQNYLDSFETDLKVLKSSKDQPYFVEYKSSNQQIASGQRDYKLDDLDARILQFIFDRVKASDELLLNEIYMAKKLKQASS
ELEKLESSKKLDEVIANSQLSQILKSQHTNGIFEQGTFLHLVCKYYKQRQRARDSRLYIMPEYRYDKKLKHKYNNTGRPDD
NQLLTYCNHKPRQKRYQLLNDLAGVLQVSPNFLKDKIGSDDDLFISKWLVEHIRGFKKACEDSLKIQKDNRGLLNHKINIA
RNTKGKCEKEIFNLICKIEGSEDKKGNYKHGLAYELGVLLFGEPNEASKPEFDRKIKKFNSIYSFAQIQQIAFAERKGNAN
TCAVCSADNAHRMQQIKITEPVEDNKDKIILSAKAQRLPAIPTRIVDGAVKKMATILAKNIVDDNWQNIKQVLSAKHQLHI
PIITESNAFEFEPALADVKGKSLKDRRKKALERISPENIFKDKNNRIKEFAKGISAYSGANLTDGDFDGAKEELDHIIPRS
HKKYGTLNDEANLICVTRGDNKNKGNRIFCLRDLADNYKLKQFETTDDLEIEKKIADTIWDANKKDFKFGNYRSFINLTPQ
EQKAFRHALFLADENPIKQAVIRAINNRNRTFVNGTQRYFAEVLANNIYLRAKKENLNTDKISFDYFGIPTIGNGRGIAEI
RQLYEKVDSDIQAYAKGDKPQASYSHLIDAMLAFCIAADEHRNDGSIGLEIDKNYSLYPLDKNTGEVFTKDIFSQIKITDN
EFSDKKLVRKKAIEGFNTHRQMTRDGIYAENYLPILIHKELNEVRKGYTWKNSEEIKIFKGKKYDIQQLNNLVYCLKFVDK
PISIDIQISTLEELRNILTTNNIAATAEYYYINLKTQKLHEYYIENYNTALGYKKYSKEMEFLRSLAYRSERVKIKSIDDV
KQVLDKDSNFIIGKITLPFKKEWQRLYREWQNTTIKDDYEFLKSFFNVKSITKLHKKVRKDFSLPISTNEGKFLVKRKTWD
NNFIYQILNDSDSRADGTKPFIPAFDISKNEIVEAIIDSFTSKNIFWLPKNIELQKVDNKNIFAIDTSKWFEVETPSDLRD
IGIATIQYKIDNNSRPKVRVKLDYVIDDDSKINYFMNHSLLKSRYPDKVLEILKQSTIIEFESSGFNKTIKEMLGMKLAGI
YNETSNN SEQ ID NO: 7
*Pasteurella multocida* Cas9
MQTTNLSYILGLDLGIASVGWAVVEINENEDPIGLIDVGVRIFERAEVPKTGESLALSRRLARSTRRLIRRRAHRLLLAKR
FLKREGILSTIDLEKGLPNQAWELRVAGLERRLSAIEWGAVLLHLIKHRGYLSKRKNESQTNNKELGALLSGVAQNHQLLQ
SDDYRTPAELALKKFAKEEGHIRNQRGAYTHTFNRLDLLAELNLLFAQQHQFGNPHCKEHIQQYMTELLMWQKPALSGEAI
LKMLGKCTHEKNEFKAAKHTYSAERFVWLTKLNNLRILEDGAERALNEEERQLLINHPYEKSKLTYAQVRKLLGLSEQAIF
KHLRYSKENAESATFMELKAWHAIRKALENQGLKDTWQDLAKKPDLLDEIGTAFSLYKTDEDIQQYLTNKVPNSVINALLV
SLNFDKFIELSLKSLRKILPLMEQGKRYDQACREIYGHHYGEANQKTSQLLPAIPAQEIRNPVVLRTLSQARKVINAIIRQ
YGSPARVHIETGRELGKSFKERREIQKQQEDNRTKRESAVQKFKELFSDFSSEPKSKDILKFRLYEQQHGKCLYSGKEINI
HRLNEKGYVEIDHALPFSRTWDDSFNNKVLVLASENQNKGNQTRYEWLQGKINSERWKNFVALVLGSQCSAAKKQRLLTQV
IDDNKFIDRNLNDTRYIARFLSNYIQENLLLVGKNKKNVFTPNGQITALLRSRWGLIKARENNNRHHALDAIVVACATPSM
QQKITRFIRFKEVHPYKIENRYEMVDQESGEIISPHFPEPWAYFRQEVNIRVFDNHPDTVLKEMLPDRPQANHQFVQPLFV
SRAPTRKMSGQGHMETIKSAKRLAEGISVLRIPLTQLKPNLLENMVNKEREPALYAGLKARLAEFNQDPAKAFATPFYKQG
GQQVKAIRVEQVQKSGVLRENNGVADNASIVRTDVFIKNNKFFLVPIYTWQVAKGILPNKAIVAHKNEDEWEEMDEGAKF
KFSLFPNDLVELKTKKEYFFGYYIGLDRATGNISLKEHDGEISKGKDGVYRVGVKLALSFEKYQVDELGKNRQICRPQQRQ
PVR -continued Sequences:

SEQ ID NO: 8
Filamentous fungal cell codon optimized *Streptococcus pyogenes* Cas9-encoding
gene; no NLS
atggacaagaagtacagcatcggcctcgacatcggcaccaactcggtgggctggccgtcatcacggacgaatataaggtc
ccgtcgaagaagttcaaggtcctcggcaatacagaccgccacagcatcaagaaaaacttgatcggcgccctcctgttcgat
agcggcgagaccgcggaggcgaccaggctcaagaggaccgccaggagacggtacactaggcgcaagaacaggatctgctac
ctgcaggagatcttcagcaacgagatggcgaaggtggacgactccttcttccaccgcctggaggaatcattcctggtggag
gaggacaagaagcatgagcggcaccaatcttcggcaacatcgtcgacgaggtggcctaccacgagaagtacccgacaatc
taccacctccggaagaaactggtggacagcacagacaaggcggacctccggctcatctaccttgccctcgcgcatatgatc
aagttccgcggccacttcctcatcgagggcgacctgaacccggacaactccgacgtggacaagctgttcatccagctcgtg
cagacgtacaatcaactgttcgaggagaaccccataaacgctagcggcgtggacgccaaggccatcctctcggccaggctc
tcgaaatcaagaaggctggagaaccttatcgcgcagttgccaggcgaaagaagaacggcctcttcggcaaccttattgcg
ctcagcctcggcctgacgccgaacttcaaatcaaacttcgacctcgcggaggacgccaagtccagctctcaaaggacacc
tacgacgacgacctcgacaacctcctggcccagataggagaccagtacgcggacctcttcctcgccgccaagaacctctcc
gacgctatcctgctcagcgacatccttcgggtcaacaccgaaattaccaaggcaccgctgtccgccagcatgattaaacgc
tacgacgagcaccatcaggacctcacgctgctcaaggcactcgtccgccagcgctccccgagaagtacaaggagatcttc
ttcgaccaatcaaaaaacggctacgcgggatatatcgacggcggtgccagccaggaagagttctacaagttcatcaaacca
atcctggagaagatggacggcaccgaggagttgctggtcaagctcaacagggaggacctcctcaggaagcagaggacctc
gacaacggctccatcccgcatcagatccacctgggcgaactgcatgccatcctgcgggcgccaggaggacttctacccgttc
ctgaaggataaccgggagaagatcgagaagatcttgacgttccgcatcccatactacgtgggcccgctggctcgcggcaac
tcccggttcgcctggatgacccggaagtcggaggagaccatcacaccctggaactttgaggaggtggtcgataagggcgct
agcgctcagagcttcatcgagcgcatgaccaacttcgataaaaacctgcccaatgaaaagtcctcccaagcactcgctg
ctctacgagtacttcaccgtgtacaacgagctcaccaaggtcaaatacgtcaccgagggcatgcggaagccggcgttcctg
agcggcgagcaagaaggcgatagtgagcctcctcttcaagaccaacaggaaggtgaccgtgaagcaattaaaagaggac
tacttcaagaaaatagagtgcttcgactccgtggagatctcgggcgtggaggatcggttcaacgcctcactcggcacgtat
cacgacctcctcaagatcattaaagacaaggacttcctcgacaacgaggagaacgaggacatcctcgaggacatcgtcctc
accctgaccctgttcgaggaccgcgaaatgatcgaggagaggctgaagacctacgcgcacctgttcgacgacaaggtcatg
aaacagctcaagaggcgccgctacactggttggggaaggctgtcccgcaagctcattaatggcatcagggacaagcagagc
ggcaagaccatcctggacttcctcaagtccgacgggttcgccaaccgcaacttcatgcagctcattcacgacgactcgctc
acgttcaaggaagacatccagaaggcacaggtgagcgggcagggtgactccctccacgaacacatcgccaacctggccggc
tcgccggccattaaaaagggcatcctgcagacggtcaaggtcgtcgacgagctcgtgaaggtgatgggcggcacaagccc
gaaaatatcgtcatagagatggccagggagaaccagaccaccccaaaagggcagaagaactcgcgcgagcggatgaaacgg
atcgaggagggcattaaagagctcgggtcccagatcctgaaggagcaccccgtggaaaataccagctccagaatgaaaag
ctctacctctactacctgcagaacggccgcgacatgtacgtggaccaggagctggacattaatcggctatcggactacgac
gtcgaccacatcgtgccgcagtcgttcctcaaggacgatagcatcgacaacaaggtgctcacccggtcggataaaaatcgg
ggcaagagcgacaacgtgcccagcgaggaggtcgtgaagaagatgaaaaactactggcgccagctcctcaacgcgaaactg
atcacccagcgcaagttcgacaacctgacgaaggcggaacgggctggcttgagcgaactcgataaggcgggcttcataaaa
aggcagctggtcgagacgcgccagatcacgaagcatgtcgcccagatcctggacagccgcatgaatactaagtacgatgaa
aacgacaagctgatccgggaggtgaaggtgatcacgctgaagtccaagctcgtgtcggacttccgcaaggacttccagttc
tacaaggtccgcgagatcaacaactaccaccacgcccacgacgcctacctgaatgcggtggtcgggaccgccctgatcaag
aagtacccgaagctggagtcggagttcgtgtacggcgactacaaggtctacgacgtgcgcaaaatgatcgccaagtccgag
caggagatcggcaaggccacggcaaaatacttcttctactcgaacatcatgaacttcttcaagaccgagatcaccctcgcg
aacggcgagatccgcaagcgcccgctcatcgaaccaacggcgagacgggcgagatcgtctgggataagggccgggatttc
gcgacggtccgcaaggtgctctccatgccgcaagtcaatatcgtgaaaaagacggaggtccagacgggcgggttcagcaag
gagtccatcctcccgaagcgcaactccgacaagctcatcgcgaggaagaaggattgggaccgaaaaaatatggccgcttc
gacagcccgaccgtcgcatacagcgtcctcgtcgtggcgaaggtggagaagggcaagtcaaagaagctcaagtccgtgaag
gagctgctcgggatcacgattatggagcggtcctccttcgagaagaacccgatcgacttcctagaggccaagggatataag
gaggtcaagaaggacctgattattaaactgccgaagtactcgctcttcgagctggaaaacggccgcaagaggatgctcgcc
tccgcaggcgagttgcagaagggcaacgagctcgccctccccgagcaaatactgcaatttcctgtacctcgctagccactat
gaaaagctcaagggcagcccggaggacaacgagcagaagcagctcttcgtggagcagcacaagcattacctggacgagatc
atcgagcagatcagcgagttctcgaagcgggtgatcctcgccgacgcgaacctggacaaggtgctgtcggcatataacaag
caccgcgacaaaccaatacgcgagcaggccgaaaatatcatccacctcttcaccctcaccaacctcggcgctccggcagcc
ttcaagtacttcgacaccacgattgaccggaagcggtacacgagcacgaaggaggtgctcgatgcgacgctgatccaccag
agcatcacagggctctatgaaacacgcatcgacctgagccagctgggcggagac SEQ ID NO: 9
Filamentous fungal cell codon optimized *Streptococcus pyogenes* Cas9-encoding
gene; with N- and C-terminal NLS sequences
atggcaccgaagaagaagcgcaaggtgatggacaagaagtacagcatcggcctcgacatcggcaccaactcggtgggctgg
gccgtcatcacggacgaatataaggtcccgtcgaagaagttcaaggtcctcggcaatacagaccgccacagcatcaagaaa
aacttgatcggcgccctcctgttcgatagcggcgagaccgcggaggcgaccaggctcaagaggaccgccaggagacggtac
actaggcgcaagaacaggatctgctacctgcaggagatcttcagcaacgagatggcgaaggtggacgactccttcttccac
cgcctggaggaatcattcctggtggaggaggacaagaagcatgagcggcaccaatcttcggcaacatcgtcgacgaggtg
gcctaccacgagaagtacccgacaatctaccacctccggaagaaactggtggacagcacagacaaggcggacctccggctc
atctaccttgccctcgcgcatatgatcaagttccgcggccacttcctcatcgagggcgacctgaacccggacaactccgac
gtggacaagctgttcatccagctcgtgcagacgtacaatcaactgttcgaggagaaccccataaacgctagcggcgtggac
gccaaggccatcctctcggccaggctctcgaaatcaagaaggctggagaaccttatcgcgcagttgccaggcgaaagaag
aacggcctcttcggcaaccttattgcgctcagcctcggcctgacgccgaacttcaaatcaaacttcgacctcgcggaggac
gccaagctccagctctcaaaggacacctacgacgacgacctcgacaacctcctggcccagataggagaccagtacgcggac
ctcttcctcgccgccaagaacctctccgacgctatcctgctcagcgacatccttcgggtcaacaccgaaattaccaaggca
ccgctgtccgccagcatgattaaacgctacgacgagcaccatcaggacctcacgctgctcaaggcactcgtccgccagcag
ctccccgagaagtacaaggagatcttcttcgaccaatcaaaaaacggctacgcgggatatatcgacggcggtgccagccag
gaagagttctacaagttcatcaaaccaatcctggagaagatggacggcaccgaggagttgctggtcaagctcaacagggag
gacctcctcaggaagcagaggaccctcgacaacggctccatcccgcatcagatccacctgggcgaactgcatgccatcctg
cggcgccaggaggacttctacccgttcctgaaggataaccgggagaagatcgagaagatcttgacgttccgcatcccatac
tacgtgggcccgctggctcgcggcaactcccggttcgcctggatgacccggaagtcggaggagaccatcacaccctggaac
tttgaggaggtggtcgataagggcgctagcgctcagagcttcatcgagcgcatgaccaacttcgataaaaacctgcccaat Sequences:

```
gaaaaagtcctccccaagcactcgctgctctacgagtacttcaccgtgtacaacgagctcaccaaggtcaaatacgtcacc
gagggcatgcgcgaagccggcgttcctgagcggcgagcagaagaaggcgatagtggacctcctcttcaagaccaacaggaag
gtgaccgtgaagcaattaaaagaggactacttcaagaaaatagagtgcttcgactccgtggagatctcgggcgtggaggat
cggttcaacgcctcactcggcacgtatcacgacctcctcaagatcattaaagacaaggacttcctcgacaacgaggagaac
gaggacatcctcgaggacatcgtcctcaccctgaccctgttcgaggaccgcgaaatgatcgaggagaggctgaagacctac
gcgcacctgttcgacgacaaggtcatgaaacagctcaagaggcgccgctacactggttggggaaggctgtcccgcaagctc
attaatggcatcagggacaagcagagcggcaagaccatcctggacttcctcaagtccgacgggttcgccaaccgcaacttc
atgcagctcattcacgacgactcgctcacgttcaaggaagacatccagaaggcacaggtgagcgggcagggtgactccctc
cacgaacacatcgccaacctggccggctcgccggccattaaaaagggcatcctgcagacggtcaaggtcgtcgacgagctc
gtgaaggtgatgggccggcacaagcccgaaaatcgtcatagagatggccagggagaaccagaccacccaaaaagggcag
aagaactcgcgcgagcggatgaaacggatcgaggagggcattaaagagctcgggtcccgatcctgaaggagcacccgtg
gaaaatacccagctccagaatgaaaagctctacctctactacctgcagaacggccgcgacatgtacgtggaccaggagctg
gacattaatcggctatcggactacgacgtcgaccacatcgtgccgcagtcgttcctcaaggacgatagcatcgacaacaag
gtgctcaccgtcggataaaaatcggcaagagcgacaacgtgcccagcgaggaggtcgtgaagaagatgaaaaactac
tgggcgccagctcctcaacgcgaaactgatcacccagcgcaagttcgacaacctgacgaaggcggaacgcggtggcttgagc
gaactcgataaggcgggcttcataaaaaggcagctggtcgagcgcgcagatcacgaagcatgtcgcccagatcctggac
agccgcatgaatactaagtacgatgaaaacgacaagctgatccggagggtgaaggtgatcacgctgaagtccaagctcgtg
tcggacttccgcaaggacttccagttctacaaggtccgcgagatcaacaactaccaccacgccacgacgcctacctgaat
gcggtggtcgggaccgccctgatcaagaagtacccgaagctggagtcggagttcgtgtacggcgactacaaggtctacgac
gtgcgcaaaatgatcgccaagtccgagcaggagatcggcaaggccacggcaaaatacttcttctactcgaacatcatgaac
ttcttcaagaccgagatcaccctcgcgaacggcgagatccgcaagcgcccgctcatcgaaaccaacggcgagacgggcgag
atcgtctgggataagggccgggatttcgcgacggtccgcaaggtgctctccatgccgcaagtcaatatcgtgaaaaagacg
gaggtccagacgggcgggttcagcaaggagtccatcctcccgaagcgcaactccgacaagctcatcgcgaggaagaaggat
tgggacccgaaaaaatatggcggcttcgacagcccgaccgtcgcatacagcgtcctcgtcgtggcgaaggtggagaagggc
aagtcaaagaagctcaagtccgtgaaggagctgctcgggatcacgattatggagcggtcctccttcgagaagaacccgatc
gacttcctagaggccaaggatataaggaggtcaagaaggacctgattatttaaactgccgaagtactcgctcttcgagctg
gaaaacggccgcaagaggatgctcgcctccgcaggcgagttgcagaagggcaacgagctcgcctcccgagcaaatacgtc
aatttcctgtacctcgctagccactatgaaaagctcaaggcagccccggaggacaacgagcagaagcagctcttcgtggag
cagcacaagcattacctggacgagatcatcgagcagatcagcgagttctcgaagcgggtgatcctcgccgacgcgaacctg
gacaaggtgctgtcggcatataacaagcaccgcgacaaaccaatacgcgagcaggccgaaaatatcatccacctcttcacc
ctcaccaacctcggcgctccggcagccttcaagtacttcgacaccacgattgaccggaagcggtacacgagcacgaaggag
gtgctcgatgcgacgctgatccaccagagcatcacagggctctatgaaacacgcatcgacctgagccagctgggcggagac
aagaagaagaagctcaagctctag
```

SEQ ID NO: 10
Streptococcus pyogenes Cas9 with N- and C-terminal NLS sequences (encoded by SEQ ID NO: 9)

```
MAPKKKRKVMDKKYSIGLDIGTNSVGWAVITDEYKVPSKKFKVLGNTDRHSIKKNLIGALLFDSGETAEATRLKRTARRRY
TRRKNRICYLQEIFSNEMAKVDDSFFHRLEESFLVEEDKKHERHPIFGNIVDEVAYHEKYPTIYHLRKKLVDSTDKADLRL
IYLALAHMIKFRGHFLIEGDLNPDNSDVDKLFIQLVQTYNQLFEENPINASGVDAKAILSARLSKSRRLENLIAQLPGEKK
NGLFGNLIALSLGLTPNFKSNFDLAEDAKLQLSKDTYDDDLDNLLAQIGDQYADLFLAAKNLSDAILLSDILRVNTEITKA
PLSASMIKRYDEHHQDLTLLKALVRQQLPEKYKEIFFDQSKNGYAGYIDGGASQEEFYKFIKPILEKMDGTEELLVKLNRE
DLLRKQRTFDNGSIPHQIHLGELHAILRRQEDFYPFLKDNREKIEKILTFRIPYYVGPLARGNSRFAWMTRKSEETITPWN
FEEVVDKGASAQSFIERMTNFDKNLPNEKVLPKHSLLYEYFTVYNELTKVKYVTEGMRKPAFLSGEQKKAIVDLLFKTNRK
VTVKQLKEDYFKKIECFDSVEISGVEDRFNASLGTYHDLLKIIKDKDFLDNEENEDILEDIVLTLTLFEDREMIEERLKTY
AHLFDDKVMKQLKRRRYTGWGRLSRKLINGIRDKQSGKTILDFLKSDGFANRNFMQLIHDDSLTFKEDIQKAQVSGQGDSL
HEHIANLAGSPAIKKGILQTVKVVDELVKVMGRHKPENIVIEMARENQTTQKGQKNSRERMKRIEEGIKELGSQILKEHPV
ENTQLQNEKLYLYYLQNGRDMYVDQELDINRLSDYDVDHIVPQSFLKDDSIDNKVLTRSDKNRGKSDNVPSEEVVKKMKNY
WRQLLNAKLITQRKFDNLTKAERGGLSELDKAGFIKRQLVETRQITKHVAQILDSRMNTKYDENDKLIREVKVITLKSKLV
SDFRKDFQFYKVREINNYHHAHDAYLNAVVGTALIKKYPKLESEFVYGDYKVYDVRKMIAKSEQEIGKATAKYFFYSNIMN
FFKTEITLANGEIRKRPLIETNGETGEIVWDKGRDFATVRKVLSMPQVNIVKKTEVQTGGFSKESILPKRNSDKLIARKKD
WDPKKYGGFDSPTVAYSVLVVAKVEKGKSKKLKSVKELLGITIMERSSFEKNPIDFLEAKGYKEVKKDLIIKLPKYSLFEL
ENGRKRMLASAGELQKGNELALPSKYVNFLYLASHYEKLKGSPEDNEQKQLFVEQHKHYLDEIIEQISEFSKRVILADANL
DKVLSAYNKHRDKPIREQAENIIHLFTLTNLGAPAAFKYFDTTIDRKRYTSTKEVLDATLIHQSITGLYETRIDLSQLGGD
KKKKLKL
```

SEQ ID NO: 11
Full U6 gene promoter sequence (not including transcription start site)

```
AAAAAACACTAGTAAGTACTTACTTATGTATTATTAACTACTTTAGCTAACTTCTGCAGTACTACCTAAGAGGCTAGGGT
AGTTTTATAGCAGACTTATAGCTATTATTTTTATTTAGTAAAGTGCTTTTAAAGTAAGGTCTTTTTTATAGCACTTTTTAT
TTATTATAATATATTTATATAATAATTTTAAGCCTGGAATAGTAAAGAGGCTTATATAATAATTTATAGTAATAAAAGCT
TAGCAGCTGTAATATAATTCCTAAAGAAACAGCATGAAATGGTATTATGTAAGAGCTATAGTCTAAAGGCACTCTGCTGGA
TAAAAATAGTGGCTATAAGTCTGCTGCAAAACTACCCCCAACCTCGTAGGTATATAAGTACTGTTTGATGGTAGTCTATC
```

SEQ ID NO: 12
Truncated/shorter U6 gene promoter sequence (not including transcription start site)

```
AATTCCTAAAGAAACAGCATGAAATGGTATTATGTAAGAGCTATAGTCTAAAGGCACTCTGCTGGATAAAAATAGTGGCTA
TAAGTCTGCTGCAAAACTACCCCCAACCTCGTAGGTATATAAGTACTGTTTGATGGTAGTCTATC
```

SEQ ID NO: 13
N-terminal His6 tag/thrombin/S•Tag ™/enterokinase region polynucleotide sequence (with start codon); encodes SEQ ID NO: 18

```
atgcaccatcatcatcatcattcttctggtctggtgccacgcggttctggtatgaaagaaaccgctgctgctaaattcgaa
cgccagcacatggacagcccagatctgggtaccgacgacgacgacaaggccatggcc
```

Sequences:

SEQ ID NO: 14
SV40 NLS coding sequence (encodes SEQ ID NO: 19)
ccaaaaaagaaacgcaaggtt SEQ ID NO: 15
*E. coli* codon-optimized Cas9 gene (no stop codon)
atggataaaaaatacagcattggtctggatatcggaaccaacagcgttgggtgggcagtaataacagatgaatacaaagtg
ccgtcaaaaaaatttaaggttctggggaatacagatcgccacagcataaaaaagaatctgattgggggcattgctgtttgat
tcgggtgagacagctgaggccacgcgtctgaaacgtacagcaagaagacgttacacacgtcgtaaaaatcgtatttgctac
ttacaggaaatttttctaacgaaatggccaaggtagatgatagtttcttccatcgtctcgaagaatcttttctggttgag
gaagataaaaaacacgaacgtcaccctatctttggcaatatcgtggatgaagtggcctatcatgaaaaatacccctacgatt
tatcatcttcgcaagaagttggttgatagtacggacaaagcggatctgcgtttaatctatcttgcgttagcgcacatgatc
aaatttcgtggtcatttcttaattgaaggtgatctgaatcctgataactctgatgtggacaaattgtttatacaattagtg
caaacctataatcagctgttcgaggaaaaccccattaatgcctctggagttgatgccaaagcgattttaagcgcgagactt
ttctaagtcccggcgtctggagaatctgatcgcccagttaccaggggaaaagaaaatggtctgtttggtaatctgattgc
cctcagtctggggcttaccccgaacttcaaatccaatttttgacctggctgaggacgcaaagctgcagctgagcaaagatac
ttatgatgatgacctcgacaatctgctcgcccagattggtgaccaatatgcggatctgtttctggcagcgaagaatctttc
ggatgctatcttgctgtcggatattctgcgtgttaataccgaaatcaccaaagcgcctctgtctgcaagtatgatcaagag
atacgacgagcaccaccaggacctgactcttcttaaggcactggtacgccaacagcttccggagaaatacaaagaaatatt
cttcgaccagtccaagaatggttacgcgggctacatcgatggtggtgcatcacaggaagagttctataaatttattaaacc
aatccttgagaaaatggatggcacggaagagttacttgttaaacttaaccgcgaagacttgcttagaaagcaacgtacatt
cgacaacggctccatcccacaccagattcatttaggtgaacttcacgccatcttgcgcagacaagaagatttctatccctt
cttaaaagacaatcgggagaaaatcgagaagatcctgacgttccgcattccctattatgtcggtcccctggcacgtggtaa
ttctcggtttgcctggatgacgcgcaaaagtgaggaaaccatcaccccttggaactttgaagaagtcgtggataaaggtgc
tagcgcgcagtcttttatagaaagaatgacgaacttcgataaaaacttgcccaacgaaaaagtcctgcccaagcactctct
tttatatgagtactttactgtgtacaacgaactgactaaagtgaaatacgttacggaaggtatgcgcaaacctgcctttct
tagtggcgagcagaaaaaagcaattgtcgatcttctctttaaaacgaatcgcaaggtaactgtaaaacagctgaaggaaga
ttatttcaaaaagatcgaatgctttgattctgtcgagatctcgggtgtcgaagatcgtttcaacgcttccttagggaccta
tcatgatttgctgaagataataaaaagacaaagactttctcgacaatgaagaaaatgaagatattctggaggatattgtttt
gaccttgaccttattcgaagatagagagatgatcgaggagcgcttaaaaacctatgcccacctgtttgatgacaaagtcat
gaagcaattaaagcgccgcagatatacggggtggggccgcttgagccgcaagttgattaacggtattagagacaagcagag
cggaaaaactatcctggatttcctcaaatctgacggatttgcgaaccgcaatttttatgcagctatcatgatgattcgct
tacattcaaagaggatattcagaaggctcaggtgtctgggcaaggtgattcactccacgaacatatagcaaattttggccgg
ctctcctgcgattaagaaggggatcctgcaaacagttaaagttgtggatgaacttgtaaaagtaatgggccgccacaagcc
ggagaatatcgtgatagaaatggcgcgcgagaatcaaacgacacaaaaggtcaaaagaactcaagagagagaatgaagcg
cattgaggagggggataaaggaacttggatctcaaattctgaaagaacatccagttgaaaacactcagctgcaaatgaaaa
attgtacctgtactacctgcagaatggaagagacatgtacgtggatcaggaattggatatcaatagactctcggactatga
cgtagatcacattgtccctcagagcttcctcaaggatgattctatagataataaagtacttacgagatcggacaaaaatcg
cggtaaatcggataacgtcccatcggaggaagtcgttaaaaagatgaaaaactattggcgtcaactgctgaacgccaagct
gatcacacagcgtaagtttgataatctgactaaagccgaacgcggtggtcttagtgaactcgataaagcaggatttataaa
acggcagttagtagaaacgcgccaaattacgaaacacgtggctcagtcctcgattctagaatgaatacaaagtacgatga
aaacgataaactgatccgtgaagtaaaagtcattacccttaaaatctaaacttgtgtccgatttccgcaaagattttcagtt
ttacaaggtccggaaatcaataactatcaccatgcacatgatgcatatttaaatgcggttgtaggcacggcccttattaa
gaaatacctaaactcgaaagtgagtttgtttatgggggattataaagtgtatgacgttcgcaaaatgatcgcgaaatcaga
acaggaaatcggtaaggctaccgctaaatactttttttattccaacattatgaatttttttaagaccgaaataactctcgc
gaatggtgaaatccgtaaacggcctcttatagaaaccaatggtgaaacgggagaaatcgtttgggataaaggtcgtgactt
tgccaccgttcgtaaagtcctctcaatgccgcaagttaacattgtcaagaagacggaagttcaaacagggggattctccaa
agaatctatcctgccgaagcgtaacagtgataaacttattgccagaaaaaagattgggatccaaaaaaatacggaggctt
tgattcccctaccgtcgcgtatagtgtgctggtggttgctaaagtcgagaaagggaaaagcaagaaattgaaatcagttaa
agaactgctgggtattacaattatggaaagatcgtcctttgagaaaaatccgatcgacttttttagaggccaaggggtataa
ggaagtgaaaaaagatctcatcatcaaattaccgaagtatagtctttttgagctggaaaacggcagaaaagaatgctggc
ctccgcgggcgagttacagaagggaaatgagctggcgctgccttccaaatatgttaattttctgtaccttgccagtcatta
tgagaaactgaagggcagccccgaagataacgaacagaaacaattattcgtggaacagcataagcactatttagatgaaat
tatagagcaaattagtgaattttctaagcgcgttatcctcgcggatgctaatttagacaaagtactgtcagcttataataa
acatcgggataagccgattagagaacaggccgaaaatatcattcatttgtttaccttaaccaaccttggagcaccagctgc
cttcaaatatttcgataccacaattgatcgtaaacggtatacaagtacaaaagaagtcttggacgcaacccctcattcatca
atctattactggattatatgagacacgcattgatcttcacagctgggcggagac SEQ ID NO: 16
nuclear localization signal coding sequence (encodes SEQ ID NO: 20)
aagaagaaaaaactgaaactg SEQ ID NO: 17
The nucleotide sequence of the SpyCas9 synthetic gene in plasmid pET30a- SpyCas9.
The oligonucleotides encoding the N-terminal His6 tag, the SV40 nuclear
localization signal, and the BLR nuclear localization signal are shown in bold
underline, italic underline, and underlined, respectively.
atgcaccatcatcatcatcatcttctggtctggtgccacgcggttctggtatgaaagaaacgctgctgctaaattcgaa
cgccagcacatggacagcccagatctgggtaccgacgacgacgacaaggccatgcc*ccaaaaaagaaacgcaaggtt*atg
gataaaaaatacagcattggtctggatatcggaaccaacagcgttgggtgggcagtaataacagatgaatacaaagtgccg
tcaaaaaaatttaaggttctggggaatacagatcgccacagcataaaaaagaatctgattgggggcattgctgtttgattcg
ggtgagacagctgaggccacgcgtctgaaacgtacagcaagaagacgttacacacgtcgtaaaaatcgtatttgctactta
caggaaatttttctaacgaaatggccaaggtagatgatagtttcttccatcgtctcgaagaatcttttctggttgaggaa
gataaaaaacacgaacgtcaccctatctttggcaatatcgtggatgaagtggcctatcatgaaaaatacccctacgatttat
catcttcgcaagaagttggttgatagtacggacaaagcggatctgcgtttaatctatcttgcgttagcgcacatgatcaaa
tttcgtggtcatttcttaattgaaggtgatctgaatcctgataactctgatgtggacaaattgtttatacaattagtgcaa
acctataatcagctgttcgaggaaaaccccattaatgcctctggagttgatgccaaagcgattttaagcgcgagactttct -continued Sequences:

```
aagtcccggcgtctggagaatctgatcgcccagttaccaggggaaaagaaaaatggtctgtttggtaatctgattgccctc
agtctgggcgcttaccccgaacttcaaatccaattttgacctggctgaggacgcaaagctgcagctgagcaaagatacttat
gatgatgacctcgacaatctgctcgcccagattggtgaccaatatgcggatctgtttctggcagcgaagaatctttcggat
gctatcttgctgtcggatattctgcgtgttaataccgaaatcaccaaagcgcctctgtctgcaagtatgatcaagagatac
gacgagcaccaccaggacctgactcttcttaaggcactggtacgccaacagctccggagaaatacaaagaaatattcttc
gaccagtccaagaatggttacgcgggctacatcgatggtggtgcatcacaggaagagttctataaatttattaaaccaatc
cttgagaaaatggatggcacggaagagttacttgttaaacttaaccgcgaagacttgcttagaaagcaacgtacattcgac
aacggctccatcccacaccagattcatttaggtgaacttcacgccatcttgcgcagacaagaagatttctatcccttctta
aaagacaatcgggagaaaatcgagaagatcctgacgttccgcattcctattatgtcggtccctggcacgtggtaattct
cggtttgcctggatgacgcgcaaaagtgaggaaaccatcacccttggaactttgaagaagtcgtggataaggtgctagc
gcgcagtcttttatagaaagaatgacgaacttcgataaaaacttgcccaacgaaaagtcctgcccaagcactctctttta
tatgagtacttactgtgtacaacgaactgactaaagtgaaatacgttacggaaggtatgcgcaaacctgcctttcttagt
ggcgagcagaaaaagcaattgtcgatcttctctttaaaacgaatcgcaaggtaactgtaaaacagctgaaggaagattat
ttcaaaaagatcgaatgctttgattctgtcgagatctcgggtgtcgaagatcgtttcaacgcttcctagggacctatcat
gatttgctgaagataataaaagacaaagacttctcgacaatgaagaaatgaagatattctggaggatattgttttgacc
ttgaccttattcgaagatagagagatgatcggaggagcgcttaaaaacctatgcccacctgtttgatgacaaagtcatgaag
caattaaagcgccgcagatatacggggtggggccgcttgagccgcaagttgattaacggtattagagacaagcagagcgga
aaaactatcctggatttcctcaaatctgacggatttgcgaaccgcaattttatgcagcttatacatgatgattcgcttaca
ttcaaagaggatattcagaaggctcaggtgtctgggcaaggtgattcactccacgaacatatagcaaatttggccggctct
cctgcgattaagaagggatcctgcaaacagttaaagttgtggatgaactttgtaaaagtaatgggccgccacaagccggag
aatatcgtgatagaaatggcgcgcgagaatcaaacgacacaaaaggtcaaaagaactcaaggagagaatgaagcgcatt
gaggaggggataaaggaacttggatctcaaattctgaaagaacatccagttgaaaacactcagctgcaaaatgaaaaattg
tacctgtactacctgcagaatggaagagacatgtacgtggatcaggaattggatatcaatagactctcggactatgacgta
gatcacattgtccctcagagcttcctcaaggatgatctatagataataagtacttacgagatcggacaaaaatcgcggt
aaatcggataacgtcccatcggaggaagtcgttaaaagatgaaaaactattggcgtcaactgctgaacgccaagctgatc
acacagcgtaagtttgataatctgactaaagccgaacgcggtggtcttagtgaactcgataaagcaggatttataaaacgg
cagttagtagaaacgcgccaaattacgaaacacgtggctcagatcctcgattctagaatgaatacaaagtacgatgaaaac
gataaactgatccgtgaagtaaaagtcattaccttaaaatctaaacttgtctccgatttccgcaaagattttcagttttac
aaggtccgggaaatcaataactatccatgcacatgatgcatatttaaatgcggttgtaggcacggccttattaagaaa
taccctaaactcgaaagtgagtttgtttatggggattataaagtgtatgacgttcgcaaaatgatcgcgaaatcagaacag
gaaatcggtaaggctaccgctaaatactttttttattccaacattatgaatttttttaagaccgaaataactctcgcgaat
ggtgaaatccgtaaacggcctcttatagaaaccaatggtgaaacgggagaaatcgtttgggataaaggtcgtgactttgcc
accgttcgtaaagtcctctcaatgccgcaagttaacattgtcgacgaagacggaagttcaaacaggggggattctccaaagaa
tctatcctgccgaagcgtaacagtgataaacttattgccagaaaaaaagattgggatccaaaaaaatacggaggctttgat
tcccctaccgtcgcgtatagtgtgctggtggttgctaaagtcgagaaagggaaaagcaagaaattgaaatcagttaaagaa
ctgctgggtattacaattatggaaagatcgtcctttgagaaaaatccgatcgactttttagaggccaagggtataaggaa
gtgaaaaaagatctcatcatcaaattaccgaagtatagtcttttttgagctggaaacgcagaaaaagatgctggcctcc
gcgggcgagttacagaagggaaatgagctggcgctgccttccaaatatgttaattttctgtaccttgccagtcattatgag
aaactgaagggcagcccgaagataacgaacagaacaattattcgtggaacagcataagcactatttagatgaaattata
gagcaaattagtgaattttctaagcgcgttatcctcgcggatgctaatttagacaaagtactgtcagcttataataaacat
cgggataagccgattagagaacgaggccgaaaatatcattcatttgtttacctaaccaacctggagcaccagctgcctc
aaatatttcgataccaattgatcgtaaacggtatacaagtacaaaagaagtcttggacgcaaccctcattcatcaatct
attactggattatatgagacacgcattgatctttcacagctgggcggagac\underline{aagaagaaaaaactgaaactg}
```

SEQ ID NO: 18
N-terminal His6 tag/thrombin/S•Tag ™/enterokinase region amino acid sequence
(with start methionine)
Mhhhhhhssglvprgsgmketaaakferqhmdspdlgtddddkama

SEQ ID NO: 19
SV40 NLS
PKKKRKV

SEQ NO: 20
T. reesei blr2 (blue light regulator 2) gene NLS
KKKKLKL

SEQ ID NO: 21
The amino acid sequence of the SpyCas9 protein expressed from plasmid pET30a-
SpyCas9. The N-terminal His6 tag, the SV40 nuclear localization signal, and the
BLR nuclear localization signal are shown in bold underline, italic underline,
and underlined, respectively.
mhhhhhhssglvprgsgmketaaakferqhmdspdlgtddddkama_pkkkrkv_mdkkysigldigtnsvgwavitdeykvp
skkfkvlgntdrhsikknligallfdsgetaeatrlkrtarrrytrrknricylqeifsnemakvddsffhrleesflvee
dkkherhpifgnivdevayhekyptiyhlrkklvdstdkadlrliylalahmikfrghfliegdlnpdnsdvdklfiqlvq
tynqlfeenpinasgvdakailsarlsksrrlenliaqlpgekknglfgnlialslgltpnfksnfdlaedaklqlskdty
dddldnllaqigdqyadlflaaknlsdaillsdilrvnteitkaplsasmikrydehhqdltlllkalvrqqlpekykeiff
dqskngyagyidggasqeefykfikp;ilekmdgteellvklnredllrkqrtfdngsiphqihlgelhailrrqedfypf
lkdnrekiekiltfripyyvgplargnsrfawmtrkseetitpwnfeevvdkgasaqsfiermtnfdknlpnekvlpkhsl
lyeyftvyneltkvkyvtegmrkpaflsgeqkkaivdllfktnrkvtvkqlkedyfkkiecfdsveisgvedrfnaslgty
hdllkiikdkdfldneenedilediv1tltlfedremieerlktyahlfddkvmkqlkrrrytgwgrlsrklingirdkqs
gktildflksdgfanrnfmqlihddsltfkediqkaqvsgqqdslhehianlagspaikkgilqtvkvvdelvkvmgrhkp
eniviemarenqttqkgqknsrermkrieegikelgsqilkephpventqlqneklylyylqngrdmyvdqeldinrlsdyd
vdhivpqsflkddsidnkvltrsdknrgksdnvpseevvkkmknyqrqllnaklitqrkfdnltkaergglseldkagfik
rqlvetrqitkhvaqildsrmntkydendklirevkvitlkslvsdfrkdfqfykvreinnyhhahdaylnavvgtalik
kypklesefvygdykvydvrkmiakseqeigkatakyffysnimnffkteitlangeirkrplietngetgeivwdkgrdf
atvrkvlsmpqvnivkktevqtggfskesilpkrnsdkliarkkdwdpkkyggfdsptvaysvlvvakekgkskklksvke

```
llgitimerssfeknpidfleakgykevkkdliikpklyslfelengrkrmlasagelqkgnelalpskyvnflylashye
klkgspedneqkqlfveqhkhyldeiieqisefskrviladanldkvlsaynkhrdkpireqaeniihlftltnlgapaaf
kyfdttidrkrytstkevldatlihqsitglyetridlsqlggdkkkklkl
```

```
SEQ ID NO: 22
Putative T. reesei U6 gene
AAAAAACACTAGTAAGTACTTACTTATGTATTATTAACTACTTTAGCTAACTTCTGCAGTACTACCTAAGAGGCTAGGGGT
AGTTTTATAGCAGACTTATAGCTATTATTTTTATTTAGTAAAGTGCTTTTAAAGTAAGGTCTTTTTTATAGCACTTTTTAT
TTATTATAATATATTTATATAATAATTTTAAGCCTGGAATAGTAAAGAGGCTTATATAATAATTTATAGTAATAAAAGCT
TAGCAGCTGTAATATAATTCCTAAAGAAACAGCATGAAATGGTATTATGTAAGAGCTATAGTCTAAAGGCACTCTGCTGGA
TAAAAATAGTGGCTATAAGTCTGCTGCAAAACTACCCCCAACCTCGTAGGTATATAAGTACTGTTTGATGGTAGTCTATCG
CCTTCGGGCATTTGGTCAATTTATAACGATACAGGTTCGTTTCGGCTTTTCCTCGGAACCCCCAGAGGTCATCAGTTCGAA
TCGCTAACAGGTCAACAGAGAAGATTAGCATGGCCCCTGCACTAAGGATGACACGCTCACTCAAAGAGAAGCTAAACATTT
TTTTTCTCTTCCAAGTCGTGATGGTTATCTTTTTGCTTAGAGAATCTATTCTTGTGGACGATTAGTATTGGTAAATCCCTG
CTGCACATTGCGGCGGATGGTCTCAACGGCATAATACCCCATTCGTGATGCAGCGGTGATCTTCAATATGTAGTGTAATAC
GTTGCATACACCACCAGGTTCGGTGCCTCCTGTATGTACAGTACTGTAGTTCGACTCCTCCGCGCAGGTGGAAACGATTCC
CTAGTGGGCAGGTATTTTGGCGGGGTCAAGAA SEQ ID NO: 23
sequence of sgRNA (N is sequence complementary to target site)
NNNNNNNNNNNNNNNNNNNNGUUUUAGAGCUAGAAAUAGCAAGUUAAAAUAAGGCUAGUCCGUUAUCAACUUGAAAAAGUG
GCACCGAGUCGGUGGUGC SEQ ID NO: 24
sgRNA: gAd3A TS1
guccucgagcaaaaggugccGUUUUAGAGCUAGAAAUAGCAAGUUAAAAUAAGGCUAGUCCGUUAUCAACUUGAAAAAGUG
GCACCGAGUCGGUGGUGC SEQ ID NO: 25
sgRNA: gTrGA TS2
guucagugcaauaggcgucuGUUUUAGAGCUAGAAAUAGCAAGUUAAAAUAAGGCUAGUCCGUUAUCAACUUGAAAAAGUG
GCACCGAGUCGGUGGUGC SEQ ID NO: 26
sgRNA: gTrGA TS11
gccaauggcgacggcagcacGUUUUAGAGCUAGAAAUAGCAAGUUAAAAUAAGGCUAGUCCGUUAUCAACUUGAAAAAGUG
GCACCGAGUCGGUGGUGC SEQ ID NO: 27
sgRNA: gPyr2 T56
gcacagcgggaugcccuuguGUUUUAGAGCUAGAAAUAGCAAGUUAAAAUAAGGCUAGUCCGUUAUCAACUUGAAAAAGUG
GCACCGAGUCGGUGGUGC SEQ ID NO: 28
Synthetic DNA: gAd3ATS1-1 (gAd3A TS1 sgRNA (SEQ ID NO: 3) with Saccharomyces
cerevisiae snr52 promoter and S. cerevisiae sup4 terminator)
gaattcggatccTCTTTGAAAAGATAATGTATGATTATGCTTTCACTCATATTTATACAGAAACTTGATGTTTTCTTTCGA
GTATATACAAGGTGATTACATGTACGTTTGAAGTACAACTCTAGATTTTGTAGTGCCCTCTTGGGCTAGCGGTAAAGGTGC
GCATTTTTTCACACCCTACAATGTTCTGTTCAAAAGATTTTGGTCAAACGCTGTAGAAGTGAAAGTTGGTGCGCATGTTTC
GGCGTTCGAAACTTCTCCGCAGTGAAAGATAAATGATCgtcctcgagcaaaaggtgccGTTTTAGAGCTAGAAATAGCAAG
TTAAAATAAGGCTAGTCCGTTATCAACTTGAAAAAGTGGCACCGAGTCGGTGGTGCTTTTTTTGTTTTTTATGTCTgaatt
cggatcc SEQ ID NO: 29
Synthetic DNA: gAd3ATS1-2 (gAd3A TS1 sgRNA (SEQ ID NO: 3) with T. reesei U6
promoter and terminator)
gaattcggatccAAAAAACACTAGTAAGTACTTACTTATGTATTATTAACTACTTTAGCTAACTTCTGCAGTACTACCTAA
GAGGCTAGGGGTAGTTTTATAGCAGACTTATAGCTATTATTTTTATTTAGTAAAGTGCTTTTAAAGTAAGGTCTTTTTTAT
AGCACTTTTTATTTATTATAATATATATTATATAATAATTTTAAGCCTGGAATAGTAAAGAGGCTTATATAATAATTTATA
GTAATAAAAGCTTAGCAGCTGTAATATAATTCCTAAAGAAACAGCATGAAATGGTATTATGTAAGAGCTATAGTCTAAAGG
CACTCTGCTGGATAAAAATAGTGGCTATAAGTCTGCTGCAAAACTACCCCCAACCTCGTAGGTATATAAGTACTGTTTGAT
GGTAGTCTATCgtcctcgagcaaaaggtgccGTTTTAGAGCTAGAAATAGCAAGTTAAAATAAGGCTAGTCCGTTATCAAC
TTGAAAAAGTGGCACCGAGTCGGTGGTGCTTTTTTTTCTCTTgaattcggatcc SEQ ID NO: 30
Synthetic DNA: gAd3ATS1-3 (gAd3A TS1 sgRNA (SEQ ID NO: 3) with T. reesei U6
promoter, terminator and intron)
gaattcggatccAAAAAACACTAGTAAGTACTTACTTATGTATTATTAACTACTTTAGCTAACTTCTGCAGTACTACCTAA
GAGGCTAGGGGTAGTTTTATAGCAGACTTATAGCTATTATTTTTATTTAGTAAAGTGCTTTTAAAGTAAGGTCTTTTTTAT
AGCACTTTTTATTTATTATAATATATATTATATAATAATTTTAAGCCTGGAATAGTAAAGAGGCTTATATAATAATTTATA
GTAATAAAAGCTTAGCAGCTGTAATATAATTCCTAAAGAAACAGCATGAAATGGTATTATGTAAGAGCTATAGTCTAAAGG
CACTCTGCTGGATAAAAATAGTGGCTATAAGTCTGCTGCAAAACTACCCCCAACCTCGTAGGTATATAAGTACTGTTTGAT
GGTAGTCTATCgtcctcgagcaaaaggtgccGTTTTAGAGCTAGAGTTCGTTTCGGCTTTTCCTCGGAACCCCCAGAGGTC
ATCAGTTCGAATCGCTAACAGAATAGCAAGTTAAAATAAGGCTAGTCCGTTATCAACTTGAAAAAGTGGCACCGAGTCGGT
GGTGCTTTTTTTCTCTTgaattcggatcc
```

Sequences:

SEQ ID NO: 31
Guide RNA expression cassettes with a shorter *T. reesei* U6 promoter region were
obtained as synthetic DNA. An example is provided here that includes the sequence
for an sgRNA targeting the *T. reesei* gla1 gene at TS11.
AATTCCTAAAGAAACAGCATGAAATGGTATTATGTAAGAGCTATAGTCTAAAGGCACTCTGCTGGATAAAAATAGTGGCTA
TAAGTCTGCTGCAAAACTACCCCCAACCTCGTAGGTATATAAGTACTGTTTGATGGTAGTCTATCgccaatggcgacggca
gcacGTTTTAGAGCTAGAGTTCGTTTCGGCTTTTCCTCGGAACCCCCAGAGGTCATCAGTTCGAATCGCTAACAGAATAGC
AAGTTAAAATAAGGCTAGTCCGTTATCAACTTGAAAAAGTGGCACCGAGTCGGTGGTGCTTTTTTTTCTCTT SEQ ID NO: 32
Primer: gRNA fwd aflII
cgtcagcttaagAATTCCTAAAGAAACAGCATGAAATGG SEQ ID NO: 33
Primer: gRNA rev sfiI
cgtcagggccacgtgggccAAGAGAAAAAAAAGCACCACCGACTCGG SEQ ID NO: 34
Primer: Ad3 5' fwd
tgaacacagccaccgacatcagc SEQ ID NO: 35
Primer: Ad3 5' rev
gctggtgagggtttgtgctattg SEQ ID NO: 36
Primer: Ad3a 5005 rev
gattgcttgggaggaggacat SEQ ID NO: 37
Primer: Ad3 3' fwd
cgaggccactgatgaagttgttc SEQ ID NO: 38
Primer: Ad3 3' rev
Cagttttccaaggctgccaacgc SEQ ID NO: 39
Primer: Ad3a 5003 fwd
ctgatcttgcaccctggaaatc SEQ ID NO: 40
Ad3mid rev
ctctctatcatttgccaccctcc SEQ ID NO: 41
Primer: Adfrag fwd
ctccattcaccctcaattctcc SEQ ID NO: 42
Primer: Adfrag rev
gttcccttggcggtgcttggatc SEQ ID NO: 43
Primer: Ad3a 2k fwd
caatagcacaaaccctcaccagc SEQ ID NO: 44
Ad3a 2k rev
gaacaacttcatcagtggcctcg SEQ ID NO: 45
Primer: glaA
ccgttagttgaagatccttgccg SEQ ID NO: 46
Primer: glaB
gtcgaggatttgcttcatacctc SEQ ID NO: 47
Primer: glaJ
tgccgactttgtccagtgattcg SEQ ID NO: 48
Primer: glaK
ttacatgtggacgcgagatagcg Sequences:

SEQ ID NO: 49
Primer: gla1repF
gtgtgtctaatgcctccaccac

SEQ ID NO: 50
Primer: gla1repR
gatcgtgctagcgctgctgttg

SEQ ID NO: 51
Primer: 1553R
CCGTGATGGAGCCCGTCTTCT

SEQ ID NO: 52
Primer: 1555F
CGCGGTGAGTTCAGGCTTTTC

SEQ ID NO: 53
Primer: pyr2F
gtataagagcaggaggagggag

SEQ ID NO: 54
Primer: pyr2R
gaacgcctcaatcagtcagtcg

SEQ ID NO: 55
Bacterial kanamycin resistance gene (with promoter and terminator) between
Trichoderma reesei telomere sequences
tcaggaaatagctttaagtagcttattaagtattaaaattatatatattttaatataactatatttctttaataaatagg
tattttaagctttatatataaatataataataaaataatatattatatagcttttttattaataaataaaatagctaaaaat
ataaaaaaaatagctttaaaatacttattttttaattagaattttatatattttaatatataagatcttttactttttat
aagcttcctaccttaaattaaattttttacttttttttttactattttactatatcttaaataaaggctttaaaaatataaaaa
aaatcttcttatatattataagctataaggattatatatatattttttttttaatttttaaagtaagtattaaagctagaat
taaagttttaattttttaaggctttatttaaaaaaaggcagtaatagcttataaaagaaatttctttttctttttatactaa
aagtacttttttttttaataaggttaggggttagggtttactcacaccgaccatcccaaccacatcttagggttagggttagg
gttagggttagggttagggttagggttagggtaagggtttaaacaaagccacgttgtgtctcaaaatctctgatgttacat
tgcacaagataaaaatatatcatcatgaacaataaaactgtctgcttacataaacagtaatacaaggggtgttatgagcca
tattcaacgggaaacgtcttgctcgaggccgcgattaaattccaacatggatgctgatttatatgggtataaatgggctcg
cgataatgtcgggcaatcaggtgcgacaatctatcgattgtatgggaagcccgatgcgccagagttgtttctgaaacatgg
caaaggtagcgttgccaatgatgttacagatgagatggtcagactaaactggctgacggaatttatgcctcttccgaccat
caagcatttatccgtactcctgatgatgcatggttactcaccactgcgatccccgggaaaacagcattccaggtattaga
agaatatcctgattcaggtgaaaatattgttgatgcgctggcagtgttcctgcgccggttgcattcgattcctgtttgtaa
ttgtccttttaacagcgatcgcgtatttcgtctcgctcaggcgcaatcacgaatgaataacggtttggttgatgcgagtga
ttttgatgacgagcgtaatggctggcctgttgaacaagtctggaaagaaatgcataagcttttgccattgttcaccggattc
agtcgtcactcatggtgatttctcacttgataaccttatttttgacgaggggaaattaatggttgtattgatgttggacg
agtcggaatcgcagaccgataccaggatcttgccatcctatggaactgcctcggtgagttttctccttcattacagaaacg
gcttttcaaaaatatggtattgataatcctgatatgaataaattgcagtttcatttgatgctcgatgagttttctcaatc
agaattggttaattggttgtaacactggcagagcattacgctgacttgacgggacggcggctttgttgaataaatcgaact
tttgctgagttgaaggatcagatcacgcatcttcccgacaacgcagaccgttccgtggcaaagcaaaagttcaaaatcacc
aactggtccacctacaacaaagctctcatcaaccgtggctccctcactttctggctggatgatggggcgattcaggcctgg
tatgagtcagcaacaccttcttcacgaggcagacctcagcggtttaaacctaaccctaaccctaaccctaaccctaaccct
aaccctaaccctaaccctaaccctaaccctaaccctaaccctaaccctaacctaaccctaatggggtcgatctgaaccgag
gatgagggttctatagactaatctacaggccgtacatggtgtgattgcagatgcgacgggcaaggtgtacagtgtccagaa
ggaggagagcggcataggtattgtaatagaccagctttacataataatcgcctgttgctactgactgatgaccttcttccc
taaccagtttcctaattaccactgcagtgaggataaccctaactcgctctggggttattattactgattagcaggtggc
ttatatagtgctgaagtactataagagtttctgcgggaggaggtggaaggactataaactggacacagttagggatagagt
gatgacaagacctgaatgttatcctccggtgtggtatagcgaattggctgaccttgcagatggtaatggtttaggcagggt
ttttgcagaggggacgagaacgcgttctgcgatttaacggctgctgccgccaagctttacggttctctaatgggcggccg
c SEQ ID NO: 56
Xyr1 Ta Target sequence (5'-3', PAM bold underlined):
GCAGCACCTCGCACAGCATGCGG

SEQ ID NO: 57
Xyr1 Ta (2) oligo 1
TAGGCAGCACCTCGCACAGCATG

SEQ ID NO: 58
Xyr1 Ta oligo 2
AAACCATGCTGTGCGAGGTGCT

SEQ ID NO: 59
Xyr1 Tc Target sequence (5'-3', PAM bold underlined):
GCTGCCAGGAAGAATTCAACGGG

Sequences:

SEQ ID NO: 60
Xyr1 To oligo 1
TAGGCTGCCAGGAAGAATTCAAC

SEQ ID NO: 61
Xyr1 To oligo 2
AAACGTTGAATTCTTCCTGGCA

SEQ ID NO: 62
Pyr4 TS2 Target sequence (5'-3', PAM bold underlined)
GCTCAAGACGCACTACGACATGG

SEQ ID NO: 63
Pyr4 TS2 oligo 1
TAGGCTCAAGACGCACTACGACA

SEQ ID NO: 64
Pyr4 TS2 oligo 2
AAACTGTCGTAGTGCGTCTTGAGC

SEQ ID NO: 65
Xyr1 Ta
taatacgactcactataggGCAGCACCTCGCACAGCATGgttttagagctagaaatagcaagttaaaataaggctagtccg
ttatcaacttgaaaaagtggcaccgagtcggtgctttttacg SEQ ID NO: 66
Xyr1 Tc
taatacgactcactataggGCTGCCAGGAAGAATTCAACgttttagagctagaaatagcaagttaaaataaggctagtccg
ttatcaacttgaaaaagtggcaccgagtcggtgctttttacg SEQ ID NO: 67
Pyr4 TS2
taatacgactcactataggGCTCAAGACGCACTACGACAgttttagagctagaaatagcaagttaaaataaggctagtccg
ttatcaacttgaaaaagtggcaccgagtcggtgctttttacg SEQ ID NO: 68
K21 control T4
tggcccgtcgattgtcgtgctcaagacgcactacgacatggtctcgg SEQ ID NO: 69
T4 4-3
tggcccgtcgattgtcgtgctcaagacgcactacgCGacatggtctcgg SEQ ID NO: 70
T4 4-13
tggcccgtcgattgtcgtgctcaagacgcactacgacatggtctcgg SEQ ID NO: 71
T4 4-11
tggcccgtcgattgtcgtgctcaagacgcactacgGacatggtctcgg SEQ ID NO: 72
T4 4-12
tggcccgtcgattgtcgtgctcaagacgcactacgacatggtctcgg SEQ ID NO: 73
T4 4-18
tggcccgtcgattgtcgtgctcaagacgcactacgGacatggtctcgg SEQ ID NO: 74
T4 4-20
tggcccgtcgattgtcgtgctcaagacgcactacgAGCCGACAGGGCGCCTGGCTAAATCCAAGGTCAAGACAGGCTGGTG
GTTGTTTAGTGCGAGTCCTCTGacatggtctcgg SEQ ID NO: 75
T4 4-19
tggcccgtcgattgtcgtgctcaagacgcactacgGacatggtctcgg SEQ ID NO: 76
T4 4-4
tggcccgtcgaatgttgtggtcaaggcgcccttcGacatggtctcgg SEQ ID NO: 77
T4 4-7
tggcccgtcgattgtcgtgctcaagacgcactacgGacatggtctcgg

```
SEQ ID NO: 78
9-96
CCGCTGACGGCTTACCTGTTCAAGCTCATGGACCTCAAGGCGTCCAACCTGTGCCTGAGCGCCGACGTGCCGACAGCGCGC
GAGCTGCTGTACCTGGCCGACAAGATTGGCCCGTCGATTGTCGTGCTCAAGACGCACTACGCAGGCCTGCGTCGAGGCCGC
CCGGGAGCACAAGGACTTTGTCATG

SEQ ID NO: 79
Pyr4 Tr
CCGCTGACGGCTTACCTGTTCAAGCTCATGGACCTCAAGGCGTCCAACCTGTGCCTGAGCGCCGACGTGCCGACAGCGCGC
GAGCTGCTGTACCTGGCCGACAAGATTGGCCCGTCGATTGTCGTGCTCAAGACGCACTACGACATGGTCTCGGGCTGGGAC
TTCCACCCGGAGACGGGCACGGGAGCCCAGCTGGCGTCGCTGGCGCGCAAGCACGGCTTCCTCATCTTCGAGGACCGCAAG
TTTGGCGACATTGGCCACACCGTCGAGCTGCAGTACACGGGCGGGTCGGCGCGCATCATCGACTGGGCGCACATTGTCAAC
GTCAACATGGTGCCCGGCAAGGCGTCGGTGGCCTCGCTGGCCCAGGGCGCCAAGCGCTGGCTCGAGCGCTACCCCTGCGAG
GTCAAGACGTCCGTCACCGTCGGCACGCCCACCATGGACTCGTTTGACGACGACGCCGACTCCAGGGACGCCGAGCCCGCC
GGCGCCGTCAACGGCATGGGCTCCATTGGCGTCCTGGACAAGCCCATCTACTCGAACCGGTCCGGCGACGGCCGCAAGGGC
AGCATCGTCTCCATCACCACCGTCACCCAGCAGTACGAGTCCGTCTCCTCGCCCCGGTTAACAAAGGCCATCGCCGAGGGC
GACGAGTCGCTCTTCCCGGGCATCGAGGAGGCGCCGCTGAGCCGCGGCCTCCTGATCCTCGCCCAAATGTCCAGCCAGGGC
AACTTCATGAACAAGGAGTACACGCAGGCCTGCGTCGAGGCCGCCCGGGAGCACAAGGACTTTGTCATG

SEQ ID NO: 80
Query
ctggccgacaagattggcccgtcgattgtcgtgctcaagacgcactacgacatggtctc

SEQ ID NO: 81
Subject
ctggccgacaagattggcccgtcgattgtcgtgctcaagacgcactacgGacatggtctc SEQ ID NO: 82
Pyr4 Tr
gacagcgcgcgagctgctgtacctggccgacaagattggcccgtcgattgtcgtgctcaagacgcactacgacatggtct
cgggctgggacttccacccgg SEQ ID NO: 83
P37 #13 4.2 rc
gacagcgcgcgagctgctgtacctggccgacaagattggcccgtcgattgtcgtgctcaagacgcactacgGacatggt
ctcgggctgggacttccacccgg SEQ ID NO: 84
P374.1 #12 rc
gacagcgcgcgagctgctgtacctggccgacaagattggcccgtcgattgtcgtgctcaagacgcactacgTacatggt
ctcgggctgggacttccacccgg SEQ ID NO: 85
P37 #15 4.4 rc
gacagcgcgcgagctgctgtacctggccgacaagattggcccgtcgattgtcgtgctcaagacgcactacgcatggtctc
gggctgggacttccacccgg SEQ ID NO: 86
P37 #14 4.3
Gacagcgcgcgagctgctgtacctggccgacaagattggcccgtcgattgtcgtgctcaagacgcactacgacatggtctc
gggctgggacttccacccgg SEQ ID NO: 87
Consensus (deletion alignment)
Gacagcgcgcgagctgctgtacctggccgacaagattggcccgtcgattgtcgtgctcaagacgcannangnnnnggnnnn
nggnngggannncnancngg SEQ ID NO: 88
Wild type pyr4 full coding sequence
Atggcaccacacccgacgctcaaggccaccttcgcggccaggagcgagacggcgacgcacccgctgacggcttacctgttc
aagctcatggacctcaaggcgtccaacctgtgcctgagcgccgacgtgccgacagcgcgcgagctgctgtacctggccgac
aagattggcccgtcgattgtcgtgctcaagacgcactacgacatggtctcgggctgggacttccacccggagacgggcacg
ggagcccagctggcgtcgctggcgcgcaagcacggcttcctcatcttcgaggaccgcaagtttggcgacattggccacacc
gtcgagctgcagtacacgggcgggtcggcgcgcatcatcgactgggcgcacattgtcaacgtcaacatggtgcccggcaag
gcgtcggtggcctcgctggcccagggcgccaagcgctggctcgagcgctaccctgcgaggtcaagacgtccgtcaccgtc
ggcacgcccaccatggactcgtttgacgacgacgccgactccagggacgccgagcccgcggcgccgtcaacggcatgggc
tccattggcgtcctggacaagcccatctactcgaaccggtccggcgacggccgcaagggcagcatcgtctccatcaccacc
gtcacccagcagtacgagtccgtcctcgcccggttaacaaaggccatcgccgagggcgacgagtcgctcttcccgggc
atcgaggaggcgccgctgagccgcggcctcctgatcctcgcccaaatgtccagccagggcaacttcatgaacaaggagtac
acgcaggcctgcgtcgaggccgcccgggagcacaaggactttgtcatgggcttcatctcgcaggagacgctcaacaccgag
cccgacgatgcctttatccacatgacgcccggctgccagctgccccccgaagacgaggaccagcagaccaacggatcggtc
ggtggagacggccagggccagcagtacaaacacgccgacaagctgattggcatcgccggcagcgacattgccattgtgggc
cggggcatcctcaaggcctcagaccccgtagaggaggcagagcggtaccgatcagcagcgtggaaagcctacaccgagagg
ctgctgcgatag
```

-continued

Sequences:

SEQ ID NO: 89
Xyr-1 gene coding sequence
atgttgtccaatcctctccgtcgctattctgcctaccccgacatctcctcggcgtcatttgacccgaactaccatggctca
cagtcgcatctccactcgatcaacgtcaacacattcggcaacagccaccccctatcccatgcagcacctcgcacagcatgcg
gagctttcgagttcacgcatgataagggccagtccggtgcagccaaagcagcgccagggctctcttattgctgccaggaag
aattcaacGGGtactgctgggcccattcggcggaggatcagtcgcgcttgtgaccagtgcaaccagcttcgtaccaagtgc
gatggcttacacccatgtgccattgtataggtatgtcccttttcctctacacagtgatgctgcgctcaagcacatgtact
gatccgatcttgtttagaattcggccttggatgcgaatatgtccgagagagaaagaacgtggcaaagcttcgcgcaaggat
attgctgcccagcaagccgcggcggctgcagcacaacactccggccaggtccaggatggtccagaggatcaacatcgcaaa
ctctcacgccagcaaagcgaatcttcgcgtggcagcgctgagcttgcccagcctgcccacgaccgcctcatggccacatt
gagggctctgtcagctccttcagcgacaatggccttcccagcatgctgccatgggcggcatggatggcctggaagatcac
catggccacgtcggagttgatcctgccctgggccgaactcagctggaagcgtcatcagcaatgggcctgggcgcatacggt
gaagtccaccccggctatgagagccccggcatgaatggccatgtgatggtgcccccgtcgtatggcgcgcagaccaccatg
gccgggtattccggtatctcgtatgctgcgcaagccccgagtccggctacgtatagcagcgacggtaactttcgactcacc
ggtcacatccatgattaccgctggcaaatgggagctcgccctcatggggagtctcgctggcctcgccttcgaaccagttc
cagcttcagctctcgcagcccatcttcaagcaaagcgatttgcgatatcctgtgcttgagcctctgctgcctcacctggga
aacatcctccccgtgtctttggcgtgcgatctgattgacctgtacttctcctcgtcttcatcagcacagatgcacccaatg
tccccatacgttctgggcttcgtcttccggaagcgctccttcttgcaccccacgaacccacgaaggtgccagcccgcgctg
cttgcgagcatgctgtgggtggcggcacagactagcgaagcgtccttcttgacgagcctgccgtcggcgaggagcaaggtc
tgccagaagctgctcgagctgaccgttgggcttcttcagccctgcatccacacgcaccaacagcccgtctccaagact
agccccgtcgtcggtgctgctgccctgggagttcttggggtggccatgccgggctcgctgaacatggattcactggccggc
gaaacgggtgctttggggccatagggagccttgacgacgtcatcacctatgtgcacctcgccacggtcgtctcggccagc
gagtacaagggcgccagcctgcggtggtggggtgcggcatggtctctcgccagagagctcaagcttggccgtgagctgccg
cctgcaatccacctgccaaccaggaggacggcgagggccttagcgaagcggatgagcacgacttgaacagaaacaac
actcgcttcgtgacggaagaggagcgcgaagagcgacggcgagcatggtggctcgtttacatcgtcgacaggcacctggcg
ctctgctacaaccgcccccttgtttcttctggacagcgagtgcagcgacttgtaccacccgatggacgacatcaagtggcag
gcaggcaaatttcgcagccacgatgcagggaactccagcatcaacatcgatagctccatgacggacgagtttggcgatagt
ccccgggcggctcgccggcgcacactacgagtgccgcggtcgtagcattttttggctacttcttgtccttgatgacaatcctg
ggcgagattgtcgatgtccaccatgctaaaagccaccccggttcggcgttggattccgctccgcgcggattgggacgag
caggttgctgaaatcacccgacacctggacatgtatgaggagagcctcaagaggttcgtggccaagcatctgccattgtcc
tcaaaggacaaggagcagcatgagatgcacgacagtggagcggtaacagacatgcaatctccactctcggtgcggaccaac
gcgtccagccgcatgacggagagcgagatccaggccagcatcgtggtggcttacagcacccatgtgatgcatgtcctccac
atcctccttgcggataagtgggatcccatcaaccttctagacgacgacgacttgtggatctcgtcggaaggattcgtgacg
gcgacgagccacgcggtatcggctgccgaagctattagccagattctcgagtttgaccctggcctggagtttatgccattc
ttctctacggcgtctatctcctgcaggggttccttcctcctcctgctcatcgccgacaagctgcaggccgaagcgtctccaagc
gtcatcaaggcttgcgagaccattgttagggcacacgaagcttgcgttgtgacgctgagcacagagtatcaggtaagccct
atcagttcaaacgtctatcttgctgtgaatcaaagactgacttggacatcagcgcaactttagcaaggtatgcgaagcgc
gctggctctgattcggggccgtgtgccggaagattagctgagcagcagcagcgacgacgcgagcttcttgcactataccg
atggactggtaacggaaccggtctggccctctaa SEQ ID NO: 90
U6 intron
GTTCGTTTCGGCTTTTCCTCGGAACCCCCAGAGGTCATCAGTTCGAATCGCTAACAG SEQ ID NO: 91
U6 gene transcriptional terminator sequence
TTTTTTTTCTCTT SEQ ID NO: 92
Target Sequence for Pyr4 TS2 guide RNA
GCTCAAGACGCACTACGACA

That which is claimed:

1. A method for modifying a DNA sequence at a target site in the genome of a filamentous fungal cell, the method comprising:
   a) introducing into a population of filamentous fungal cells a Cas endonuclease and a guide RNA, wherein the Cas endonuclease and guide RNA are capable of forming a complex that enables the Cas endonuclease to introduce a double-strand break at a target site in the genome of the fungal cells, wherein the introducing step comprises introducing a DNA construct comprising an expression cassette for the guide RNA into the filamentous fungal cells, wherein the expression cassette for the guide RNA comprises a RNA polymerase III dependent promoter derived from a *Trichoderma* U6 snRNA gene and functional in a Euascomycete or Pezizomycete, and wherein the promoter is operably linked to the DNA encoding the guide RNA; and,
   b) an identification step, the identifying step comprises culturing the population of cells from step (a) under conditions to screen for unstable transformants and identifying at least one fungal cell from the unstable transformants that has a modification of the DNA sequence at the target site,
   wherein the Cas endonuclease, the guide RNA, or both are introduced transiently into the population of fungal cells, and wherein the modification of the DNA sequence at the target site is not caused by homologous recombination between a donor DNA and the genome of the filamentous fungal cell.

2. The method of claim 1, wherein the promoter comprises a nucleotide sequence with at least 70% identity to SEQ ID NO: 11 or 12.

3. The method of claim 1, wherein the expression cassette for the guide RNA comprises a guide RNA-encoding DNA with an intron sequence from a *Trichoderma* U6 snRNA gene.

4. The method of claim 3, wherein the intron sequence derived from *Trichoderma* U6 snRNA gene comprises a nucleotide sequence with at least 70% identity to SEQ ID NO: 90.

5. An engineered nucleic acid encoding a guide RNA which enables a Cas endonuclease to introduce a double-strand break at a target site in the genome of a filamentous fungal cell, wherein the nucleic acid encoding the guide RNA comprises a RNA polymerase III dependent promoter functional in a Euascomycete or Pezizomycete, and the promoter is derived from a *Trichoderma* U6 snRNA gene.

6. The engineered nucleic acid of claim 5, wherein the promoter comprises a nucleotide sequence with at least 70% identity to SEQ ID NO: 11 or 12.

7. An engineered nucleic acid encoding a guide RNA which enables a Cas endonuclease to introduce a double-strand break at a target site in the genome of a filamentous fungal cell, wherein the nucleic acid encoding the guide RNA comprises a guide RNA-encoding DNA with an intron sequence derived from a *Trichoderma* U6 snRNA gene.

8. The engineered nucleic acid of claim 7, wherein the intron sequence derived from *Trichoderma* U6 snRNA gene comprises a nucleotide sequence with at least 70% identity to SEQ ID NO: 90.

9. The engineered nucleic acid of claim 5 or 7, wherein the nucleic acid encoding the guide RNA comprises both a promoter derived from a Trichoderma U6 snRNA gene and an intron sequence derived from a *Trichoderma* U6 snRNA gene, wherein the promoter comprises a nucleotide sequence with at least 70% identity to SEQ ID NO: 11 or 12, and wherein the intron sequence derived from *Trichoderma* U6 snRNA gene comprises a nucleotide sequence with at least 70% identity to SEQ ID NO: 90.

* * * * *

SEQUENCE LISTING

<160> NUMBER OF SEQ ID NOS: 92

<210> SEQ ID NO 1
<211> LENGTH: 1368
<212> TYPE: PRT
<213> ORGANISM: Streptococcus pyogenes

<400> SEQUENCE: 1

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu

```
              50                  55                  60
Lys Arg Thr Ala Arg Arg Tyr Thr Arg Lys Asn Arg Ile Cys
 65                  70                  75                  80

Tyr Leu Gln Glu Ile Phe Ser Asn Glu Met Ala Lys Val Asp Asp Ser
                     85                  90                  95

Phe Phe His Arg Leu Glu Glu Ser Phe Leu Val Glu Glu Asp Lys Lys
                    100                 105                 110

His Glu Arg His Pro Ile Phe Gly Asn Ile Val Asp Glu Val Ala Tyr
                    115                 120                 125

His Glu Lys Tyr Pro Thr Ile Tyr His Leu Arg Lys Lys Leu Val Asp
                    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                    165                 170                 175

Asp Asn Ser Asp Val Asp Lys Leu Phe Ile Gln Leu Val Gln Thr Tyr
                    180                 185                 190

Asn Gln Leu Phe Glu Glu Asn Pro Ile Asn Ala Ser Gly Val Asp Ala
                    195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                    245                 250                 255

Asp Leu Ala Glu Asp Ala Lys Leu Gln Leu Ser Lys Asp Thr Tyr Asp
                    260                 265                 270

Asp Asp Leu Asp Asn Leu Leu Ala Gln Ile Gly Asp Gln Tyr Ala Asp
                    275                 280                 285

Leu Phe Leu Ala Ala Lys Asn Leu Ser Asp Ala Ile Leu Leu Ser Asp
                    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                    325                 330                 335

Ala Leu Val Arg Gln Gln Leu Pro Glu Lys Tyr Lys Glu Ile Phe Phe
                    340                 345                 350

Asp Gln Ser Lys Asn Gly Tyr Ala Gly Tyr Ile Asp Gly Gly Ala Ser
                    355                 360                 365

Gln Glu Glu Phe Tyr Lys Phe Ile Lys Pro Ile Leu Glu Lys Met Asp
                    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                    405                 410                 415

Gly Glu Leu His Ala Ile Leu Arg Arg Gln Glu Asp Phe Tyr Pro Phe
                    420                 425                 430

Leu Lys Asp Asn Arg Glu Lys Ile Glu Lys Ile Leu Thr Phe Arg Ile
                    435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480
```

-continued

Val Val Asp Lys Gly Ala Ser Ala Gln Ser Phe Ile Glu Arg Met Thr
            485             490             495

Asn Phe Asp Lys Asn Leu Pro Asn Glu Lys Val Leu Pro Lys His Ser
            500             505             510

Leu Leu Tyr Glu Tyr Phe Thr Val Tyr Asn Glu Leu Thr Lys Val Lys
            515             520             525

Tyr Val Thr Glu Gly Met Arg Lys Pro Ala Phe Leu Ser Gly Glu Gln
            530             535             540

Lys Lys Ala Ile Val Asp Leu Leu Phe Lys Thr Asn Arg Lys Val Thr
545             550             555             560

Val Lys Gln Leu Lys Glu Asp Tyr Phe Lys Lys Ile Glu Cys Phe Asp
            565             570             575

Ser Val Glu Ile Ser Gly Val Glu Asp Arg Phe Asn Ala Ser Leu Gly
            580             585             590

Thr Tyr His Asp Leu Leu Lys Ile Ile Lys Asp Lys Asp Phe Leu Asp
            595             600             605

Asn Glu Glu Asn Glu Asp Ile Leu Glu Asp Ile Val Leu Thr Leu Thr
            610             615             620

Leu Phe Glu Asp Arg Glu Met Ile Glu Glu Arg Leu Lys Thr Tyr Ala
625             630             635             640

His Leu Phe Asp Asp Lys Val Met Lys Gln Leu Lys Arg Arg Arg Tyr
            645             650             655

Thr Gly Trp Gly Arg Leu Ser Arg Lys Leu Ile Asn Gly Ile Arg Asp
            660             665             670

Lys Gln Ser Gly Lys Thr Ile Leu Asp Phe Leu Lys Ser Asp Gly Phe
            675             680             685

Ala Asn Arg Asn Phe Met Gln Leu Ile His Asp Asp Ser Leu Thr Phe
            690             695             700

Lys Glu Asp Ile Gln Lys Ala Gln Val Ser Gly Gln Gly Asp Ser Leu
705             710             715             720

His Glu His Ile Ala Asn Leu Ala Gly Ser Pro Ala Ile Lys Lys Gly
            725             730             735

Ile Leu Gln Thr Val Lys Val Val Asp Glu Leu Val Lys Val Met Gly
            740             745             750

Arg His Lys Pro Glu Asn Ile Val Ile Glu Met Ala Arg Glu Asn Gln
            755             760             765

Thr Thr Gln Lys Gly Gln Lys Asn Ser Arg Glu Arg Met Lys Arg Ile
770             775             780

Glu Glu Gly Ile Lys Glu Leu Gly Ser Gln Ile Leu Lys Glu His Pro
785             790             795             800

Val Glu Asn Thr Gln Leu Gln Asn Glu Lys Leu Tyr Leu Tyr Tyr Leu
            805             810             815

Gln Asn Gly Arg Asp Met Tyr Val Asp Gln Glu Leu Asp Ile Asn Arg
            820             825             830

Leu Ser Asp Tyr Asp Val Asp His Ile Val Pro Gln Ser Phe Leu Lys
            835             840             845

Asp Asp Ser Ile Asp Asn Lys Val Leu Thr Arg Ser Asp Lys Asn Arg
850             855             860

Gly Lys Ser Asp Asn Val Pro Ser Glu Glu Val Val Lys Lys Met Lys
865             870             875             880

Asn Tyr Trp Arg Gln Leu Leu Asn Ala Lys Leu Ile Thr Gln Arg Lys
            885             890             895

-continued

```
Phe Asp Asn Leu Thr Lys Ala Glu Arg Gly Gly Leu Ser Glu Leu Asp
            900                 905                 910
Lys Ala Gly Phe Ile Lys Arg Gln Leu Val Glu Thr Arg Gln Ile Thr
        915                 920                 925
Lys His Val Ala Gln Ile Leu Asp Ser Arg Met Asn Thr Lys Tyr Asp
    930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
            980                 985                 990
Val Gly Thr Ala Leu Ile Lys Lys Tyr Pro Lys Leu Glu Ser Glu Phe
        995                 1000                1005
Val Tyr Gly Asp Tyr Lys Val Tyr Asp Val Arg Lys Met Ile Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Asp Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Leu Gly Ile Thr Ile Met Glu Arg Ser Ser
    1160                1165                1170
Phe Glu Lys Asn Pro Ile Asp Phe Leu Glu Ala Lys Gly Tyr Lys
    1175                1180                1185
Glu Val Lys Lys Asp Leu Ile Ile Lys Leu Pro Lys Tyr Ser Leu
    1190                1195                1200
Phe Glu Leu Glu Asn Gly Arg Lys Arg Met Leu Ala Ser Ala Gly
    1205                1210                1215
Glu Leu Gln Lys Gly Asn Glu Leu Ala Leu Pro Ser Lys Tyr Val
    1220                1225                1230
Asn Phe Leu Tyr Leu Ala Ser His Tyr Glu Lys Leu Lys Gly Ser
    1235                1240                1245
Pro Glu Asp Asn Glu Gln Lys Gln Leu Phe Val Glu Gln His Lys
    1250                1255                1260
His Tyr Leu Asp Glu Ile Ile Glu Gln Ile Ser Glu Phe Ser Lys
    1265                1270                1275
Arg Val Ile Leu Ala Asp Ala Asn Leu Asp Lys Val Leu Ser Ala
    1280                1285                1290
Tyr Asn Lys His Arg Asp Lys Pro Ile Arg Glu Gln Ala Glu Asn
```

```
               1295               1300                1305
Ile  Ile  His  Leu  Phe  Thr  Leu  Thr  Asn  Leu  Gly  Ala  Pro  Ala  Ala
    1310                1315               1320

Phe  Lys  Tyr  Phe  Asp  Thr  Thr  Ile  Asp  Arg  Lys  Arg  Tyr  Thr  Ser
    1325                1330                1335

Thr  Lys  Glu  Val  Leu  Asp  Ala  Thr  Leu  Ile  His  Gln  Ser  Ile  Thr
    1340                1345               1350

Gly  Leu  Tyr  Glu  Thr  Arg  Ile  Asp  Leu  Ser  Gln  Leu  Gly  Gly  Asp
    1355                1360               1365

<210> SEQ ID NO 2
<211> LENGTH: 1388
<212> TYPE: PRT
<213> ORGANISM: Streptococcus thermophilus

<400> SEQUENCE: 2

Met  Thr  Lys  Pro  Tyr  Ser  Ile  Gly  Leu  Asp  Ile  Gly  Thr  Asn  Ser
 1                 5                  10                  15

Val  Gly  Trp  Ala  Val  Thr  Thr  Asp  Asn  Tyr  Lys  Val  Pro  Ser  Lys  Lys  Met
                    20                  25                  30

Lys  Val  Leu  Gly  Asn  Thr  Ser  Lys  Lys  Tyr  Ile  Lys  Lys  Asn  Leu  Leu
            35                  40                  45

Gly  Val  Leu  Leu  Phe  Asp  Ser  Gly  Ile  Thr  Ala  Glu  Gly  Arg  Arg  Leu
        50                  55                  60

Lys  Arg  Thr  Ala  Arg  Arg  Arg  Tyr  Thr  Arg  Arg  Arg  Asn  Arg  Ile  Leu
 65                  70                  75                  80

Tyr  Leu  Gln  Glu  Ile  Phe  Ser  Thr  Glu  Met  Ala  Thr  Leu  Asp  Asp  Ala
                    85                  90                  95

Phe  Phe  Gln  Arg  Leu  Asp  Asp  Ser  Phe  Leu  Val  Pro  Asp  Asp  Lys  Arg
            100                 105                 110

Asp  Ser  Lys  Tyr  Pro  Ile  Phe  Gly  Asn  Leu  Val  Glu  Glu  Lys  Ala  Tyr
        115                 120                 125

His  Asp  Glu  Phe  Pro  Thr  Ile  Tyr  His  Leu  Arg  Lys  Tyr  Leu  Ala  Asp
        130                 135                 140

Ser  Thr  Lys  Lys  Ala  Asp  Leu  Arg  Leu  Val  Tyr  Leu  Ala  Leu  Ala  His
145                 150                 155                 160

Met  Ile  Lys  Tyr  Arg  Gly  His  Phe  Leu  Ile  Glu  Gly  Glu  Phe  Asn  Ser
                    165                 170                 175

Lys  Asn  Asn  Asp  Ile  Gln  Lys  Asn  Phe  Gln  Asp  Phe  Leu  Asp  Thr  Tyr
            180                 185                 190

Asn  Ala  Ile  Phe  Glu  Ser  Asp  Leu  Ser  Leu  Glu  Asn  Ser  Lys  Gln  Leu
        195                 200                 205

Glu  Glu  Ile  Val  Lys  Asp  Lys  Ile  Ser  Lys  Leu  Glu  Lys  Lys  Asp  Arg
        210                 215                 220

Ile  Leu  Lys  Leu  Phe  Pro  Gly  Glu  Lys  Asn  Ser  Gly  Ile  Phe  Ser  Glu
225                 230                 235                 240

Phe  Leu  Lys  Leu  Ile  Val  Gly  Asn  Gln  Ala  Asp  Phe  Arg  Lys  Cys  Phe
                    245                 250                 255

Asn  Leu  Asp  Glu  Lys  Ala  Ser  Leu  His  Phe  Ser  Lys  Glu  Ser  Tyr  Asp
            260                 265                 270

Glu  Asp  Leu  Glu  Thr  Leu  Leu  Gly  Tyr  Ile  Gly  Asp  Asp  Tyr  Ser  Asp
        275                 280                 285

Val  Phe  Leu  Lys  Ala  Lys  Lys  Leu  Tyr  Asp  Ala  Ile  Leu  Leu  Ser  Gly
        290                 295                 300
```

```
Phe Leu Thr Val Thr Asp Asn Glu Thr Glu Ala Pro Leu Ser Ser Ala
305                 310                 315                 320

Met Ile Lys Arg Tyr Asn Glu His Lys Glu Asp Leu Ala Leu Leu Lys
            325                 330                 335

Glu Tyr Ile Arg Asn Ile Ser Leu Lys Thr Tyr Asn Glu Val Phe Lys
                340                 345                 350

Asp Asp Thr Lys Asn Gly Tyr Ala Gly Tyr Ile Asp Gly Lys Thr Asn
                355                 360                 365

Gln Glu Asp Phe Tyr Val Tyr Leu Lys Lys Leu Leu Ala Glu Phe Glu
            370                 375                 380

Gly Ala Asp Tyr Phe Leu Glu Lys Ile Asp Arg Glu Asp Phe Leu Arg
385                 390                 395                 400

Lys Gln Arg Thr Phe Asp Asn Gly Ser Ile Pro Tyr Gln Ile His Leu
                405                 410                 415

Gln Glu Met Arg Ala Ile Leu Asp Lys Gln Ala Lys Phe Tyr Pro Phe
            420                 425                 430

Leu Ala Lys Asn Lys Glu Arg Ile Glu Lys Ile Leu Thr Phe Arg Ile
                435                 440                 445

Pro Tyr Tyr Val Gly Pro Leu Ala Arg Gly Asn Ser Asp Phe Ala Trp
450                 455                 460

Ser Ile Arg Lys Arg Asn Glu Lys Ile Thr Pro Trp Asn Phe Glu Asp
465                 470                 475                 480

Val Ile Asp Lys Glu Ser Ser Ala Glu Ala Phe Ile Asn Arg Met Thr
                485                 490                 495

Ser Phe Asp Leu Tyr Leu Pro Glu Glu Lys Val Leu Pro Lys His Ser
            500                 505                 510

Leu Leu Tyr Glu Thr Phe Asn Val Tyr Asn Glu Leu Thr Lys Val Arg
            515                 520                 525

Phe Ile Ala Glu Ser Met Arg Asp Tyr Gln Phe Leu Asp Ser Lys Gln
            530                 535                 540

Lys Lys Asp Ile Val Arg Leu Tyr Phe Lys Asp Lys Arg Lys Val Thr
545                 550                 555                 560

Asp Lys Asp Ile Ile Glu Tyr Leu His Ala Ile Tyr Gly Tyr Asp Gly
                565                 570                 575

Ile Glu Leu Lys Gly Ile Glu Lys Gln Phe Asn Ser Ser Leu Ser Thr
            580                 585                 590

Tyr His Asp Leu Leu Asn Ile Ile Asn Asp Lys Glu Phe Leu Asp Asp
            595                 600                 605

Ser Ser Asn Glu Ala Ile Ile Glu Glu Ile Ile His Thr Leu Thr Ile
            610                 615                 620

Phe Glu Asp Arg Glu Met Ile Lys Gln Arg Leu Ser Lys Phe Glu Asn
625                 630                 635                 640

Ile Phe Asp Lys Ser Val Leu Lys Lys Leu Ser Arg Arg His Tyr Thr
                645                 650                 655

Gly Trp Gly Lys Leu Ser Ala Lys Leu Ile Asn Gly Ile Arg Asp Glu
            660                 665                 670

Lys Ser Gly Asn Thr Ile Leu Asp Tyr Leu Ile Asp Asp Gly Ile Ser
            675                 680                 685

Asn Arg Asn Phe Met Gln Leu Ile His Asp Asp Ala Leu Ser Phe Lys
            690                 695                 700

Lys Lys Ile Gln Lys Ala Gln Ile Ile Gly Asp Glu Asp Lys Gly Asn
705                 710                 715                 720

Ile Lys Glu Val Val Lys Ser Leu Pro Gly Ser Pro Ala Ile Lys Lys
```

725                 730                 735
Gly Ile Leu Gln Ser Ile Lys Ile Val Asp Glu Leu Val Lys Val Met
                740                 745                 750
Gly Gly Arg Lys Pro Glu Ser Ile Val Val Glu Met Ala Arg Glu Asn
                755                 760                 765
Gln Tyr Thr Asn Gln Gly Lys Ser Asn Ser Gln Gln Arg Leu Lys Arg
                770                 775                 780
Leu Glu Lys Ser Leu Lys Glu Leu Gly Ser Lys Ile Leu Lys Glu Asn
785                 790                 795                 800
Ile Pro Ala Lys Leu Ser Lys Ile Asp Asn Asn Ala Leu Gln Asn Asp
                805                 810                 815
Arg Leu Tyr Leu Tyr Tyr Leu Gln Asn Gly Lys Asp Met Tyr Thr Gly
                820                 825                 830
Asp Asp Leu Asp Ile Asp Arg Leu Ser Asn Tyr Asp Ile Asp His Ile
                835                 840                 845
Ile Pro Gln Ala Phe Leu Lys Asp Asn Ser Ile Asp Asn Lys Val Leu
                850                 855                 860
Val Ser Ser Ala Ser Asn Arg Gly Lys Ser Asp Asp Val Pro Ser Leu
865                 870                 875                 880
Glu Val Val Lys Lys Arg Lys Thr Phe Trp Tyr Gln Leu Leu Lys Ser
                    885                 890                 895
Lys Leu Ile Ser Gln Arg Lys Phe Asp Asn Leu Thr Lys Ala Glu Arg
                900                 905                 910
Gly Gly Leu Ser Pro Glu Asp Lys Ala Gly Phe Ile Gln Arg Gln Leu
                915                 920                 925
Val Glu Thr Arg Gln Ile Thr Lys His Val Ala Arg Leu Leu Asp Glu
                930                 935                 940
Lys Phe Asn Asn Lys Lys Asp Glu Asn Asn Arg Ala Val Arg Thr Val
945                 950                 955                 960
Lys Ile Ile Thr Leu Lys Ser Thr Leu Val Ser Gln Phe Arg Lys Asp
                965                 970                 975
Phe Glu Leu Tyr Lys Val Arg Glu Ile Asn Asp Phe His His Ala His
                980                 985                 990
Asp Ala Tyr Leu Asn Ala Val Val Ala Ser Ala Leu Leu Lys Lys Tyr
                995                 1000                1005
Pro Lys Leu Glu Pro Glu Phe Val Tyr Gly Asp Tyr Pro Lys Tyr
                1010                1015                1020
Asn Ser Phe Arg Glu Arg Lys Ser Ala Thr Glu Lys Val Tyr Phe
                1025                1030                1035
Tyr Ser Asn Ile Met Asn Ile Phe Lys Lys Ser Ile Ser Leu Ala
                1040                1045                1050
Asp Gly Arg Val Ile Glu Arg Pro Leu Ile Glu Val Asn Glu Glu
                1055                1060                1065
Thr Gly Glu Ser Val Trp Asn Lys Glu Ser Asp Leu Ala Thr Val
                1070                1075                1080
Arg Arg Val Leu Ser Tyr Pro Gln Val Asn Val Val Lys Lys Val
                1085                1090                1095
Glu Glu Gln Asn His Gly Leu Asp Arg Gly Lys Pro Lys Gly Leu
                1100                1105                1110
Phe Asn Ala Asn Leu Ser Ser Lys Pro Lys Pro Asn Ser Asn Glu
                1115                1120                1125
Asn Leu Val Gly Ala Lys Glu Tyr Leu Asp Pro Lys Lys Tyr Gly
                1130                1135                1140

-continued

Gly Tyr Ala Gly Ile Ser Asn Ser Phe Thr Val Leu Val Lys Gly
    1145                1150                1155

Thr Ile Glu Lys Gly Ala Lys Lys Ile Thr Asn Val Leu Glu
    1160                1165                1170

Phe Gln Gly Ile Ser Ile Leu Asp Arg Ile Asn Tyr Arg Lys Asp
    1175                1180                1185

Lys Leu Asn Phe Leu Leu Glu Lys Gly Tyr Lys Asp Ile Glu Leu
    1190                1195                1200

Ile Ile Glu Leu Pro Lys Tyr Ser Leu Phe Glu Leu Ser Asp Gly
    1205                1210                1215

Ser Arg Arg Met Leu Ala Ser Ile Leu Ser Thr Asn Asn Lys Arg
    1220                1225                1230

Gly Glu Ile His Lys Gly Asn Gln Ile Phe Leu Ser Gln Lys Phe
    1235                1240                1245

Val Lys Leu Leu Tyr His Ala Lys Arg Ile Ser Asn Thr Ile Asn
    1250                1255                1260

Glu Asn His Arg Lys Tyr Val Glu Asn His Lys Lys Glu Phe Glu
    1265                1270                1275

Glu Leu Phe Tyr Tyr Ile Leu Glu Phe Asn Glu Asn Tyr Val Gly
    1280                1285                1290

Ala Lys Lys Asn Gly Lys Leu Leu Asn Ser Ala Phe Gln Ser Trp
    1295                1300                1305

Gln Asn His Ser Ile Asp Glu Leu Cys Ser Ser Phe Ile Gly Pro
    1310                1315                1320

Thr Gly Ser Glu Arg Lys Gly Leu Phe Glu Leu Thr Ser Arg Gly
    1325                1330                1335

Ser Ala Ala Asp Phe Glu Phe Leu Gly Val Lys Ile Pro Arg Tyr
    1340                1345                1350

Arg Asp Tyr Thr Pro Ser Ser Leu Leu Lys Asp Ala Thr Leu Ile
    1355                1360                1365

His Gln Ser Val Thr Gly Leu Tyr Glu Thr Arg Ile Asp Leu Ala
    1370                1375                1380

Lys Leu Gly Glu Gly
    1385

<210> SEQ ID NO 3
<211> LENGTH: 1345
<212> TYPE: PRT
<213> ORGANISM: Streptococcus mutans

<400> SEQUENCE: 3

Met Lys Lys Pro Tyr Ser Ile Gly Leu Asp Ile Gly Thr Asn Ser Val
1               5                   10                  15

Gly Trp Ala Val Val Thr Asp Asp Tyr Lys Val Pro Ala Lys Lys Met
            20                  25                  30

Lys Val Leu Gly Asn Thr Asp Lys Ser His Ile Glu Lys Asn Leu Leu
        35                  40                  45

Gly Ala Leu Leu Phe Asp Ser Gly Asn Thr Ala Glu Asp Arg Arg Leu
    50                  55                  60

Lys Arg Thr Ala Arg Arg Arg Tyr Thr Arg Arg Arg Asn Arg Ile Leu
65                  70                  75                  80

Tyr Leu Gln Glu Ile Phe Ser Glu Glu Met Gly Lys Val Asp Asp Ser
                85                  90                  95

Phe Phe His Arg Leu Glu Asp Ser Phe Leu Val Thr Glu Asp Lys Arg

-continued

```
                100             105             110
Gly Glu Arg His Pro Ile Phe Gly Asn Leu Glu Glu Val Lys Tyr
            115                 120             125
His Glu Asn Phe Pro Thr Ile Tyr His Leu Arg Gln Tyr Leu Ala Asp
            130                 135             140
Asn Pro Glu Lys Val Asp Leu Arg Leu Val Tyr Leu Ala Leu Ala His
145                 150                 155                 160
Ile Ile Lys Phe Arg Gly His Phe Leu Ile Glu Gly Lys Phe Asp Thr
                165                 170                 175
Arg Asn Asn Asp Val Gln Arg Leu Phe Gln Glu Phe Leu Ala Val Tyr
                180                 185                 190
Asp Asn Thr Phe Glu Asn Ser Ser Leu Gln Glu Gln Asn Val Gln Val
                195                 200                 205
Glu Glu Ile Leu Thr Asp Lys Ile Ser Lys Ser Ala Lys Lys Asp Arg
            210                 215                 220
Val Leu Lys Leu Phe Pro Asn Glu Lys Ser Asn Gly Arg Phe Ala Glu
225                 230                 235                 240
Phe Leu Lys Leu Ile Val Gly Asn Gln Ala Asp Phe Lys Lys His Phe
                245                 250                 255
Glu Leu Glu Glu Lys Ala Pro Leu Gln Phe Ser Lys Asp Thr Tyr Glu
            260                 265                 270
Glu Glu Leu Glu Val Leu Leu Ala Gln Ile Gly Asp Asn Tyr Ala Glu
            275                 280                 285
Leu Phe Leu Ser Ala Lys Lys Leu Tyr Asp Ser Ile Leu Leu Ser Gly
            290                 295                 300
Ile Leu Thr Val Thr Asp Val Gly Thr Lys Ala Pro Leu Ser Ala Ser
305                 310                 315                 320
Met Ile Gln Arg Tyr Asn Glu His Gln Met Asp Leu Ala Gln Leu Lys
                325                 330                 335
Gln Phe Ile Arg Gln Lys Leu Ser Asp Lys Tyr Asn Glu Val Phe Ser
                340                 345                 350
Asp Val Ser Lys Asp Gly Tyr Ala Gly Tyr Ile Asp Gly Lys Thr Asn
                355                 360                 365
Gln Glu Ala Phe Tyr Lys Tyr Leu Lys Gly Leu Leu Asn Lys Ile Glu
            370                 375                 380
Gly Ser Gly Tyr Phe Leu Asp Lys Ile Glu Arg Glu Asp Phe Leu Arg
385                 390                 395                 400
Lys Gln Arg Thr Phe Asp Asn Gly Ser Ile Pro His Gln Ile His Leu
                405                 410                 415
Gln Glu Met Arg Ala Ile Ile Arg Arg Gln Ala Glu Phe Tyr Pro Phe
                420                 425                 430
Leu Ala Asp Asn Gln Asp Arg Ile Glu Lys Leu Leu Thr Phe Arg Ile
                435                 440                 445
Pro Tyr Tyr Val Gly Pro Leu Ala Arg Gly Lys Ser Asp Phe Ala Trp
            450                 455                 460
Leu Ser Arg Lys Ser Ala Asp Lys Ile Thr Pro Trp Asn Phe Asp Glu
465                 470                 475                 480
Ile Val Asp Lys Glu Ser Ser Ala Glu Ala Phe Ile Asn Arg Met Thr
                485                 490                 495
Asn Tyr Asp Leu Tyr Leu Pro Asn Gln Lys Val Leu Pro Lys His Ser
                500                 505                 510
Leu Leu Tyr Glu Lys Phe Thr Val Tyr Asn Glu Leu Thr Lys Val Lys
            515                 520                 525
```

Tyr Lys Thr Glu Gln Gly Lys Thr Ala Phe Phe Asp Ala Asn Met Lys
    530                 535                 540

Gln Glu Ile Phe Asp Gly Val Phe Lys Val Tyr Arg Lys Val Thr Lys
545                 550                 555                 560

Asp Lys Leu Met Asp Phe Leu Glu Lys Glu Phe Asp Glu Phe Arg Ile
                565                 570                 575

Val Asp Leu Thr Gly Leu Asp Lys Glu Asn Lys Val Phe Asn Ala Ser
            580                 585                 590

Tyr Gly Thr Tyr His Asp Leu Cys Lys Ile Leu Asp Lys Asp Phe Leu
        595                 600                 605

Asp Asn Ser Lys Asn Glu Lys Ile Leu Glu Asp Ile Val Leu Thr Leu
    610                 615                 620

Thr Leu Phe Glu Asp Arg Glu Met Ile Arg Lys Arg Leu Glu Asn Tyr
625                 630                 635                 640

Ser Asp Leu Leu Thr Lys Glu Gln Val Lys Lys Leu Glu Arg Arg His
                645                 650                 655

Tyr Thr Gly Trp Gly Arg Leu Ser Ala Glu Leu Ile His Gly Ile Arg
            660                 665                 670

Asn Lys Glu Ser Arg Lys Thr Ile Leu Asp Tyr Leu Ile Asp Asp Gly
        675                 680                 685

Asn Ser Asn Arg Asn Phe Met Gln Leu Ile Asn Asp Asp Ala Leu Ser
    690                 695                 700

Phe Lys Glu Glu Ile Ala Lys Ala Gln Val Ile Gly Glu Thr Asp Asn
705                 710                 715                 720

Leu Asn Gln Val Val Ser Asp Ile Ala Gly Ser Pro Ala Ile Lys Lys
                725                 730                 735

Gly Ile Leu Gln Ser Leu Lys Ile Val Asp Glu Leu Val Lys Ile Met
            740                 745                 750

Gly His Gln Pro Glu Asn Ile Val Val Glu Met Ala Arg Glu Asn Gln
        755                 760                 765

Phe Thr Asn Gln Gly Arg Arg Asn Ser Gln Gln Arg Leu Lys Gly Leu
    770                 775                 780

Thr Asp Ser Ile Lys Glu Phe Gly Ser Gln Ile Leu Lys Glu His Pro
785                 790                 795                 800

Val Glu Asn Ser Gln Leu Gln Asn Asp Arg Leu Phe Leu Tyr Tyr Leu
                805                 810                 815

Gln Asn Gly Arg Asp Met Tyr Thr Gly Glu Glu Leu Asp Ile Asp Tyr
            820                 825                 830

Leu Ser Gln Tyr Asp Ile Asp His Ile Ile Pro Gln Ala Phe Ile Lys
        835                 840                 845

Asp Asn Ser Ile Asp Asn Arg Val Leu Thr Ser Ser Lys Glu Asn Arg
    850                 855                 860

Gly Lys Ser Asp Asp Val Pro Ser Lys Asp Val Val Arg Lys Met Lys
865                 870                 875                 880

Ser Tyr Trp Ser Lys Leu Leu Ser Ala Lys Leu Ile Thr Gln Arg Lys
                885                 890                 895

Phe Asp Asn Leu Thr Lys Ala Glu Arg Gly Gly Leu Thr Asp Asp Asp
            900                 905                 910

Lys Ala Gly Phe Ile Lys Arg Gln Leu Val Glu Thr Arg Gln Ile Thr
        915                 920                 925

Lys His Val Ala Arg Ile Leu Asp Glu Arg Phe Asn Thr Glu Thr Asp
    930                 935                 940

-continued

```
Glu Asn Asn Lys Lys Ile Arg Gln Val Lys Ile Val Thr Leu Lys Ser
945                 950                 955                 960

Asn Leu Val Ser Asn Phe Arg Lys Glu Phe Glu Leu Tyr Lys Val Arg
                965                 970                 975

Glu Ile Asn Asp Tyr His His Ala His Asp Ala Tyr Leu Asn Ala Val
                980                 985                 990

Ile Gly Lys Ala Leu Leu Gly Val Tyr Pro Gln Leu Glu Pro Glu Phe
        995                 1000                1005

Val Tyr Gly Asp Tyr Pro His Phe His Gly His Lys Glu Asn Lys
    1010                1015                1020

Ala Thr Ala Lys Lys Phe Phe Tyr Ser Asn Ile Met Asn Phe Phe
    1025                1030                1035

Lys Lys Asp Asp Val Arg Thr Asp Lys Asn Gly Glu Ile Ile Trp
    1040                1045                1050

Lys Lys Asp Glu His Ile Ser Asn Ile Lys Lys Val Leu Ser Tyr
    1055                1060                1065

Pro Gln Val Asn Ile Val Lys Lys Val Glu Glu Gln Thr Gly Gly
    1070                1075                1080

Phe Ser Lys Glu Ser Ile Leu Pro Lys Gly Asn Ser Asp Lys Leu
    1085                1090                1095

Ile Pro Arg Lys Thr Lys Lys Phe Tyr Trp Asp Thr Lys Lys Tyr
    1100                1105                1110

Gly Gly Phe Asp Ser Pro Ile Val Ala Tyr Ser Ile Leu Val Ile
    1115                1120                1125

Ala Asp Ile Glu Lys Gly Lys Ser Lys Lys Leu Lys Thr Val Lys
    1130                1135                1140

Ala Leu Val Gly Val Thr Ile Met Glu Lys Met Thr Phe Glu Arg
    1145                1150                1155

Asp Pro Val Ala Phe Leu Glu Arg Lys Gly Tyr Arg Asn Val Gln
    1160                1165                1170

Glu Glu Asn Ile Ile Lys Leu Pro Lys Tyr Ser Leu Phe Lys Leu
    1175                1180                1185

Glu Asn Gly Arg Lys Arg Leu Leu Ala Ser Ala Arg Glu Leu Gln
    1190                1195                1200

Lys Gly Asn Glu Ile Val Leu Pro Asn His Leu Gly Thr Leu Leu
    1205                1210                1215

Tyr His Ala Lys Asn Ile His Lys Val Asp Glu Pro Lys His Leu
    1220                1225                1230

Asp Tyr Val Asp Lys His Lys Asp Glu Phe Lys Glu Leu Leu Asp
    1235                1240                1245

Val Val Ser Asn Phe Ser Lys Lys Tyr Thr Leu Ala Glu Gly Asn
    1250                1255                1260

Leu Glu Lys Ile Lys Glu Leu Tyr Ala Gln Asn Asn Gly Glu Asp
    1265                1270                1275

Leu Lys Glu Leu Ala Ser Ser Phe Ile Asn Leu Leu Thr Phe Thr
    1280                1285                1290

Ala Ile Gly Ala Pro Ala Thr Phe Lys Phe Phe Asp Lys Asn Ile
    1295                1300                1305

Asp Arg Lys Arg Tyr Thr Ser Thr Thr Glu Ile Leu Asn Ala Thr
    1310                1315                1320

Leu Ile His Gln Ser Ile Thr Gly Leu Tyr Glu Thr Arg Ile Asp
    1325                1330                1335

Leu Asn Lys Leu Gly Gly Asp
```

1340              1345

<210> SEQ ID NO 4
<211> LENGTH: 984
<212> TYPE: PRT
<213> ORGANISM: Campylobacter jejuni

<400> SEQUENCE: 4

Met Ala Arg Ile Leu Ala Phe Asp Ile Gly Ile Ser Ser Ile Gly Trp
1               5                   10                  15

Ala Phe Ser Glu Asn Asp Glu Leu Lys Asp Cys Gly Val Arg Ile Phe
                20                  25                  30

Thr Lys Val Glu Asn Pro Lys Thr Gly Glu Ser Leu Ala Leu Pro Arg
            35                  40                  45

Arg Leu Ala Arg Ser Ala Arg Lys Arg Leu Ala Arg Arg Lys Ala Arg
        50                  55                  60

Leu Asn His Leu Lys His Leu Ile Ala Asn Glu Phe Lys Leu Asn Tyr
65                  70                  75                  80

Glu Asp Tyr Gln Ser Phe Asp Glu Ser Leu Ala Lys Ala Tyr Lys Gly
                85                  90                  95

Ser Leu Ile Ser Pro Tyr Glu Leu Arg Phe Arg Ala Leu Asn Glu Leu
            100                 105                 110

Leu Ser Lys Gln Asp Phe Ala Arg Val Ile Leu His Ile Ala Lys Arg
        115                 120                 125

Arg Gly Tyr Asp Asp Ile Lys Asn Ser Asp Asp Lys Glu Lys Gly Ala
130                 135                 140

Ile Leu Lys Ala Ile Lys Gln Asn Glu Glu Lys Leu Ala Asn Tyr Gln
145                 150                 155                 160

Ser Val Gly Glu Tyr Leu Tyr Lys Glu Tyr Phe Gln Lys Phe Lys Glu
                165                 170                 175

Asn Ser Lys Glu Phe Thr Asn Val Arg Asn Lys Lys Glu Ser Tyr Glu
            180                 185                 190

Arg Cys Ile Ala Gln Ser Phe Leu Lys Asp Glu Leu Lys Leu Ile Phe
        195                 200                 205

Lys Lys Gln Arg Glu Phe Gly Phe Ser Phe Ser Lys Lys Phe Glu Glu
    210                 215                 220

Glu Val Leu Ser Val Ala Phe Tyr Lys Arg Ala Leu Lys Asp Phe Ser
225                 230                 235                 240

His Leu Val Gly Asn Cys Ser Phe Phe Thr Asp Glu Lys Arg Ala Pro
                245                 250                 255

Lys Asn Ser Pro Leu Ala Phe Met Phe Val Ala Leu Thr Arg Ile Ile
            260                 265                 270

Asn Leu Leu Asn Asn Leu Lys Asn Thr Glu Gly Ile Leu Tyr Thr Lys
        275                 280                 285

Asp Asp Leu Asn Ala Leu Leu Asn Glu Val Leu Lys Asn Gly Thr Leu
    290                 295                 300

Thr Tyr Lys Gln Thr Lys Lys Leu Leu Gly Leu Ser Asp Asp Tyr Glu
305                 310                 315                 320

Phe Lys Gly Glu Lys Gly Thr Tyr Phe Ile Glu Phe Lys Lys Tyr Lys
                325                 330                 335

Glu Phe Ile Lys Ala Leu Gly Glu His Asn Leu Ser Gln Asp Asp Leu
            340                 345                 350

Asn Glu Ile Ala Lys Asp Ile Thr Leu Ile Lys Asp Glu Ile Lys Leu
        355                 360                 365

-continued

```
Lys Lys Ala Leu Ala Lys Tyr Asp Leu Asn Gln Asn Gln Ile Asp Ser
370                 375                 380

Leu Ser Lys Leu Glu Phe Lys Asp His Leu Asn Ile Ser Phe Lys Ala
385                 390                 395                 400

Leu Lys Leu Val Thr Pro Leu Met Leu Glu Gly Lys Lys Tyr Asp Glu
                405                 410                 415

Ala Cys Asn Glu Leu Asn Leu Lys Val Ala Ile Asn Glu Asp Lys Lys
                420                 425                 430

Asp Phe Leu Pro Ala Phe Asn Glu Thr Tyr Tyr Lys Asp Glu Val Thr
            435                 440                 445

Asn Pro Val Val Leu Arg Ala Ile Lys Glu Tyr Arg Lys Val Leu Asn
450                 455                 460

Ala Leu Leu Lys Lys Tyr Gly Lys Val His Lys Ile Asn Ile Glu Leu
465                 470                 475                 480

Ala Arg Glu Val Gly Lys Asn His Ser Gln Arg Ala Lys Ile Glu Lys
                485                 490                 495

Glu Gln Asn Glu Asn Tyr Lys Ala Lys Lys Asp Ala Glu Leu Glu Cys
                500                 505                 510

Glu Lys Leu Gly Leu Lys Ile Asn Ser Lys Asn Ile Leu Lys Leu Arg
                515                 520                 525

Leu Phe Lys Glu Gln Lys Glu Phe Cys Ala Tyr Ser Gly Glu Lys Ile
530                 535                 540

Lys Ile Ser Asp Leu Gln Asp Glu Lys Met Leu Glu Ile Asp His Ile
545                 550                 555                 560

Tyr Pro Tyr Ser Arg Ser Phe Asp Asp Ser Tyr Met Asn Lys Val Leu
                565                 570                 575

Val Phe Thr Lys Gln Asn Gln Glu Lys Leu Asn Gln Thr Pro Phe Glu
                580                 585                 590

Ala Phe Gly Asn Asp Ser Ala Lys Trp Gln Lys Ile Glu Val Leu Ala
            595                 600                 605

Lys Asn Leu Pro Thr Lys Lys Gln Lys Arg Ile Leu Asp Lys Asn Tyr
            610                 615                 620

Lys Asp Lys Glu Gln Lys Asn Phe Lys Asp Arg Asn Leu Asn Asp Thr
625                 630                 635                 640

Arg Tyr Ile Ala Arg Leu Val Leu Asn Tyr Thr Lys Asp Tyr Leu Asp
                645                 650                 655

Phe Leu Pro Leu Ser Asp Asp Glu Asn Thr Lys Leu Asn Asp Thr Gln
            660                 665                 670

Lys Gly Ser Lys Val His Val Glu Ala Lys Ser Gly Met Leu Thr Ser
            675                 680                 685

Ala Leu Arg His Thr Trp Gly Phe Ser Ala Lys Asp Arg Asn Asn His
690                 695                 700

Leu His His Ala Ile Asp Ala Val Ile Ile Ala Tyr Ala Asn Asn Ser
705                 710                 715                 720

Ile Val Lys Ala Phe Ser Asp Phe Lys Lys Glu Gln Glu Ser Asn Ser
                725                 730                 735

Ala Glu Leu Tyr Ala Lys Lys Ile Ser Glu Leu Asp Tyr Lys Asn Lys
            740                 745                 750

Arg Lys Phe Phe Glu Pro Phe Ser Gly Phe Arg Gln Lys Val Leu Asp
            755                 760                 765

Lys Ile Asp Glu Ile Phe Val Ser Lys Pro Glu Arg Lys Lys Pro Ser
770                 775                 780

Gly Ala Leu His Glu Glu Thr Phe Arg Lys Glu Glu Glu Phe Tyr Gln
```

```
             785                 790                 795                 800
        Ser Tyr Gly Gly Lys Glu Gly Val Leu Lys Ala Leu Glu Leu Gly Lys
                        805                 810                 815

Ile Arg Lys Val Asn Gly Lys Ile Val Lys Asn Gly Asp Met Phe Arg
                        820                 825                 830

Val Asp Ile Phe Lys His Lys Lys Thr Asn Lys Phe Tyr Ala Val Pro
                        835                 840                 845

Ile Tyr Thr Met Asp Phe Ala Leu Lys Val Leu Pro Asn Lys Ala Val
                        850                 855                 860

Ala Arg Ser Lys Lys Gly Glu Ile Lys Asp Trp Ile Leu Met Asp Glu
        865                 870                 875                 880

Asn Tyr Glu Phe Cys Phe Ser Leu Tyr Lys Asp Ser Leu Ile Leu Ile
                        885                 890                 895

Gln Thr Lys Asp Met Gln Glu Pro Glu Phe Val Tyr Tyr Asn Ala Phe
                        900                 905                 910

Thr Ser Ser Thr Val Ser Leu Ile Val Ser Lys His Asp Asn Lys Phe
                        915                 920                 925

Glu Thr Leu Ser Lys Asn Gln Lys Ile Leu Phe Lys Asn Ala Asn Glu
                        930                 935                 940

Lys Glu Val Ile Ala Lys Ser Ile Gly Ile Gln Asn Leu Lys Val Phe
        945                 950                 955                 960

Glu Lys Tyr Ile Val Ser Ala Leu Gly Glu Val Thr Lys Ala Glu Phe
                        965                 970                 975

Arg Gln Arg Glu Asp Phe Lys Lys
                        980

<210> SEQ ID NO 5
<211> LENGTH: 1082
<212> TYPE: PRT
<213> ORGANISM: Neisseria meningitides

<400> SEQUENCE: 5

Met Ala Ala Phe Lys Pro Asn Ser Ile Asn Tyr Ile Leu Gly Leu Asp
1               5                   10                  15

Ile Gly Ile Ala Ser Val Gly Trp Ala Met Val Glu Ile Asp Glu Glu
                20                  25                  30

Glu Asn Pro Ile Arg Leu Ile Asp Leu Gly Val Arg Val Phe Glu Arg
                35                  40                  45

Ala Glu Val Pro Lys Thr Gly Asp Ser Leu Ala Met Ala Arg Arg Leu
        50                  55                  60

Ala Arg Ser Val Arg Arg Leu Thr Arg Arg Arg Ala His Arg Leu Leu
65                  70                  75                  80

Arg Thr Arg Arg Leu Leu Lys Arg Glu Gly Val Leu Gln Ala Ala Asn
                85                  90                  95

Phe Asp Glu Asn Gly Leu Ile Lys Ser Leu Pro Asn Thr Pro Trp Gln
                100                 105                 110

Leu Arg Ala Ala Ala Leu Asp Arg Lys Leu Thr Pro Leu Glu Trp Ser
                115                 120                 125

Ala Val Leu Leu His Leu Ile Lys His Arg Gly Tyr Leu Ser Gln Arg
                130                 135                 140

Lys Asn Glu Gly Glu Thr Ala Asp Lys Glu Leu Gly Ala Leu Leu Lys
145                 150                 155                 160

Gly Val Ala Gly Asn Ala His Ala Leu Gln Thr Gly Asp Phe Arg Thr
                165                 170                 175
```

-continued

```
Pro Ala Glu Leu Ala Leu Asn Lys Phe Glu Lys Glu Ser Gly His Ile
            180                 185                 190

Arg Asn Gln Arg Ser Asp Tyr Ser His Thr Phe Ser Arg Lys Asp Leu
        195                 200                 205

Gln Ala Glu Leu Ile Leu Leu Phe Glu Lys Gln Lys Glu Phe Gly Asn
    210                 215                 220

Pro His Val Ser Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
                245                 250                 255

His Cys Thr Phe Glu Pro Ala Glu Pro Lys Ala Ala Lys Asn Thr Tyr
            260                 265                 270

Thr Ala Glu Arg Phe Ile Trp Leu Thr Lys Leu Asn Asn Leu Arg Ile
        275                 280                 285

Leu Glu Gln Gly Ser Glu Arg Pro Leu Thr Asp Thr Glu Arg Ala Thr
    290                 295                 300

Leu Met Asp Glu Pro Tyr Arg Lys Ser Lys Leu Thr Tyr Ala Gln Ala
305                 310                 315                 320

Arg Lys Leu Leu Gly Leu Glu Asp Thr Ala Phe Phe Lys Gly Leu Arg
                325                 330                 335

Tyr Gly Lys Asp Asn Ala Glu Ala Ser Thr Leu Met Glu Met Lys Ala
            340                 345                 350

Tyr His Ala Ile Ser Arg Ala Leu Glu Lys Glu Gly Leu Lys Asp Lys
        355                 360                 365

Lys Ser Pro Leu Asn Leu Ser Pro Glu Leu Gln Asp Glu Ile Gly Thr
    370                 375                 380

Ala Phe Ser Leu Phe Lys Thr Asp Glu Asp Ile Thr Gly Arg Leu Lys
385                 390                 395                 400

Asp Arg Ile Gln Pro Glu Ile Leu Glu Ala Leu Leu Lys His Ile Ser
                405                 410                 415

Phe Asp Lys Phe Val Gln Ile Ser Leu Lys Ala Leu Arg Arg Ile Val
            420                 425                 430

Pro Leu Met Glu Gln Gly Lys Arg Tyr Asp Glu Ala Cys Ala Glu Ile
        435                 440                 445

Tyr Gly Asp His Tyr Gly Lys Lys Asn Thr Glu Glu Lys Ile Tyr Leu
    450                 455                 460

Pro Pro Ile Pro Ala Asp Glu Ile Arg Asn Pro Val Val Leu Arg Ala
465                 470                 475                 480

Leu Ser Gln Ala Arg Lys Val Ile Asn Gly Val Val Arg Arg Tyr Gly
                485                 490                 495

Ser Pro Ala Arg Ile His Ile Glu Thr Ala Arg Glu Val Gly Lys Ser
            500                 505                 510

Phe Lys Asp Arg Lys Glu Ile Glu Lys Arg Gln Glu Glu Asn Arg Lys
        515                 520                 525

Asp Arg Glu Lys Ala Ala Ala Lys Phe Arg Glu Tyr Phe Pro Asn Phe
    530                 535                 540

Val Gly Glu Pro Lys Ser Lys Asp Ile Leu Lys Leu Arg Leu Tyr Glu
545                 550                 555                 560

Gln Gln His Gly Lys Cys Leu Tyr Ser Gly Lys Glu Ile Asn Leu Gly
                565                 570                 575

Arg Leu Asn Glu Lys Gly Tyr Val Glu Ile Asp His Ala Leu Pro Phe
            580                 585                 590

Ser Arg Thr Trp Asp Asp Ser Phe Asn Asn Lys Val Leu Val Leu Gly
```

```
                    595                 600                 605
Ser Glu Asn Gln Asn Lys Gly Asn Gln Thr Pro Tyr Glu Tyr Phe Asn
610                 615                 620

Gly Lys Asp Asn Ser Arg Glu Trp Gln Glu Phe Lys Ala Arg Val Glu
625                 630                 635                 640

Thr Ser Arg Phe Pro Arg Ser Lys Lys Gln Arg Ile Leu Leu Gln Lys
                    645                 650                 655

Phe Asp Glu Asp Gly Phe Lys Glu Arg Asn Leu Asn Asp Thr Arg Tyr
            660                 665                 670

Val Asn Arg Phe Leu Cys Gln Phe Val Ala Asp Arg Met Arg Leu Thr
            675                 680                 685

Gly Lys Gly Lys Lys Arg Val Phe Ala Ser Asn Gly Gln Ile Thr Asn
            690                 695                 700

Leu Leu Arg Gly Phe Trp Gly Leu Arg Lys Val Arg Ala Glu Asn Asp
705                 710                 715                 720

Arg His His Ala Leu Asp Ala Val Val Ala Cys Ser Thr Val Ala
            725                 730                 735

Met Gln Gln Lys Ile Thr Arg Phe Val Arg Tyr Lys Glu Met Asn Ala
                    740                 745                 750

Phe Asp Gly Lys Thr Ile Asp Lys Glu Thr Gly Glu Val Leu His Gln
            755                 760                 765

Lys Thr His Phe Pro Gln Pro Trp Glu Phe Phe Ala Gln Glu Val Met
770                 775                 780

Ile Arg Val Phe Gly Lys Pro Asp Gly Lys Pro Glu Phe Glu Ala
785                 790                 795                 800

Asp Thr Leu Glu Lys Leu Arg Thr Leu Leu Ala Glu Lys Leu Ser Ser
            805                 810                 815

Arg Pro Glu Ala Val His Glu Tyr Val Thr Pro Leu Phe Val Ser Arg
            820                 825                 830

Ala Pro Asn Arg Lys Met Ser Gly Gln Gly His Met Glu Thr Val Lys
            835                 840                 845

Ser Ala Lys Arg Leu Asp Glu Gly Val Ser Val Leu Arg Val Pro Leu
850                 855                 860

Thr Gln Leu Lys Leu Lys Asp Leu Glu Lys Met Val Asn Arg Glu Arg
865                 870                 875                 880

Glu Pro Lys Leu Tyr Glu Ala Leu Lys Ala Arg Leu Glu Ala His Lys
                    885                 890                 895

Asp Asp Pro Ala Lys Ala Phe Ala Glu Pro Phe Tyr Lys Tyr Asp Lys
            900                 905                 910

Ala Gly Asn Arg Thr Gln Gln Val Lys Ala Val Arg Val Glu Gln Val
            915                 920                 925

Gln Lys Thr Gly Val Trp Val Arg Asn His Asn Gly Ile Ala Asp Asn
            930                 935                 940

Ala Thr Met Val Arg Val Asp Val Phe Glu Lys Gly Asp Lys Tyr Tyr
945                 950                 955                 960

Leu Val Pro Ile Tyr Ser Trp Gln Val Ala Lys Gly Ile Leu Pro Asp
                    965                 970                 975

Arg Ala Val Val Gln Gly Lys Asp Glu Glu Asp Trp Gln Leu Ile Asp
            980                 985                 990

Asp Ser Phe Asn Phe Lys Phe Ser Leu His Pro Asn Asp Leu Val Glu
            995                 1000                1005

Val Ile Thr Lys Lys Ala Arg Met Phe Gly Tyr Phe Ala Ser Cys
            1010                1015                1020
```

-continued

```
His Arg Gly Thr Gly Asn Ile Asn Ile Arg Ile His Asp Leu Asp
    1025                1030                1035

His Lys Ile Gly Lys Asn Gly Ile Leu Glu Gly Ile Gly Val Lys
    1040                1045                1050

Thr Ala Leu Ser Phe Gln Lys Tyr Gln Ile Asp Glu Leu Gly Lys
    1055                1060                1065

Glu Ile Arg Pro Cys Arg Leu Lys Lys Arg Pro Pro Val Arg
    1070                1075                1080

<210> SEQ ID NO 6
<211> LENGTH: 1629
<212> TYPE: PRT
<213> ORGANISM: Francisella tularensis

<400> SEQUENCE: 6

Met Asn Phe Lys Ile Leu Pro Ile Ala Ile Asp Leu Gly Val Lys Asn
1               5                   10                  15

Thr Gly Val Phe Ser Ala Phe Tyr Gln Lys Gly Thr Ser Leu Glu Arg
            20                  25                  30

Leu Asp Asn Lys Asn Gly Lys Val Tyr Glu Leu Ser Lys Asp Ser Tyr
        35                  40                  45

Thr Leu Leu Met Asn Asn Arg Thr Ala Arg Arg His Gln Arg Arg Gly
    50                  55                  60

Ile Asp Arg Lys Gln Leu Val Lys Arg Leu Phe Lys Leu Ile Trp Thr
65                  70                  75                  80

Glu Gln Leu Asn Leu Glu Trp Asp Lys Asp Thr Gln Gln Ala Ile Ser
                85                  90                  95

Phe Leu Phe Asn Arg Arg Gly Phe Ser Phe Ile Thr Asp Gly Tyr Ser
            100                 105                 110

Pro Glu Tyr Leu Asn Ile Val Pro Glu Gln Val Lys Ala Ile Leu Met
        115                 120                 125

Asp Ile Phe Asp Asp Tyr Asn Gly Glu Asp Asp Leu Asp Ser Tyr Leu
    130                 135                 140

Lys Leu Ala Thr Glu Gln Glu Ser Lys Ile Ser Glu Ile Tyr Asn Lys
145                 150                 155                 160

Leu Met Gln Lys Ile Leu Glu Phe Lys Leu Met Lys Leu Cys Thr Asp
                165                 170                 175

Ile Lys Asp Asp Lys Val Ser Thr Lys Thr Leu Lys Glu Ile Thr Ser
            180                 185                 190

Tyr Glu Phe Glu Leu Leu Ala Asp Tyr Leu Ala Asn Tyr Ser Glu Ser
        195                 200                 205

Leu Lys Thr Gln Lys Phe Ser Tyr Thr Asp Lys Gln Gly Asn Leu Lys
    210                 215                 220

Glu Leu Ser Tyr Tyr His His Asp Lys Tyr Asn Ile Gln Glu Phe Leu
225                 230                 235                 240

Lys Arg His Ala Thr Ile Asn Asp Arg Ile Leu Asp Thr Leu Leu Thr
                245                 250                 255

Asp Asp Leu Asp Ile Trp Asn Phe Asn Phe Glu Lys Phe Asp Phe Asp
            260                 265                 270

Lys Asn Glu Glu Lys Leu Gln Asn Gln Glu Asp Lys Asp His Ile Gln
        275                 280                 285

Ala His Leu His His Phe Val Phe Ala Val Asn Lys Ile Lys Ser Glu
    290                 295                 300

Met Ala Ser Gly Gly Arg His Arg Ser Gln Tyr Phe Gln Glu Ile Thr
```

```
                305                 310                 315                 320
        Asn Val Leu Asp Glu Asn Asn His Gln Glu Gly Tyr Leu Lys Asn Phe
                        325                 330                 335
        Cys Glu Asn Leu His Asn Lys Lys Tyr Ser Asn Leu Ser Val Lys Asn
                        340                 345                 350
        Leu Val Asn Leu Ile Gly Asn Leu Ser Asn Leu Glu Leu Lys Pro Leu
                        355                 360                 365
        Arg Lys Tyr Phe Asn Asp Lys Ile His Ala Lys Ala Asp His Trp Asp
                        370                 375                 380
        Glu Gln Lys Phe Thr Glu Thr Tyr Cys His Trp Ile Leu Gly Glu Trp
        385                 390                 395                 400
        Arg Val Gly Val Lys Asp Gln Asp Lys Lys Asp Gly Ala Lys Tyr Ser
                            405                 410                 415
        Tyr Lys Asp Leu Cys Asn Glu Leu Lys Gln Lys Val Thr Lys Ala Gly
                        420                 425                 430
        Leu Val Asp Phe Leu Leu Glu Leu Asp Pro Cys Arg Thr Ile Pro Pro
                        435                 440                 445
        Tyr Leu Asp Asn Asn Arg Lys Pro Pro Lys Cys Gln Ser Leu Ile
                        450                 455                 460
        Leu Asn Pro Lys Phe Leu Asp Asn Gln Tyr Pro Asn Trp Gln Gln Tyr
        465                 470                 475                 480
        Leu Gln Glu Leu Lys Lys Leu Gln Ser Ile Gln Asn Tyr Leu Asp Ser
                            485                 490                 495
        Phe Glu Thr Asp Leu Lys Val Leu Lys Ser Ser Lys Asp Gln Pro Tyr
                        500                 505                 510
        Phe Val Glu Tyr Lys Ser Ser Asn Gln Gln Ile Ala Ser Gly Gln Arg
                        515                 520                 525
        Asp Tyr Lys Asp Leu Asp Ala Arg Ile Leu Gln Phe Ile Phe Asp Arg
                        530                 535                 540
        Val Lys Ala Ser Asp Glu Leu Leu Leu Asn Glu Ile Tyr Phe Gln Ala
        545                 550                 555                 560
        Lys Lys Leu Lys Gln Lys Ala Ser Ser Glu Leu Glu Lys Leu Glu Ser
                            565                 570                 575
        Ser Lys Lys Leu Asp Glu Val Ile Ala Asn Ser Gln Leu Ser Gln Ile
                        580                 585                 590
        Leu Lys Ser Gln His Thr Asn Gly Ile Phe Glu Gln Gly Thr Phe Leu
                        595                 600                 605
        His Leu Val Cys Lys Tyr Tyr Lys Gln Arg Gln Arg Ala Arg Asp Ser
                        610                 615                 620
        Arg Leu Tyr Ile Met Pro Glu Tyr Arg Tyr Asp Lys Lys Leu His Lys
        625                 630                 635                 640
        Tyr Asn Asn Thr Gly Arg Phe Asp Asp Asn Gln Leu Leu Thr Tyr
                            645                 650                 655
        Cys Asn His Lys Pro Arg Gln Lys Arg Tyr Gln Leu Leu Asn Asp Leu
                        660                 665                 670
        Ala Gly Val Leu Gln Val Ser Pro Asn Phe Leu Lys Asp Lys Ile Gly
                        675                 680                 685
        Ser Asp Asp Asp Leu Phe Ile Ser Lys Trp Leu Val Glu His Ile Arg
                        690                 695                 700
        Gly Phe Lys Lys Ala Cys Glu Asp Ser Leu Lys Ile Gln Lys Asp Asn
        705                 710                 715                 720
        Arg Gly Leu Leu Asn His Lys Ile Asn Ile Ala Arg Asn Thr Lys Gly
                            725                 730                 735
```

Lys Cys Glu Lys Glu Ile Phe Asn Leu Ile Cys Lys Ile Glu Gly Ser
                740                 745                 750

Glu Asp Lys Lys Gly Asn Tyr Lys His Gly Leu Ala Tyr Glu Leu Gly
                755                 760                 765

Val Leu Leu Phe Gly Pro Asn Glu Ala Ser Lys Pro Glu Phe Asp
770                 775                 780

Arg Lys Ile Lys Lys Phe Asn Ser Ile Tyr Ser Phe Ala Gln Ile Gln
785                 790                 795                 800

Gln Ile Ala Phe Ala Glu Arg Lys Gly Asn Ala Asn Thr Cys Ala Val
                805                 810                 815

Cys Ser Ala Asp Asn Ala His Arg Met Gln Gln Ile Lys Ile Thr Glu
                820                 825                 830

Pro Val Glu Asp Asn Lys Asp Lys Ile Ile Leu Ser Ala Lys Ala Gln
                835                 840                 845

Arg Leu Pro Ala Ile Pro Thr Arg Ile Val Asp Gly Ala Val Lys Lys
                850                 855                 860

Met Ala Thr Ile Leu Ala Lys Asn Ile Val Asp Asp Asn Trp Gln Asn
865                 870                 875                 880

Ile Lys Gln Val Leu Ser Ala Lys His Gln Leu His Ile Pro Ile Ile
                885                 890                 895

Thr Glu Ser Asn Ala Phe Glu Phe Glu Pro Ala Leu Ala Asp Val Lys
                900                 905                 910

Gly Lys Ser Leu Lys Asp Arg Arg Lys Lys Ala Leu Glu Arg Ile Ser
                915                 920                 925

Pro Glu Asn Ile Phe Lys Asp Lys Asn Asn Arg Ile Lys Glu Phe Ala
                930                 935                 940

Lys Gly Ile Ser Ala Tyr Ser Gly Ala Asn Leu Thr Asp Gly Asp Phe
945                 950                 955                 960

Asp Gly Ala Lys Glu Glu Leu Asp His Ile Ile Pro Arg Ser His Lys
                965                 970                 975

Lys Tyr Gly Thr Leu Asn Asp Glu Ala Asn Leu Ile Cys Val Thr Arg
                980                 985                 990

Gly Asp Asn Lys Asn Lys Gly Asn Arg Ile Phe Cys Leu Arg Asp Leu
                995                 1000                1005

Ala Asp Asn Tyr Lys Leu Lys Gln Phe Glu Thr Thr Asp Asp Leu
        1010                1015                1020

Glu Ile Glu Lys Lys Ile Ala Asp Thr Ile Trp Asp Ala Asn Lys
        1025                1030                1035

Lys Asp Phe Lys Phe Gly Asn Tyr Arg Ser Phe Ile Asn Leu Thr
        1040                1045                1050

Pro Gln Glu Gln Lys Ala Phe Arg His Ala Leu Phe Leu Ala Asp
        1055                1060                1065

Glu Asn Pro Ile Lys Gln Ala Val Ile Arg Ala Ile Asn Asn Arg
        1070                1075                1080

Asn Arg Thr Phe Val Asn Gly Thr Gln Arg Tyr Phe Ala Glu Val
        1085                1090                1095

Leu Ala Asn Asn Ile Tyr Leu Arg Ala Lys Lys Glu Asn Leu Asn
        1100                1105                1110

Thr Asp Lys Ile Ser Phe Asp Tyr Phe Gly Ile Pro Thr Ile Gly
        1115                1120                1125

Asn Gly Arg Gly Ile Ala Glu Ile Arg Gln Leu Tyr Glu Lys Val
        1130                1135                1140

```
Asp Ser Asp Ile Gln Ala Tyr Ala Lys Gly Asp Lys Pro Gln Ala
    1145                1150                1155

Ser Tyr Ser His Leu Ile Asp Ala Met Leu Ala Phe Cys Ile Ala
    1160                1165                1170

Ala Asp Glu His Arg Asn Asp Gly Ser Ile Gly Leu Glu Ile Asp
    1175                1180                1185

Lys Asn Tyr Ser Leu Tyr Pro Leu Asp Lys Asn Thr Gly Glu Val
    1190                1195                1200

Phe Thr Lys Asp Ile Phe Ser Gln Ile Lys Ile Thr Asp Asn Glu
    1205                1210                1215

Phe Ser Asp Lys Lys Leu Val Arg Lys Lys Ala Ile Glu Gly Phe
    1220                1225                1230

Asn Thr His Arg Gln Met Thr Arg Asp Gly Ile Tyr Ala Glu Asn
    1235                1240                1245

Tyr Leu Pro Ile Leu Ile His Lys Glu Leu Asn Glu Val Arg Lys
    1250                1255                1260

Gly Tyr Thr Trp Lys Asn Ser Glu Glu Ile Lys Ile Phe Lys Gly
    1265                1270                1275

Lys Lys Tyr Asp Ile Gln Gln Leu Asn Asn Leu Val Tyr Cys Leu
    1280                1285                1290

Lys Phe Val Asp Lys Pro Ile Ser Ile Asp Ile Gln Ile Ser Thr
    1295                1300                1305

Leu Glu Glu Leu Arg Asn Ile Leu Thr Thr Asn Asn Ile Ala Ala
    1310                1315                1320

Thr Ala Glu Tyr Tyr Tyr Ile Asn Leu Lys Thr Gln Lys Leu His
    1325                1330                1335

Glu Tyr Tyr Ile Glu Asn Tyr Asn Thr Ala Leu Gly Tyr Lys Lys
    1340                1345                1350

Tyr Ser Lys Glu Met Glu Phe Leu Arg Ser Leu Ala Tyr Arg Ser
    1355                1360                1365

Glu Arg Val Lys Ile Lys Ser Ile Asp Asp Val Lys Gln Val Leu
    1370                1375                1380

Asp Lys Asp Ser Asn Phe Ile Ile Gly Lys Ile Thr Leu Pro Phe
    1385                1390                1395

Lys Lys Glu Trp Gln Arg Leu Tyr Arg Glu Trp Gln Asn Thr Thr
    1400                1405                1410

Ile Lys Asp Asp Tyr Glu Phe Leu Lys Ser Phe Phe Asn Val Lys
    1415                1420                1425

Ser Ile Thr Lys Leu His Lys Lys Val Arg Lys Asp Phe Ser Leu
    1430                1435                1440

Pro Ile Ser Thr Asn Glu Gly Lys Phe Leu Val Lys Arg Lys Thr
    1445                1450                1455

Trp Asp Asn Asn Phe Ile Tyr Gln Ile Leu Asn Asp Ser Asp Ser
    1460                1465                1470

Arg Ala Asp Gly Thr Lys Pro Phe Ile Pro Ala Phe Asp Ile Ser
    1475                1480                1485

Lys Asn Glu Ile Val Glu Ala Ile Ile Asp Ser Phe Thr Ser Lys
    1490                1495                1500

Asn Ile Phe Trp Leu Pro Lys Asn Ile Glu Leu Gln Lys Val Asp
    1505                1510                1515

Asn Lys Asn Ile Phe Ala Ile Asp Thr Ser Lys Trp Phe Glu Val
    1520                1525                1530

Glu Thr Pro Ser Asp Leu Arg Asp Ile Gly Ile Ala Thr Ile Gln
```

```
    1535                1540                1545

Tyr Lys  Ile Asp Asn Asn Ser  Arg Pro Lys Val Arg  Val Lys Leu
    1550                1555                1560

Asp Tyr  Val Ile Asp Asp Asp  Ser Lys Ile Asn Tyr  Phe Met Asn
    1565                1570                1575

His Ser  Leu Leu Lys Ser Arg  Tyr Pro Asp Lys Val  Leu Glu Ile
    1580                1585                1590

Leu Lys  Gln Ser Thr Ile Ile  Glu Phe Glu Ser Ser  Gly Phe Asn
    1595                1600                1605

Lys Thr  Ile Lys Glu Met Leu  Gly Met Lys Leu Ala  Gly Ile Tyr
    1610                1615                1620

Asn Glu  Thr Ser Asn Asn
    1625

<210> SEQ ID NO 7
<211> LENGTH: 1056
<212> TYPE: PRT
<213> ORGANISM: Pasteurella multocida

<400> SEQUENCE: 7

Met Gln Thr Thr Asn Leu Ser Tyr Ile Leu Gly Leu Asp Leu Gly Ile
1               5                   10                  15

Ala Ser Val Gly Trp Ala Val Val Glu Ile Asn Glu Asn Glu Asp Pro
            20                  25                  30

Ile Gly Leu Ile Asp Val Gly Val Arg Ile Phe Glu Arg Ala Glu Val
        35                  40                  45

Pro Lys Thr Gly Glu Ser Leu Ala Leu Ser Arg Arg Leu Ala Arg Ser
    50                  55                  60

Thr Arg Arg Leu Ile Arg Arg Arg Ala His Arg Leu Leu Leu Ala Lys
65                  70                  75                  80

Arg Phe Leu Lys Arg Glu Gly Ile Leu Ser Thr Ile Asp Leu Glu Lys
                85                  90                  95

Gly Leu Pro Asn Gln Ala Trp Glu Leu Arg Val Ala Gly Leu Glu Arg
            100                 105                 110

Arg Leu Ser Ala Ile Glu Trp Gly Ala Val Leu Leu His Leu Ile Lys
        115                 120                 125

His Arg Gly Tyr Leu Ser Lys Arg Lys Asn Glu Ser Gln Thr Asn Asn
    130                 135                 140

Lys Glu Leu Gly Ala Leu Leu Ser Gly Val Ala Gln Asn His Gln Leu
145                 150                 155                 160

Leu Gln Ser Asp Asp Tyr Arg Thr Pro Ala Glu Leu Ala Leu Lys Lys
                165                 170                 175

Phe Ala Lys Glu Glu Gly His Ile Arg Asn Gln Arg Gly Ala Tyr Thr
            180                 185                 190

His Thr Phe Asn Arg Leu Asp Leu Leu Ala Glu Leu Asn Leu Leu Phe
        195                 200                 205

Ala Gln Gln His Gln Phe Gly Asn Pro His Cys Lys Glu His Ile Gln
    210                 215                 220

Gln Tyr Met Thr Glu Leu Leu Met Trp Gln Lys Pro Ala Leu Ser Gly
225                 230                 235                 240

Glu Ala Ile Leu Lys Met Leu Gly Lys Cys Thr His Glu Lys Asn Glu
                245                 250                 255

Phe Lys Ala Ala Lys His Thr Tyr Ser Ala Glu Arg Phe Val Trp Leu
            260                 265                 270
```

```
Thr Lys Leu Asn Asn Leu Arg Ile Leu Glu Asp Gly Ala Glu Arg Ala
            275                 280                 285

Leu Asn Glu Glu Glu Arg Gln Leu Leu Ile Asn His Pro Tyr Glu Lys
        290                 295                 300

Ser Lys Leu Thr Tyr Ala Gln Val Arg Lys Leu Leu Gly Leu Ser Glu
305                 310                 315                 320

Gln Ala Ile Phe Lys His Leu Arg Tyr Ser Lys Glu Asn Ala Glu Ser
                325                 330                 335

Ala Thr Phe Met Glu Leu Lys Ala Trp His Ala Ile Arg Lys Ala Leu
                340                 345                 350

Glu Asn Gln Gly Leu Lys Asp Thr Trp Gln Asp Leu Ala Lys Lys Pro
        355                 360                 365

Asp Leu Leu Asp Glu Ile Gly Thr Ala Phe Ser Leu Tyr Lys Thr Asp
370                 375                 380

Glu Asp Ile Gln Gln Tyr Leu Thr Asn Lys Val Pro Asn Ser Val Ile
385                 390                 395                 400

Asn Ala Leu Leu Val Ser Leu Asn Phe Asp Lys Phe Ile Glu Leu Ser
                405                 410                 415

Leu Lys Ser Leu Arg Lys Ile Leu Pro Leu Met Glu Gln Gly Lys Arg
        420                 425                 430

Tyr Asp Gln Ala Cys Arg Glu Ile Tyr Gly His His Tyr Gly Glu Ala
            435                 440                 445

Asn Gln Lys Thr Ser Gln Leu Leu Pro Ala Ile Pro Ala Gln Glu Ile
        450                 455                 460

Arg Asn Pro Val Val Leu Arg Thr Leu Ser Gln Ala Arg Lys Val Ile
465                 470                 475                 480

Asn Ala Ile Ile Arg Gln Tyr Gly Ser Pro Ala Arg Val His Ile Glu
                485                 490                 495

Thr Gly Arg Glu Leu Gly Lys Ser Phe Lys Glu Arg Arg Glu Ile Gln
                500                 505                 510

Lys Gln Gln Glu Asp Asn Arg Thr Lys Arg Glu Ser Ala Val Gln Lys
            515                 520                 525

Phe Lys Glu Leu Phe Ser Asp Phe Ser Ser Glu Pro Lys Ser Lys Asp
        530                 535                 540

Ile Leu Lys Phe Arg Leu Tyr Glu Gln Gln His Gly Lys Cys Leu Tyr
545                 550                 555                 560

Ser Gly Lys Glu Ile Asn Ile His Arg Leu Asn Glu Lys Gly Tyr Val
                565                 570                 575

Glu Ile Asp His Ala Leu Pro Phe Ser Arg Thr Trp Asp Asp Ser Phe
            580                 585                 590

Asn Asn Lys Val Leu Val Leu Ala Ser Glu Asn Gln Asn Lys Gly Asn
        595                 600                 605

Gln Thr Pro Tyr Glu Trp Leu Gln Gly Lys Ile Asn Ser Glu Arg Trp
        610                 615                 620

Lys Asn Phe Val Ala Leu Val Leu Gly Ser Gln Cys Ser Ala Ala Lys
625                 630                 635                 640

Lys Gln Arg Leu Leu Thr Gln Val Ile Asp Asp Asn Lys Phe Ile Asp
                645                 650                 655

Arg Asn Leu Asn Asp Thr Arg Tyr Ile Ala Arg Phe Leu Ser Asn Tyr
                660                 665                 670

Ile Gln Glu Asn Leu Leu Leu Val Gly Lys Asn Lys Lys Asn Val Phe
            675                 680                 685

Thr Pro Asn Gly Gln Ile Thr Ala Leu Leu Arg Ser Arg Trp Gly Leu
```

```
                    690             695             700
Ile Lys Ala Arg Glu Asn Asn Arg His His Ala Leu Asp Ala Ile
705                 710             715                 720
Val Val Ala Cys Ala Thr Pro Ser Met Gln Gln Lys Ile Thr Arg Phe
                725             730             735
Ile Arg Phe Lys Glu Val His Pro Tyr Lys Ile Glu Asn Arg Tyr Glu
            740             745             750
Met Val Asp Gln Glu Ser Gly Glu Ile Ile Ser Pro His Phe Pro Glu
        755             760             765
Pro Trp Ala Tyr Phe Arg Gln Glu Val Asn Ile Arg Val Phe Asp Asn
770             775             780
His Pro Asp Thr Val Leu Lys Glu Met Leu Pro Asp Arg Pro Gln Ala
785             790             795             800
Asn His Gln Phe Val Gln Pro Leu Phe Val Ser Arg Ala Pro Thr Arg
                805             810             815
Lys Met Ser Gly Gln Gly His Met Glu Thr Ile Lys Ser Ala Lys Arg
                820             825             830
Leu Ala Glu Gly Ile Ser Val Leu Arg Ile Pro Leu Thr Gln Leu Lys
            835             840             845
Pro Asn Leu Leu Glu Asn Met Val Asn Lys Glu Arg Glu Pro Ala Leu
850             855             860
Tyr Ala Gly Leu Lys Ala Arg Leu Ala Glu Phe Asn Gln Asp Pro Ala
865             870             875             880
Lys Ala Phe Ala Thr Pro Phe Tyr Lys Gln Gly Gly Gln Gln Val Lys
                885             890             895
Ala Ile Arg Val Glu Gln Val Gln Lys Ser Gly Val Leu Val Arg Glu
                900             905             910
Asn Asn Gly Val Ala Asp Asn Ala Ser Ile Val Arg Thr Asp Val Phe
            915             920             925
Ile Lys Asn Asn Lys Phe Phe Leu Val Pro Ile Tyr Thr Trp Gln Val
930             935             940
Ala Lys Gly Ile Leu Pro Asn Lys Ala Ile Val Ala His Lys Asn Glu
945             950             955             960
Asp Glu Trp Glu Glu Met Asp Glu Gly Ala Lys Phe Lys Phe Ser Leu
                965             970             975
Phe Pro Asn Asp Leu Val Glu Leu Lys Thr Lys Glu Tyr Phe Phe
            980             985             990
Gly Tyr Tyr Ile Gly Leu Asp Arg Ala Thr Gly Asn Ile Ser Leu Lys
            995             1000            1005
Glu His Asp Gly Glu Ile Ser Lys Gly Lys Asp Gly Val Tyr Arg
    1010            1015            1020
Val Gly Val Lys Leu Ala Leu Ser Phe Glu Lys Tyr Gln Val Asp
    1025            1030            1035
Glu Leu Gly Lys Asn Arg Gln Ile Cys Arg Pro Gln Gln Arg Gln
    1040            1045            1050
Pro Val Arg
    1055

<210> SEQ ID NO 8
<211> LENGTH: 4104
<212> TYPE: DNA
<213> ORGANISM: Artificial sequence
<220> FEATURE:
<223> OTHER INFORMATION: codon optimized gene
```

<400> SEQUENCE: 8

```
atggacaaga agtacagcat cggcctcgac atcggcacca actcggtggg ctgggccgtc      60
atcacggacg aatataaggt cccgtcgaag aagttcaagg tcctcggcaa tacagaccgc     120
cacagcatca agaaaaactt gatcggcgcc ctcctgttcg atagcggcga gaccgcggag     180
gcgaccaggc tcaagaggac cgccaggaga cggtacacta ggcgcaagaa caggatctgc     240
tacctgcagg agatcttcag caacgagatg gcgaaggtgg acgactcctt cttccaccgc     300
ctggaggaat cattcctggt ggaggaggac aagaagcatg agcggcaccc aatcttcggc     360
aacatcgtcg acgaggtggc ctaccacgag aagtacccga caatctacca cctccggaag     420
aaactggtgg acagcacaga caaggcggac ctccggctca tctaccttgc cctcgcgcat     480
atgatcaagt ccgcggcca cttcctcatc gagggcgacc tgaacccgga caactccgac     540
gtggacaagc tgttcatcca gctcgtgcag acgtacaatc aactgttcga ggagaacccc     600
ataaacgcta gcggcgtgga cgccaaggcc atcctctcgg ccaggctctc gaaatcaaga     660
aggctggaga accttatcgc gcagttgcca ggcgaaaaga gaacggcct cttcggcaac      720
cttattgcgc tcagcctcgg cctgacgccg aacttcaaat caaacttcga cctcgcggag     780
gacgccaagc tccagctctc aaaggacacc tacgacgacg acctcgacaa cctcctggcc     840
cagataggag accagtacgc ggacctcttc ctcgccgcca gaaacctctc cgacgctatc     900
ctgctcagcg acatccttcg ggtcaacacc gaaattacca aggcaccgct gtccgccagc     960
atgattaaac gctacgacga gcaccatcag gacctcacgc tgctcaaggc actcgtccgc    1020
cagcagctcc ccgagaagta caaggagatc ttcttcgacc aatcaaaaaa cggctacgcg    1080
ggatatatcg acggcggtgc cagccaggaa gagttctaca gttcatcaa accaatcctg     1140
gagaagatgg acggcaccga ggagttgctg gtcaagctca cagggagga cctcctcagg     1200
aagcagagga ccttcgacaa cggctccatc ccgcatcaga tccacctggg cgaactgcat    1260
gccatcctgc ggcgcagga ggacttctac ccgttcctga aggataaccg ggagaagatc     1320
gagaagatct tgacgttccg catcccatac tacgtgggcc cgctggctcg cggcaactcc    1380
cggttcgcct ggatgacccg gaagtcggag gagaccatca cacccctggaa cttttgaggag    1440
gtggtcgata agggcgctag cgctcagagc ttcatcgagc gcatgaccaa cttcgataaa    1500
aacctgccca tgaaaaagt cctccccaag cactcgctgc tctacgagta cttcaccgtg    1560
tacaacgagc tcaccaaggt caaatacgtc accgagggca tgcggaagcc ggcgttcctg    1620
agcggcgagg agaagaaggc gatagtggac ctcctcttca agaccaacag gaaggtgacc    1680
gtgaagcaat taaaagagga ctacttcaag aaaatagagt gcttcgactc cgtggagatc    1740
tcgggcgtgg aggatcggtt caacgcctca ctcggcacgt atcacgacct cctcaagatc    1800
attaaagaca aggacttcct cgacaacgag gagaacgagg acatcctcga ggacatcgtc    1860
ctcacccctga ccctgttcga ggaccgcgaa atgatcgagg agaggctgaa gacctacgcg    1920
cacctgttcg acgacaaggt catgaaacag ctcaagaggg gccgctacac tggttgggga    1980
aggctgtccc gcaagctcat taatggcatc agggacaagc agagcggcaa gaccatcctg    2040
gacttcctca gtccgacgg gttcgccaac cgcaacttca tgcagctcat tcacgacgac    2100
tcgctcacgt tcaaggaaga catccagaag gcacaggtga gcgggcaggg tgactccctc    2160
cacgaacaca tcgccaacct ggccggctcg ccggccatta aaaagggcat cctgcagacg    2220
gtcaaggtcg tcgacgagct cgtgaaggtg atggccgc acaagcccga aaatatcgtc     2280
atagagatgg ccagggagaa ccagaccacc caaaaagggc agaagaactc gcgcgagcgg    2340
```

| atgaaacgga tcgaggaggg cattaaagag ctcgggtccc agatcctgaa ggagcacccc | 2400 |
| gtggaaaata cccagctcca gaatgaaaag ctctacctct actacctgca gaacggccgc | 2460 |
| gacatgtacg tggaccagga gctggacatt aatcggctat cggactacga cgtcgaccac | 2520 |
| atcgtgccgc agtcgttcct caaggacgat agcatcgaca acaaggtgct cacccggtcg | 2580 |
| gataaaaatc ggggcaagag cgacaacgtg cccagcgagg aggtcgtgaa gaagatgaaa | 2640 |
| aactactggc gccagctcct caacgcgaaa ctgatcaccc agcgcaagtt cgacaacctg | 2700 |
| acgaaggcgg aacgcggtgg cttgagcgaa ctcgataagg cgggcttcat aaaaaggcag | 2760 |
| ctggtcgaga cgcgccagat cacgaagcat gtcgcccaga tcctggacag ccgcatgaat | 2820 |
| actaagtacg atgaaaacga caagctgatc cgggaggtga aggtgatcac gctgaagtcc | 2880 |
| aagctcgtgt cggacttccg caaggacttc cagttctaca aggtccgcga tcaacaac | 2940 |
| taccaccacg cccacgacgc ctacctgaat gcggtggtcg ggaccgccct gatcaagaag | 3000 |
| tacccgaagc tggagtcgga gttcgtgtac ggcgactaca aggtctacga cgtgcgcaaa | 3060 |
| atgatcgcca agtccgagca ggagatcggc aaggccacgg caaaatactt cttctactcg | 3120 |
| aacatcatga acttcttcaa gaccgagatc accctcgcga acggcgagat ccgcaagcgc | 3180 |
| ccgctcatcg aaaccaacgg cgagacgggc gagatcgtct gggataaggg ccgggatttc | 3240 |
| gcgacggtcc gcaaggtgct ctccatgccg caagtcaata tcgtgaaaaa gacggaggtc | 3300 |
| cagacgggcg ggttcagcaa ggagtccatc ctcccgaagc gcaactccga caagctcatc | 3360 |
| gcgaggaaga aggattggga cccgaaaaaa tatggcggct cgacagcccg accgtcgca | 3420 |
| tacagcgtcc tcgtcgtggc gaaggtggag aagggcaagt caaagaagct caagtccgtg | 3480 |
| aaggagctgc tcgggatcac gattatgagc cggtcctcct cgagaagaa cccgatcgac | 3540 |
| ttcctagagg ccaagggata taaggaggtc aagaaggacc tgattattaa actgccgaag | 3600 |
| tactcgctct tcgagctgga aaacggccgc aagaggatgc tcgcctccgc aggcgagttg | 3660 |
| cagaagggca acgagctcgc cctcccgagc aaatacgtca atttcctgta cctcgctagc | 3720 |
| cactatgaaa agctcaaggg cagcccggag gacaacgagc agaagcagct cttcgtggag | 3780 |
| cagcacaagc attacctgga cgagatcatc gagcagatca gcgagttctc gaagcgggtg | 3840 |
| atcctcgccg acgcgaacct ggacaaggtg ctgtcggcat ataacaagca ccgcgacaaa | 3900 |
| ccaatacgcg agcaggccga aaatatcatc cacctcttca ccctcaccaa cctcggcgct | 3960 |
| ccggcagcct tcaagtactt cgacaccacg attgaccgga agcggtacac gagcacgaag | 4020 |
| gaggtgctcg atgcgacgct gatccaccag agcatcacag ggctctatga acacgcatc | 4080 |
| gacctgagcc agctgggcgg agac | 4104 |

<210> SEQ ID NO 9
<211> LENGTH: 4155
<212> TYPE: DNA
<213> ORGANISM: Artificial sequence
<220> FEATURE:
<223> OTHER INFORMATION: codon optimized gene

<400> SEQUENCE: 9

| atggcaccga agaagaagcg caaggtgatg gacaagaagt acagcatcgg cctcgacatc | 60 |
| ggcaccaact cggtgggctg gccgtcatc acggacgaat ataaggtccc gtcgaagaag | 120 |
| ttcaaggtcc tcggcaatac agaccgccac agcatcaaga aaaacttgat cggcgccctc | 180 |
| ctgttcgata gcggcgagac cgcggaggcg accaggctca gaggaccgc caggagacgg | 240 |

```
tacactaggc gcaagaacag gatctgctac ctgcaggaga tcttcagcaa cgagatggcg    300
aaggtggacg actccttctt ccaccgcctg gaggaatcat tcctggtgga ggaggacaag    360
aagcatgagc ggcacccaat cttcggcaac atcgtcgacg aggtggccta ccacgagaag    420
tacccgacaa tctaccacct ccggaagaaa ctggtggaca gcacagacaa ggcggacctc    480
cggctcatct accttgccct cgcgcatatg atcaagttcc gcggccactt cctcatcgag    540
ggcgacctga acccggacaa ctccgacgtg acaagctgt tcatccagct cgtgcagacg    600
tacaatcaac tgttcgagga aaccccata aacgctagcg gcgtggacgc caaggccatc    660
ctctcggcca ggctctcgaa atcaagaagg ctggagaacc ttatcgcgca gttgccaggc    720
gaaaagaaga acggcctctt cggcaaccttt attgcgctca gcctcggcct gacgccgaac    780
ttcaaatcaa acttcgacct cgcggaggac gccaagctcc agctctcaaa ggacacctac    840
gacgacgacc tcgacaacct cctggcccag ataggagacc agtacgcgga cctcttcctc    900
gccgccaaga acctctccga cgctatcctg ctcagcgaca tccttcgggt caacaccgaa    960
attaccaagg caccgctgtc cgccagcatg attaaacgct acgacgagca ccatcaggac   1020
ctcacgctgc tcaaggcact cgtccgccag cagctccccg agaagtacaa ggagatcttc   1080
ttcgaccaat caaaaaacgg ctacgcggga tatatcgacg gcggtgccag ccaggaagag   1140
ttctacaagt tcatcaaacc aatcctggag aagatggacg gcaccgagga gttgctggtc   1200
aagctcaaca gggaggacct cctcaggaag cagaggacct tcgacaacgg ctccatcccg   1260
catcagatcc acctgggcga actgcatgcc atcctgcggc gccaggagga cttctacccg   1320
ttcctgaagg ataaccggga gaagatcgag aagatcttga cgttccgcat cccatactac   1380
gtgggcccgc tggctcgcgg caactcccgg ttcgcctgga tgacccggaa gtcggaggag   1440
accatcacac cctggaactt tgaggaggtg gtcgataagg gcgctagcgc tcagagcttc   1500
atcgagcgca tgaccaactt cgataaaaac ctgcccaatg aaaaagtcct ccccaagcac   1560
tcgctgctct acgagtactt caccgtgtac aacgagctca ccaaggtcaa atacgtcacc   1620
gagggcatgc ggaagccggc gttcctgagc ggcgagcaga agaaggcgat agtggacctc   1680
ctcttcaaga ccaacaggaa ggtgaccgtg aagcaattaa aagaggacta cttcaagaaa   1740
atagagtgct tcgactccgt ggagatctcg ggcgtggagg atcggttcaa cgcctcactc   1800
ggcacgtatc acgacctcct caagatcatt aaagacaagg acttcctcga caacgaggag   1860
aacgaggaca tcctcgagga catcgtcctc accctgaccc tgttcgagga ccgcgaaatg   1920
atcgaggaga ggctgaagac ctacgcgcac ctgttcgacg acaaggtcat gaaacagctc   1980
aagaggcgcc gctacactgg ttggggaagg ctgtcccgca agctcattaa tggcatcagg   2040
gacaagcaga gcggcaagac catcctggac ttcctcaagt ccgacgggtt cgccaaccgc   2100
aacttcatgc agctcattca cgacgactcg ctcacgttca aggaagacat ccagaaggca   2160
caggtgagcg gcagggtga ctccctccac gaacacatcg ccaacctggc cggctcgccg   2220
gccattaaaa agggcatcct gcagacggtc aaggtcgtcg acgagctcgt gaaggtgatg   2280
ggccggcaca gcccgaaaa tatcgtcata gagatggcca gggagaacca gaccacccaa   2340
aaagggcaga agaactcgcg cgagcggatg aacggatcg aggagggcat taaagagctc   2400
gggtcccaga tcctgaagga gcaccccgtg gaaaatacccc agctccagaa tgaaaagctc   2460
tacctctact acctgcagaa cggccgcgac atgtacgtgg accaggagct ggacattaat   2520
cggctatcgg actacgacgt cgaccacatc gtgccgcagt cgttcctcaa ggacgatagc   2580
atcgacaaca aggtgctcac ccggtcggat aaaaatcggg gcaagagcga caacgtgccc   2640
```

-continued

```
agcgaggagg tcgtgaagaa gatgaaaaac tactggcgcc agctcctcaa cgcgaaactg    2700
atcacccagc gcaagttcga caacctgacg aaggcggaac gcggtggctt gagcgaactc    2760
gataaggcgg gcttcataaa aaggcagctg gtcgagacgc gccagatcac gaagcatgtc    2820
gcccagatcc tggacagccg catgaatact aagtacgatg aaaacgacaa gctgatccgg    2880
gaggtgaagg tgatcacgct gaagtccaag ctcgtgtcgg acttccgcaa ggacttccag    2940
ttctacaagg tccgcgagat caacaactac caccacgccc acgacgccta cctgaatgcg    3000
gtggtcggga ccgccctgat caagaagtac ccgaagctgg agtcggagtt cgtgtacggc    3060
gactacaagg tctacgacgt gcgcaaaatg atcgccaagt ccgagcagga gatcggcaag    3120
gccacggcaa atacttcttc tactcgaac atcatgaact tcttcaagac cgagatcacc    3180
ctcgcgaacg gcgagatccg caagcgcccg ctcatcgaaa ccaacggcga cgggcgag    3240 atcgtctggg ataagggccg ggatttcgcg acggtccgca aggtgctctc catgccgcaa    3300
gtcaatatcg tgaaaaagac ggaggtccag acgggcgggt tcagcaagga gtccatcctc    3360
ccgaagcgca actccgacaa gctcatcgcg aggaagaagg attgggaccc gaaaaaatat    3420
ggcggcttcg acagcccgac cgtcgcatac agcgtcctcg tcgtggcgaa ggtggagaag    3480
ggcaagtcaa agaagctcaa gtccgtgaag gagctgctcg ggatcacgat tatggagcgg    3540
tcctccttcg agaagaaccc gatcgacttc ctagaggcca agggatataa ggaggtcaag    3600
aaggacctga ttattaaact gccgaagtac tcgctcttcg agctggaaaa cggccgcaag    3660
aggatgctcg cctccgcagg cgagttgcag aagggcaacg agctcgccct cccgagcaaa    3720
tacgtcaatt tcctgtacct cgctagccac tatgaaaagc tcaagggcag cccggaggac    3780
aacgagcaga agcagctctt cgtggagcag cacaagcatt acctggacga gatcatcgag    3840
cagatcagcg agttctcgaa gcgggtgatc ctcgccgacg cgaacctgga caaggtgctg    3900
tcggcatata acaagcaccg cgacaaacca atacgcgagc aggccgaaaa tatcatccac    3960
ctcttcaccc tcaccaacct cggcgctccg gcagccttca gtacttcga caccacgatt    4020 gaccggaagc ggtacacgag cacgaaggag gtgctcgatg cgacgctgat ccaccagagc    4080
atcacagggc tctatgaaac acgcatcgac ctgagccagc tgggcggaga caagaagaag    4140
aagctcaagc tctag                                                     4155
```

<210> SEQ ID NO 10
<211> LENGTH: 1384
<212> TYPE: PRT
<213> ORGANISM: Artificial sequence
<220> FEATURE:
<223> OTHER INFORMATION: synthetic construct

<400> SEQUENCE: 10

```
Met Ala Pro Lys Lys Lys Arg Lys Val Met Asp Lys Lys Tyr Ser Ile
1               5                   10                  15

Gly Leu Asp Ile Gly Thr Asn Ser Val Gly Trp Ala Val Ile Thr Asp
            20                  25                  30

Glu Tyr Lys Val Pro Ser Lys Lys Phe Lys Val Leu Gly Asn Thr Asp
        35                  40                  45

Arg His Ser Ile Lys Lys Asn Leu Ile Gly Ala Leu Leu Phe Asp Ser
    50                  55                  60

Gly Glu Thr Ala Glu Ala Thr Arg Leu Lys Arg Thr Ala Arg Arg Arg
65                  70                  75                  80

Tyr Thr Arg Arg Lys Asn Arg Ile Cys Tyr Leu Gln Glu Ile Phe Ser
```

-continued

```
                    85                  90                  95
Asn Glu Met Ala Lys Val Asp Asp Ser Phe Phe His Arg Leu Glu Glu
                100                 105                 110

Ser Phe Leu Val Glu Glu Asp Lys Lys His Glu Arg His Pro Ile Phe
                115                 120                 125

Gly Asn Ile Val Asp Glu Val Ala Tyr His Glu Lys Tyr Pro Thr Ile
            130                 135                 140

Tyr His Leu Arg Lys Lys Leu Val Asp Ser Thr Asp Lys Ala Asp Leu
145                 150                 155                 160

Arg Leu Ile Tyr Leu Ala Leu Ala His Met Ile Lys Phe Arg Gly His
                165                 170                 175

Phe Leu Ile Glu Gly Asp Leu Asn Pro Asp Asn Ser Asp Val Asp Lys
                180                 185                 190

Leu Phe Ile Gln Leu Val Gln Thr Tyr Asn Gln Leu Phe Glu Glu Asn
                195                 200                 205

Pro Ile Asn Ala Ser Gly Val Asp Ala Lys Ala Ile Leu Ser Ala Arg
            210                 215                 220

Leu Ser Lys Ser Arg Arg Leu Glu Asn Leu Ile Ala Gln Leu Pro Gly
225                 230                 235                 240

Glu Lys Lys Asn Gly Leu Phe Gly Asn Leu Ile Ala Leu Ser Leu Gly
                245                 250                 255

Leu Thr Pro Asn Phe Lys Ser Asn Phe Asp Leu Ala Glu Asp Ala Lys
                260                 265                 270

Leu Gln Leu Ser Lys Asp Thr Tyr Asp Asp Asp Leu Asp Asn Leu Leu
                275                 280                 285

Ala Gln Ile Gly Asp Gln Tyr Ala Asp Leu Phe Leu Ala Ala Lys Asn
            290                 295                 300

Leu Ser Asp Ala Ile Leu Leu Ser Asp Ile Leu Arg Val Asn Thr Glu
305                 310                 315                 320

Ile Thr Lys Ala Pro Leu Ser Ala Ser Met Ile Lys Arg Tyr Asp Glu
                325                 330                 335

His His Gln Asp Leu Thr Leu Leu Lys Ala Leu Val Arg Gln Gln Leu
                340                 345                 350

Pro Glu Lys Tyr Lys Glu Ile Phe Phe Asp Gln Ser Lys Asn Gly Tyr
            355                 360                 365

Ala Gly Tyr Ile Asp Gly Gly Ala Ser Gln Glu Glu Phe Tyr Lys Phe
            370                 375                 380

Ile Lys Pro Ile Leu Glu Lys Met Asp Gly Thr Glu Glu Leu Leu Val
385                 390                 395                 400

Lys Leu Asn Arg Glu Asp Leu Leu Arg Lys Gln Arg Thr Phe Asp Asn
                405                 410                 415

Gly Ser Ile Pro His Gln Ile His Leu Gly Glu Leu His Ala Ile Leu
            420                 425                 430

Arg Arg Gln Glu Asp Phe Tyr Pro Phe Leu Lys Asp Asn Arg Glu Lys
                435                 440                 445

Ile Glu Lys Ile Leu Thr Phe Arg Ile Pro Tyr Tyr Val Gly Pro Leu
            450                 455                 460

Ala Arg Gly Asn Ser Arg Phe Ala Trp Met Thr Arg Lys Ser Glu Glu
465                 470                 475                 480

Thr Ile Thr Pro Trp Asn Phe Glu Glu Val Val Asp Lys Gly Ala Ser
                485                 490                 495

Ala Gln Ser Phe Ile Glu Arg Met Thr Asn Phe Asp Lys Asn Leu Pro
            500                 505                 510
```

```
Asn Glu Lys Val Leu Pro Lys His Ser Leu Leu Tyr Glu Tyr Phe Thr
            515                 520                 525
Val Tyr Asn Glu Leu Thr Lys Val Lys Tyr Val Thr Glu Gly Met Arg
            530                 535             540
Lys Pro Ala Phe Leu Ser Gly Glu Gln Lys Lys Ala Ile Val Asp Leu
545                 550                 555                 560
Leu Phe Lys Thr Asn Arg Lys Val Thr Val Lys Gln Leu Lys Glu Asp
            565                 570                 575
Tyr Phe Lys Lys Ile Glu Cys Phe Asp Ser Val Glu Ile Ser Gly Val
            580                 585                 590
Glu Asp Arg Phe Asn Ala Ser Leu Gly Thr Tyr His Asp Leu Leu Lys
            595                 600                 605
Ile Ile Lys Asp Lys Asp Phe Leu Asp Asn Glu Glu Asn Glu Asp Ile
            610                 615                 620
Leu Glu Asp Ile Val Leu Thr Leu Thr Leu Phe Glu Asp Arg Glu Met
625                 630                 635                 640
Ile Glu Glu Arg Leu Lys Thr Tyr Ala His Leu Phe Asp Asp Lys Val
                645                 650                 655
Met Lys Gln Leu Lys Arg Arg Arg Tyr Thr Gly Trp Gly Arg Leu Ser
            660                 665                 670
Arg Lys Leu Ile Asn Gly Ile Arg Asp Lys Gln Ser Gly Lys Thr Ile
            675                 680                 685
Leu Asp Phe Leu Lys Ser Asp Gly Phe Ala Asn Arg Asn Phe Met Gln
            690                 695                 700
Leu Ile His Asp Asp Ser Leu Thr Phe Lys Glu Asp Ile Gln Lys Ala
705                 710                 715                 720
Gln Val Ser Gly Gln Gly Asp Ser Leu His Glu His Ile Ala Asn Leu
            725                 730                 735
Ala Gly Ser Pro Ala Ile Lys Lys Gly Ile Leu Gln Thr Val Lys Val
            740                 745                 750
Val Asp Glu Leu Val Lys Val Met Gly Arg His Lys Pro Glu Asn Ile
            755                 760                 765
Val Ile Glu Met Ala Arg Glu Asn Gln Thr Thr Gln Lys Gly Gln Lys
            770                 775                 780
Asn Ser Arg Glu Arg Met Lys Arg Ile Glu Glu Gly Ile Lys Glu Leu
785                 790                 795                 800
Gly Ser Gln Ile Leu Lys Glu His Pro Val Glu Asn Thr Gln Leu Gln
            805                 810                 815
Asn Glu Lys Leu Tyr Leu Tyr Tyr Leu Gln Asn Gly Arg Asp Met Tyr
            820                 825                 830
Val Asp Gln Glu Leu Asp Ile Asn Arg Leu Ser Asp Tyr Asp Val Asp
            835                 840                 845
His Ile Val Pro Gln Ser Phe Leu Lys Asp Asp Ser Ile Asp Asn Lys
            850                 855                 860
Val Leu Thr Arg Ser Asp Lys Asn Arg Gly Lys Ser Asp Asn Val Pro
865                 870                 875                 880
Ser Glu Glu Val Val Lys Lys Met Lys Asn Tyr Trp Arg Gln Leu Leu
                885                 890                 895
Asn Ala Lys Leu Ile Thr Gln Arg Lys Phe Asp Asn Leu Thr Lys Ala
            900                 905                 910
Glu Arg Gly Gly Leu Ser Glu Leu Asp Lys Ala Gly Phe Ile Lys Arg
            915                 920                 925
```

```
Gln Leu Val Glu Thr Arg Gln Ile Thr Lys His Val Ala Gln Ile Leu
    930                 935                 940

Asp Ser Arg Met Asn Thr Lys Tyr Asp Glu Asn Asp Lys Leu Ile Arg
945                 950                 955                 960

Glu Val Lys Val Ile Thr Leu Lys Ser Lys Leu Val Ser Asp Phe Arg
                965                 970                 975

Lys Asp Phe Gln Phe Tyr Lys Val Arg Glu Ile Asn Asn Tyr His His
            980                 985                 990

Ala His Asp Ala Tyr Leu Asn Ala Val Val Gly Thr Ala Leu Ile Lys
            995                 1000                1005

Lys Tyr Pro Lys Leu Glu Ser Glu Phe Val Tyr Gly Asp Tyr Lys
    1010            1015            1020

Val Tyr Asp Val Arg Lys Met Ile Ala Lys Ser Glu Gln Glu Ile
    1025            1030            1035

Gly Lys Ala Thr Ala Lys Tyr Phe Phe Tyr Ser Asn Ile Met Asn
    1040            1045            1050

Phe Phe Lys Thr Glu Ile Thr Leu Ala Asn Gly Glu Ile Arg Lys
    1055            1060            1065

Arg Pro Leu Ile Glu Thr Asn Gly Glu Thr Gly Glu Ile Val Trp
    1070            1075            1080

Asp Lys Gly Arg Asp Phe Ala Thr Val Arg Lys Val Leu Ser Met
    1085            1090            1095

Pro Gln Val Asn Ile Val Lys Lys Thr Glu Val Gln Thr Gly Gly
    1100            1105            1110

Phe Ser Lys Glu Ser Ile Leu Pro Lys Arg Asn Ser Asp Lys Leu
    1115            1120            1125

Ile Ala Arg Lys Lys Asp Trp Asp Pro Lys Lys Tyr Gly Gly Phe
    1130            1135            1140

Asp Ser Pro Thr Val Ala Tyr Ser Val Leu Val Val Ala Lys Val
    1145            1150            1155

Glu Lys Gly Lys Ser Lys Lys Leu Lys Ser Val Lys Glu Leu Leu
    1160            1165            1170

Gly Ile Thr Ile Met Glu Arg Ser Ser Phe Glu Lys Asn Pro Ile
    1175            1180            1185

Asp Phe Leu Glu Ala Lys Gly Tyr Lys Glu Val Lys Lys Asp Leu
    1190            1195            1200

Ile Ile Lys Leu Pro Lys Tyr Ser Leu Phe Glu Leu Glu Asn Gly
    1205            1210            1215

Arg Lys Arg Met Leu Ala Ser Ala Gly Glu Leu Gln Lys Gly Asn
    1220            1225            1230

Glu Leu Ala Leu Pro Ser Lys Tyr Val Asn Phe Leu Tyr Leu Ala
    1235            1240            1245

Ser His Tyr Glu Lys Leu Lys Gly Ser Pro Glu Asp Asn Glu Gln
    1250            1255            1260

Lys Gln Leu Phe Val Glu Gln His Lys His Tyr Leu Asp Glu Ile
    1265            1270            1275

Ile Glu Gln Ile Ser Glu Phe Ser Lys Arg Val Ile Leu Ala Asp
    1280            1285            1290

Ala Asn Leu Asp Lys Val Leu Ser Ala Tyr Asn Lys His Arg Asp
    1295            1300            1305

Lys Pro Ile Arg Glu Gln Ala Glu Asn Ile Ile His Leu Phe Thr
    1310            1315            1320

Leu Thr Asn Leu Gly Ala Pro Ala Ala Phe Lys Tyr Phe Asp Thr
```

```
                 1325                1330                1335
Thr Ile Asp Arg Lys Arg Tyr Thr Ser Thr Lys Glu Val Leu Asp
     1340                1345                 1350

Ala Thr Leu Ile His Gln Ser Ile Thr Gly Leu Tyr Glu Thr Arg
     1355                1360                 1365

Ile Asp Leu Ser Gln Leu Gly Gly Asp Lys Lys Lys Leu Lys
     1370                1375                 1380

Leu

<210> SEQ ID NO 11
<211> LENGTH: 404
<212> TYPE: DNA
<213> ORGANISM: Trichoderma reesei

<400> SEQUENCE: 11
aaaaaacact agtaagtact tacttatgta ttattaacta ctttagctaa cttctgcagt    60
actacctaag aggctagggg tagttttata gcagacttat agctattatt tttatttagt   120
aaagtgcttt taaagtaagg tctttttttat agcacttttt atttattata atatatatta  180
tataataatt ttaagcctgg aatagtaaag aggcttatat aataatttat agtaataaaa   240
gcttagcagc tgtaatataa ttcctaaaga aacagcatga aatggtatta tgtaagagct   300
atagtctaaa ggcactctgc tggataaaaa tagtggctat aagtctgctg caaaactacc   360
cccaacctcg taggtatata agtactgttt gatggtagtc tatc                   404

<210> SEQ ID NO 12
<211> LENGTH: 146
<212> TYPE: DNA
<213> ORGANISM: Trichoderma reesei

<400> SEQUENCE: 12
aattcctaaa gaaacagcat gaaatggtat tatgtaagag ctatagtcta aaggcactct    60
gctggataaa aatagtggct ataagtctgc tgcaaaacta cccccaacct cgtaggtata   120
taagtactgt ttgatggtag tctatc                                       146

<210> SEQ ID NO 13
<211> LENGTH: 138
<212> TYPE: DNA
<213> ORGANISM: Artificial sequence
<220> FEATURE:
<223> OTHER INFORMATION: synthetic construct

<400> SEQUENCE: 13
atgcaccatc atcatcatca ttcttctggt ctggtgccac gcggttctgg tatgaaagaa    60
accgctgctg ctaaattcga acgccagcac atggacagcc cagatctggg taccgacgac   120
gacgacaagg ccatggcc                                                138

<210> SEQ ID NO 14
<211> LENGTH: 21
<212> TYPE: DNA
<213> ORGANISM: SV40

<400> SEQUENCE: 14
ccaaaaaaga aacgcaaggt t                                             21

<210> SEQ ID NO 15
<211> LENGTH: 4104
<212> TYPE: DNA
```

<213> ORGANISM: Artificial sequence
<220> FEATURE:
<223> OTHER INFORMATION: synthetic construct

<400> SEQUENCE: 15

| | | | | | |
|---|---|---|---|---|---|
| atggataaaa | aatacagcat | tggtctggat | atcggaacca | acagcgttgg | gtgggcagta | 60 |
| ataacagatg | aatacaaagt | gccgtcaaaa | aaatttaagg | ttctggggaa | tacagatcgc | 120 |
| cacagcataa | aaaagaatct | gattggggca | ttgctgtttg | attcgggtga | dacagctgag | 180 |
| gccacgcgtc | tgaaacgtac | agcaagaaga | cgttacacac | gtcgtaaaaa | tcgtatttgc | 240 |
| tacttacagg | aaatttttc | taacgaaatg | gccaaggtag | atgatagttt | cttccatcgt | 300 |
| ctcgaagaat | cttttctggt | tgaggaagat | aaaaaacacg | aacgtcaccc | tatctttggc | 360 |
| aatatcgtgg | atgaagtggc | ctatcatgaa | aaatacccta | cgatttatca | tcttcgcaag | 420 |
| aagttggttg | atagtacgga | caaagcggat | ctgcgtttaa | tctatcttgc | gttagcgcac | 480 |
| atgatcaaat | tcgtggtca | tttcttaatt | gaaggtgatc | tgaatcctga | taactctgat | 540 |
| gtggacaaat | tgtttataca | attagtgcaa | acctataatc | agctgttcga | ggaaaacccc | 600 |
| attaatgcct | ctggagttga | tgccaaagcg | attttaagcg | cgagactttc | taagtcccgg | 660 |
| cgtctggaga | atctgatcgc | ccagttacca | ggggaaaaga | aaaatggtct | gtttggtaat | 720 |
| ctgattgccc | tcagtctggg | gcttacccg | aacttcaaat | ccaattttga | cctggctgag | 780 |
| gacgcaaagc | tgcagctgag | caaagatact | tatgatgatg | acctcgacaa | tctgctcgcc | 840 |
| cagattggtg | accaatatgc | ggatctgttt | ctggcagcga | agaatctttc | ggatgctatc | 900 |
| ttgctgtcgg | atattctgcg | tgttaatacc | gaaatcacca | agcgcctct | gtctgcaagt | 960 |
| atgatcaaga | gatacgacga | gcaccaccag | gacctgactc | ttcttaaggc | actggtacgc | 1020 |
| caacagcttc | cggagaaata | caagaaaata | ttcttcgacc | agtccaagaa | tggttacgcg | 1080 |
| ggctacatcg | atggtggtgc | atcacaggaa | gagttctata | aatttattaa | accaatcctt | 1140 |
| gagaaaatgg | atggcacgga | agagttactt | gttaaactta | accgcgaaga | cttgcttaga | 1200 |
| aagcaacgta | cattcgacaa | cggctccatc | ccacaccaga | ttcatttagg | tgaacttcac | 1260 |
| gccatcttgc | gcagacaaga | agatttctat | cccttcttaa | aagacaatcg | ggagaaaatc | 1320 |
| gagaagatcc | tgacgttccg | cattccctat | tatgtcggtc | ccctggcacg | tggtaattct | 1380 |
| cggtttgcct | ggatgacgcg | caaaagtgag | gaaaccatca | ccccttggaa | ctttgaagaa | 1440 |
| gtcgtggata | aggtgctag | cgcgcagtct | tttatagaaa | gaatgacgaa | cttcgataaa | 1500 |
| aacttgccca | cgaaaaaagt | cctgcccaag | cactctcttt | tatatgagta | ctttactgtg | 1560 |
| tacaacgaac | tgactaaagt | gaaatacgtt | acggaaggta | tgcgcaaacc | tgcctttctt | 1620 |
| agtggcgagc | agaaaaaagc | aattgtcgat | cttctcttta | aaacgaatcg | caaggtaact | 1680 |
| gtaaaacagc | tgaaggaaga | ttatttcaaa | aagatcgaat | gctttgattc | tgtcgagatc | 1740 |
| tcgggtgtcg | aagatcgttt | caacgcttcc | ttagggacct | atcatgattt | gctgaagata | 1800 |
| ataaaagaca | aagactttct | cgacaatgaa | gaaaatgaag | atattctgga | ggatattgtt | 1860 |
| ttgaccttga | ccttattcga | agatagagag | atgatcgagg | agcgcttaaa | aacctatgcc | 1920 |
| cacctgtttg | atgacaaagt | catgaagcaa | ttaaagcgcc | gcagatatac | ggggtggggc | 1980 |
| cgcttgagcc | gcaagttgat | taacggtatt | agagacaagc | agagcggaaa | aactatcctg | 2040 |
| gatttcctca | aatctgacgg | atttgcgaac | cgcaatttta | tgcagcttat | acatgatgat | 2100 |
| tcgcttacat | tcaaagagga | tattcagaag | gctcaggtgt | ctgggcaagg | tgattcactc | 2160 |
| cacgaacata | tagcaaattt | ggccggctct | cctgcgatta | agaagggat | cctgcaaaca | 2220 |

```
gttaaagttg tggatgaact tgtaaaagta atgggccgcc acaagccgga gaatatcgtg    2280
atagaaatgg cgcgcgagaa tcaaacgaca caaaaaggtc aaaagaactc aagagagaga    2340
atgaagcgca ttgaggaggg gataaaggaa cttggatctc aaattctgaa agaacatcca    2400
gttgaaaaca ctcagctgca aaatgaaaaa ttgtacctgt actacctgca gaatggaaga    2460
gacatgtacg tggatcagga attggatatc aatagactct cggactatga cgtagatcac    2520
attgtccctc agagcttcct caaggatgat tctatagata ataaagtact tacgagatcg    2580
gacaaaaatc gcggtaaatc ggataacgtc ccatcggagg aagtcgttaa aaagatgaaa    2640
aactattggc gtcaactgct gaacgccaag ctgatcacac agcgtaagtt tgataatctg    2700
actaaagccg aacgcggtgg tcttagtgaa ctcgataaag caggatttat aaaacggcag    2760
ttagtagaaa cgcgccaaat tacgaaacac gtggctcaga tcctcgattc tagaatgaat    2820
acaaagtacg atgaaaacga taaactgatc cgtgaagtaa aagtcattac cttaaaatct    2880
aaacttgtgt ccgatttccg caaagatttt cagttttaca aggtccggga atcaataac     2940 tatcaccatg cacatgatgc atatttaaat gcggttgtag gcacggccct tattaagaaa    3000
taccctaaac tcgaaagtga gtttgtttat ggggattata aagtgtatga cgttcgcaaa    3060
atgatcgcga aatcagaaca ggaaatcggt aaggctaccg ctaaatactt ttttattcc    3120 aacattatga attttttaa gaccgaaata actctcgcga atggtgaaat ccgtaaacgg    3180
cctcttatag aaaccaatgg tgaaacggga gaaatcgttt gggataaagg tcgtgactttt    3240 gccaccgttc gtaaagtcct ctcaatgccg caagttaaca ttgtcaagaa gacggaagtt    3300
caaacagggg gattctccaa agaatctatc ctgccgaagc gtaacagtga taaacttatt    3360
gccagaaaaa aagattggga tccaaaaaaa tacggaggct tgattcccc taccgtcgcg    3420 tatagtgtgc tggtggttgc taaagtcgag aaagggaaaa gcaagaaatt gaaatcagtt    3480
aaagaactgc tgggtattac aattatgaaa agatcgtcct ttgagaaaaa tccgatcgac    3540
tttttagagg ccaaggggta taaggaagtg aaaaaagatc tcatcatcaa attaccgaag    3600 tatagtctttt ttgagctgga aaacggcaga aaaagaatgc tggcctccgc gggcgagtta    3660
cagaagggaa atgagctggc gctgccttcc aaatatgtta attttctgta ccttgccagt    3720
cattatgaga aactgaaggg cagccccgaa gataacgaac agaaacaatt attcgtggaa    3780
cagcataagc actatttaga tgaaattata gagcaaatta gtgaatttttc taagcgcgtt    3840 atcctcgcgg atgctaattt agacaaagta ctgtcagctt ataataaaca tcgggataag    3900
ccgattagag aacaggccga aaatatcatt catttgttta ccttaaccaa ccttggagca    3960
ccagctgcct tcaaatattt cgataccaca attgatcgta aacggtatac aagtacaaaa    4020
gaagtcttgg acgcaaccct cattcatcaa tctattactg gattatatga gacacgcatt    4080
gatctttcac agctgggcgg agac                                           4104
```

<210> SEQ ID NO 16
<211> LENGTH: 21
<212> TYPE: DNA
<213> ORGANISM: Trichoderma reesei

<400> SEQUENCE: 16

```
aagaagaaaa aactgaaact g                                                21
```

<210> SEQ ID NO 17
<211> LENGTH: 4284
<212> TYPE: DNA

<213> ORGANISM: Artificial sequence
<220> FEATURE:
<223> OTHER INFORMATION: synthetic construct

<400> SEQUENCE: 17

| | | | | | |
|---|---|---|---|---|---|
| atgcaccatc | atcatcatca | ttcttctggt | ctggtgccac | gcggttctgg | tatgaaagaa | 60 |
| accgctgctg | ctaaattcga | acgccagcac | atggacagcc | agatctggg | taccgacgac | 120 |
| gacgacaagg | ccatggcccc | aaaaaagaaa | cgcaaggtta | tggataaaaa | atacagcatt | 180 |
| ggtctggata | tcggaaccaa | cagcgttggg | tgggcagtaa | taacagatga | atacaaagtg | 240 |
| ccgtcaaaaa | aatttaaggt | tctggggaat | acagatcgcc | acagcataaa | aaagaatctg | 300 |
| attgggcat | tgctgtttga | ttcgggtgag | acagctgagg | ccacgcgtct | gaaacgtaca | 360 |
| gcaagaagac | gttacacacg | tcgtaaaaat | cgtatttgct | acttacagga | aattttttct | 420 |
| aacgaaatgg | ccaaggtaga | tgatagtttc | ttccatcgtc | tcgaagaatc | ttttctggtt | 480 |
| gaggaagata | aaaacacga | acgtcaccct | atctttggca | atatcgtgga | tgaagtggcc | 540 |
| tatcatgaaa | atacccctac | gatttatcat | cttcgcaaga | agttggttga | tagtacggac | 600 |
| aaagcggatc | tgcgtttaat | ctatcttgcg | ttagcgcaca | tgatcaaatt | tcgtggtcat | 660 |
| ttcttaattg | aaggtgatct | gaatcctgat | aactctgatg | tggacaaatt | gtttatacaa | 720 |
| ttagtgcaaa | cctataatca | gctgttcgag | gaaaaccccca | ttaatgcctc | tggagttgat | 780 |
| gccaaagcga | ttttaagcgc | gagactttct | aagtcccggc | gtctggagaa | tctgatcgcc | 840 |
| cagttaccag | ggaaaagaa | aaatggtctg | tttggtaatc | tgattgccct | cagtctgggg | 900 |
| cttaccccga | acttcaaatc | caattttgac | ctggctgagg | acgcaaagct | gcagctgagc | 960 |
| aaagatactt | atgatgatga | cctcgacaat | ctgctcgccc | agattggtga | ccaatatgcg | 1020 |
| gatctgtttc | tggcagcgaa | gaatctttcg | gatgctatct | tgctgtcgga | tattctgcgt | 1080 |
| gttaataccg | aaatcaccaa | agcgcctctg | tctgcaagta | tgatcaagag | atacgacgag | 1140 |
| caccaccagg | acctgactct | tcttaaggca | ctggtacgcc | aacagcttcc | ggagaaatac | 1200 |
| aaagaaatat | tcttcgacca | gtccaagaat | ggttacgcgg | gctacatcga | tggtggtgca | 1260 |
| tcacaggaag | agttctataa | atttattaaa | ccaatccttg | agaaaatgga | tggcacggaa | 1320 |
| gagttacttg | ttaaacttaa | ccgcgaagac | ttgcttagaa | agcaacgtac | attcgacaac | 1380 |
| ggctccatcc | cacaccagat | tcatttaggt | gaacttcacg | ccatcttgcg | cagacaagaa | 1440 |
| gatttctatc | ccttcttaaa | agacaatcgg | gagaaaatcg | agaagatcct | gacgttccgc | 1500 |
| attccctatt | atgtcggtcc | cctggcacgt | ggtaattctc | ggtttgcctg | gatgacgcgc | 1560 |
| aaaagtgagg | aaaccatcac | cccttggaac | tttgaagaag | tcgtggataa | aggtgctagc | 1620 |
| gcgcagtctt | ttatagaaag | aatgacgaac | ttcgataaaa | acttgcccaa | cgaaaaagtc | 1680 |
| ctgcccaagc | actctctttt | atatgagtac | tttactgtgt | acaacgaact | gactaaagtg | 1740 |
| aaatacgtta | cggaaggtat | gcgcaaacct | gcctttctta | gtggcgagca | gaaaaaagca | 1800 |
| attgtcgatc | ttctctttaa | aacgaatcgc | aaggtaactg | taaaacagct | gaaggaagat | 1860 |
| tatttcaaaa | agatcgaatg | ctttgattct | gtcgagatct | cgggtgtcga | agatcgtttc | 1920 |
| aacgcttcct | tagggaccta | tcatgatttg | ctgaagataa | taaagacaa | agactttctc | 1980 |
| gacaatgaag | aaaatgaaga | tattctggag | gatattgttt | tgaccttgac | cttattcgaa | 2040 |
| gatagagaga | tgatcgagga | gcgcttaaaa | acctatgccc | acctgtttga | tgacaaagtc | 2100 |
| atgaagcaat | taaagcgccg | cagatatacg | gggtggggcc | gcttgagccg | caagttgatt | 2160 |
| aacggtatta | gagacaagca | gagcggaaaa | actatcctgg | atttcctcaa | atctgacgga | 2220 |

```
tttgcgaacc gcaatttat gcagcttata catgatgatt cgcttacatt caaagaggat    2280
attcagaagg ctcaggtgtc tgggcaaggt gattcactcc acgaacatat agcaaatttg    2340
gccggctctc ctgcgattaa gaaggggatc ctgcaaacag ttaaagttgt ggatgaactt    2400
gtaaaagtaa tgggccgcca caagccggag aatatcgtga tagaaatggc gcgcgagaat    2460
caaacgacac aaaaaggtca aagaactca agagagagaa tgaagcgcat tgaggagggg    2520
ataaaggaac ttgatctca aattctgaaa gaacatccag ttgaaaacac tcagctgcaa    2580
aatgaaaaat tgtacctgta ctacctgcag aatggaagag acatgtacgt ggatcaggaa    2640
ttggatatca atagactctc ggactatgac gtagatcaca ttgtccctca gagcttcctc    2700
aaggatgatt ctatagataa taaagtactt acgagatcgg acaaaaatcg cggtaaatcg    2760
gataacgtcc catcggagga agtcgttaaa aagatgaaaa actattggcg tcaactgctg    2820
aacgccaagc tgatcacaca gcgtaagttt gataatctga ctaaagccga acgcggtggt    2880
cttagtgaac tcgataaagc aggatttata aaacggcagt tagtagaaac gcgccaaatt    2940
acgaaacacg tggctcagat cctcgattct agaatgaata caaagtacga tgaaaacgat    3000
aaactgatcc gtgaagtaaa agtcattacc ttaaaatcta acttgtgtc cgatttccgc    3060 aaagatttc agttttacaa ggtccgggaa atcaataact atcaccatgc acatgatgca    3120
tatttaaatg cggttgtagg cacggcccctt attaagaaat accctaaaact cgaaagtgag    3180 tttgtttatg gggattataa agtgtatgac gttcgcaaaa tgatcgcgaa atcagaacag    3240
gaaatcggta aggctaccgc taaatacttt ttttattcca acattatgaa ttttttttaag    3300 accgaaataa ctctcgcgaa tggtgaaatc cgtaaacggc ctcttataga aaccaatggt    3360
gaaacgggag aaatcgtttg ggataaaggt cgtgactttg ccaccgttcg taaagtcctc    3420
tcaatgccgc aagttaacat tgtcaagaag acggaagttc aaacaggggg attctccaaa    3480
gaatctatcc tgccgaagcg taacagtgat aaacttattg ccagaaaaaa agattgggat    3540
ccaaaaaaat acggaggctt tgattcccct accgtcgcgt atagtgtgct ggtggttgct    3600
aaagtcgaga aagggaaaag caagaaattg aaatcagtta agaactgct gggtattaca    3660 attatggaaa gatcgtcctt tgagaaaaat ccgatcgact ttttagaggc caaggggtat    3720
aaggaagtga aaaagatct catcatcaaa ttaccgaagt atagtctttt tgagctggaa    3780
aacggcagaa aaagaatgct ggcctccgcg ggcgagttac agaagggaaa tgagctggcg    3840
ctgccttcca aatatgttaa ttttctgtac cttgccagtc attatgagaa actgaagggc    3900
agccccgaag ataacgaaca gaaacaatta ttcgtggaac agcataagca ctatttagat    3960
gaaattatag agcaaattag tgaatttctt aagcgcgtta tcctcgcgga tgctaattta    4020
gacaaagtac tgtcagctta taataaacat cgggataagc cgattagaga acaggccgaa    4080
aatatcattc atttgtttac cttaaccaac cttggagcac cagctgcctt caaatatttc    4140
gataccacaa ttgatcgtaa acggtataca agtacaaaag aagtcttgga cgcaaccctc    4200
attcatcaat ctattactgg attatatgag acacgcattg atctttcaca gctgggcgga    4260
gacaagaaga aaaaactgaa actg                                            4284
```

<210> SEQ ID NO 18
<211> LENGTH: 46
<212> TYPE: PRT
<213> ORGANISM: Artificial sequence
<220> FEATURE:
<223> OTHER INFORMATION: synthetic construct

```
<400> SEQUENCE: 18

Met His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Ala Met Ala
        35                  40                  45

<210> SEQ ID NO 19
<211> LENGTH: 7
<212> TYPE: PRT
<213> ORGANISM: SV40

<400> SEQUENCE: 19

Pro Lys Lys Lys Arg Lys Val
1               5

<210> SEQ ID NO 20
<211> LENGTH: 7
<212> TYPE: PRT
<213> ORGANISM: Trichoderma reesei

<400> SEQUENCE: 20

Lys Lys Lys Lys Leu Lys Leu
1               5

<210> SEQ ID NO 21
<211> LENGTH: 1428
<212> TYPE: PRT
<213> ORGANISM: Artificial sequence
<220> FEATURE:
<223> OTHER INFORMATION: protein expressed from synthetic construct

<400> SEQUENCE: 21

Met His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Ala Met Ala Pro Lys
        35                  40                  45

Lys Lys Arg Lys Val Met Asp Lys Lys Tyr Ser Ile Gly Leu Asp Ile
    50                  55                  60

Gly Thr Asn Ser Val Gly Trp Ala Val Ile Thr Asp Glu Tyr Lys Val
65                  70                  75                  80

Pro Ser Lys Lys Phe Lys Val Leu Gly Asn Thr Asp Arg His Ser Ile
                85                  90                  95

Lys Lys Asn Leu Ile Gly Ala Leu Leu Phe Asp Ser Gly Glu Thr Ala
            100                 105                 110

Glu Ala Thr Arg Leu Lys Arg Thr Ala Arg Arg Arg Tyr Thr Arg Arg
        115                 120                 125

Lys Asn Arg Ile Cys Tyr Leu Gln Glu Ile Phe Ser Asn Glu Met Ala
    130                 135                 140

Lys Val Asp Asp Ser Phe Phe His Arg Leu Glu Glu Ser Phe Leu Val
145                 150                 155                 160

Glu Glu Asp Lys Lys His Glu Arg His Pro Ile Phe Gly Asn Ile Val
                165                 170                 175

Asp Glu Val Ala Tyr His Glu Lys Tyr Pro Thr Ile Tyr His Leu Arg
            180                 185                 190
```

-continued

```
Lys Lys Leu Val Asp Ser Thr Asp Lys Ala Asp Leu Arg Leu Ile Tyr
            195                 200                 205
Leu Ala Leu Ala His Met Ile Lys Phe Arg Gly His Phe Leu Ile Glu
        210                 215                 220
Gly Asp Leu Asn Pro Asp Asn Ser Asp Val Asp Lys Leu Phe Ile Gln
225                 230                 235                 240
Leu Val Gln Thr Tyr Asn Gln Leu Phe Glu Glu Asn Pro Ile Asn Ala
                245                 250                 255
Ser Gly Val Asp Ala Lys Ala Ile Leu Ser Ala Arg Leu Ser Lys Ser
                260                 265                 270
Arg Arg Leu Glu Asn Leu Ile Ala Gln Leu Pro Gly Glu Lys Lys Asn
            275                 280                 285
Gly Leu Phe Gly Asn Leu Ile Ala Leu Ser Leu Gly Leu Thr Pro Asn
        290                 295                 300
Phe Lys Ser Asn Phe Asp Leu Ala Glu Asp Ala Lys Leu Gln Leu Ser
305                 310                 315                 320
Lys Asp Thr Tyr Asp Asp Asp Leu Asp Asn Leu Leu Ala Gln Ile Gly
                325                 330                 335
Asp Gln Tyr Ala Asp Leu Phe Leu Ala Ala Lys Asn Leu Ser Asp Ala
            340                 345                 350
Ile Leu Leu Ser Asp Ile Leu Arg Val Asn Thr Glu Ile Thr Lys Ala
        355                 360                 365
Pro Leu Ser Ala Ser Met Ile Lys Arg Tyr Asp Glu His His Gln Asp
        370                 375                 380
Leu Thr Leu Leu Lys Ala Leu Val Arg Gln Gln Leu Pro Glu Lys Tyr
385                 390                 395                 400
Lys Glu Ile Phe Phe Asp Gln Ser Lys Asn Gly Tyr Ala Gly Tyr Ile
                405                 410                 415
Asp Gly Gly Ala Ser Gln Glu Glu Phe Tyr Lys Phe Ile Lys Pro Ile
            420                 425                 430
Leu Glu Lys Met Asp Gly Thr Glu Glu Leu Leu Val Lys Leu Asn Arg
        435                 440                 445
Glu Asp Leu Leu Arg Lys Gln Arg Thr Phe Asp Asn Gly Ser Ile Pro
450                 455                 460
His Gln Ile His Leu Gly Glu Leu His Ala Ile Leu Arg Arg Gln Glu
465                 470                 475                 480
Asp Phe Tyr Pro Phe Leu Lys Asp Asn Arg Glu Lys Ile Glu Lys Ile
                485                 490                 495
Leu Thr Phe Arg Ile Pro Tyr Tyr Val Gly Pro Leu Ala Arg Gly Asn
            500                 505                 510
Ser Arg Phe Ala Trp Met Thr Arg Lys Ser Glu Glu Thr Ile Thr Pro
        515                 520                 525
Trp Asn Phe Glu Glu Val Val Asp Lys Gly Ala Ser Ala Gln Ser Phe
        530                 535                 540
Ile Glu Arg Met Thr Asn Phe Asp Lys Asn Leu Pro Asn Glu Lys Val
545                 550                 555                 560
Leu Pro Lys His Ser Leu Leu Tyr Glu Tyr Phe Thr Val Tyr Asn Glu
                565                 570                 575
Leu Thr Lys Val Lys Tyr Val Thr Glu Gly Met Arg Lys Pro Ala Phe
            580                 585                 590
Leu Ser Gly Glu Gln Lys Lys Ala Ile Val Asp Leu Leu Phe Lys Thr
        595                 600                 605
Asn Arg Lys Val Thr Val Lys Gln Leu Lys Glu Asp Tyr Phe Lys Lys
```

-continued

```
            610                 615                 620

Ile Glu Cys Phe Asp Ser Val Glu Ile Ser Gly Val Glu Asp Arg Phe
625                 630                 635                 640

Asn Ala Ser Leu Gly Thr Tyr His Asp Leu Leu Lys Ile Ile Lys Asp
                645                 650                 655

Lys Asp Phe Leu Asp Asn Glu Glu Asn Glu Asp Ile Leu Glu Asp Ile
                660                 665                 670

Val Leu Thr Leu Thr Leu Phe Glu Asp Arg Glu Met Ile Glu Glu Arg
                675                 680                 685

Leu Lys Thr Tyr Ala His Leu Phe Asp Asp Lys Val Met Lys Gln Leu
                690                 695                 700

Lys Arg Arg Tyr Thr Gly Trp Gly Arg Leu Ser Arg Lys Leu Ile
705                 710                 715                 720

Asn Gly Ile Arg Asp Lys Gln Ser Gly Lys Thr Ile Leu Asp Phe Leu
                725                 730                 735

Lys Ser Asp Gly Phe Ala Asn Arg Asn Phe Met Gln Leu Ile His Asp
                740                 745                 750

Asp Ser Leu Thr Phe Lys Glu Asp Ile Gln Lys Ala Gln Val Ser Gly
                755                 760                 765

Gln Gly Asp Ser Leu His Glu His Ile Ala Asn Leu Ala Gly Ser Pro
                770                 775                 780

Ala Ile Lys Lys Gly Ile Leu Gln Thr Val Lys Val Val Asp Glu Leu
785                 790                 795                 800

Val Lys Val Met Gly Arg His Lys Pro Glu Asn Ile Val Ile Glu Met
                805                 810                 815

Ala Arg Glu Asn Gln Thr Thr Gln Lys Gly Gln Lys Asn Ser Arg Glu
                820                 825                 830

Arg Met Lys Arg Ile Glu Glu Gly Ile Lys Glu Leu Gly Ser Gln Ile
                835                 840                 845

Leu Lys Glu His Pro Val Glu Asn Thr Gln Leu Gln Asn Glu Lys Leu
                850                 855                 860

Tyr Leu Tyr Tyr Leu Gln Asn Gly Arg Asp Met Tyr Val Asp Gln Glu
865                 870                 875                 880

Leu Asp Ile Asn Arg Leu Ser Asp Tyr Asp Val Asp His Ile Val Pro
                885                 890                 895

Gln Ser Phe Leu Lys Asp Asp Ser Ile Asp Asn Lys Val Leu Thr Arg
                900                 905                 910

Ser Asp Lys Asn Arg Gly Lys Ser Asp Asn Val Pro Ser Glu Glu Val
                915                 920                 925

Val Lys Lys Met Lys Asn Tyr Trp Arg Gln Leu Leu Asn Ala Lys Leu
930                 935                 940

Ile Thr Gln Arg Lys Phe Asp Asn Leu Thr Lys Ala Glu Arg Gly Gly
945                 950                 955                 960

Leu Ser Glu Leu Asp Lys Ala Gly Phe Ile Lys Arg Gln Leu Val Glu
                965                 970                 975

Thr Arg Gln Ile Thr Lys His Val Ala Gln Ile Leu Asp Ser Arg Met
                980                 985                 990

Asn Thr Lys Tyr Asp Glu Asn Asp Lys Leu Ile Arg Glu Val Lys Val
                995                 1000                1005

Ile Thr Leu Lys Ser Lys Leu Val Ser Asp Phe Arg Lys Asp Phe
            1010                1015                1020

Gln Phe Tyr Lys Val Arg Glu Ile Asn Asn Tyr His His Ala His
            1025                1030                1035
```

```
Asp Ala Tyr Leu Asn Ala Val Val Gly Thr Ala Leu Ile Lys Lys
1040                1045                1050

Tyr Pro Lys Leu Glu Ser Glu Phe Val Tyr Gly Asp Tyr Lys Val
    1055                1060                1065

Tyr Asp Val Arg Lys Met Ile Ala Lys Ser Glu Gln Glu Ile Gly
1070                1075                1080

Lys Ala Thr Ala Lys Tyr Phe Phe Tyr Ser Asn Ile Met Asn Phe
1085                1090                1095

Phe Lys Thr Glu Ile Thr Leu Ala Asn Gly Glu Ile Arg Lys Arg
1100                1105                1110

Pro Leu Ile Glu Thr Asn Gly Glu Thr Gly Glu Ile Val Trp Asp
    1115                1120                1125

Lys Gly Arg Asp Phe Ala Thr Val Arg Lys Val Leu Ser Met Pro
1130                1135                1140

Gln Val Asn Ile Val Lys Lys Thr Glu Val Gln Thr Gly Gly Phe
1145                1150                1155

Ser Lys Glu Ser Ile Leu Pro Lys Arg Asn Ser Asp Lys Leu Ile
1160                1165                1170

Ala Arg Lys Lys Asp Trp Asp Pro Lys Lys Tyr Gly Gly Phe Asp
1175                1180                1185

Ser Pro Thr Val Ala Tyr Ser Val Leu Val Val Ala Lys Val Glu
1190                1195                1200

Lys Gly Lys Ser Lys Lys Leu Lys Ser Val Lys Glu Leu Leu Gly
1205                1210                1215

Ile Thr Ile Met Glu Arg Ser Ser Phe Glu Lys Asn Pro Ile Asp
1220                1225                1230

Phe Leu Glu Ala Lys Gly Tyr Lys Glu Val Lys Lys Asp Leu Ile
1235                1240                1245

Ile Lys Leu Pro Lys Tyr Ser Leu Phe Glu Leu Glu Asn Gly Arg
1250                1255                1260

Lys Arg Met Leu Ala Ser Ala Gly Glu Leu Gln Lys Gly Asn Glu
1265                1270                1275

Leu Ala Leu Pro Ser Lys Tyr Val Asn Phe Leu Tyr Leu Ala Ser
1280                1285                1290

His Tyr Glu Lys Leu Lys Gly Ser Pro Glu Asp Asn Glu Gln Lys
1295                1300                1305

Gln Leu Phe Val Glu Gln His Lys His Tyr Leu Asp Glu Ile Ile
1310                1315                1320

Glu Gln Ile Ser Glu Phe Ser Lys Arg Val Ile Leu Ala Asp Ala
1325                1330                1335

Asn Leu Asp Lys Val Leu Ser Ala Tyr Asn Lys His Arg Asp Lys
1340                1345                1350

Pro Ile Arg Glu Gln Ala Glu Asn Ile Ile His Leu Phe Thr Leu
1355                1360                1365

Thr Asn Leu Gly Ala Pro Ala Ala Phe Lys Tyr Phe Asp Thr Thr
1370                1375                1380

Ile Asp Arg Lys Arg Tyr Thr Ser Thr Lys Glu Val Leu Asp Ala
1385                1390                1395

Thr Leu Ile His Gln Ser Ile Thr Gly Leu Tyr Glu Thr Arg Ile
1400                1405                1410

Asp Leu Ser Gln Leu Gly Gly Asp Lys Lys Lys Lys Leu Lys Leu
1415                1420                1425
```

<210> SEQ ID NO 22
<211> LENGTH: 842
<212> TYPE: DNA
<213> ORGANISM: Trichoderma reesei

<400> SEQUENCE: 22

```
aaaaaacact agtaagtact tacttatgta ttattaacta ctttagctaa cttctgcagt      60
actacctaag aggctagggg tagttttata gcagacttat agctattatt tttatttagt    120
aaagtgcttt taaagtaagg tcttttttat agcactttt atttattata atatatatta     180
tataataatt ttaagcctgg aatagtaaag aggcttatat aataatttat agtaataaaa    240
gcttagcagc tgtaatataa ttcctaaaga aacagcatga aatggtatta tgtaagagct    300
atagtctaaa ggcactctgc tggataaaaa tagtggctat aagtctgctg caaaactacc    360
cccaacctcg taggtatata agtactgttt gatggtagtc tatcgccttc gggcatttgg    420
tcaatttata acgatacagg ttcgtttcgg cttttcctcg aaccccag aggtcatcag      480
ttcgaatcgc taacaggtca acagagaaga ttagcatggc ccctgcacta aggatgacac    540
gctcactcaa agagaagcta acatttttt ttctcttcca agtcgtgatg gttatctttt     600
tgcttagaga atctattctt gtggacgatt agtattggta aatccctgct gcacattgcg    660
gcggatggtc tcaacggcat aataccccat tcgtgatgca gcggtgatct tcaatatgta    720
gtgtaatacg ttgcatacac caccaggttc ggtgcctcct gtatgtacag tactgtagtt    780
cgactcctcc gcgcaggtgg aaacgattcc ctagtgggca ggtattttgg cggggtcaag    840
aa                                                                    842
```

<210> SEQ ID NO 23
<211> LENGTH: 99
<212> TYPE: RNA
<213> ORGANISM: Artificial sequence
<220> FEATURE:
<223> OTHER INFORMATION: sg RNA
<220> FEATURE:
<221> NAME/KEY: misc_feature
<222> LOCATION: (1)..(20)
<223> OTHER INFORMATION: N region - complementary to target site

<400> SEQUENCE: 23

```
nnnnnnnnnn nnnnnnnnnn guuuuagagc uagaaauagc aaguuaaaau aaggcuaguc      60
cguuaucaac uugaaaaagu ggcaccgagu cggugguc                               99
```

<210> SEQ ID NO 24
<211> LENGTH: 99
<212> TYPE: RNA
<213> ORGANISM: Artificial sequence
<220> FEATURE:
<223> OTHER INFORMATION: Synthetic construct

<400> SEQUENCE: 24

```
guccucgagc aaaaggugcc guuuuagagc uagaaauagc aaguuaaaau aaggcuaguc      60
cguuaucaac uugaaaaagu ggcaccgagu cggugguc                               99
```

<210> SEQ ID NO 25
<211> LENGTH: 99
<212> TYPE: RNA
<213> ORGANISM: Artificial sequence
<220> FEATURE:
<223> OTHER INFORMATION: Synthetic construct

<400> SEQUENCE: 25

```
guucagugca auaggcgucu guuuuagagc uagaaauagc aaguuaaaau aaggcuaguc      60
cguuaucaac uugaaaaagu ggcaccgagu cgguggugc                            99

<210> SEQ ID NO 26
<211> LENGTH: 99
<212> TYPE: RNA
<213> ORGANISM: Artificial sequence
<220> FEATURE:
<223> OTHER INFORMATION: Synthetic construct

<400> SEQUENCE: 26
gccaauggcg acggcagcac guuuuagagc uagaaauagc aaguuaaaau aaggcuaguc      60
cguuaucaac uugaaaaagu ggcaccgagu cgguggugc                            99

<210> SEQ ID NO 27
<211> LENGTH: 99
<212> TYPE: RNA
<213> ORGANISM: Artificial sequence
<220> FEATURE:
<223> OTHER INFORMATION: Synthetic construct

<400> SEQUENCE: 27
gcacagcggg augcccuugu guuuuagagc uagaaauagc aaguuaaaau aaggcuaguc      60
cguuaucaac uugaaaaagu ggcaccgagu cgguggugc                            99

<210> SEQ ID NO 28
<211> LENGTH: 412
<212> TYPE: DNA
<213> ORGANISM: Artificial sequence
<220> FEATURE:
<223> OTHER INFORMATION: Synthetic construct

<400> SEQUENCE: 28
gaattcggat cctctttgaa aagataatgt atgattatgc tttcactcat atttatacag      60
aaacttgatg ttttctttcg agtatataca aggtgattac atgtacgttt gaagtacaac     120
tctagatttt gtagtgccct cttgggctag cggtaaaggt gcgcattttt tcacaccta     180 caatgttctg ttcaaaagat tttggtcaaa cgctgtagaa gtgaaagttg gtgcgcatgt     240
ttcggcgttc gaaacttctc cgcagtgaaa gataaatgat cgtcctcgag caaaaggtgc     300
cgttttagag ctagaaatag caagttaaaa taaggctagt ccgttatcaa cttgaaaaag     360
tggcaccgag tcggtggtgc tttttttgtt ttttatgtct gaattcggat cc             412

<210> SEQ ID NO 29
<211> LENGTH: 540
<212> TYPE: DNA
<213> ORGANISM: Artificial sequence
<220> FEATURE:
<223> OTHER INFORMATION: Synthetic construct

<400> SEQUENCE: 29
gaattcggat ccaaaaaaca ctagtaagta cttacttatg tattattaac tactttagct      60
aacttctgca gtactaccta agaggctagg ggtagtttta tagcagactt atagctatta     120
tttttattta gtaaagtgct tttaaagtaa ggtcttttt atgcactttt ttatttatta     180
taatatatat tatataataa ttttaagcct ggaatagtaa agaggcttat ataataattt     240
atagtaataa aagcttagca gctgtaatat aattcctaaa gaaacagcat gaaatggtat     300
tatgtaagag ctatagtcta aaggcactct gctggataaa aatagtggct ataagtctgc     360
```

```
tgcaaaacta ccccaacct cgtaggtata aagtactgt ttgatggtag tctatcgtcc      420
tcgagcaaaa ggtgccgttt tagagctaga aatagcaagt taaaataagg ctagtccgtt      480
atcaacttga aaaagtggca ccgagtcggt ggtgctttt tttctcttga attcggatcc      540
```

<210> SEQ ID NO 30
<211> LENGTH: 597
<212> TYPE: DNA
<213> ORGANISM: Artificial sequence
<220> FEATURE:
<223> OTHER INFORMATION: Synthetic construct

<400> SEQUENCE: 30

```
gaattcggat ccaaaaaaca ctagtaagta cttacttatg tattattaac tactttagct      60
aacttctgca gtactaccta agaggctagg ggtagtttta tagcagactt atagctatta     120
tttttattta gtaaagtgct tttaaagtaa ggtctttttt atagcacttt ttatttatta     180
taatatatat tatataataa ttttaagcct ggaatagtaa agaggcttat ataataattt     240
atagtaataa aagcttagca gctgtaatat aattcctaaa gaaacagcat gaaatggtat     300
tatgtaagag ctatagtcta aaggcactct gctggataaa aatagtggct ataagtctgc     360
tgcaaaacta ccccaacct cgtaggtata aagtactgt ttgatggtag tctatcgtcc      420
tcgagcaaaa ggtgccgttt tagagctaga gttcgtttcg gcttttcctc ggaacccca      480 gaggtcatca gttcgaatcg ctaacagaat agcaagttaa aataaggcta gtccgttatc     540
aacttgaaaa agtggcaccg agtcggtggt gctttttttt ctcttgaatt cggatcc        597
```

<210> SEQ ID NO 31
<211> LENGTH: 315
<212> TYPE: DNA
<213> ORGANISM: Artificial sequence
<220> FEATURE:
<223> OTHER INFORMATION: Synthetic construct

<400> SEQUENCE: 31

```
aattcctaaa gaaacagcat gaaatggtat tatgtaagag ctatagtcta aaggcactct      60
gctggataaa aatagtggct ataagtctgc tgcaaaacta ccccaacct cgtaggtata     120 taagtactgt ttgatggtag tctatcgcca atggcgacgg cagcacgttt tagagctaga     180
gttcgtttcg gcttttcctc ggaacccca gaggtcatca gttcgaatcg ctaacagaat     240
agcaagttaa aataaggcta gtccgttatc aacttgaaaa agtggcaccg agtcggtggt     300 gcttttttt ctctt                                                       315
```

<210> SEQ ID NO 32
<211> LENGTH: 39
<212> TYPE: DNA
<213> ORGANISM: Artificial sequence
<220> FEATURE:
<223> OTHER INFORMATION: primer

<400> SEQUENCE: 32

```
cgtcagctta agaattccta aagaaacagc atgaaatgg                            39
```

<210> SEQ ID NO 33
<211> LENGTH: 47
<212> TYPE: DNA
<213> ORGANISM: Artificial sequence
<220> FEATURE:
<223> OTHER INFORMATION: primer

<400> SEQUENCE: 33
cgtcagggcc acgtgggcca agagaaaaaa aagcaccacc gactcgg        47

<210> SEQ ID NO 34
<211> LENGTH: 23
<212> TYPE: DNA
<213> ORGANISM: Artificial sequence
<220> FEATURE:
<223> OTHER INFORMATION: primer

<400> SEQUENCE: 34
tgaacacagc caccgacatc agc        23

<210> SEQ ID NO 35
<211> LENGTH: 23
<212> TYPE: DNA
<213> ORGANISM: Artificial sequence
<220> FEATURE:
<223> OTHER INFORMATION: primer

<400> SEQUENCE: 35
gctggtgagg gtttgtgcta ttg        23

<210> SEQ ID NO 36
<211> LENGTH: 21
<212> TYPE: DNA
<213> ORGANISM: Artificial sequence
<220> FEATURE:
<223> OTHER INFORMATION: primer

<400> SEQUENCE: 36
gattgcttgg gaggaggaca t        21

<210> SEQ ID NO 37
<211> LENGTH: 23
<212> TYPE: DNA
<213> ORGANISM: Artificial sequence
<220> FEATURE:
<223> OTHER INFORMATION: primer

<400> SEQUENCE: 37
cgaggccact gatgaagttg ttc        23

<210> SEQ ID NO 38
<211> LENGTH: 23
<212> TYPE: DNA
<213> ORGANISM: Artificial sequence
<220> FEATURE:
<223> OTHER INFORMATION: primer

<400> SEQUENCE: 38
cagttttcca aggctgccaa cgc        23

<210> SEQ ID NO 39
<211> LENGTH: 22
<212> TYPE: DNA
<213> ORGANISM: Artificial sequence
<220> FEATURE:
<223> OTHER INFORMATION: primer

<400> SEQUENCE: 39
ctgatcttgc accctggaaa tc        22

<210> SEQ ID NO 40
<211> LENGTH: 23
<212> TYPE: DNA

```
<213> ORGANISM: Artificial sequence
<220> FEATURE:
<223> OTHER INFORMATION: primer

<400> SEQUENCE: 40
ctctctatca tttgccaccc tcc                                              23

<210> SEQ ID NO 41
<211> LENGTH: 22
<212> TYPE: DNA
<213> ORGANISM: Artificial sequence
<220> FEATURE:
<223> OTHER INFORMATION: primer

<400> SEQUENCE: 41
ctccattcac cctcaattct cc                                               22

<210> SEQ ID NO 42
<211> LENGTH: 23
<212> TYPE: DNA
<213> ORGANISM: Artificial sequence
<220> FEATURE:
<223> OTHER INFORMATION: primer

<400> SEQUENCE: 42
gttcccttgg cggtgcttgg atc                                              23

<210> SEQ ID NO 43
<211> LENGTH: 23
<212> TYPE: DNA
<213> ORGANISM: Artificial sequence
<220> FEATURE:
<223> OTHER INFORMATION: primer

<400> SEQUENCE: 43
caatagcaca aaccctcacc agc                                              23

<210> SEQ ID NO 44
<211> LENGTH: 23
<212> TYPE: DNA
<213> ORGANISM: Artificial sequence
<220> FEATURE:
<223> OTHER INFORMATION: primer

<400> SEQUENCE: 44
gaacaacttc atcagtggcc tcg                                              23

<210> SEQ ID NO 45
<211> LENGTH: 23
<212> TYPE: DNA
<213> ORGANISM: Artificial sequence
<220> FEATURE:
<223> OTHER INFORMATION: primer

<400> SEQUENCE: 45
ccgttagttg aagatccttg ccg                                              23

<210> SEQ ID NO 46
<211> LENGTH: 23
<212> TYPE: DNA
<213> ORGANISM: Artificial sequence
<220> FEATURE:
<223> OTHER INFORMATION: primer

<400> SEQUENCE: 46
gtcgaggatt tgcttcatac ctc                                              23
```

```
<210> SEQ ID NO 47
<211> LENGTH: 23
<212> TYPE: DNA
<213> ORGANISM: Artificial sequence
<220> FEATURE:
<223> OTHER INFORMATION: primer

<400> SEQUENCE: 47 tgccgactttt gtccagtgat tcg                                              23

<210> SEQ ID NO 48
<211> LENGTH: 23
<212> TYPE: DNA
<213> ORGANISM: Artificial sequence
<220> FEATURE:
<223> OTHER INFORMATION: primer

<400> SEQUENCE: 48
ttacatgtgg acgcgagata gcg                                               23

<210> SEQ ID NO 49
<211> LENGTH: 22
<212> TYPE: DNA
<213> ORGANISM: Artificial sequence
<220> FEATURE:
<223> OTHER INFORMATION: primer

<400> SEQUENCE: 49
gtgtgtctaa tgcctccacc ac                                                22

<210> SEQ ID NO 50
<211> LENGTH: 22
<212> TYPE: DNA
<213> ORGANISM: Artificial sequence
<220> FEATURE:
<223> OTHER INFORMATION: primer

<400> SEQUENCE: 50
gatcgtgcta gcgctgctgt tg                                                22

<210> SEQ ID NO 51
<211> LENGTH: 21
<212> TYPE: DNA
<213> ORGANISM: Artificial sequence
<220> FEATURE:
<223> OTHER INFORMATION: primer

<400> SEQUENCE: 51
ccgtgatgga gcccgtcttc t                                                 21

<210> SEQ ID NO 52
<211> LENGTH: 22
<212> TYPE: DNA
<213> ORGANISM: Artificial sequence
<220> FEATURE:
<223> OTHER INFORMATION: primer

<400> SEQUENCE: 52
cgcggtgagt tcaggctttt tc                                                22

<210> SEQ ID NO 53
<211> LENGTH: 22
<212> TYPE: DNA
<213> ORGANISM: Artificial sequence
<220> FEATURE:
```

<223> OTHER INFORMATION: primer

<400> SEQUENCE: 53
gtataagagc aggaggaggg ag				22

<210> SEQ ID NO 54
<211> LENGTH: 22
<212> TYPE: DNA
<213> ORGANISM: Artificial sequence
<220> FEATURE:
<223> OTHER INFORMATION: primer

<400> SEQUENCE: 54
gaacgcctca atcagtcagt cg				22

<210> SEQ ID NO 55
<211> LENGTH: 2431
<212> TYPE: DNA
<213> ORGANISM: Artificial sequence
<220> FEATURE:
<223> OTHER INFORMATION: Synthetic construct

<400> SEQUENCE: 55

```
tcaggaaata gctttaagta gcttattaag tattaaaatt atatatattt ttaatataac    60
tatatttctt taataaatag gtattttaag ctttatatat aaatataata ataaaataat   120
atattatata gctttttatt aataaataaa atagctaaaa atataaaaaa aatagcttta   180
aaatacttat ttttaattag aattttatat atttttaata taagatctc tttactttt   240
tataagcttc ctaccttaaa ttaaattttt actttttttt actattttac tatatcttaa   300
ataaaggctt taaaatata aaaaaaatct tcttatatat tataagctat aaggattata   360
tatatatttt ttttaattt ttaaagtaag tattaaagct agaattaaag ttttaattt   420
ttaaggcttt atttaaaaaa aggcagtaat agcttataaa agaaatttct ttttctttta   480
tactaaaagt actttttttt taataaggtt agggttaggg tttactcaca ccgaccatcc   540
caaccacatc ttagggttag ggttagggtt agggttaggg ttagggttag ggttagggta   600
agggtttaaa caaagccacg ttgtgtctca aaatctctga tgttacattg cacaagataa   660
aaatatatca tcatgaacaa taaaactgtc tgcttacata aacagtaata caagggggtgt   720
tatgagccat attcaacggg aaacgtcttg ctcgaggccg cgattaaatt ccaacatgga   780
tgctgattta tatgggtata aatgggctcg cgataatgtc gggcaatcag gtgcgacaat   840
ctatcgattg tatgggaagc ccgatgcgcc agagttgttt ctgaaacatg gcaaaggtag   900
cgttgccaat gatgttacag atgagatggt cagactaaac tggctgacgg aatttatgcc   960
tcttccgacc atcaagcatt ttatccgtac tcctgatgat gcatggttac tcaccactgc  1020
gatccccggg aaaacagcat tccaggtatt agaagaatat cctgattcag gtgaaaatat  1080
tgttgatgcg ctggcagtgt tcctgcgccg gttgcattcg attcctgttt gtaattgtcc  1140
ttttaacagc gatcgcgtat ttcgtctcgc tcaggcgcaa tcacgaatga ataacggttt  1200
ggttgatgcg agtgattttg atgacgagcg taatggctgg cctgttgaac aagtctggaa  1260
agaaatgcat aagcttttgc cattctcacc ggattcagtc gtcactcatg gtgatttctc  1320
acttgataac cttattttg acgaggggaa attaataggt tgtattgatg ttggacgagt  1380
cggaatcgca gaccgatacc aggatcttgc catcctatgg aactgcctcg gtgagttttc  1440
tccttcatta cagaaacggc tttttcaaaa atatggtatt gataatcctg atatgaataa  1500
attgcagttt catttgatgc tcgatgagtt tttctaatca gaattggtta attggttgta  1560
```

-continued

```
acactggcag agcattacgc tgacttgacg ggacggcggc tttgttgaat aaatcgaact    1620
tttgctgagt tgaaggatca gatcacgcat cttcccgaca acgcagaccg ttccgtggca    1680
aagcaaaagt tcaaaatcac caactggtcc acctacaaca aagctctcat caaccgtggc    1740
tccctcactt tctggctgga tgatggggcg attcaggcct ggtatgagtc agcaacacct    1800
tcttcacgag gcagacctca gcggtttaaa cctaacccta accctaaccc taaccctaac    1860
cctaacccta accctaaccc taaccctaac cctaacccta accctaaccc taacctaacc    1920
ctaatggggt cgatctgaac cgaggatgag ggttctatag actaatctac aggccgtaca    1980
tggtgtgatt gcagatgcga cgggcaaggt gtacagtgtc cagaaggagg agagcggcat    2040
aggtattgta atagaccagc tttacataat aatcgcctgt tgctactgac tgatgacctt    2100
cttccctaac cagtttccta attaccactg cagtgaggat aacccctaact cgctctgggg    2160 ttattattat actgattagc aggtggctta tatagtgctg aagtactata agagtttctg    2220
cgggaggagg tggaaggact ataaactgga cacagttagg gatagagtga tgacaagacc    2280
tgaatgttat cctccggtgt ggtatagcga attggctgac cttgcagatg gtaatggttt    2340
aggcagggtt tttgcagagg gggacgagaa cgcgttctgc gatttaacgg ctgctgccgc    2400
caagctttac ggttctctaa tgggcggccg c                                  2431
```

<210> SEQ ID NO 56  
<211> LENGTH: 23  
<212> TYPE: DNA  
<213> ORGANISM: Trichoderma reesei

<400> SEQUENCE: 56

```
gcagcacctc gcacagcatg cgg                                             23
```

<210> SEQ ID NO 57  
<211> LENGTH: 23  
<212> TYPE: DNA  
<213> ORGANISM: Artificial sequence  
<220> FEATURE:  
<223> OTHER INFORMATION: linker

<400> SEQUENCE: 57

```
taggcagcac ctcgcacagc atg                                             23
```

<210> SEQ ID NO 58  
<211> LENGTH: 22  
<212> TYPE: DNA  
<213> ORGANISM: Artificial sequence  
<220> FEATURE:  
<223> OTHER INFORMATION: linker

<400> SEQUENCE: 58

```
aaaccatgct gtgcgaggtg ct                                              22
```

<210> SEQ ID NO 59  
<211> LENGTH: 23  
<212> TYPE: DNA  
<213> ORGANISM: Trichoderma reesei

<400> SEQUENCE: 59

```
gctgccagga agaattcaac ggg                                             23
```

<210> SEQ ID NO 60  
<211> LENGTH: 23  
<212> TYPE: DNA

```
<213> ORGANISM: Artificial sequence
<220> FEATURE:
<223> OTHER INFORMATION: linker

<400> SEQUENCE: 60
taggctgcca ggaagaattc aac                                              23

<210> SEQ ID NO 61
<211> LENGTH: 22
<212> TYPE: DNA
<213> ORGANISM: Artificial sequence
<220> FEATURE:
<223> OTHER INFORMATION: linker

<400> SEQUENCE: 61
aaacgttgaa ttcttcctgg ca                                               22

<210> SEQ ID NO 62
<211> LENGTH: 23
<212> TYPE: DNA
<213> ORGANISM: Trichoderma reesei

<400> SEQUENCE: 62
gctcaagacg cactacgaca tgg                                              23

<210> SEQ ID NO 63
<211> LENGTH: 23
<212> TYPE: DNA
<213> ORGANISM: Artificial sequence
<220> FEATURE:
<223> OTHER INFORMATION: linker

<400> SEQUENCE: 63
taggctcaag acgcactacg aca                                              23

<210> SEQ ID NO 64
<211> LENGTH: 24
<212> TYPE: DNA
<213> ORGANISM: Artificial sequence
<220> FEATURE:
<223> OTHER INFORMATION: linker

<400> SEQUENCE: 64
aaactgtcgt agtgcgtctt gagc                                             24

<210> SEQ ID NO 65
<211> LENGTH: 123
<212> TYPE: DNA
<213> ORGANISM: Artificial sequence
<220> FEATURE:
<223> OTHER INFORMATION: Synthetic construct

<400> SEQUENCE: 65
taatacgact cactataggg cagcacctcg cacagcatgg ttttagagct agaaatagca      60
agttaaaata aggctagtcc gttatcaact tgaaaaagtg gcaccgagtc ggtgcttttt     120
acg                                                                  123

<210> SEQ ID NO 66
<211> LENGTH: 123
<212> TYPE: DNA
<213> ORGANISM: Artificial sequence
<220> FEATURE:
<223> OTHER INFORMATION: Synthetic construct

<400> SEQUENCE: 66
```

```
taatacgact cactataggg ctgccaggaa gaattcaacg ttttagagct agaaatagca      60
agttaaaata aggctagtcc gttatcaact tgaaaaagtg gcaccgagtc ggtgcttttt     120
acg                                                                  123
```

<210> SEQ ID NO 67
<211> LENGTH: 123
<212> TYPE: DNA
<213> ORGANISM: Artificial sequence
<220> FEATURE:
<223> OTHER INFORMATION: Synthetic construct

<400> SEQUENCE: 67

```
taatacgact cactataggg ctcaagacgc actacgacag ttttagagct agaaatagca      60
agttaaaata aggctagtcc gttatcaact tgaaaaagtg gcaccgagtc ggtgcttttt     120
acg                                                                  123
```

<210> SEQ ID NO 68
<211> LENGTH: 47
<212> TYPE: DNA
<213> ORGANISM: Trichoderma reesei

<400> SEQUENCE: 68

```
tggcccgtcg attgtcgtgc tcaagacgca ctacgacatg gtctcgg                   47
```

<210> SEQ ID NO 69
<211> LENGTH: 49
<212> TYPE: DNA
<213> ORGANISM: unknown
<220> FEATURE:
<223> OTHER INFORMATION: mutant T4 4-3

<400> SEQUENCE: 69

```
tggcccgtcg attgtcgtgc tcaagacgca ctacgcgaca tggtctcgg                 49
```

<210> SEQ ID NO 70
<211> LENGTH: 47
<212> TYPE: DNA
<213> ORGANISM: unknown
<220> FEATURE:
<223> OTHER INFORMATION: mutant T4 4-13

<400> SEQUENCE: 70

```
tggcccgtcg attgtcgtgc tcaagacgca ctacgacatg gtctcgg                   47
```

<210> SEQ ID NO 71
<211> LENGTH: 48
<212> TYPE: DNA
<213> ORGANISM: unknown
<220> FEATURE:
<223> OTHER INFORMATION: mutant T4 4-11

<400> SEQUENCE: 71

```
tggcccgtcg attgtcgtgc tcaagacgca ctacggacat ggtctcgg                  48
```

<210> SEQ ID NO 72
<211> LENGTH: 47
<212> TYPE: DNA
<213> ORGANISM: unknown
<220> FEATURE:
<223> OTHER INFORMATION: mutant T4 4-12

<400> SEQUENCE: 72

```
tggcccgtcg attgtcgtgc tcaagacgca ctacgacatg gtctcgg        47
```

<210> SEQ ID NO 73
<211> LENGTH: 48
<212> TYPE: DNA
<213> ORGANISM: unknown
<220> FEATURE:
<223> OTHER INFORMATION: mutant T4 4-18

<400> SEQUENCE: 73

```
tggcccgtcg attgtcgtgc tcaagacgca ctacggacat ggtctcgg       48
```

<210> SEQ ID NO 74
<211> LENGTH: 115
<212> TYPE: DNA
<213> ORGANISM: unknown
<220> FEATURE:
<223> OTHER INFORMATION: mutant T4 4-20

<400> SEQUENCE: 74

```
tggcccgtcg attgtcgtgc tcaagacgca ctacgagccg acagggcgcc tggctaaatc    60
caaggtcaag acaggctggt ggttgtttag tgcgagtcct ctgacatggt ctcgg        115
```

<210> SEQ ID NO 75
<211> LENGTH: 48
<212> TYPE: DNA
<213> ORGANISM: unknown
<220> FEATURE:
<223> OTHER INFORMATION: mutant T4 4-19

<400> SEQUENCE: 75

```
tggcccgtcg attgtcgtgc tcaagacgca ctacggacat ggtctcgg       48
```

<210> SEQ ID NO 76
<211> LENGTH: 48
<212> TYPE: DNA
<213> ORGANISM: unknown
<220> FEATURE:
<223> OTHER INFORMATION: mutant T4 4-4

<400> SEQUENCE: 76

```
tggcccgtcg aatgttgtgg tcaaggcgcc cttcggacat ggtctcgg       48
```

<210> SEQ ID NO 77
<211> LENGTH: 48
<212> TYPE: DNA
<213> ORGANISM: unknown
<220> FEATURE:
<223> OTHER INFORMATION: mutant T4 4-7

<400> SEQUENCE: 77

```
tggcccgtcg attgtcgtgc tcaagacgca ctacggacat ggtctcgg       48
```

<210> SEQ ID NO 78
<211> LENGTH: 187
<212> TYPE: DNA
<213> ORGANISM: unknown
<220> FEATURE:
<223> OTHER INFORMATION: mutant T4 2.2

<400> SEQUENCE: 78

```
ccgctgacgg cttacctgtt caagctcatg gacctcaagg cgtccaacct gtgcctgagc    60
gccgacgtgc cgacagcgcg cgagctgctg tacctggccg acaagattgg cccgtcgatt    120
gtcgtgctca agacgcacta cgcaggcctg cgtcgaggcc gcccgggagc acaaggactt    180
```

<210> SEQ ID NO 79
<211> LENGTH: 798
<212> TYPE: DNA
<213> ORGANISM: Trichoderma reesei

<400> SEQUENCE: 79

```
ccgctgacgg cttacctgtt caagctcatg gacctcaagg cgtccaacct gtgcctgagc      60
gccgacgtgc cgacagcgcg cgagctgctg tacctggccg acaagattgg cccgtcgatt     120
gtcgtgctca agacgcacta cgacatggtc tcgggctggg acttccaccc ggagacgggc     180
acgggagccc agctggcgtc gctggcgcgc aagcacggct tcctcatctt cgaggaccgc     240
aagtttggcg acattggcca caccgtcgag ctgcagtaca cgggcgggtc ggcgcgcatc     300
atcgactggg cgcacattgt caacgtcaac atggtgcccg gcaaggcgtc ggtggcctcg     360
ctggcccagg gcgccaagcg ctggctcgag cgctacccct gcgaggtcaa gacgtccgtc     420
accgtcggca cgcccaccat ggactcgttt gacgacgacg ccgactccag ggacgccgag     480
cccgccggcg ccgtcaacgg catgggctcc attggcgtcc tggacaagcc catctactcg     540
aaccggtccg gcgacggccg caagggcagc atcgtctcca tcaccaccgt cacccagcag     600
tacgagtccg tctcctcgcc ccggttaaca aaggccatcg ccgagggcga cgagtcgctc     660
ttcccgggca tcgaggaggc gccgctgagc cgcggcctcc tgatcctcgc ccaaatgtcc     720
agccagggca acttcatgaa caaggagtac acgcaggcct gcgtcgaggc cgcccgggag     780
cacaaggact ttgtcatg                                                  798
```

<210> SEQ ID NO 80
<211> LENGTH: 59
<212> TYPE: DNA
<213> ORGANISM: Trichoderma reesei

<400> SEQUENCE: 80

```
ctggccgaca agattggccc gtcgattgtc gtgctcaaga cgcactacga catggtctc      59
```

<210> SEQ ID NO 81
<211> LENGTH: 60
<212> TYPE: DNA
<213> ORGANISM: unknown
<220> FEATURE:
<223> OTHER INFORMATION: mutant T4 2.4

<400> SEQUENCE: 81

```
ctggccgaca agattggccc gtcgattgtc gtgctcaaga cgcactacgg acatggtctc      60
```

<210> SEQ ID NO 82
<211> LENGTH: 101
<212> TYPE: DNA
<213> ORGANISM: Artificial sequence
<220> FEATURE:
<223> OTHER INFORMATION: consensus sequence

<400> SEQUENCE: 82

```
gacagcgcgc gagctgctgt acctggccga caagattggc ccgtcgattg tcgtgctcaa      60
gacgcactac gacatggtct cgggctggga cttccacccg g                         101
```

<210> SEQ ID NO 83
<211> LENGTH: 102
<212> TYPE: DNA

```
<213> ORGANISM: unknown
<220> FEATURE:
<223> OTHER INFORMATION: mutant P37 #13 4.2

<400> SEQUENCE: 83
gacagcgcgc gagctgctgt acctggccga caagattggc ccgtcgattg tcgtgctcaa      60
gacgcactac ggacatggtc tcgggctggg acttccaccc gg                        102

<210> SEQ ID NO 84
<211> LENGTH: 102
<212> TYPE: DNA
<213> ORGANISM: unknown
<220> FEATURE:
<223> OTHER INFORMATION: mutant P37 4.1 #12

<400> SEQUENCE: 84
gacagcgcgc gagctgctgt acctggccga caagattggc ccgtcgattg tcgtgctcaa      60
gacgcactac gtacatggtc tcgggctggg acttccaccc gg                        102

<210> SEQ ID NO 85
<211> LENGTH: 100
<212> TYPE: DNA
<213> ORGANISM: unknown
<220> FEATURE:
<223> OTHER INFORMATION: mutant P37 #15 4.4

<400> SEQUENCE: 85
gacagcgcgc gagctgctgt acctggccga caagattggc ccgtcgattg tcgtgctcaa      60
gacgcactac gcatggtctc gggctgggac ttccacccgg                           100

<210> SEQ ID NO 86
<211> LENGTH: 101
<212> TYPE: DNA
<213> ORGANISM: unknown
<220> FEATURE:
<223> OTHER INFORMATION: mutant P37 #14 4.3

<400> SEQUENCE: 86
gacagcgcgc gagctgctgt acctggccga caagattggc ccgtcgattg tcgtgctcaa      60
gacgcactac gacatggtct cgggctggga cttccacccg g                         101

<210> SEQ ID NO 87
<211> LENGTH: 101
<212> TYPE: DNA
<213> ORGANISM: Artificial sequence
<220> FEATURE:
<223> OTHER INFORMATION: consensus sequence
<220> FEATURE:
<221> NAME/KEY: misc_feature
<222> LOCATION: (67)..(68)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (72)..(75)
<223> OTHER INFORMATION: n is a, c, g, or t
<220> FEATURE:
<221> NAME/KEY: misc_feature
<222> LOCATION: (78)..(82)
<223> OTHER INFORMATION: n is a, c, g, or t
<220> FEATURE:
<221> NAME/KEY: misc_feature
<222> LOCATION: (85)..(86)
<223> OTHER INFORMATION: n is a, c, g, or t
```

```
<220> FEATURE:
<221> NAME/KEY: misc_feature
<222> LOCATION: (91)..(93)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t
<220> FEATURE:
<221> NAME/KEY: misc_feature
<222> LOCATION: (97)..(97)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t

<400> SEQUENCE: 87
gacagcgcgc gagctgctgt acctggccga caagattggc ccgtcgattg tcgtgctcaa      60
gacgcannan gnnnggnnn nnggnnggga nnncnancng g                          101

<210> SEQ ID NO 88
<211> LENGTH: 1146
<212> TYPE: DNA
<213> ORGANISM: Trichoderma reesei

<400> SEQUENCE: 88
atggcaccac acccgacgct caaggccacc ttcgcggcca ggagcgagac ggcgacgcac      60
ccgctgacgg cttacctgtt caagctcatg gacctcaagg cgtccaacct gtgcctgagc     120
gccgacgtgc cgacagcgcg cgagctgctg tacctggccg acaagattgg cccgtcgatt     180
gtcgtgctca agacgcacta cgacatggtc tcgggctggg acttccaccc ggagacgggc     240
acgggagccc agctggcgtc gctggcgcgc aagcacggct tcctcatctt cgaggaccgc     300
aagtttggcg acattggcca caccgtcgag ctgcagtaca cgggcgggtc ggcgcgcatc     360
atcgactggg cgcacattgt caacgtcaac atggtgcccg gcaaggcgtc ggtggcctcg     420
ctggcccagg gcgccaagcg ctggctcgag cgctaccccc tgcgaggtca gacgtccgtc     480
accgtcggca cgcccaccat ggactcgttt gacgacgacg ccgactccag ggacgccgag     540
cccgccggcg ccgtcaacgg catgggctcc attggcgtcc tggacaagcc catctactcg     600
aaccggtccg cgcgacggccg caagggcagc atcgtctcca tcaccaccgt cacccagcag     660
tacgagtccg tctcctcgcc ccggttaaca aaggccatcg ccgagggcga cgagtcgctc     720
ttcccgggca tcgaggaggc gccgctgagc cgcggcctcc tgatcctcgc ccaaatgtcc     780
agccagggca acttcatgaa caaggagtac acgcaggcct gcgtcgaggc cgcccgggag     840
cacaaggact ttgtcatggg cttcatctcg caggagacgc tcaacaccga gcccgacgat     900
gcctttatcc acatgacgcc cggctgccag ctgccccccg aagacgagga ccagcagacc     960
aacggatcgg tcggtggaga cggccagggc cagcagtaca acacgccgca caagctgatt    1020
ggcatcgccg gcagcgacat tgccattgtg ggcggggca tcctcaaggc ctcagacccc     1080
gtagaggagg cagagcggta ccgatcagca gcgtggaaag cctacaccga gaggctgctg    1140
cgatag                                                                1146

<210> SEQ ID NO 89
<211> LENGTH: 2950
<212> TYPE: DNA
<213> ORGANISM: Trichoderma reesei

<400> SEQUENCE: 89
```

```
atgttgtcca atcctctccg tcgctattct gcctaccccg acatctcctc ggcgtcattt    60
gacccgaact accatggctc acagtcgcat ctccactcga tcaacgtcaa cacattcggc   120
aacagccacc cctatcccat gcagcacctc gcacagcatg cggagctttc gagttcacgc   180
atgataaggg ccagtccggt gcagccaaag cagcgccagg gctctcttat tgctgccagg   240
aagaattcaa cgggtactgc tgggcccatt cggcggagga tcagtcgcgc ttgtgaccag   300
tgcaaccagc ttcgtaccaa gtgcgatggc ttacacccat gtgcccattg tataggtatg   360
tcccttttcc tctacacagt gatgctgcgc tcaagcacat gtactgatcg atcttgttta   420
gaattcggcc ttggatgcga atatgtccga gagagaaaga agcgtggcaa agcttcgcgc   480
aaggatattg ctgcccagca agccgcggcg gctgcagcac aacactccgg ccaggtccag   540
gatggtccag aggatcaaca tcgcaaactc tcacgccagc aaagcgaatc ttcgcgtggc   600
agcgctgagc ttgcccagcc tgcccacgac ccgcctcatg ccacattga gggctctgtc   660
agctccttca gcgacaatgg cctttcccag catgctgcca tgggcggcat ggatggcctg   720
gaagatcacc atggccacgt cggagttgat cctgccctgg gccgaactca gctggaagcg   780
tcatcagcaa tgggcctggg cgcatacggt gaagtccacc ccggctatga gagccccggc   840
atgaatggcc atgtgatggt gccccgtcg tatggcgcgc agaccaccat ggccgggtat   900
tccggtatct cgtatgctgc gcaagccccg agtccggcta cgtatagcag cgacggtaac   960
tttcgactca ccggtcacat ccatgattac ccgctggcaa atgggagctc gccctcatgg  1020
ggagtctcgc tggcctcgcc ttcgaaccag ttccagcttc agctctcgca gcccatcttc  1080
aagcaaagcg atttgcgata tcctgtgctt gagcctctgc tgcctcacct gggaaacatc  1140
ctccccgtgt ctttggcgtg cgatctgatt gacctgtact tctcctcgtc ttcatcagca  1200
cagatgcacc caatgtcccc atacgttctg ggcttcgtct tccggaagcg ctccttcttg  1260
cacccacga acccacgaag gtgccagccc gcgctgcttg cgagcatgct gtgggtggcg  1320
gcacagacta gcgaagcgtc cttcttgacg agcctgccgt cggcgaggag caaggtctgc  1380
cagaagctgc tcgagctgac cgttgggctt cttcagcccc tgatccacac cggcaccaac  1440
agcccgtctc ccaagactag ccccgtcgtc ggtgctgctg ccctgggagt tcttggggtg  1500
gccatgccgg gctcgctgaa catggattca ctggccggcg aaacgggtgc ttttggggcc  1560
atagggagcc ttgacgacgt catcacctat gtgcacctcg ccacggtcgt ctcggccagc  1620
gagtacaagg gcgccagcct gcggtggtgg ggtgcggcat ggtctctcgc cagagagctc  1680
aagcttggcc gtgagctgcc gcctggcaat ccacctgcca accaggagga cggcgagggc  1740
cttagcgaag acgtggatga gcacgacttg aacagaaaca cactcgcttc gtgacggaa   1800
gaggagcgcg aagagcgacg gcgagcatgg tggctcgttt acatcgtcga caggcacctg  1860
gcgctctgct acaaccgccc cttgtttctt ctggacagcg agtgcagcga cttgtaccac  1920
ccgatggacg acatcaagtg gcaggcaggc aaatttcgca gccacgatgc agggaactcc  1980
agcatcaaca tcgatagctc catgacggac gagtttggcg atagtccccg gcggctcgc   2040
ggcgcacact acgagtgccg cggtcgtagc atttttggct acttcttgtc cttgatgaca  2100
atcctgggca gattgtcga tgtccaccat gctaaaagcc accccggtt cggcgttgga   2160
ttccgctccg cgcgggattg ggacgagcag gttgctgaaa tcacccgaca cctggacatg  2220
tatgaggaga gcctcaagag gttcgtggcc aagcatctgc cattgtcctc aaaggacaag  2280
gagcagcatg agatgcacga cagtggagcg gtaacagaca tgcaatctcc actctcggtg  2340
cggaccaacg cgtccagccg catgacggag agcgagatcc aggccagcat cgtggtggct  2400
```

```
tacagcaccc atgtgatgca tgtcctccac atcctccttg cggataagtg ggatcccatc    2460
aaccttctag acgacgacga cttgtggatc tcgtcggaag gattcgtgac ggcgacgagc    2520
cacgcggtat cggctgccga agctattagc cagattctcg agtttgaccc tggcctggag    2580
tttatgccat tcttctacgg cgtctatctc ctgcagggtt ccttcctcct cctgctcatc    2640
gccgacaagc tgcaggccga agcgtctcca agcgtcatca aggcttgcga gaccattgtt    2700
agggcacacg aagcttgcgt tgtgacgctg agcacagagt atcaggtaag ccctatcagt    2760
tcaaacgtct atcttgctgt gaatcaaaga ctgacttgga catcagcgca actttagcaa    2820
ggttatgcga agcgcgctgg ctctgattcg gggccgtgtg ccggaagatt tagctgagca    2880
gcagcagcga cgacgcgagc ttcttgcact ataccgatgg actggtaacg gaaccggtct    2940
ggccctctaa                                                           2950

<210> SEQ ID NO 90
<211> LENGTH: 57
<212> TYPE: DNA
<213> ORGANISM: Trichoderma reesei

<400> SEQUENCE: 90
gttcgtttcg gcttttcctc ggaaccccca gaggtcatca gttcgaatcg ctaacag      57

<210> SEQ ID NO 91
<211> LENGTH: 13
<212> TYPE: DNA
<213> ORGANISM: Trichoderma reesei

<400> SEQUENCE: 91
ttttttttct ctt                                                      13

<210> SEQ ID NO 92
<211> LENGTH: 20
<212> TYPE: DNA
<213> ORGANISM: T. Reesei

<400> SEQUENCE: 92
gctcaagacg cactacgaca                                               20
```